(12) United States Patent
Chong et al.

(10) Patent No.: US 8,338,593 B2
(45) Date of Patent: Dec. 25, 2012

(54) MODULATORS OF TOLL-LIKE RECEPTOR 7

(75) Inventors: Lee S. Chong, Newark, CA (US);
Manoj C. Desai, Pleasant Hill, CA (US);
Brian Gallagher, Goleta, CA (US);
Michael Graupe, Pacifica, CA (US);
Randall L. Halcomb, Foster City, CA (US); Hong Yang, Fremont, CA (US);
Jennifer R. Zhang, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 297 days.

(21) Appl. No.: 12/303,214

(22) PCT Filed: Jul. 6, 2007

(86) PCT No.: PCT/US2007/015615
§ 371 (c)(1),
(2), (4) Date: Feb. 19, 2009

(87) PCT Pub. No.: WO2008/005555
PCT Pub. Date: Jan. 10, 2008

(65) Prior Publication Data
US 2009/0202484 A1    Aug. 13, 2009

Related U.S. Application Data

(60) Provisional application No. 60/819,490, filed on Jul. 7, 2006, provisional application No. 60/832,851, filed on Jul. 24, 2006.

(51) Int. Cl.
*C07F 9/6561* (2006.01)
*C07D 473/16* (2006.01)
*A61K 31/675* (2006.01)
*A61P 31/20* (2006.01)
*C07D 473/40* (2006.01)

(52) U.S. Cl. ......... 544/157; 544/244; 544/277; 544/276
(58) Field of Classification Search .................. 544/157, 544/244; 514/81
See application file for complete search history.

(56) References Cited

U.S. PATENT DOCUMENTS

| 5,994,321 | A | 11/1999 | Lewis et al. | |
|---|---|---|---|---|
| 2006/0030545 | A1* | 2/2006 | Cheng et al. | 514/81 |
| 2008/0008682 | A1* | 1/2008 | Chong et al. | 424/85.6 |
| 2010/0210598 | A1* | 8/2010 | Carson et al. | 514/81 |

FOREIGN PATENT DOCUMENTS

WO    WO-92/05180    4/1992

OTHER PUBLICATIONS

Holy, Journal of Medicinal Chemistry (1999), 42(12), 2064-2086.*

Hemmi et al. (2002) "Small Anti-ciral Compounds Activate Immune Cells via the TLR7 MyD88-Dependent Signaling Pathway," *Nature Immunology* 392:196-200.

International Union of Pure and Applied Chemistry (1960) Definitive Rules for Nomenclature of Organic Chemistry, pp. 5566-5574.

Jin et al. (2006) Synthesis and Immunostimulatory Activity of 8-substituted amino 9-benzylacienines as potent Toll-Like Receptor .. *Bioorg Med Chem Lett* 16:4559-4563.

Klunder et al. (1989) "Arenesulfonate Derivatives of Homochiral Glycidol: Versatile Chiral Building Blocks for Organic Syntheses," *J Org. Chem* 54:1295-1304.

Paquette, Leo A. "The Diazines and S-Triazine," Chapter 9: Principals of Modern Heterocyclic Chemistry, 1968.

Paquette, Leo A. (1968) "Furan, Pyrrole, and Thiophene," Chapter 4: Principals of Modern Heterocyclic Chemistry.

Paquette, Leo A. (1968) "The Azoles" Chapter 6: Principals of Modern Heterocyclic Chemistry.

Paquette, Leo A. (1968) "The Four-Membered Heterocycles," Chapter 3: Principles of Modern Heterocyclic Chemistry.

(Continued)

*Primary Examiner* — Mark Berch

(57) ABSTRACT

The present application provides for a compound of Formula (I) or (II): or a pharmaceutically acceptable salt, solvate, and/or ester thereof, compositions containing such compounds, therapeutic methods that include the administration of such compounds, and therapeutic methods that include the administration of such compounds with at least one additional active agent.

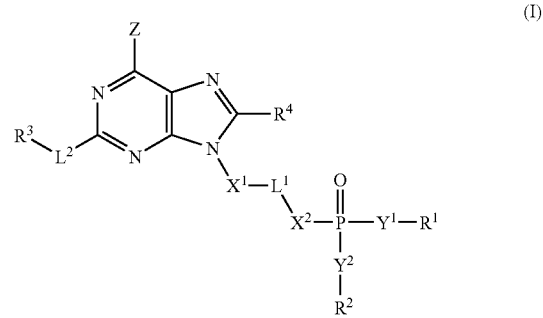

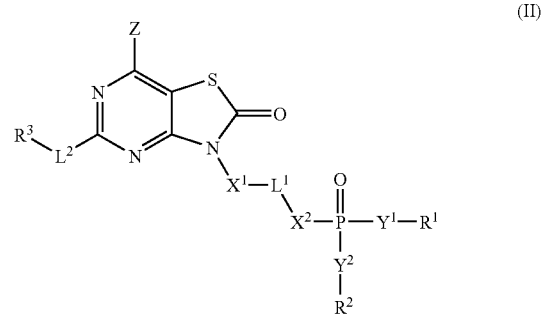

1 Claim, No Drawings

OTHER PUBLICATIONS

Paquette, Leo A. (1968) "The Pyridine Group," Chapter 7: Principals of Modern Heterocyclic Chemistry.

Paquette, Leo A. (1968) "Three-membered Rings with One Hetero Atom," Chapter 1: Principals of Modern Heterocyclic Chemistry.

Smeisters et al. (1999) "Inhibition of the in vitro growth of *Plasmodium falciparum* by acyclic nucleoside phosphonates," *International Journal of Antimicrobial Agents* 12:53-61.

Solinova et al. (2006) "Determination of Acid-Base Dissociation Constants of Amino- and Guanidinpurine Nucleotide Analogs and Related Compounds by Capillary Zone Electrophoresis," *Electrophoresis* 27:10056-1019.

Stuttgart, Georg Thiem Verlag (1994) "Diol Protecting Groups," Protecting Groups pp. 95-117.

Stuttgart, Georg Thieme Verlag (1994) "Hydroxyl Protecting Groups," Protecting Groups pp. 21-94.

Stuttgart, Georg Thieme Verlag (1994) "Carboxyl Protecting Groups" Protecting Groups, pp. 155-184.

Stuttgart, Georg Thieme Verlag (1994) "Carboxyl Protecting Groups" Protecting Groups, pp. 118-154.

Stuttgart, Georg Thieme Verlag, (1994) "An Overview" Protecting Groups, pp. 1-20.

Examination Report from New Zealand Intellectual Property Office, for Application No. 572983, dated Apr. 7, 2011.

Examination Report from the European Patent Office, for Application No. 07836017.9-1211, dated Mar. 11, 2011.

Office Action dated Jul. 11, 2011 for European Patent Application No. 07 836 017.9—1211.

Office Action dated Mar. 21, 2012 in Australian Patent App. No. 2007269557.

\* cited by examiner

MODULATORS OF TOLL-LIKE RECEPTOR 7

FIELD OF THE INVENTION

This application relates generally to compounds and pharmaceutical compositions which selectively activates toll-like receptor 7 (TLR7), and methods of making and using them.

BACKGROUND OF THE INVENTION

The innate immune system provides the body with a first line defense against invading pathogens. In an innate immune response, an invading pathogen is recognized by a germline-encoded receptor, the activation of which initiates a signaling cascade that leads to the induction of cytokine expression. Innate immune system receptors have broad specificity, recognizing molecular structures that are highly conserved among different pathogens. One family of these receptors is known as Toll-like receptors (TLRs), due to their homology with receptors that were first identified and named in *Drosophila*, and are present in cells such as macrophages, dendritic cells, and epithelial cells.

There are at least ten different TLRs in mammals. Ligands and corresponding signaling cascades have been identified for some of these receptors. For example, TLR2 is activated by the lipoprotein of bacteria (e.g., *E. coli.*), TLR3 is activated by double-stranded RNA, TLR4 is activated by lipopolysaccharide (i.e., LPS or endotoxin) of Gram-negative bacteria (e.g., *Salmonella* and *E. coli* O157:H7), TLR5 is activated by flagellin of motile bacteria (e.g., *Listeria*), TLR7 recognizes and responds to imiquimod and TLR9 is activated by unmethylated CpG sequences of pathogen DNA. The stimulation of each of these receptors leads to activation of the transcription factor NF-κB, and other signaling molecules that are involved in regulating the expression of cytokine genes, including those encoding tumor necrosis factor-alpha (TNF-α), interleukin-1 (IL-1), and certain chemokines.

SUMMARY OF THE INVENTION

The present invention is based, in part, on the discovery by the applicants that a number of small molecules can alter TLR-mediated immunostimulatory signaling. Accordingly, the present application is directed to compounds and pharmaceutical compositions, and methods for use in preventing or treating diseases or conditions characterized by Toll-like receptor 7 (TLR7) activation in patients. In one embodiment, the invention features a compound of formula I or II:

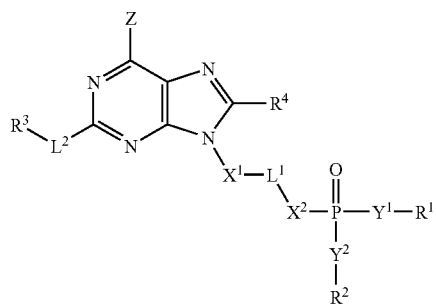

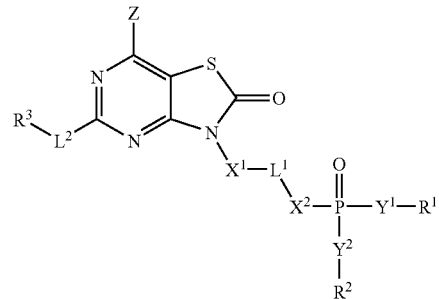

wherein:

Z is —$NH_2$ or —OH;

$X^1$ is alkylene, substituted alkylene, alkenylene, substituted alkenylene, alkynylene, substituted alkynylene, carbocyclylene, substituted carbocyclylene, heterocyclylene, or substituted heterocyclylene;

$L^1$ is a covalent bond, arylene, substituted arylene, heterocyclylene, substituted heterocyclylene, carbocyclylene, substituted carbocyclylene, —S—, —S(O)—, $S(O)_2$, —$NR^5$—, or —O—;

$X^2$ is a covalent bond, alkylene, or substituted alkylene;

$L^2$ is —$NR^5$—, —$N(R^5)C(O)$—, —O—, —S—, —S(O)—, $S(O)_2$, or a covalent bond;

$R^3$ is H, alkyl, substituted alkyl, heteroalkyl, substituted heteroalkyl, alkenyl, substituted alkenyl, aryl, substituted aryl, arylalkyl, substituted arylalkyl, heterocyclyl, substituted heterocyclyl, heterocyclylalkyl, or substituted heterocyclylalkyl;

$Y^1$ and $Y^2$ are each independently a covalent bond, —O— or —$NR^5$—; or —$Y^1$—$R^1$ and —$Y^2$—$R^2$ are each independently —O—N=$C(R^6R^7)$;

$R^1$ and $R^2$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^5$, -(substituted alkylene)-C(O)—O—$R^5$, -alkylene-O—C(O)—$R^5$, -(substituted alkylene)-O—C(O)—$R^5$, -alkylene-O—C(O)—O—$R^5$, or -(substituted alkylene)-O—C(O)—O—$R^5$;

$R^4$ is H, halogen, —OH, O-alkyl, —O-alkylene-O—C(O)—O—$R^1$, —O—C(O)—O—$R^5$, —SH, or —NH($R^5$);

each $R^5$, $R^6$, and $R^7$ are independently H, alkyl, substituted alkyl, carbocyclyl, substituted carbocyclyl, heterocyclyl substituted heterocyclyl, alkenyl, substituted alkenyl, alkynyl, substituted alkynyl, arylalkyl, substituted arylalkyl, heterocyclylalkyl, or substituted heterocyclylalkyl; and with the following provisos:
  (a) when $R^4$ is —OH, and
    $X^1$ is $C_1$-$C_2$ alkylene, and
    $L^1$ is phenylene or heterocylylene, and
    $X^2$ is a covalent bond or a $C_1$-$C_2$ alkylene, and
    $L^2$ is a covalent bond, —NH—, —O—, or —S—, and
    $R^3$ is alkyl or substituted alkyl, and
    $Y^1$ and $Y^2$ are both —O—;
    then:
    neither $R^1$ nor $R^2$ are alkyl, substituted alkyl or cycloalkyl;
  (b) when -$L^2$-$R^3$ is alkyl, amino, aminoalkyl, amidoalkyl, or thioalkyl, and
R⁴ is H, and
X¹ is alkylene or substituted alkylene, and
L¹ is —O—, and
X² is —CH₂—, and
Y¹ and Y² are both —O—;
then:
R¹ and R² are not both H or both alkyl;
(c) when L² is a covalent bond; then R³ is not H;
(d) when Y¹ is a covalent bond; then R¹ is not H;
(e) when Y² is a covalent bond, then R² is not H; and
(f) R⁶ and R⁷ are not both H.

In another embodiment, Formula I can be represented by Formula Ia:

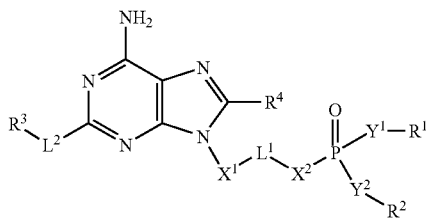

Ia wherein:
X¹ is alkylene, substituted alkylene, alkenylene, substituted alkenylene, alkynylene, substituted alkynylene, carbocyclylene, substituted carbocyclylene, heterocyclylene, or substituted heterocyclylene;
X² is a covalent bond, alkylene, or substituted alkylene;
Y¹ and Y² are each independently a covalent bond, —O— or —NR⁵—; or —Y—R¹ and —Y²—R² are each independently —O—N=C(R⁶R⁷);
L¹ is a covalent bond, arylene, substituted arylene, heterocyclylene, substituted heterocyclylene, carbocyclylene, substituted carbocyclylene, —S—, —S(O)—, S(O)₂, —NR⁵—, or —O—;
L² is —NR⁵—, —N(R⁵)C(O)—, —O—, —S—, —S(O)—, S(O)₂, or a covalent bond;
R¹ and R² are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—R⁵, -(substituted alkylene)-C(O)—O—R⁵, -alkylene-O—C(O)—R⁵, -(substituted alkylene)-O—C(O)—R⁵, -alkylene-O—C(O)—O—R⁵, or -(substituted alkylene)-O—C(O)—O—R⁵;
R³ is H, alkyl, substituted alkyl, heteroalkyl substituted heteroalkyl, alkenyl, substituted alkenyl, aryl, substituted aryl arylalkyl, substituted arylalkyl, heterocyclyl, substituted heterocyclyl, heterocyclylalkyl, or substituted heterocyclylalkyl;
R⁴ is H, halogen, —OH, —O-alkyl, —O-alkylene-O—C(O)—O—R⁵, —O—C(O)—O—R⁵, —SH, or —NH(R⁵);
R⁵ is H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; and
with the following provisos:
(a) when R⁴ is —OH, and
X¹ is C₁-C₂ alkylene, and
L¹ is phenylene or heterocyclylene, and
X² is a covalent bond or a C₁-C₂ alkylene, and L² is a covalent bond, —NH—, —O—, or —S—, and
R³ is alkyl or substituted alkyl, and
Y¹ and Y² are both —O—;
then:
neither R¹ nor R² are alkyl, substituted alkyl or cycloalkyl;
(b) when -L²-R³ is alkyl, amino, aminoalkyl, amidoalkyl, or
thioalkyl, and
R⁴ is H, and
X¹ is alkylene or substituted alkylene, and
L¹ is —O—, and
X² is —CH₂—, and
Y¹ and Y² are both —O—;
then:
R¹ and R² are not both H or both alkyl;
(c) when L² is a covalent bond; then R³ is not H;
(d) when Y¹ is a covalent bond; then R¹ is not H;
(e) when Y² is a covalent bond, then R² is not H; and
(f) R⁶ and R⁷ are not both H.

In another embodiment, Formula II can be represented by Formula IIa:

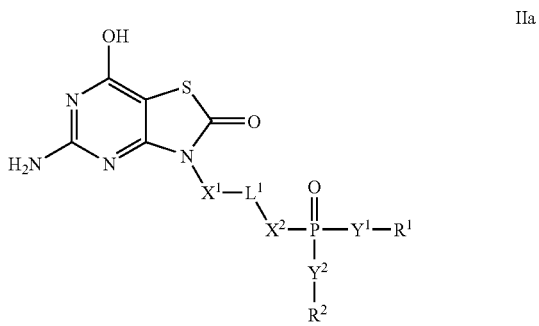

IIa or a pharmaceutically acceptable tautomer, salt, solvate, and/or ester thereof, wherein:
X¹ is alkylene, substituted alkylene, alkenylene, substituted alkenylene, alkynylene, substituted alkynylene; carbocyclylene, substituted carbocyclylene, heterocyclylene, or substituted heterocyclylene;
X² is a covalent bond, alkylene, or substituted alkylene;
L¹ is a covalent bond, arylene, substituted arylene, heterocyclylene, substituted heterocyclylene, carbocyclylene, substituted carbocyclylene, —S—, —S(O)—, S(O)₂, —NR³—, or —O—;
Y¹ and Y⁷ are each independently a covalent bond, —O—, or —NR⁴—;
R¹ and R² are each independently H, alkyl substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—R⁵, -(substituted alkylene)-C(O)—O—R⁵, -alkylene-O—C(O)—O—R⁵, or -(substituted alkylene)-O—C(O)—O—R⁵; and
R³, R⁴, and R⁵ are each independently H, alkyl, substituted alkyl, carbocyclyl, substituted carbocyclyl, heterocyclyl, substituted heterocyclyl, alkenyl, substituted alkenyl alkynyl, substituted alkynyl, arylalkyl, substituted arylalkyl, heterocyclylalkyl, or substituted heterocyclylalkyl;

with the following provisos:

(a) $Y^1$ and $Y^2$ are not both covalent bonds;

(b) when $Y^1$ is a covalent bond, then $R^1$ is not H; and (c) when $Y^2$ is a covalent bond, then $R^2$ is not H.

In another embodiment, the present application provides for a pharmaceutical composition comprising a compound of Formula I or II, or a pharmaceutically acceptable salt, solvate, and/or ester thereof; and a pharmaceutically acceptable carrier or excipient.

In another embodiment, the present application provides for a pharmaceutical composition comprising a compound of Formula I or II, or a pharmaceutically acceptable salt, solvate, and/or ester thereof; at least one additional active agent; and a pharmaceutically acceptable carrier or excipient.

In another embodiment, the present application provides for a method for treating or preventing a viral infection comprising administering, to a patient in need thereof, a therapeutically effective amount of at least one compound of Formula I or II, or a pharmaceutically acceptable salt, solvate, and/or ester thereof.

In another embodiment, the present application provides for a combination pharmaceutical agent comprising:

a) a first pharmaceutical composition comprising a compound of Formula I or II, or a pharmaceutically acceptable salt, solvate, and/or ester thereof; and b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HBV/HCV, another drug for treating HBV/HCV, and combinations thereof.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended to limit the invention to those claims. On the contrary, the invention is intended to cover all alternatives, modifications, and equivalents, which may be included within the scope of the present invention as defined by the claims.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of formula I or II" means a compound of formula I or II, or a pharmaceutically acceptable salt, solvate, or physiologically functional derivative thereof. Similarly, with respect to isolatable intermediates such as for example, compounds of formula (IX), the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{17}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene, vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CF_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aminoalkyl" refers to an acyclic alkyl radical in which one of the hydrogen atoms bonded to a carbon atom, typically a terminal or sp$^3$ carbon atom, is replaced with an amino radical.

"Amidoalkyl" refers to an acyclic alkyl radical in which one of the hydrogen atoms bonded to a carbon atom, typically a terminal or sp$^3$ carbon atom, is replaced with a —NRCOR$^a$ group where R is hydrogen or alkyl and R$^a$ is alkyl, substituted alkyl, aryl, or substituted aryl as defined herein, e.g., —(CH$_2$)$_2$—NHC(O)CH$_3$, —(CH$_2$)$_3$—NH—C(O)—CH$_3$, and the like.

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene.

"Arylalkyl" refers to an acyclic alkyl radical in which one of the hydrogen atoms bonded to a carbon atom, typically a terminal or Sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$; ═O, —OR, —SR, —S$^-$, —N$_2$, —N$^+$R$_3$, ═NR, —CX$_3$, —CN, —OCN, —SCN, —N═C═O, —NCS, —NO, —NO$_2$, ═N$_2$, —N$_3$, —NHC(═O)R, —C(═O)NRR—S(═O)$_2$O$^-$, —S(═O)$_2$OH, —S(═O)$_2$R, —OS(═O)$_2$OR, —S(═O)$_2$NR, —S(═O)R, —OP(═O)(OR)$_2$, —P(═O)(OR)$_2$, —P(═O)(O$^-$)$_2$, —P(═O)(OH)$_2$, —P(O)(OR)(O$^-$), —C(═O)R, —C(S)R, —C(O)OR, —C(O)O—, —C(S)OR, —C(O)SR, —C(S)SR, —C(O)NRR, —C(S)NRR, —C(═NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I or II should be selected in order to provide a compound which is sufficiently stable to provide a pharmaceutically useful compound which can be formulated into an acceptably stable pharmaceutical composition. Compounds of Formula I or U which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle"

includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

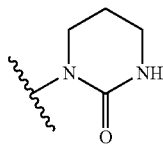

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisbxazolyl, oxindolyl, benzoxazolinyl, isatinoyl, and bis-tetrahydrofuranyl:

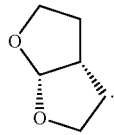

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or $Sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 2 to 20 carbon atoms, e.g., the alkyl portion of the arylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $Sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 2 to 20 carbon atoms, e.g., the alkenyl portion of the heterocyclyl alkenyl group comprises 1 to 6 carbon atoms and the heterocyclyl moiety comprises 1 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 2 to 20 carbon atoms, e.g., the alkynyl portion of the heterocyclyl alkynyl group comprises 1 to 6 carbon atoms and the heterocyclyl moiety comprises 1 to 14 carbon atoms.

"Heteroaryl" refers to a monovalent aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo (4,5), (5,5), (5,6) or (6,6) system, or 9 or 10 ring atoms arranged as a bicyclo (5,6) or (6,6) system. Examples of monocyclic carbocycles include cyclopropyl, cyclobutyl cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl.

"Carbocyclylene" refers to a carbocyclyl or carbocycle as defined above having two monovalent radical centers derived by the removal of two hydrogen atoms from the same or two different carbon atoms of a parent carbocyclyl. Typical carbocyclylene radicals include, but are not limited to, phenylene.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, $CH_2$-furanyl, $CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I (e.g., an optionally substituted aryl group) refers to a moiety having 0, 1, 2, or more substituents.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereo-selection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I or II

In one embodiment, the present application provides compounds according to Formula I or II, as described herein.

In another embodiment of the compounds of formula I or II, $-L^2-R^3$ is $-NH_2$.

In another embodiment of the compounds of formula I or II, $L^2$ is $-NR^5$ or $-O-$; and $R^3$ is heteroalkyl or substituted heteroalkyl.

In another embodiment of the compounds of formula I or II, $L^2$ is $-NR^5$ or $-O-$; and $R^3$ is alkyl or substituted alkyl.

In another embodiment of the compounds of formula I or II, $L^2$ is $-NR^5$ or $-O-$; and $R^3$ is arylalkyl, substituted arylalkyl, heterocyclylalkyl, or substituted heterocyclylalkyl.

In another embodiment of the compounds of formula I or II, $X^1$ is alkylene or substituted alkylene; $L^1$ is arylene, substituted arylene, heterocyclylene, substituted heterocyclylene, carbocyclylene, or substituted carbocyclylene; and $X^2$ is alkylene or substituted alkylene.

In another embodiment of the compounds of formula I or II, $X^1$ is alkylene or substituted alkylene; $L^1$ is $-S-$, $-NR$ %, or $-O-$; and $X^2$ is alkylene or substituted alkylene.

In another embodiment of the compounds of formula I or II, $X^1$ is alkylene or substituted alkylene; $L^1$ is a covalent bond; and $X^2$ is a covalent bond, alkylene or substituted alkylene.

In another embodiment of the compounds of formula I or II, $X^1$ is carbocyclylene, substituted carbocyclylene, heterocyclylene, or substituted heterocyclylene; $L^1$ is a covalent bond; and $X^2$ is alkylene or substituted alkylene.

In another embodiment of the compounds of formula I or II, $Y^1$ is $-O-$ or $-NR^5-$; 2 is a covalent bond; $R^1$ is H, alkyl, or substituted alkyl; and $R^2$ is alkyl or substituted alkyl.

In another embodiment of the compounds of formula I or II, $Y^1$ and $Y^2$ are each independently $-O-$ or $-NR^5-$; and $R^1$ and $R^2$ are each independently H, alkyl, or substituted alkyl.

In another embodiment of the compounds of formula I or II, $Y^1$ is $-O-$ or $-NR-9$; $Y^2$ is a covalent bond; $R^1$ is -alkylene-C(O)$-O-R^5$, -(substituted alkylene)-C(O)$-O-R^5$, -alkylene-O$-C(O)-R^5$, -(substituted alkylene)-O$-C(O)-R^5$, -alkylene-O$-C(O)-O-R^5$, or -(substituted alkylene)-O$-C(O)-O-R^5$; and $R^2$ is alkyl or substituted alkyl.

In another embodiment of the compounds of formula I or U, $Y^1$ and $Y^2$ are each independently $-O-$ or $-NR^5-$; and $R^1$ and $R^2$ are each independently -alkylene-C(O)$-O-R^5$, -(substituted alkylene)-C(O)$-O-R^5$, -alkylene-O$-C$(O)$-R^5$, -(substituted alkylene)-O$-C(O)-R^5$"-alkylene-O$-C(O)-O-R^5$, or -(substituted alkylene)-O$-C(O)-O-R^5$.

In another embodiment of the compounds of formula I or II, $Y^1$ is $-O-$ or $-NR^5-$; $Y^2$ is a covalent bond; and $R^2$ is carbocyclyl, substituted carbocyclyl, heterocyclyl, or substituted heterocyclyl.

In another embodiment of the compounds of formula I or II, $Y^1$ is $-O-$ or $-NR^5-$; $Y^2$ is a covalent bond; and $R^2$ is aryl, substituted aryl, substituted or unsubstituted 5- to 7-membered non-aromatic heterocyclyl containing one to 4 hetero atoms selected from a group consisting of N, O, S, and a combination thereof.

In another embodiment of the compounds of formula I or II, $Y^1$ and $Y^2$ are each independently $-O-$ or $-NR^5-$; and $R^2$ is carbocyclyl, substituted carbocyclyl, heterocyclyl, or substituted heterocyclyl.

In another embodiment of the compounds of formula I or II, $Y^1$ and $Y^2$ are each independently $-O-$ or $-NR^5-$; $R^2$ is aryl, substituted aryl, heteroaryl, or substituted heteroaryl.

In another embodiment of the compounds of formula I or II, $-Y^1-R^1$ is $-O-N=C(R^6R^7)$.

In another embodiment of the compounds of formula I or II, —Y$^1$—R$^1$ is —O—N=C(R$^6$R$^7$); Y$^2$ is —O— or —NR$^5$—.

In the above embodiments of the compounds of formula I or II, each R$^5$, R$^6$, and R$^7$ are independently H, alkyl substituted alkyl carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl.

Compounds of Formula Ia

In one embodiment, the present application provides compounds according to Formula Ia, as described herein.

In another embodiment of the compounds of formula Ia, —Y$^1$—R$^1$ is —OH.

In another embodiment of the compounds of formula Ia, —Y$^2$—R$^2$ is —OH.

In another embodiment of the compounds of formula Ia, —Y$^1$—R$^1$ and —Y$^2$—R$^2$ are both —OH.

In another embodiment of the compounds of formula Ia, Y$^1$ and Y$^2$ are each independently —O— or —NR$^5$—; and R$^1$ and R$^2$ are each independently -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$.

In another embodiment of the compounds of formula Ia, L$^2$ is —O—, —N(R$^5$)—, or —S—.

In another embodiment of the compounds of formula Ia, L$^2$ is —O—, —N(R$^5$)—, or —S—; and R$^3$ is alkyl, arylalkyl, or heteroalkyl.

In another embodiment of the compounds of formula Ia, L$^2$ is —O—, —N(R$^5$)—, or —S—, and R$^3$ is —CH$_2$CH$_2$CH$_2$CH$_3$.

In another embodiment of the compounds of formula Ia, L$^2$ is —O—, —N(R$^5$)—, or —S—; and R$^3$ is -alkylene-O-alkyl.

In another embodiment of the compounds of formula Ia, L$^2$ is —O—, —N(R$^5$)—, or —S—; and R$^3$ is —CH$_2$CH$_2$—O—CH$_3$.

In another embodiment of the compounds of formula Ia, L$^2$ is —O—, —N(R$^5$)—, or —S—; and R$^3$ is benzyl.

In another embodiment of the compounds of formula Ia, L$^2$ is —O—, —N(R$^5$)—, or —S—; and X$^1$ is alkylene.

In another embodiment of the compounds of formula Ia, L$^2$ is —O—, —N(R$^5$)—, or —S—; X$^1$ is CH$_2$—, —CH$_2$CH$_2$—, —CH$_2$CH$_2$CH$_2$—, or —CH$_2$CH(CH$_2$)—.

In another embodiment of the compounds of formula Ia, R$^4$ is —OH.

In another embodiment of the compounds of formula Ia, L$^1$ is arylene or substituted arylene.

In another embodiment of the compounds of formula Ia, —X$^1$-L$^1$- is —CH$_2$-phenylene-.

In another embodiment of the compounds of formula Ia, X$^1$ is alkylene; L$^1$ is —O—.

In another embodiment of the compounds of formula Ia, —X$^1$-L$^1$- is —CH$_2$CH$_2$—O— or —CH$_2$CH(CH$_3$)—O—.

In another embodiment of the compounds of formula Ia, X$^1$ is alkylene; L$^1$ is a covalent bond.

In another embodiment of the compounds of formula Ia, X$^1$ is alkylene, L$^1$ is arylene or substituted arylene, X$^2$ is alkylene.

In another embodiment of the compounds of formula Ia, X$^1$-L$^1$-X$^2$— is —CH$_2$-phenylene-CH$_2$—.

In another embodiment of the compounds of formula Ia, X$^1$-L$^1$-X$^2$— is —CH$_2$-(1,3-phenylene)-CH$_2$—.

In another embodiment of the compounds of formula Ia, X$^1$ is alkylene; L$^1$ is arylene or substituted arylene; X$^2$ is a covalent bond.

In another embodiment of the compounds of formula Ia, X$^1$-L$^1$-X$^2$— is —CH$_2$-phenylene-.

In another embodiment of the compounds of formula Ia, X$^1$-L$^1$-X$^2$— is —CH$_2$-(1,3-phenylene)- or —CH$_2$-(1,4-phenylene)-.

In another embodiment of the compounds of formula Ia, X$^1$ is alkylene; L$^1$ is —O—; X$^2$ is alkylene.

In another embodiment of the compounds of formula Ia, X$^1$ is alkylene; L$^1$ is —O—; X$^2$ is —CH$_2$—.

In another embodiment of the compounds of formula Ia, X$^1$-L$^1$-X$^2$— is —CH$_2$CH$_2$—O—CH$_2$— or —CH$_2$CH(CH$_3$)—O—CH$_2$—.

In another embodiment of the compounds of formula Ia, Y$^1$ and Y$^2$ are each independently —O— or —NR$^5$—.

In another embodiment of the compounds of formula Ia, Y$^1$ and Y$^2$ are both —O—.

In another embodiment of the compounds of formula Ia, Y$^1$ and Y$^2$ are each independently —O— or a covalent bond.

In another embodiment of the compounds of formula Ia, R$^1$ and R$^2$ are each independently H, alkyl, -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, -(substituted alkylene)-O—C(O)—O—R$^5$, aryl, or substituted aryl.

In another embodiment of the compounds of formula Ia, Y$^1$ and Y$^2$ are both —O—; R$^1$ and R$^2$ are each independently H or alkyl.

In another embodiment of the compounds of formula Ia, Y$^1$ and Y$^2$ are both —O—; R$^1$ and R$^2$ are each H.

In another embodiment of the compounds of formula Ia, Y$^1$ and Y$^2$ are each independently —O— or —NR$^5$—; R$^1$ and R$^2$ are each independently H, alkyl, -alkylene-C(O)—O—R, -(substituted alkylene)-C(O)—O—R$^5$, -alkylene-O—C(O)—R$^5$, -(substituted alkylene)-O—C(O)—R$^5$, -alkylene-O—C(O)—O—R$^5$, -(substituted alkylene)-O—C(O)—O—R$^5$, aryl, or substituted aryl.

In another embodiment of the compounds of formula Ia, Y$^1$ and Y$^2$ are each independently —O— or —NR$^5$—; and R$^1$ and R$^2$ are each H.

In another embodiment of the compounds of formula Ia, Y$^1$ is —NR$^5$—; Y$^2$ is —O—; R$^1$ is alkyl, -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$; and R$^2$ is aryl or substituted aryl.

In another embodiment of the compounds of formula Ia, Y$^1$ is —O—; Y$^2$ is a covalent bond; R$^1$ is H; and R$^2$ is alkyl, aryl, or substituted aryl.

In another embodiment of the compounds of formula Ia, Y$^2$ is a covalent bond; and R$^2$ is carbocyclyl, substituted carbocyclyl heterocyclyl, or substituted heterocyclyl.

In another embodiment of the compounds of formula Ia, Y$^2$ is a covalent bond; and R$^2$ is aryl, substituted aryl, substituted or unsubstituted 5- to 7-membered non-aromatic heterocyclyl containing 1 to 4 heteroatoms selected from a group consisting of N, O, S, and a combination thereof.

In another embodiment of the compounds of formula Ia, Y$^1$ and Y$^2$ are each independently —O— or —NR$^5$—; and R$^2$ is carbocyclyl, substituted carbocyclyl, heterocyclyl, or substituted heterocyclyl.

In another embodiment of the compounds of formula Ia, Y$^1$ and Y$^2$ are each independently —O— or —NR$^5$—; and R$^2$ is aryl, substituted aryl, heteroaryl, or substituted heteroaryl.

In another embodiment of the compounds of formula Ia, —Y$^1$—R$^1$ is —O—N=C(R$^6$R$^7$).

In another embodiment of the compounds of formula Ia, —Y$^1$—R$^1$ is —O—N=C(CH$_3$)$_2$.

In another embodiment of the compounds of formula Ia, —Y$^1$—R$^1$ is —O—N=C(R$^6$R$^7$); Y$^2$ is —O— or —NR$^5$—.

In another embodiment of the compounds of formula Ia, —Y$^1$—R$^1$ is —O—N=C(CH$_3$)$_2$; Y$^2$ is —O— or —NR$^5$—.

In another embodiment of the compounds of formula Ia, R$^4$ is —OH, —O—C(O)—O—CH$_2$CH$_3$, —O—CH$_2$—O—C(O)—O—CH(CH$_3$)$_2$, —NH—CH$_2$CH$_2$CH$_2$CH$_3$, —NH$_2$—CH$_2$CH$_2$—N(CH$_2$CH$_2$)$_2$O, or —SH.

In another embodiment of the compounds of formula Ia, X$^1$ is alkylene; Y$^1$ is —O— or —NR$^5$—; Y$^2$ is —O— or a covalent bond; L$^1$ is a covalent bond or arylene; L$^2$ is —O—; R$^1$ is H, alkyl, -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$; R$^2$ is H, alkyl, or aryl; R$^3$ is heteroalkyl; and R$^4$ is —OH.

In another embodiment of the compounds of formula Ia, X$^1$ and X$^2$ are alkylene; Y$^1$ is —O— or —NR$^5$—; Y$^2$ is —O— or —NR$^5$—; L$^1$ is arylene; L$^2$ is —O—; R$^1$ is H, alkyl, -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$; R$^2$ is H, alkyl, or aryl; R$^3$ is alkyl or heteroalkyl; and R$^4$ is —NH(R$^5$).

In another embodiment of the compounds of formula Ia, X$^1$ and X$^2$ are alkylene or substituted alkylene; Y$^1$ is —O— or —NR$^5$—; Y$^2$ is a covalent bond; and L$^1$ is arylene or —O—; L$^2$ is —O—; R$^1$ is H, alkyl, or substituted alkyl; and R$^2$ is carbocyclyl, substituted carbocyclyl, heterocyclyl, or substituted heterocyclyl.

In another embodiment of the compounds of formula Ia, X$^1$ and X$^2$ are alkylene or substituted alkylene; Y$^1$ and Y$^2$ are each independently —O— or —NR$^5$—; L$^1$ is arylene or —O—; L$^2$ is —O—; R$^1$ is -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$; and R$^2$ is carbocyclyl, substituted carbocyclyl, heterocyclyl, or substituted heterocyclyl.

In another embodiment of the compounds of formula Ia, X$^1$ and X$^2$ are alkylene or substituted alkylene; Y$^1$—R$^1$ is —O—N=C(R$^6$R$^7$); Y$^2$ is —O— or —NR$^5$—; L$^1$ is arylene or —O—; L$^2$ is —O—, and R$^2$ is -alkylene-C(O)—O—R$^5$, -(substituted alkylene)-C(O)—O—R$^5$, -alkylene-O—C(O)—R$^5$, -(substituted alkylene)-O—C(O)—R$^5$, -alkylene-O—C(O)—O—R$^5$, or -(substituted alkylene)-O—C(O)—O—R$^5$.

In another embodiment of the compounds of formula Ia, L$^2$ is —O—, —N(R$^5$)—, or —S—.

In another embodiment of the compounds of formula Ia, L$^2$ is —O—, —N(R$^5$)—, or —S—, R$^3$ is alkyl or heteroalkyl.

In another embodiment of the compounds of formula Ia, L$^2$ is —O—, —N(R$^5$)—, or —S—, R$^3$ is -alkylene-O-alkyl.

In another embodiment of the compounds of formula Ia, L$^2$ is —O—, —N(R$^5$)—, or —S—, R$^3$ is —CH$_2$CH$_2$—O—CH$_3$.

In another embodiment of the compounds of formula Ia, X$^1$ is alkylene.

In another embodiment of the compounds of formula Ia, X$^1$ is —CH$_2$—, —CH$_2$CH$_2$—, —CH$_2$CH$_2$CH$_2$—, or —CH$_2$CH(CH$_2$)—.

In another embodiment of the compounds of formula Ia, R$^4$ is —OH.

In another embodiment of the compounds of formula Ia, X$^1$ is alkylene, L$^1$ is arylene or substituted arylene.

In another embodiment of the compounds of formula Ia, —X$^1$-L$^1$- is —CH$_2$-phenylene-.

In another embodiment of the compounds of formula Ia, X$^1$ is alkylene, L$^1$ is —O—.

In another embodiment of the compounds of formula Ia, —X$^1$-L$^1$- is —CH$_2$CH$_2$—O— or —CH$_2$CH(CH$_3$)—O—.

In another embodiment of the compounds of formula Ia, X$^1$ is alkylene, L$^1$ is a covalent bond.

In another embodiment of the compounds of formula Ia, X$^1$ is alkylene, L$^1$ is arylene or substituted arylene, X$^2$ is alkylene.

In another embodiment of the compounds of formula Ia, X$^1$-L$^1$-X$^2$— is —CH$_2$-phenylene-CH$_2$—.

In another embodiment of the compounds of formula Ia, X$^1$-L$^1$-X$^2$— is —CH$_2$-(1,3-phenylene)-CH$_2$—.

In another embodiment of the compounds of formula Ia, X$^1$ is alkylene, L$^1$ is arylene or substituted arylene, X$^2$ is a covalent bond.

In another embodiment of the compounds of formula Ia, X$^1$ is alkylene, L$^1$ is arylene or substituted arylene, X$^2$ is a covalent bond, X$^1$-L$^1$-X$^2$— is —CH$_2$-phenylene-.

In another embodiment of the compounds of formula Ia, X$^1$ is alkylene, L$^1$ is arylene or substituted arylene, X$^2$ is a covalent bond, X$^1$-L$^1$-X$^2$— is —CH$_2$-(1,3-phenylene)- or —CH$_2$-(1,4-phenylene)-.

In another embodiment of the compounds of formula Ia, X$^1$ is alkylene, L$^1$ is —O—, X$^2$ is alkylene.

In another embodiment of the compounds of formula Ia, X$^1$ is alkylene, L$^1$ is —O—, X$^2$ is —CH$_2$—.

In another embodiment of the compounds of formula Ia, X$^1$ is alkylene, L$^1$ is —O—, X$^2$ is —CH$_2$—, X$^1$-L$^1$-X$^2$— is —CH$_2$CH$_2$—O—CH$_2$— or —CH$_2$CH(CH$_3$)—O—CH$_2$—.

In another embodiment of the compounds of formula Ia, Y$^1$ and Y$^2$ are each independently —O— or —NR$^5$—.

In another embodiment of the compounds of formula Ia, Y$^1$ and Y$^2$ are both —O—.

In another embodiment of the compounds of formula Ia, Y$^1$ and Y$^2$ are each independently —O— or a covalent bond.

In another embodiment of the compounds of formula Ia, R$^1$ and R$^2$ are each independently H, alkyl, -alkylene-C(O)—O—R$^5$, aryl, or substituted aryl.

In another embodiment of the compounds of formula Ia, Y$^1$ and Y$^2$ are both —O—, R$^1$ and R$^2$ are each independently H or alkyl.

In another embodiment of the compounds of formula Ia, Y$^1$ and Y$^2$ are both —O—, R$^1$ and R$^2$ are each H.

In another embodiment of the compounds of formula Ia, Y$^1$ and Y$^2$ are each independently —O— or —NR$^5$—, R$^1$ and R$^2$ are each independently H, alkyl, -alkylene-C(O)—O—R$^5$, aryl, or substituted aryl.

In another embodiment of the compounds of formula Ia, Y$^1$ is —NR$^5$—; Y$^2$ is —O—; R$^1$ is alkyl or -alkylene-C(O)—O—R$^5$; and R$^2$ is aryl or substituted aryl.

In another embodiment of the compounds of formula Ia, Y$^1$ is —NR$^5$—; Y$^2$ is —O—; R$^1$ is -alkylene-C(O)—O—R$^5$; and R$^2$ is aryl.

In another embodiment of the compounds of formula Ia, Y$^1$ is —O—; Y$^2$ is a covalent bond; R$^1$ is H; and R$^2$ is alkyl, aryl, or substituted aryl.

In another embodiment of the compounds of formula Ia, X$^1$ is alkylene; Y$^1$ is —O— or —NR$^5$—; Y$^2$ is —O— or a covalent bond; L$^1$ is a covalent bond or arylene; L$^2$ is —O—, R$^1$ is H, alkyl, or -alkylene-C(O)—O—R$^5$; R$^2$ is H, alkyl, or aryl; R$^3$ is heteroalkyl; and R$^4$ is —OH.

In another embodiment of the compounds of formula Ia, X$^1$ is alkylene; Y$^1$ and Y$^2$ are both —O—; R$^1$ and R$^2$ are both H; and L$^1$ is phenylene.

In another embodiment of the compounds of formula Ia, $X^1$ is alkylene; $Y^1$ and $Y^2$ are both —O—, $R^1$ and $R^2$ are both H; and $L^1$ and $X^2$ are both a covalent bond.

In another embodiment of the compounds of formula Ia, $X^1$ is alkylene; $Y^1$ and $Y^2$ are both —O—; $L^1$ is —O—; $R^1$ is H or alkyl; $R^2$ is H; and $X^2$ is alkylene.

In another embodiment of the compounds of formula Ia, $X^1$ is alkylene; $Y^1$ is —O—; $Y^2$ is a covalent bond; $L^1$ is phenylene; $R^1$ is H; $R^2$ is aryl; and $X^2$ is alkylene.

In another embodiment of the compounds of formula Ia, $X^1$ is alkylene; $Y^1$ is —NH—; $Y^2$ is —O—; $L^1$ is phenylene; $X^2$ is alkylene; $R^1$ is -alkylene-C(O)—O—$R^5$; and $R^2$ is phenyl.

In another embodiment of the compounds of formula Ia, $X^1$ and $X^2$ are alkylene; $Y^1$ is —O— or —NR$^5$—, $Y^2$ is —O— or —NR$^5$—; $L^1$ is arylene; $L^2$ is —O—; $R^1$ is H, alkyl, or -alkylene-C(O)—O—$R^5$; $R^2$ is H, alkyl, or aryl; $R^3$ is alkyl or heteroalkyl; and $R^4$ is —NH($R^5$).

In another embodiment of the compounds of formula Ia, $R^4$ is OH, $L^2$ is —O—, —N($R^5$)—, or —S—.

In another embodiment of the compounds of formula Ia, $R^4$ is OH, $L^2$ is —O—, —N($R^5$)—, or —S—, $R^3$ is alkyl or heteroalkyl, wherein the alkyl and heteroalkyl are any alkyl and heteroalkyl defined and exemplified herein. Non-limiting examples of alkyl or substituted alkyl include —CH$_3$, —CH(CH$_3$)$_2$, —C(CH$_3$)$_3$, —CH(alkyl), —CH(substituted alkyl), —CH(heteroalkyl), —C(alkyl)$_2$, —C(substituted alkyl)$_2$, —C(heteroalkyl)$_2$, —C(alkyl)(substituted alkyl), —C(heteroalkyl)(substituted alkyl), and —C(alkyl)(heteroalkyl), wherein alkyl, substituted alkyl, and heteroalkyl are as defined and exemplified herein. Non-limiting examples of alkyl or substituted alkyl include —OCH$_3$, —NHCH$_3$, —N(CH$_3$)$_2$, —SCH$_3$, —CH$_2$CH$_2$—O—CH$_3$, —CH$_2$NHCH$_3$, —CH$_2$N(CH$_3$)$_2$, —CH$_2$—S—CH$_3$, —CH$_2$CH$_2$—OH, —CH$_2$NH$_2$, and —CH$_2$CH$_2$—SH.

In another embodiment of the compounds of formula Ia, $R^4$ is OH, $L^2$ is —O—, —N($R^5$)—, or —S—, $R^3$ is -alkylene-O-alkyl.

In another embodiment of the compounds of formula Ia, $R^4$ is OH, $L^2$ is —O—, —N($R^5$)—, or —S—, $R^3$ is —CH$_2$CH$_2$—O—CH$_3$.

In another embodiment of the compounds of formula Ia, $R^4$ is OH, $X^1$ is alkylene.

In another embodiment of the compounds of formula Ia, $R^4$ is OH, $X^1$ is —CH$_2$—, —CH$_2$CH$_2$—, —CH$_2$CH$_2$CH$_2$—, or —CH$_2$CH(CH$_2$)—.

In another embodiment of the compounds of formula Ia, $R^4$ is OH, $X^1$ is alkylene, $L^1$ is arylene or substituted arylene.

In another embodiment of the compounds of formula Ia, $R^4$ is OH, —$X^1$-$L^1$- is —CH$_2$-phenylene-.

In another embodiment of the compounds of formula Ia, $R^4$ is OH, $X^1$ is alkylene, $L^1$ is —O—.

In another embodiment of the compounds of formula Ia, $R^4$ is OH, —$X^1$-$L^1$- is —CH$_2$CH$_2$—O— or —CH$_2$CH(CH$_3$)—O—.

In another embodiment of the compounds of formula Ia, $R^4$ is OH, $X^1$ is alkylene, $L^1$ is a covalent bond.

In another embodiment of the compounds of formula Ia, $R^4$ is OH, $X^1$ is alkylene, $L^1$ is arylene or substituted arylene, $X^2$ is alkylene.

In another embodiment of the compounds of formula Ia, $R^4$ is OH, $X^1$-$L^1$-$X^2$— is —CH$_2$-phenylene-CH$_2$—.

In another embodiment of the compounds of formula Ia, $R^4$ is OH, $X^1$-$L^1$-$X^2$— is —CH$_2$—(1,3-phenylene)-CH$_2$—.

In another embodiment of the compounds of formula Ia, $R^4$ is OH, $X^1$ is alkylene, $L^1$ is arylene or substituted arylene, $X^2$ is a covalent bond.

In another embodiment of the compounds of formula Ia, $R^4$ is OH, $X^1$ is alkylene, $L^1$ is arylene or substituted arylene, $X^2$ is a covalent bond, $X^1$-$L^1$-$X^2$— is —CH$_2$-phenylene-.

In another embodiment of the compounds of formula Ia, $R^4$ is OH, $X^1$ is alkylene, $L^1$ is arylene or substituted arylene, $X^2$ is a covalent bond, $X^1$-$L^1$-$X^2$— is —CH$_2$-(1,3-phenylene)- or —CH$_2$-(1,4-phenylene)-.

In another embodiment of the compounds of formula Ia, $R^4$ is OH, $X^1$ is alkylene, $L^1$ is —O—, $X^2$ is alkylene.

In another embodiment of the compounds of formula Ia, $R^4$ is OH, $X^1$ is alkylene, $L^1$ is —O—, $X^2$ is —CH$_2$—.

In another embodiment of the compounds of formula Ia, $R^4$ is OH, $X^1$-$L^1$-$X^2$— is —CH$_2$CH$_2$—O—CH$_2$— or —CH$_2$CH(CH$_3$)—O—CH$_2$—.

In another embodiment of the compounds of formula Ia, $R^4$ is OH, $X^1$-$L^1$-$X^2$— is —CH$_2$—O—CH$_2$CH$_2$— or —CH(CH$_3$)—O—CH$_2$CH$_2$—.

In another embodiment of the compounds of formula Ia, $R^4$ is OH, $X^1$-$L^1$-$X^2$— is —CH$_2$CH(aryl)-O—CH$_2$— or —CH$_2$CH(substituted-aryl)-O—CH$_2$—.

In another embodiment of the compounds of formula Ia, $R^4$ is OH, $X^1$-$L^1$-$X^2$— is —CH(aryl)CH$_2$—O—CH$_2$— or —CH(substituted-aryl)CH$_2$—O—CH$_2$—.

In another embodiment of the compounds of formula Ia, $R^4$ is OH, $X^1$-$L^1$-$X^2$— is —CH$_2$—O—CH(aryl)CH$_2$— or —CH$_2$—O—CH(substituted-aryl)CH$_2$—.

In another embodiment of the compounds of formula Ia, $R^4$ is OH, $X^1$-$L^1$-$X^2$— is —CH$_2$—O—CH$_2$CH(aryl)- or —CH$_2$—O—CH$_2$CH(substituted-aryl)-.

In another embodiment of the compounds of formula Ia, $R^4$ is OH, $X^1$-$L^1$-$X^2$— is —CH$_2$CH(arylalkyl)-O—CH$_2$— or —CH$_2$CH(substituted-arylalkyl)-O—CH$_2$—.

In another embodiment of the compounds of formula Ia, $R^4$ is OH, $X^1$-$L^1$-$X^2$— is —CH(arylalkyl)CH$_2$—O—CH$_2$— or —CH(substituted-arylalkyl)CH$_2$—O—CH$_2$—.

In another embodiment of the compounds of formula Ia, $R^4$ is OH, $X^1$-$L^1$-$X^2$— is —CH$_2$—O—CH(arylalkyl)CH$_2$— or —CH$_2$—O—CH(substituted arylalkyl)CH$_2$—.

In another embodiment of the compounds of formula Ia, $R^4$ is OH, $X^1$-$L^1$-$X^2$— is —CH$_2$—O—CH$_2$CH(arylalkyl)- or —CH$_2$—O—CH$_2$CH(substituted-arylalkyl)-.

In another embodiment of the compounds of formula Ia, $R^4$ is OH, $X^1$-$L^1$-$X^2$— is —CH$_2$CH(—O-arylalkyl)-O—CH$_2$— or CH$_2$CH(substituted —O-arylalkyl)-O—CH$_2$—.

In another embodiment of the compounds of formula Ia, $R^4$ is OH, $X^1$-$L^1$-$X^2$— is —CH(—O-arylalkyl)CH$_2$—O—CH$_2$— or —CH(substituted —O-arylalkyl)CH$_2$—O—CH$_2$—.

In another embodiment of the compounds of formula Ia, $R^4$ is OH, $X^1$-$L^1$-$X^2$— is —CH$_2$—O—CH(—O-arylalkyl)CH$_2$— or —CH$_2$—O—CH(substituted-O-arylalkyl)CH$_2$—.

In another embodiment of the compounds of formula Ia, $R^4$ is OH, $X^1$-$L^1$-$X^2$— is —CH$_2$—O—CH$_2$CH(—O-arylalkyl)- or —CH$_2$—O—CH$_2$CH(substituted —O-arylalkyl)-.

In another embodiment of the compounds of formula Ia, $R^4$ is OH, $X^1$-$L^1$-$X^2$— is —CH$_2$CH(-alkylene-O-arylalkyl)-O—CH$_2$— or H$_2$CH(substituted -alkylene-O-arylalkyl)-O—CH$_2$—.

In another embodiment of the compounds of formula Ia, $R^4$ is OH, $X^1$-$L^1$-$X^2$— is —CH(-alkylene-O-arylalkyl)CH$_2$—O—CH$_2$— or —CH(substituted -alkylene-O-arylalkyl)CH$_2$—O—CH$_2$—.

In another embodiment of the compounds of formula Ia, $R^4$ is OH, $X^1$-$L^1$-$X^2$— is —$CH_2$—O—CH(-alkylene-O-arylalkyl)$CF_2$— or $CH_2$—O—CH(substituted alkylene-O-arylalkyl)$CH_2$—.

In another embodiment of the compounds of formula Ia, $R^4$ is OH, $X^1$-$L^1$-$X^2$— is —$CH_2$—O—$CF_2$CH(-alkylene-O-arylalkyl)- or —$CH_2$—O—$CH_2$CH(substituted alkylene-O-arylalkyl)-.

In another embodiment of the compounds of formula Ia, $R^4$ is OH, $Y^1$ and $Y^2$ are each independently —O— or —$NR^5$—.

In another embodiment of the compounds of formula Ia, $R^4$ is OH, $Y^1$ and $Y^2$ are both —O—.

In another embodiment of the compounds of formula Ia, $R^4$ is OH, $Y^1$ and $Y^2$ are each independently —O— or a covalent bond.

In another embodiment of the compounds of formula Ia, $R^4$ is OH, $R^1$ and $R^2$ are each independently H, alkyl, -alkylene-C(O)—O—$R^5$, aryl, or substituted aryl.

In another embodiment of the compounds of formula Ia, $R^4$ is OH, $Y^1$ and $Y^2$ are both —O—, $R^1$ and $R^2$ are each independently H or alkyl.

In another embodiment of the compounds of formula Ia, $R^4$ is OH, $Y^1$ and $Y^2$ are both —O—, $R^1$ and $R^2$ are each H.

In another embodiment of the compounds of formula Ia, $R^4$ is OH, $Y^1$ and $Y^2$ are each independently —O— or —$NR^5$—, $R^1$ and $R^2$ are each independently H, alkyl, -alkylene-C(O)—O—$R^5$, aryl, or substituted aryl.

In another embodiment of the compounds of formula Ia, $R^4$ is OH, $Y^1$ is —$NR^5$—, $Y^2$ is —O—; $R^1$ is alkyl or -alkylene-C(O)—O—$R^5$; and $R^2$ is aryl or substituted aryl.

In another embodiment of the compounds of formula Ia, $R^4$ is OH, $Y^1$ is —$NR^5$—;
$Y^2$ is —O—; $R^1$ is -alkylene-C(O)—O—$R^5$; and $R^2$ is aryl.

In another embodiment of the compounds of formula Ia, $R^4$ is OH, $Y^1$ is —O—;
$Y^2$ is a covalent bond; $R^1$ is H; and $R^2$ is alkyl, aryl, or substituted aryl.

In another embodiment of the compounds of formula Ia, $R^4$ is OH, $X^1$ is alkylene; $Y^1$ and $Y^2$ are both —O—, $R^1$ and $R^2$ are both H; and $L^1$ is phenylene.

In another embodiment of the compounds of formula Ia, $R^4$ is OH, $X^1$ is alkylene; $Y^1$ and $Y^2$ are both —O—; $R^1$ and $R^2$ are both H; and $L^1$ and $X^2$ are both a covalent bond.

In another embodiment of the compounds of formula Ia, $R^4$ is OH, $X^1$ is alkylene; $Y^1$ and $Y^2$ are both —O—; $L^1$ is —O—; $R^1$ is H or alkyl; $R^2$ is H; and $X^2$ is alkylene.

In another embodiment of the compounds of formula Ia, $R^4$ is OH, $X^1$ is alkylene; $Y^1$ is —O—; $Y^2$ is a covalent bond; $L^1$ is phenylene; $R^1$ is H; $R^2$ is aryl; and $X^2$ is alkylene.

In another embodiment of the compounds of formula Ia, $R^4$ is OH, $X^1$ is alkylene; $Y^1$ is —NH—; $Y^2$ is —O—; $L^1$ is phenylene; $X^2$ is alkylene; $R^1$ is -alkylene-C(O)—O—$R^5$; and $R^2$ is phenyl.

In another embodiment of the compounds of formula Ia, $X^1$ and $X^2$ are alkylene; $Y^1$ is —O— or —$NR^5$—; $Y^2$ is —O— or —$NR^5$—; $L^1$ is arylene; $L^2$ is —O—, $R^1$ is H, alkyl, or -alkylene-C(O)—O—$R^5$; $R^2$ is H, alkyl, or aryl; $R^3$ is alkyl or heteroalkyl; and $R^4$ is —NH($R^5$).

In another embodiment of the compounds of formula Ia, $R^4$ is —NH($R^5$), $L^2$ is —O—, —N($R^5$)—, or —S—.

In another embodiment of the compounds of formula Ia, $R^4$ is —NH($R^5$), $L^2$ is —O—, —N($R^5$)—, or —S—, $R^3$ is alkyl or heteroalkyl, wherein the alkyl and heteroalkyl are any alkyl and heteroalkyl defined and exemplified herein.

In another embodiment of the compounds of formula Ia, $R^4$ is —NH($R^5$), $L^2$ is —O—, —N($R^5$)—, or —S—, $R^3$ is -alkylene-O-alkyl.

In another embodiment of the compounds of formula Ia, $R^4$ is —NH($R^5$), $L^2$ is —O—, —N($R^5$)—, or —S—, $R^3$ is —$CH_2CH_2$—O—$CH_3$.

In another embodiment of the compounds of formula Ia, $R^4$ is —NH($R^5$), $X^1$ is alkylene.

In another embodiment of the compounds of formula Ia, $R^4$ is —NH($R^5$), $X^1$ is —$CH_2$—, —$CH_2CH_2$—, —$CH_2CH_2CH_2$—, or —$CH_2CH(CH_2)$—.

In another embodiment of the compounds of formula Ia, $R^4$ is —NH($R^5$), $X^1$ is alkylene, $L^1$ is arylene or substituted arylene.

In another embodiment of the compounds of formula Ia, $R^4$ is —NH($R^5$), —$X^1$-$L^1$- is —$CH_2$-phenylene-.

In another embodiment of the compounds of formula Ia, $R^4$ is —NH($R^5$), $X^1$ is alkylene, $L^1$ is —O—.

In another embodiment of the compounds of formula Ia, $R^4$ is —NH($R^5$), —$X^1$-$L^1$- is —$CH_2CH_2$O— or —$CH_2$CH($CH_3$)—O—.

In another embodiment of the compounds of formula Ia, $R^4$ is —NH($R^5$), $X^1$ is alkylene, $L^1$ is a covalent bond.

In another embodiment of the compounds of formula Ia, $R^4$ is —NH($R^5$), $X^1$ is alkylene, $L^1$ is arylene or substituted arylene, $X^2$ is alkylene.

In another embodiment of the compounds of formula Ia, $R^4$ is —NH($R^5$), $X^1$-$L^1$-$X^2$— is —$CH_2$-phenylene-$CH_2$—.

In another embodiment of the compounds of formula Ia, $R^4$ is —NH($R^5$), $X^1$-$L^1$-$X^2$— is —$CH_2$-(1,3-phenylene)-$CH_2$—.

In another embodiment of the compounds of formula Ia, $R^4$ is —NH($R^5$), $X^1$ is alkylene, $L^1$ is arylene or substituted arylene, $X^1$ is a covalent bond.

In another embodiment of the compounds of formula Ia, $R^4$ is —NH($R^5$), $X^1$ is alkylene, $L^1$ is arylene or substituted arylene, $X^2$ is a covalent bond, $X^1$-$L^1$-$X^2$— is —$CH_2$-phenylene-.

In another embodiment of the compounds of formula Ia, $R^4$ is —NH($R^5$), $X^1$ is alkylene, $L^1$ is arylene or substituted arylene, $X^2$ is a covalent bond, $X^1$-$L^1$-$X^2$— is —$CH_2$-(1,3-phenylene)- or —$CH_2$-(1,4-phenylene)-.

In another embodiment of the compounds of formula Ia, $R^4$ is —NH($R^5$), $X^1$ is alkylene, $L^1$ is —O—, $X^2$ is alkylene.

In another embodiment of the compounds of formula Ia, $R^4$ is —NH($R^5$), $X^1$ is alkylene, $L^1$ is —O—, $X^2$ is —$CH_2$—.

In another embodiment of the compounds of formula Ia, $R^4$ is —NH($R^5$), $X^1$-$L^1$-$X^2$— is —$CH_2CH_2$—O—$CH_2$— or —$CH_2CH(CH_3)$—O—$CH_2$—.

In another embodiment of the compounds of formula Ia, $R^4$ is —NH($R^5$), $X^1$-$L^1$-$X^2$— is —$CH_2$—O—$CH_2CH_2$— or —CH($CH_3$)—O—$CH_2CH_2$—.

In another embodiment of the compounds of formula Ia, $R^4$ is —NH($R^5$), $X^1$-$L^1$-$X^2$— is —$CH_2$CH(aryl)-O—$CH_2$— or —$CH_2$CH(substituted-aryl)-O—CH—.

In another embodiment of the compounds of formula Ia, $R^4$ is —NH($R^5$), $X^1$-$L^1$-$X^2$— is —CH(aryl)$CH_2$—O—$CH_2$— or —CH(substituted-aryl)$CH_2$—O—$CH_2$—.

In another embodiment of the compounds of formula Ia, $R^4$ is —NH($R^5$), $X^1$-$L^1$-$X^2$— is —$CH_2$—O—CH(aryl)$CH_2$— or —$CH_2$—O—CH(substituted-aryl)$CH_2$—.

In another embodiment of the compounds of formula Ia, $R^4$ is —NH($R^5$), $X^1$-$L^1$-$X^2$— is —$CH_2$—O—$CH_2$CH(aryl)- or —$CH_2$—O—$CH_2$CH(substituted-aryl)-.

In another embodiment of the compounds of formula Ia, $R^4$ is —NH($R^5$), $X^1$-$L^1$-$X^2$— is —$CH_2$CH(arylalkyl)-O—$CH_2$— or —$CH_2$CH(substituted-arylalkyl)-O—$CH_2$—.

In another embodiment of the compounds of formula Ia, $R^4$ is —NH($R^5$), $X^1$-$L^1$-$X^2$— is —CH(arylalkyl)$CH_2$—O—$CH_2$— or —CH(substituted-arylalkyl)$CH_2$—O—$CH_2$—.

In another embodiment of the compounds of formula Ia, $R^4$ is —NH($R^5$), $X^1$-$L^1$-$X^2$— is —CH$_2$—O—CH(arylalkyl)CH$_2$— or —CH$_2$—O—CH(substituted arylalkyl)CH$_2$—.

In another embodiment of the compounds of formula Ia, $R^4$ is —NH($R^5$), $X^1$-$L^1$-$X^2$— is —CH$_2$—O—CH$_2$CH(arylalkyl)- or —CH$_2$—O—CH$_2$CH(substituted-arylalkyl)-.

In another embodiment of the compounds of formula Ia, $R^4$ is —NH($R^5$), $X^1$-$L^1$-$X^2$— is —CH$_2$CH(—O-arylalkyl)-O—CH$_2$— or —CH$_2$CH(substituted—O-arylalkyl)-O—CH$_2$—.

In another embodiment of the compounds of formula Ia, $R^4$ is —NH($R^5$), $X^1$-$L^1$-$X^2$— is —CH(—O-arylalkyl)CH$_2$—O—CH$_2$— or —CH(substituted —O-arylalkyl)CH$_2$—O—CH$_2$—.

In another embodiment of the compounds of formula Ia, $R^4$ is —NH($R^5$), $X^1$-$L^1$-$X^2$— is —CH$_2$—O—CH(—O-arylalkyl)CH$_2$— or —CH$_2$—O—CH(substituted-O-arylalkyl)CH$_2$—.

In another embodiment of the compounds of formula Ia, $R^4$ is —NH($R^5$), $X^1$-$L^1$-$X^2$— is —CH$_2$—O—CH$_2$CH(—O-arylalkyl)- or —CH—O—CH$_2$CH(substituted —O-arylalkyl)-.

In another embodiment of the compounds of formula Ia, $R^4$ is —NH($R^5$), $X^1$-$L^1$-$X^2$— is —CH$_2$CH(-alkylene-O-arylalkyl)-O—CH$_2$— or —CH$_2$CH(substituted-alkylene-O-arylalkyl)-O—CH$_2$—.

In another embodiment of the compounds of formula Ia, $R^4$ is —NH($R^5$), $X^1$-$L^1$-$X^2$— is —CH(-alkylene-O-arylalkyl)CH$_2$—O—CH$_2$— or —CH(substituted-alkylene-O-arylalkyl)CH$_2$—O—CH$_2$—.

In another embodiment of the compounds of formula Ia, $R^4$ is —NH($R^5$), $X^1$-$L^1$-$X^2$— is ~2-O—CH(-alkylene-O-arylalkyl)CH$_2$— or —CH$_2$—O—CH(substituted alkylene-O-arylalkyl)CH$_2$—.

In another embodiment of the compounds of formula Ia, $R^4$ is —NH($R^5$), $X^1$-$L^1$-$X^2$— is —CH$_2$—O—CH$_2$CH(-alkylene-O-arylalkyl)- or —CH$_2$—O—CH$_2$CH(substituted alkylene-O-arylalkyl)-.

In another embodiment of the compounds of formula Ia, $R^4$ is —NH($R^5$), $Y^1$ and $Y^2$ are each independently —O— or —NR$^5$—.

In another embodiment of the compounds of formula Ia, $R^4$ is —NH($R^5$), $Y^1$ and $Y^2$ are both —O—.

In another embodiment of the compounds of formula Ia, $R^4$ is —NH($R^5$), $Y^1$ and $Y^2$ are each independently —O— or a covalent bond.

In another embodiment of the compounds of formula Ia, $R^4$ is —NH($R^5$), $R^1$ and $R^2$ are each independently H, alkyl, -alkylene-C(O)—O—$R^5$, aryl, or substituted aryl.

In another embodiment of the compounds of formula Ia, $R^4$ is —NH($R^5$), $Y^1$ and $Y^2$ are both —O—, $R^1$ and $R^2$ are each independently H or alkyl.

In another embodiment of the compounds of formula Ia, $R^4$ is —NH($R^5$), $Y^1$ and $Y^2$ are both —O—, $R^1$ and $R^2$ are each H.

In another embodiment of the compounds of formula Ia, $R^4$ is —NH($R^5$), $Y^1$ and $Y^2$ are each independently —O— or —NR$^5$—, $R^1$ and $R^7$ are each independently H, alkyl, -alkylene-C(O)—O—$R^5$, aryl, or substituted aryl.

In another embodiment of the compounds of formula Ia, $R^4$ is —NH($R^5$), $Y^1$ is —NR$^5$—; $Y^2$ is —O—; $R^1$ is alkyl or -alkylene-C(O)—O—$R^5$; and $R^2$ is aryl or substituted aryl.

In another embodiment of the compounds of formula Ia, $R^4$ is —NH($R^5$), $Y^1$ is —NR$^5$—; 2 is —; $R^1$ is -alkylene-C(O)—O—$R^5$; and $R^2$ is aryl.

In another embodiment of the compounds of formula Ia, $R^4$ is —NH($R^5$), $Y^1$ is —O—; $Y^2$ is a covalent bond; $R^1$ is H; and $R^2$ is alkyl, aryl, or substituted aryl.

In another embodiment of the compounds of formula Ia, $R^4$ is —NH($R^5$), $X^1$ is alkylene; $Y^1$ and $Y^2$ are both —O—; $R^1$ and $R^2$ are both H; and $L^1$ is phenylene.

In another embodiment of the compounds of formula Ia, $R^4$ is —NH($R^5$), $X^1$ is alkylene; $Y^1$ and $Y^2$ are both —O—; $R^1$ and $R^2$ are both H; and $L^1$ and $X^2$ are both a covalent bond.

In another embodiment of the compounds of formula Ia, $R^4$ is —NH($R^5$), $X^1$ is alkylene; $Y^1$ and $Y^2$ are both —O—; $L^1$ is —O—; $R^1$ is H or alkyl; $R^2$ is H; and $X^2$ is alkylene.

In another embodiment of the compounds of formula Ia, $R^4$ is —NH($R^5$), $X^1$ is alkylene; $Y^1$ is —O—; $Y^2$ is a covalent bond; $L^1$ is phenylene; $R^1$ is H; $R^2$ is aryl; and $X^2$ is alkylene.

In another embodiment of the compounds of formula Ia, $R^4$ is —NH($R^5$), $X^1$ is alkylene; $Y^1$ is —NH—; $Y^2$ is —O—; $L^1$ is phenylene; $X^2$ is alkylene; $R^1$ is -alkylene-C(O)—O—$R^5$; and $R^2$ is phenyl.

In another embodiment of the compounds of formula Ia, $X^1$ and $X^2$ are alkylene; $Y^1$ is —O— or —NR$^5$—; $Y^2$ is —O— or —NR$^5$—; $L^1$ is arylene; $L^2$ is —O—; $R^1$ is H, alkyl, or -alkylene-C(O)—O—$R^5$; $R^2$ is H, alkyl, or aryl; $R^3$ is alkyl or heteroalkyl; and $R^4$ is —SH.

In another embodiment of the compounds of formula Ia, $R^4$ is —SH, $L^2$ is —O—, —N($R^5$)—, or —S—.

In another embodiment of the compounds of formula Ia, $R^4$ is —SH, $L^2$ is —O—, —N($R^5$)—, or —S—, $R^3$ is alkyl or heteroalkyl, wherein the alkyl and heteroalkyl are any alkyl and heteroalkyl defined and exemplified herein.

In another embodiment of the compounds of formula Ia, $R^4$ is —SH, $L^2$ is —O—, —N($R^5$)—, or —S—, $R^3$ is -alkylene-O-alkyl.

In another embodiment of the compounds of formula Ia, $R^4$ is —SH, $L^2$ is —O—, —N($R^5$)—, or —S—, $R^3$ is —CH$_2$CH$_2$—O—CH$_3$.

In another embodiment of the compounds of formula Ia, $R^4$ is —SH, $X^1$ is alkylene.

In another embodiment of the compounds of formula Ia, $R^4$ is —SH, $X^1$ is —CH$_2$—, —CH$_2$CH$_2$—, —CH$_2$CH$_2$—CH$_2$—, or —CH$_2$CH(CH$_3$)—.

In another embodiment of the compounds of formula Ia, $R^4$ is —SH, $X^1$ is alkylene, $L^1$ is arylene or substituted arylene.

In another embodiment of the compounds of formula Ia, $R^4$ is —SH, —$X^1$-$L^1$- is —CH$_2$-phenylene-.

In another embodiment of the compounds of formula Ia, $R^4$ is —SH, $X^1$ is alkylene, $L^1$ is —O—.

In another embodiment of the compounds of formula Ia, $R^4$ is —SH, —$X^1$-L- is —CH$_2$CH$_2$—O— or —CH$_2$CH(CH$_3$)—O—.

In another embodiment of the compounds of formula Ia, $R^4$ is —SH, $X^1$ is alkylene, $L^1$ is a covalent bond.

In another embodiment of the compounds of formula Ia, $R^4$ is —SH, $X^1$ is alkylene, $L^1$ is arylene or substituted arylene, $X^2$ is alkylene.

In another embodiment of the compounds of formula Ia, $R^4$ is —SH, $X^1$-$L^1$-$X^2$— is —CH$_2$-phenylene-CH$_2$—.

In another embodiment of the compounds of formula Ia, $R^4$ is —SH, $X^1$-$L^1$-$X^2$— is —CH$_2$-(1,3-phenylene)-CH—.

In another embodiment of the compounds of formula Ia, $R^4$ is —SH, $X^1$ is alkylene, $L^1$ is arylene or substituted arylene, $X^2$ is a covalent bond.

In another embodiment of the compounds of formula Ia, $R^4$ is —SH, $X^1$ is alkylene, $L^1$ is arylene or substituted arylene, $X^2$ is a covalent bond, $X^1$-$L^1$-$X^2$— is —CH$_2$-phenylene-.

In another embodiment of the compounds of formula Ia, $R^4$ is —SH, $X^1$ is alkylene, $L^1$ is arylene or substituted arylene, $X^2$ is a covalent bond, $X^1$-$L^1$-$X^2$— is —CH$_2$-(1,3-phenylene)- or —C$_1$-(1,4-phenylene)-.

In another embodiment of the compounds of formula Ia, $R^4$ is —SH, $X^1$ is alkylene, $L^1$ is —O—, $X^2$ is alkylene.

In another embodiment of the compounds of formula Ia, $R^4$ is —SH, $X^1$ is alkylene, $L^1$ is —O—, $X^2$ is —CH$_2$—.

In another embodiment of the compounds of formula Ia, $R^4$ is —SH, $X^1$-$L^1$-$X^2$— is —CH$_2$CH$_2$—O—CH$_2$— or —CH$_2$CH(CH$_3$)—O—CH$_2$—.

In another embodiment of the compounds of formula Ia, $R^4$ is —SH, $X^1$-$L^1$-$X^2$— is —CH$_2$—O—CH$_2$CH$_2$— or —CH(CH$_3$)—O—CH$_2$CH$_2$—.

In another embodiment of the compounds of formula Ia, $R^4$ is —SH, $X^1$-$L^1$-$X^2$— is —CH$_2$CH(aryl)-O—CH$_2$— or H$_2$CH(substituted-aryl)-O—CH$_2$—.

In another embodiment of the compounds of formula Ia, $R^4$ is —SH, $X^1$-$L^1$-$X^2$— is —CH(aryl)CH$_2$—O—CH$_2$— or —CH(substituted-aryl)CH$_2$—O—CH$_2$—.

In another embodiment of the compounds of formula Ia, $R^4$ is —SH, $X^1$-$L^1$-$X^2$— is —CH$_2$—O—CH(aryl)CH$_2$— or —CH$_2$—O—CH(substituted-aryl)CH$_2$—.

In another embodiment of the compounds of formula Ia, $R^4$ is —SH, $X^1$-$L^1$-$X^2$— is —CH$_2$—O—CH$_2$CH(aryl)- or —CH$_2$—O—CH$_2$CH(substituted-aryl)-.

In another embodiment of the compounds of formula Ia, $R^4$ is —SH, $X^1$-$L^1$-$X^2$— is —CH$_2$CH(arylalkyl)-O—CH— or —CH$_2$CH(substituted-arylalkyl)-O—CH$_2$—.

In another embodiment of the compounds of formula Ia, $R^4$ is —SH, $X^1$-$L^1$-$X^2$— is —CH(arylalkyl)CH$_2$—O—CH$_2$— or —CH(substituted-arylalkyl)CH$_2$—O—CH$_2$—.

In another embodiment of the compounds of formula Ia, $R^4$ is —SH, $X^1$-$L^1$-$X^2$— is —CH$_2$—O—CH(arylalkyl)CH$_2$— or —CH$_2$—O—CH(substituted arylalkyl)CH$_2$—.

In another embodiment of the compounds of formula Ia, $R^4$ is —SH, $X^1$-$L^1$-$X^2$— is —CH$_2$—O—OCH$_2$CH(arylalkyl)- or —CH$_2$—O—CH$_2$CH(substituted-arylalkyl)-.

In another embodiment of the compounds of formula Ia, $R^4$ is —SH, $X^1$-$L^1$-$X^2$— is —CH$_2$CH(—O-arylalkyl)-O—CH$_2$— or —CH$_2$CH(substituted —O-arylalkyl)-O—CH$_2$—.

In another embodiment of the compounds of formula Ia, $R^4$ is —SH, $X^1$-$L^1$-$X^2$— is —CH(—O-arylalkyl)CH$_2$—O—CH$_2$— or —CH(substituted —O-arylalkyl)CH$_2$—O—CH$_2$—.

In another embodiment of the compounds of formula Ia, $R^4$ is —SH, $X^1$-$L^1$-$X^2$— is —CH$_2$—O—CH(—O-arylalkyl)CH$_2$— or —CH$_2$—O—CH(substituted-O-arylalkyl)CH$_2$—.

In another embodiment of the compounds of formula Ia, $R^4$ is —SH, $X^1$-$L^1$-$X^2$— is —CH$_2$—O—CH$_2$CH(—O-arylalkyl)- or —CH$_2$—O—CH$_2$CH(substituted —O-arylalkyl)-.

In another embodiment of the compounds of formula Ia, $R^4$ is —SH, $X^1$-$L^1$-$X^2$— is —CH$_2$CH(-alkylene-O-arylalkyl)-O—CH— or —CH$_2$CH(substituted -alkylene-O-arylalkyl)-O—CH$_2$—.

In another embodiment of the compounds of formula Ia, $R^4$ is —SH, $X^1$-$L^1$-$X^2$— is —CH(-alkylene-O-arylalkyl)CH$_2$—O—CH$_2$— or —CH(substituted -alkylene-O-arylalkyl)CH$_2$—O—CH$_2$—.

In another embodiment of the compounds of formula Ia, $R^4$ is —SH, $X^1$-$L^1$-$X^2$— is —CH$_2$—O—CH(-alkylene-O-arylalkyl)CH$_2$— or —CH$_2$—O—CH(substituted alkylene-O-arylalkyl)CH$_2$—.

In another embodiment of the compounds of formula Ia, $R^4$ is —SH, $X^1$-$L^1$-$X^2$— is —CH$_2$—O—CH$_2$CH(-alkylene-O-arylalkyl)- or —CH—O—CH$_2$CH(substituted alkylene-O-arylalkyl)-.

In another embodiment of the compounds of formula Ia, $R^4$ is —SH, $Y^1$ and $Y^2$ are each independently —O— or —NR$^5$—.

In another embodiment of the compounds of formula Ia, $R^4$ is —SH, $Y^1$ and $Y^2$ are both —O—.

In another embodiment of the compounds of formula Ia, $R^4$ is —SH, $Y^1$ and $Y^2$ are each independently —O— or a covalent bond.

In another embodiment of the compounds of formula Ia, $R^4$ is —SH, $R^1$ and $R^2$ are each independently H, alkyl, -alkylene-C(O)—O—R$^5$, aryl, or substituted aryl.

In another embodiment of the compounds of formula Ia, $R^4$ is —SH, $Y^1$ and $Y^2$ are both —O—, $R^1$ and $R^2$ are each independently H or alkyl.

In another embodiment of the compounds of formula Ia, $R^4$ is —SH, $Y^1$ and $Y^2$ are both —, $R^1$ and $R^2$ are each H.

In another embodiment of the compounds of formula Ia, $R^4$ is —SH, $Y^1$ and $Y^2$ are each independently —O— or —NR$^5$—, $R^1$ and $R^2$ are each independently H, alkyl, -alkylene-C(O)—O—R$^5$, aryl, or substituted aryl.

In another embodiment of the compounds of formula Ia, $R^4$ is —SH, $Y^1$ is —NR$^5$—, $Y^2$ is —O—, $R^1$ is alkyl or -alkylene-C(O)—O—R$^5$; and $R^7$ is aryl or substituted aryl.

In another embodiment of the compounds of formula Ia, $R^4$ is —SH, $Y^1$ is —NR$^5$—; $Y^2$ is —O—; $R^1$ is -alkylene-C(O)—O—R$^5$; and $R^2$ is aryl.

In another embodiment of the compounds of formula Ia, $R^4$ is —SH, $Y^1$ is —;

$Y^2$ is a covalent bond; $R^1$ is H; and $R^2$ is alkyl, aryl, or substituted aryl.

In another embodiment of the compounds of formula Ia, $R^4$ is —SH, $X^1$ is alkylene; $Y^1$ and $Y^2$ are both —O—; $R^1$ and $R^2$ are both H; and $L^1$ is phenylene.

In another embodiment of the compounds of formula Ia, $R^4$ is —SH, $X^1$ is alkylene; $Y^1$ and $Y^2$ are both —O—; $R^1$ and $R^2$ are both H; and $L^1$ and $X^2$ are both a covalent bond.

In another embodiment of the compounds of formula Ia, $R^4$ is —SH, $X^1$ is alkylene; $Y^1$ and $Y^2$ are both —O—; $L^1$ is —O—; $R^1$ is H or alkyl; $R^2$ is H; and $X^2$ is alkylene.

In another embodiment of the compounds of formula Ia, $R^4$ is —SH, $X^1$ is alkylene; $Y^1$ is —O—; $Y^2$ is a covalent bond; $L^1$ is phenylene; $R^1$ is H; $R^2$ is aryl; and $X^2$ is alkylene.

In another embodiment of the compounds of formula Ia, $R^4$ is —SH, $X^1$ is alkylene; $Y^1$ is —NH—; $Y^2$ is —O—; $L^1$ is phenylene; $X^2$ is alkylene; $R^1$ is -alkylene-C(O)—O—R$^5$; and $R^2$ is phenyl.

In another embodiment of the compounds of Formula Ia, $R^4$ is OH, and $X^1$-$L_1$-$X^2$—P(O)($Y^1R^1$)($Y^2R^2$) is:

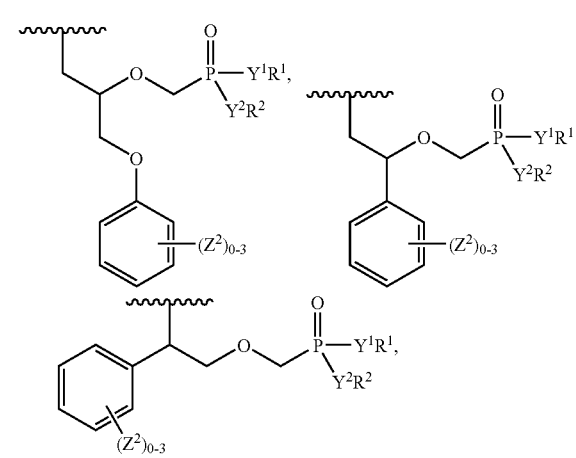

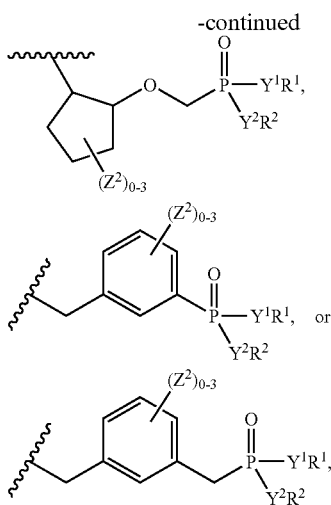

wherein $Z^2$ is selected from the group consisting of halo, alkyl, haloalkyl, and alkoxy.

In another embodiment of the compounds of formula Ia, $R^4$ is OH, —SH, —NH($R^5$), $X^1$ and $X^2$ are alkylene; $Y^1$ is —O— or —N$R^5$—, $Y^2$ is —O— or —N$R^5$—; $L^1$ is arylene; $R^1$ is H, alkyl, or -alkylene-C(O)—O—$R^5$; $R^2$ is H, alkyl, or aryl; $R^3$ is alkyl or heteroalkyl; $L^2$ is a bond, $R^3$ is a substituted alkyl, wherein the substituted alkyl is alkyl defined or exemplified herein. The substituents may include amino, amido, heteroalkyl, etc. Non-limiting examples of substituted alkyl include —CH$_2$—NH$_2$, —CH$_2$—NH—C(O)—CH$_3$, —CH$_2$—C(O)—NH—CH$_3$, —CH$_2$—CH$_2$—NH—C(O)—CH$_3$, —CH$_2$—CH$_2$—C(O)—NH—CH$_3$, —CH$_2$—NH—C(O)—CH$_2$—CH$_3$, —CH$_2$—C(O)—NH—CH$_2$—CH$_3$, —CH$_2$CH$_2$—O—CH$_3$, —CH$_2$CH(CH$_3$)—O—CH$_3$, —CH$_2$—O—CH$_2$—CH$_3$, —CH$_2$—O—CH(CH$_3$)CH$_3$, —CH$_2$CH$_2$—S—CH$_3$ or —CH—S—CH(CH$_3$)CH$_3$, —CH$_2$—S—CH$_2$CH$_3$ or —CH$_2$CH$_2$—NH$_7$—CH$_3$, —CH$_2$CH(CH$_3$)—NH$_2$—CH$_3$, —CH$_2$—NH$_2$—CH$_2$CH$_3$, —CH$_2$—NH$_2$—CH(CH$_3$)CH$_3$.

In another embodiment of the compounds of formula Ia, $R^4$ is OH, —SH, or —NH($R^5$), $L^2$ is a covalent, $R^3$ is —CH$_2$—NH$_2$, —CH$_2$—NH—C(O)—CH$_3$, $X^1$ is —CH$_2$—, —CH$_2$CH$_2$—, —CH$_2$CH$_2$CH$_2$—, or —CH$_2$CH(CH$_2$)—.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $L^1$ is arylene or substituted arylene.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, —$X^1$-$L^1$- is —CH$_2$-phenylene-.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $L^1$ is —O—.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, —$X^1$-$L^1$- is —CH$_2$CH$_2$—O— or —CH$_2$CH(CH$_3$)—.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, $X^1$ is alkylene, $L^1$ is a covalent bond.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, $X^1$ is alkylene, $L^1$ is arylene or substituted arylene, $X^2$ is alkylene.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, $X^1$-$L^1$-$X^2$— is —CH$_2$-phenylene-CH$_2$—.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, $X^1$-$L^1$-$X^2$— is —CH$_2$-(1,3-phenylene)-CH$_2$—.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, $X^1$ is alkylene, $L^1$ is arylene or substituted arylene, $X^2$ is a covalent bond.

In another embodiment of the compounds of formula Ia, $R^4$ is OH, —SH, or —NH($R^5$), $L^2$ is a covalent bond, $R^3$ is —CH$_2$—NH$_2$, or —CH$_2$—NH—C(O)—CH$_3$, $X^1$ is alkylene, $L^1$ is arylene or substituted arylene, $X^2$ is a covalent bond, $X^1$-$L^1$-$X^2$— is —CH$_2$-phenylene-.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $L^1$ is arylene or substituted arylene, $X^2$ is a covalent bond, $X^1$-$L^1$-$X^2$— is —CH$_2$-(1,3-phenylene)- or —CH$_2$-(1,4-phenylene)-.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $L^1$ is —, $X^2$ is alkylene.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $L^1$ is —O—, $X^2$ is —CH$_2$—.

In another embodiment of the compounds of formula Ia, $R^4$ is OH, —SH, or —NH($R^5$), $L^2$ is a covalent bond, $R^3$ is —CH$_2$—NH$_2$ or —CF$_2$—NH—C(O)—CH$_3$, $X^1$ is alkylene, $X^1$-$L^1$-$X^2$— is —CH$_2$CH$_2$—O—CH$_2$— or —CH$_2$CH(CH$_3$)—O—CH$_2$—.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $X^1$-$L^1$-$X^2$— is —CH$_2$—O—CH$_2$CH$_2$— or —CH(CH$_3$)—O—CH$_2$CH$_2$—.

In another embodiment of the compounds of formula Ia, $R^4$ is OH, —SH, or —NH($R^3$), $L^2$ is a covalent bond, $R^3$ is —CH$_2$—NH$_2$ or —CH$_2$—NH—C(O)—CH$_3$, $X^1$ is alkylene, $X^1$-$L^1$-$X^2$— is —CH$_2$CH(aryl)-O—CH$_2$— or —CH$_2$CH(substituted-aryl)-O—CH$_2$—.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $X^1$-$L^1$-$X^2$— is —CH(aryl)CH$_2$—O—CH$_2$— or —CH(substituted-aryl)CH$_2$—O—CH$_2$—.

In another embodiment of the compounds of formula Ia, $R^4$ is OH, —SH, or —NH($R^5$), $L^2$ is a covalent bond, $R^3$ is —CH$_2$—NH or —CH$_2$—NH—C(O)—CH$_3$, $X^1$ is alkylene, $X^1$-$L^1$-$X^2$— is —CH$_2$—O—CH(aryl)CH$_2$— or —CH$_2$—O—CH(substituted-aryl)CH$_2$—.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $X^1$-$L^1$-$X^2$— is CH$_2$—O—CH$_2$CH(aryl)- or —CH$_2$—O—CH$_2$CH(substituted-aryl)-.

In another embodiment of the compounds of formula Ia, $R^4$ is OH, —SH, or —NH($R^5$), $L^2$ is a covalent bond, $R^3$ is —CH$_2$—NH$_2$ or —CH$_2$—NH—C(O)—CH$_3$, $X^1$ is alkylene, $X^1$-$L^1$-$X^2$— is —$CH_2CH$(arylalkyl)-O—$CH_2$— or —$CH_2CH$(substituted-arylalkyl)-O—$CH_2$—.

In another embodiment of the compounds of formula Ia, $R^4$ is OH, —SH, or —NH($R^5$), $L^2$ is a covalent bond, $R^3$ is $CH_2$—NM or —$CH_2$—NH—C(O)—$CH_3$, $X^1$ is alkylene, $X^1$-$L^1$-$X^2$— is —CH(arylalkyl)$CH_2$—O—$CH_2$— or —CH(substituted-arylalkyl)$CH_2$—O—CH—.

In another embodiment of the compounds of formula Ia, $R^4$ is OH, —SH, or —NH($R^5$), $L^2$ is a covalent bond, $R^3$ is $CH_2$—$NH_2$ or —$CH_2$—NH—C(O)—$CH_3$, $X^1$ is alkylene, $X^1$-$L^1$-$X^2$— is —$C_2$—O—CH(arylalkyl)$CH_2$— or CH—O—CH(substituted arylalkyl)$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$—O—$CH_2$CH(arylalkyl)- or —$CH_2$—O—$CH_2$CH(substituted-arylalkyl)-.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$CH(—O-arylalkyl)-O—CH— or $H_2$CH(substituted —O-arylalkyl)-O—$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —CH(—O-arylalkyl)$CH_2$—O—$CH_2$— or —CH(substituted —O-arylalkyl)$CH_2$—O—$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$—O—CH(—O-arylalkyl)CH— or —$CH_2$—O—CH(substituted-O-arylalkyl)$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$—O—$CH_2$CH(—O-arylalkyl)- or —$CH_2$—O—$CH_2$CH(substituted —O-arylalkyl)-.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$CH(-alkylene-O-arylalkyl)-O—$CH_2$— or —$CH_2$CH(substituted-alkylene-O-arylalkyl)-O—$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —CH(-alkylene-O-arylalkyl)$CH_2$—O—$CH_2$— or —CH(substituted -alkylene-O-arylalkyl)$CH_2$—O—$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$—O—CH(-alkylene-O-arylalkyl)$CH_2$— or —CH—O—CH(substituted alkylene-O-arylalkyl)$CH_2$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene, $X^1$-$L^1$-$X^2$— is —$CH_2$—O—$CH_2$CH(-alkylene-O-arylalkyl)- or —$CH_2$—O—$CH_2$CH(substituted alkylene-O-arylalkyl)-.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ and $Y^2$ are each independently —O— or —$NR^c$—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ and $Y^2$ are both —O—.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ and $Y^2$ are each independently —O— or a covalent bond.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $R^1$ and $R^2$ are each independently H, alkyl, -alkylene-C(O)—O—$R^5$, aryl, or substituted aryl.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ and $Y^2$ are both —, $R^1$ and $R^2$ are each independently H or alkyl.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ and $Y^2$ are both —O—, $R^1$ and $R^2$ are each H.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ and $Y^2$ are each independently —O— or —$NR^5$—, $R^1$ and $R^2$ are each independently H, alkyl, -alkylene-C(O)—O—$R^5$, aryl, or substituted aryl.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ is —$NR^5$—; $Y^2$ is —O—; $R^1$ is alkyl or -alkylene-C(O)—O—$R^5$; and $R^2$ is aryl or substituted aryl.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $Y^1$ is —$NR^5$—; $Y^2$ is —O—; $R^1$ is -alkylene-C(O)—O—$R^5$; and $R^2$ is aryl.

In another embodiment of the compounds of formula Ia, $R^4$ is OH, —SH, or —NH($R^5$), $L^2$ is a covalent bond, $R^3$ is $CH_2$—$NH_2$ or —$CH_2$—NH—C(O)—$CH_3$, $Y^1$ is —O—; $Y^2$ is a covalent bond; $R^1$ is H; and $R^2$ is alkyl, aryl, or substituted aryl.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene; $Y^1$ and $Y^2$ are both —O—; $R^1$ and $R^2$ are both H; and $L^1$ is phenylene.

In another embodiment of the compounds of formula Ia, $R^4$ is OH, —SH, or —NH($R^5$), $L^2$ is a covalent bond, $R^3$ is $CH_2$—$NH_2$ or —$CH_2$—NH—C(O)—$CH_3$, $X^1$ is alkylene; $Y^1$ and $Y^2$ are both —O—, $R^1$ and $R^2$ are both H; and $L^1$ and $X^2$ are both a covalent bond.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene; $Y^1$ and $Y^2$ are both —O—; $L^1$ is —O—; $R^1$ is H or alkyl; $R^2$ is H; and $X^2$ is alkylene.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene; $Y^1$ is —O—; $Y^2$ is a covalent bond; $L^1$ is phenylene; $R^1$ is H; $R^2$ is aryl; and $X^2$ is alkylene.

In another embodiment of the compounds of formula Ia, $R^4$ is OH, —SH, or —NH($R^5$), $L^2$ is a covalent bond, $R^3$ is —$CH_2$—$NH_2$ or —$CH_2$—NH—C(O)—$CH_3$, $X^1$ is alkylene; $Y^1$ is —NH—; $Y^2$ is —O—; $L^1$ is phenylene; $X^2$ is alkylene; $R^1$ is -alkylene-C(O)—O—$R^5$; and $R^2$ is phenyl.

In the above embodiments of the compounds of formula Ia, each $R^5$, $R^6$, and $R^7$ are independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl.

In another embodiment of the compounds of formula Ia, the compound is selected from the group consisting of:

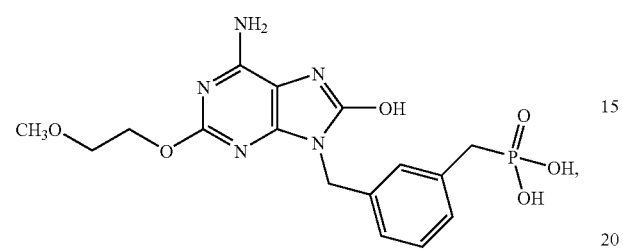

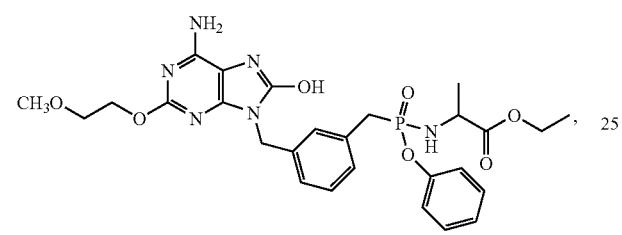

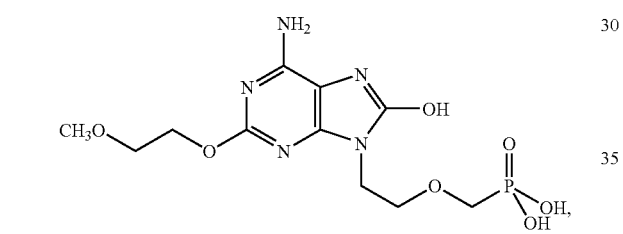

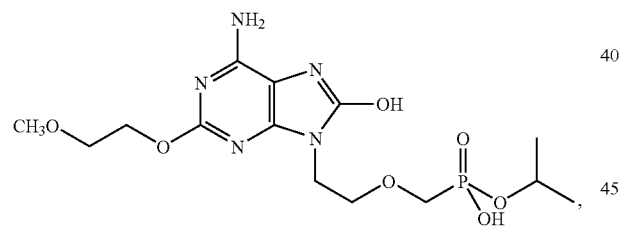

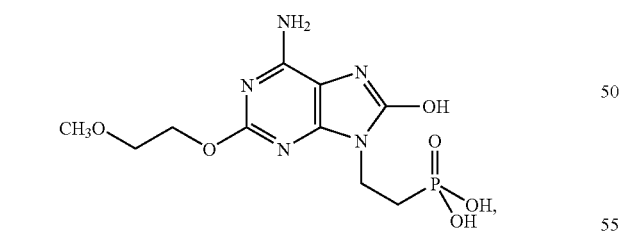

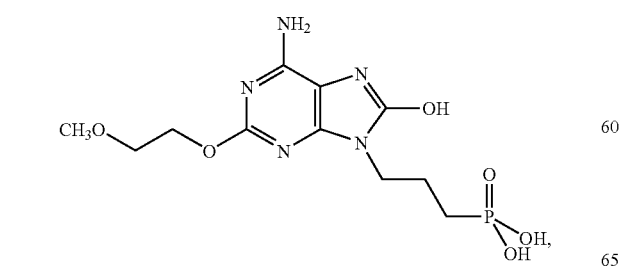

-continued

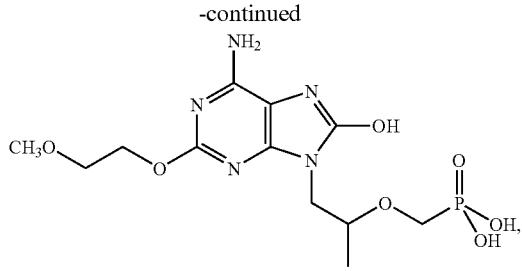

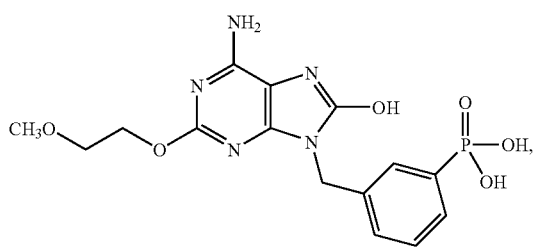

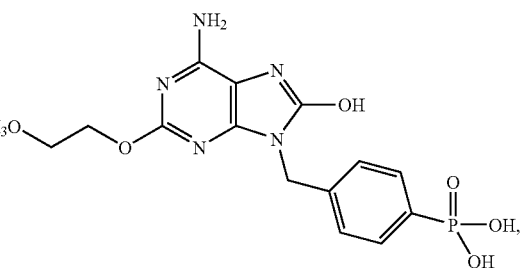

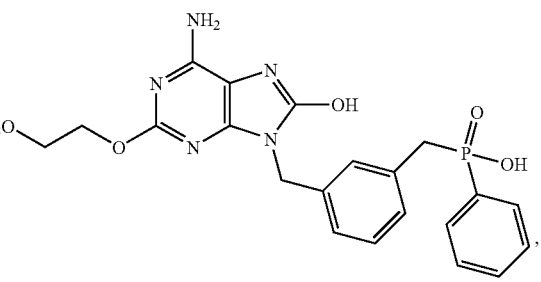

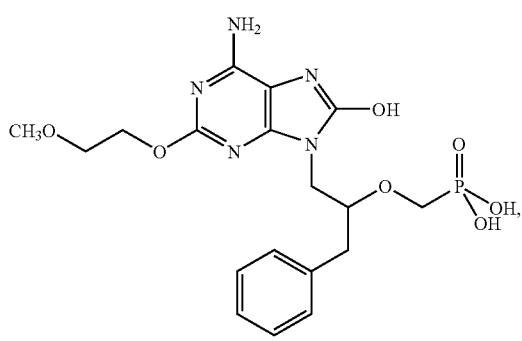

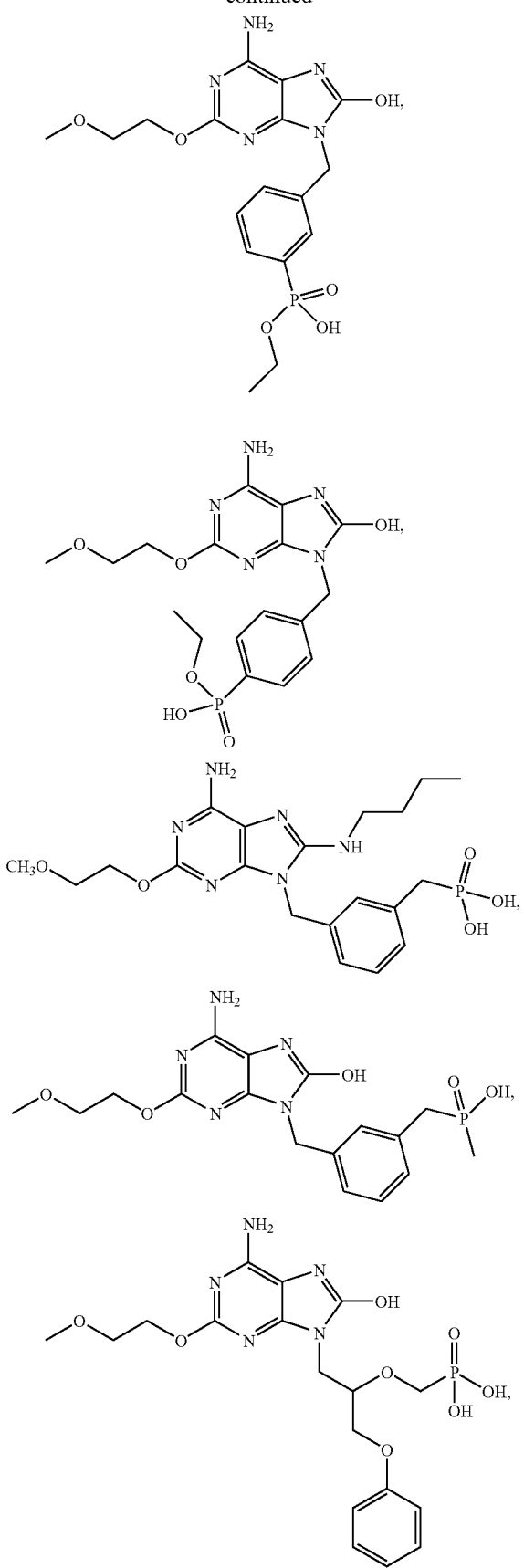

35
-continued
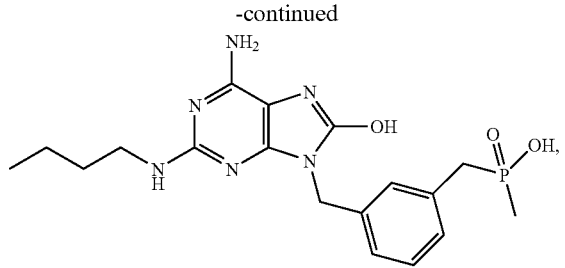
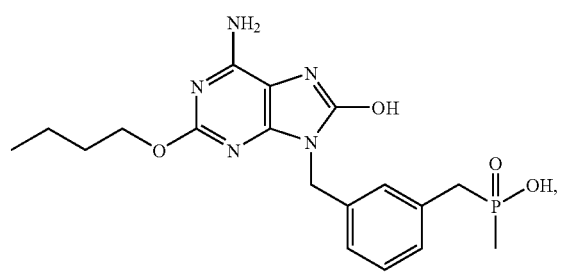
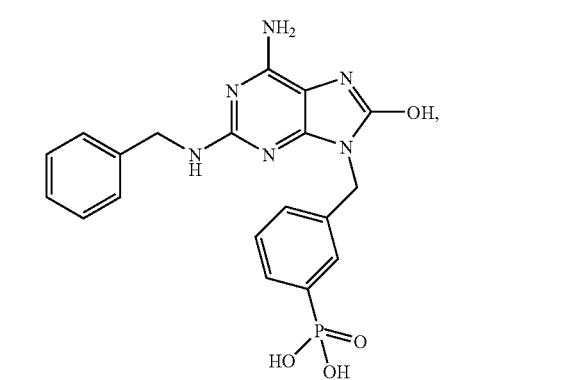
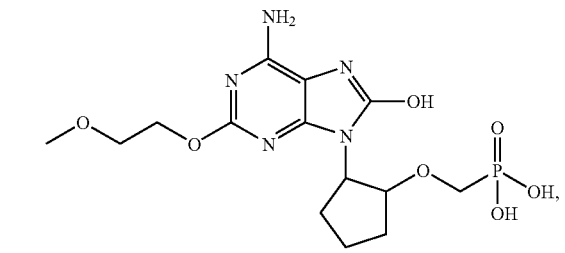
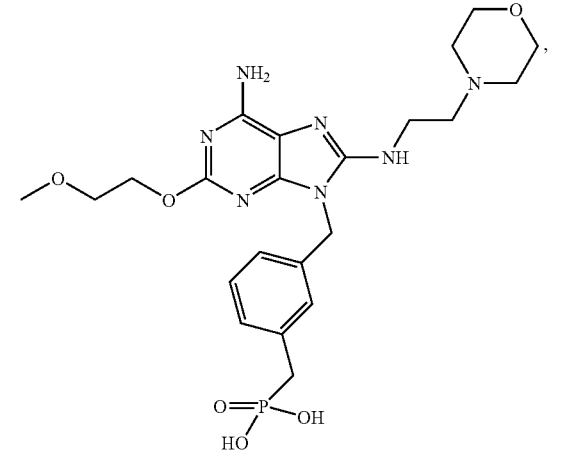
36
-continued
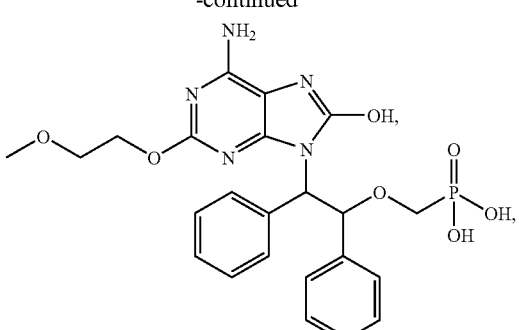
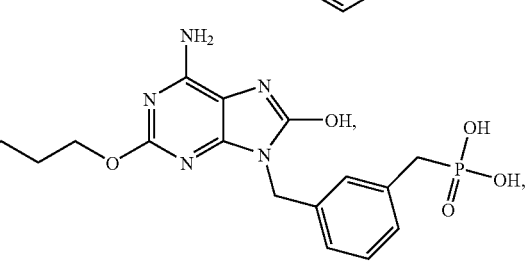
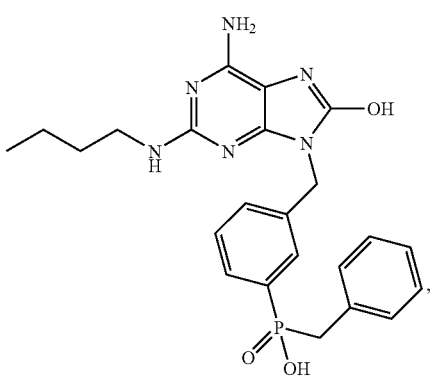
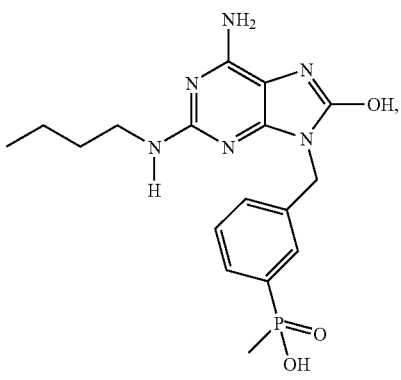
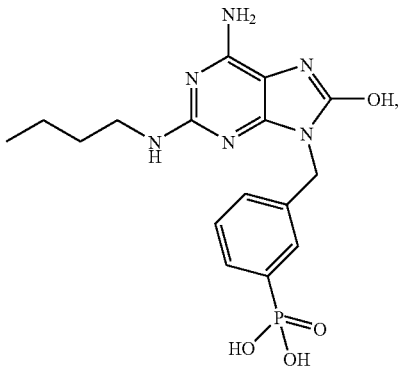

37
-continued
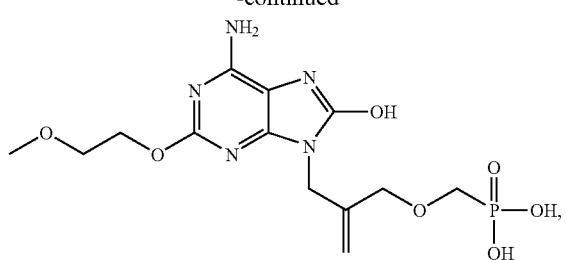
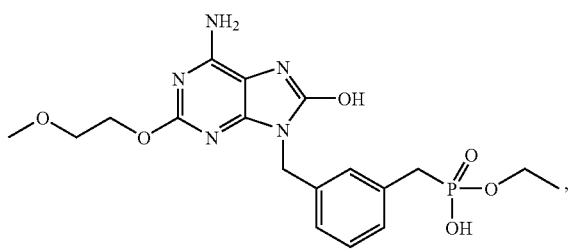
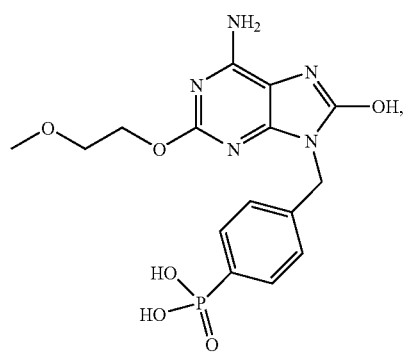
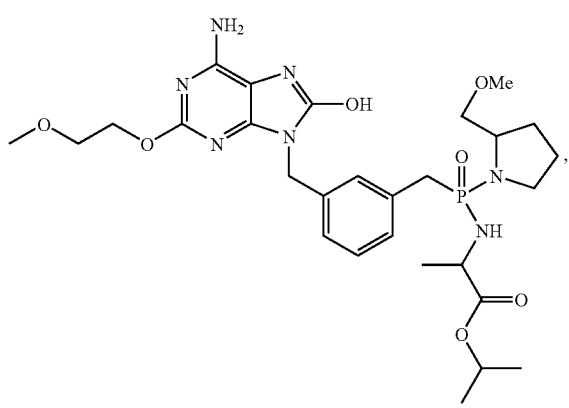
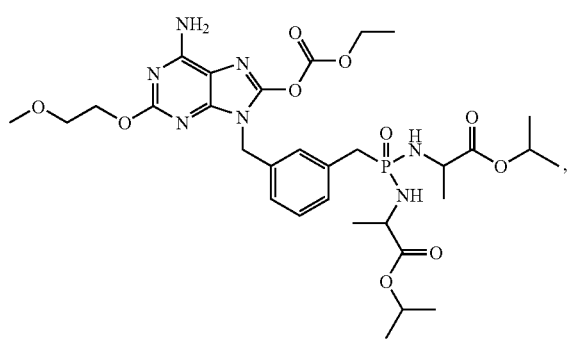
38
-continued
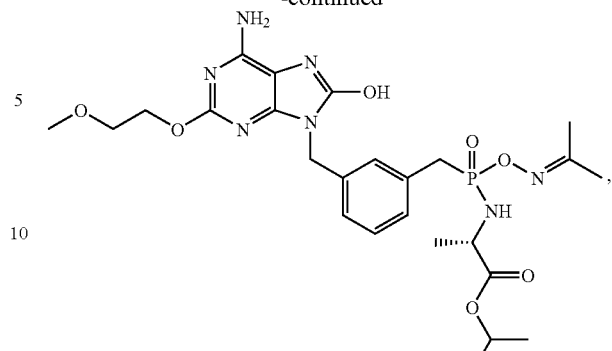
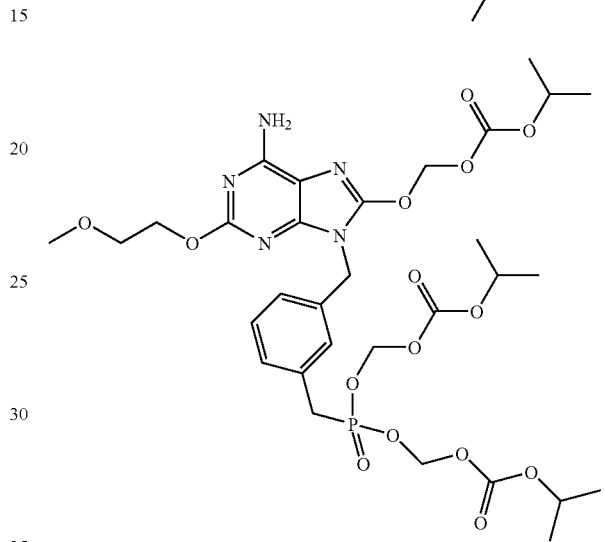
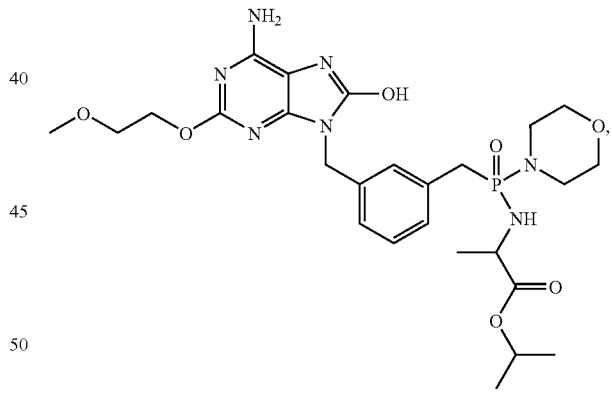
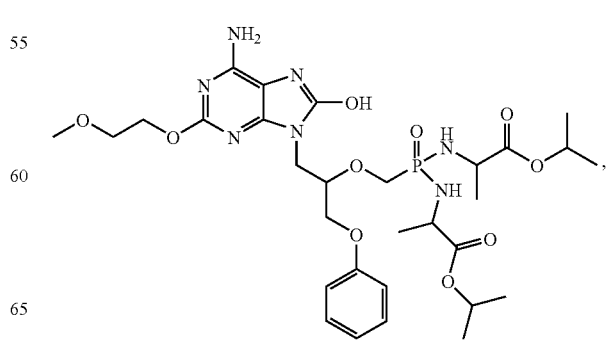

39
-continued
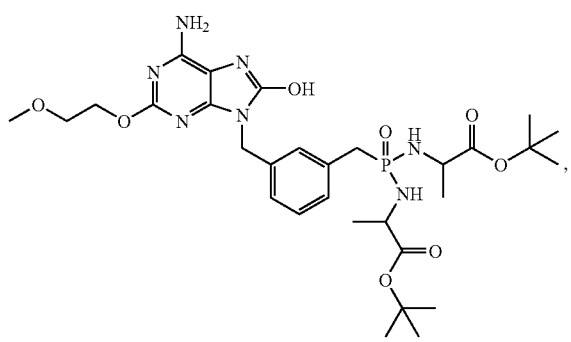
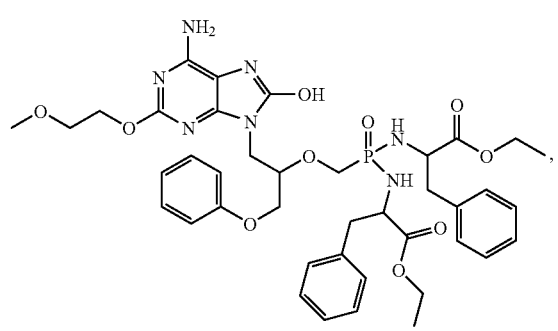
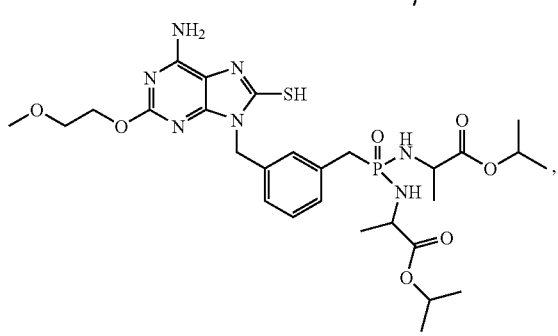
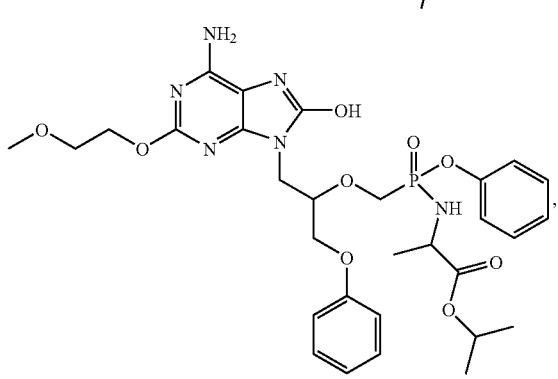
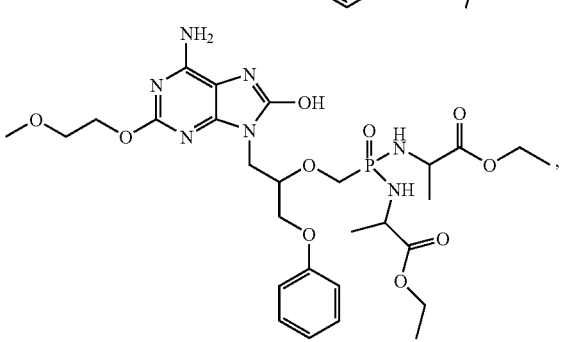
40
-continued
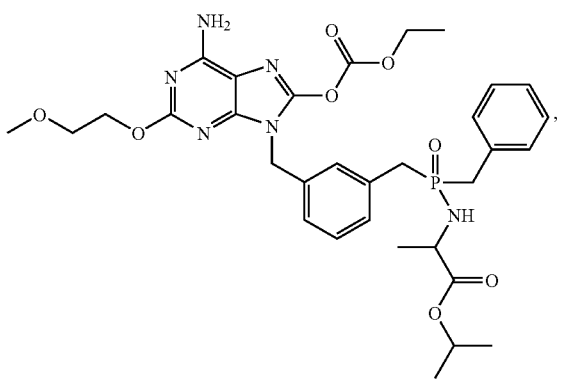
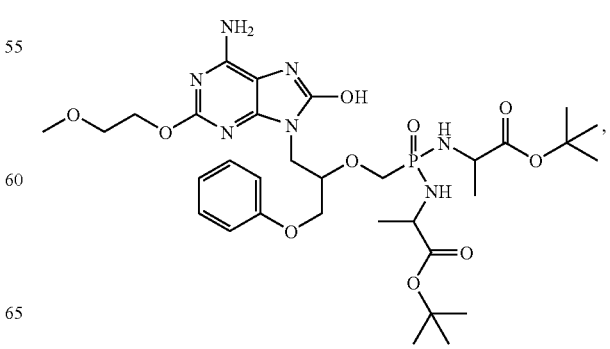

-continued

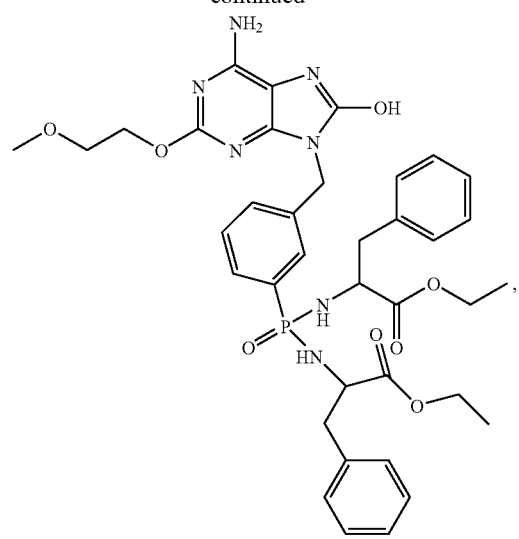

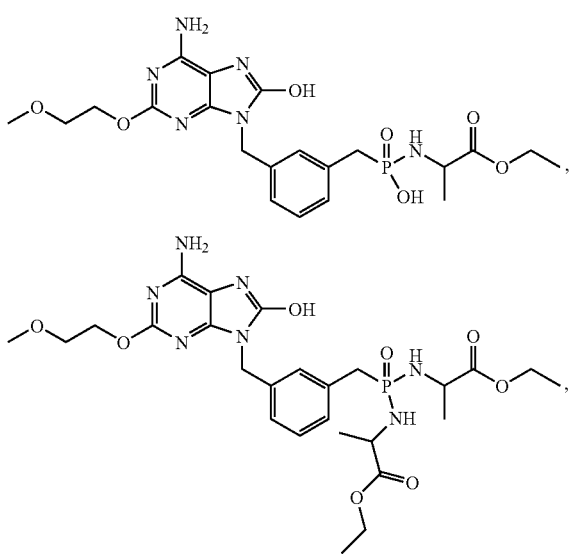

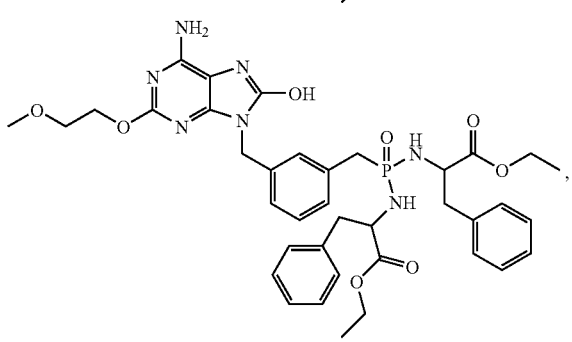

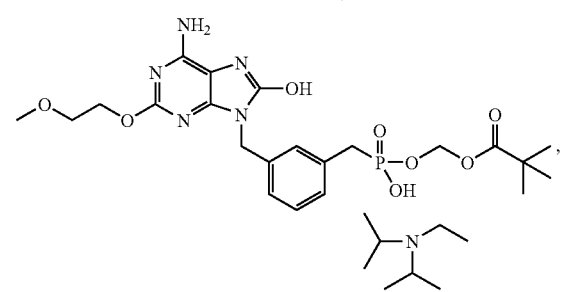

-continued

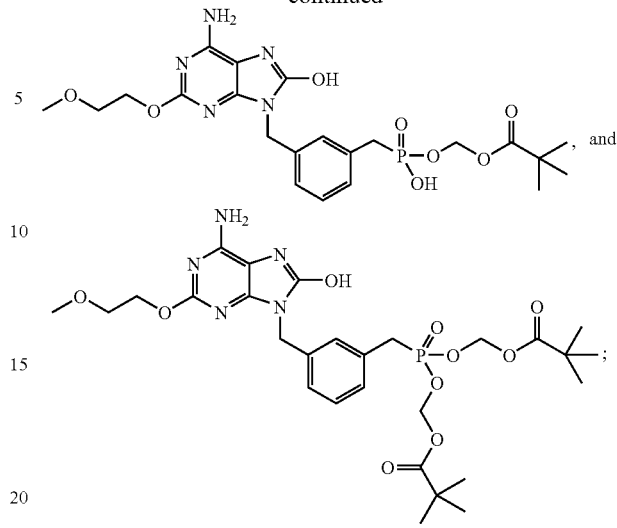

or pharmaceutically acceptable salts, solvates, and/or esters thereof. Compounds of Formula IIa In one embodiment, the present application provides compounds according to Formula IIa, as described herein.

In another embodiment of the compounds of formula Ia, $X^1$ is alkylene, substituted alkylene, alkenylene, substituted alkenylene, alkynylene, or substituted alkynylene.

In another embodiment of the compounds of formula IIa, $X^1$ is —CH$_2$— or —CH$_2$CH$_2$—.

In another embodiment of the compounds of formula IIa, $X^1$ is carbocyclylene, substituted carbocyclylene, heterocyclylene, or substituted heterocyclylene.

In another embodiment of the compounds of formula Ia, $X^1$ is

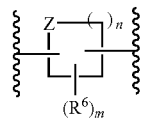

wherein Z is O, NR$^7$ or S; each R$^6$ is independently halo, hydroxyl, amino, cyano, alkyl, substituted alkyl, alkoxy, N-alkyl amino, N,N-dialkyl amino, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; R$^7$ is H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; n is 1, 2, 3, 4, or 5; and when n is 1, then m is 0, 1, or 2; when n is 2, then m is 0, 1, 2, or 3; when n is 3, then m is 0, 1, 2, 3, or 4; when n is 4, then m is 0, 1, 2, 3, 4, or 5; and when n is 5, then m is 0, 1, 2, 3, 4, 5, or 6.

In another embodiment of the compounds of formula Ia, $L^1$ is a covalent bond.

In another embodiment of the compounds of formula IIa, $L^1$ is —NR$^3$— or —O—.

In another embodiment of the compounds of formula IIa, $L^1$ is arylene, substituted arylene, heterocyclylene, substituted heterocyclylene, carbocyclylene, or substituted carbocyclylene.

In another embodiment of the compounds of formula IIa, $L^1$ is

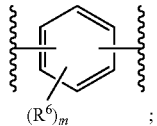

wherein m is 0, 1, 2, 3, or 4; and each $R^6$ is independently H, halo, hydroxyl, amino, cyano, alkyl, substituted alkyl, alkoxy, N-alkyl amino, N,N-dialkyl amino, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl.

In another embodiment of the compounds of formula IIa, $Y^1$ is a covalent bond; and $Y^2$ is —O— or —$NR^4$—.

In another embodiment of the compounds of formula IIa, $Y^1$ is —O—; and $Y^2$—$NR^4$—.

In another embodiment of the compounds of formula Ia, $Y^1$ and $Y^2$ are both —O—.

In another embodiment of the compounds of formula IIa, $Y^1$ and $Y^2$ are both —$NR^4$—.

In another embodiment of the compounds of formula Ia, $R^1$ and $R^2$ are each independently H, alkyl or substituted alkyl.

In another embodiment of the compounds of formula IIa, $X^1$ is alkylene or substituted alkylene; $L^1$ is a covalent bond; and $X^2$ is a covalent bond, alkylene, or substituted alkylene.

In another embodiment of the compounds of formula IIa, —$X^1$-$L^1$-$X^2$— is —$CH_2CH$.

In another embodiment of the compounds of formula IIa, $X^1$ is alkylene or substituted alkylene; $L^1$ is a covalent bond; and $X^2$ is a covalent bond, alkylene, or substituted alkylene; $Y^1$ and $Y^2$ are both —O—; and $R^1$ and $R^2$ are each independently H, alkyl, or substituted alkyl.

In another embodiment of the compounds of formula IIa, $X^1$ is alkylene or substituted alkylene; $L^1$ is —$NR^3$— or —O—; and $X^2$ is a covalent bond, alkylene, or substituted alkylene.

In another embodiment of the compounds of formula IIa, —$X^1$-$L^1$-$X^2$ is —$CH_2CH_2$—O—$CH_2$—.

In another embodiment of the compounds of formula IIa, $X^1$ is alkylene or substituted alkylene; $L^1$ is —$NR^3$— or —O—; and $X^2$ is a covalent bond, alkylene, or substituted alkylene; $Y^1$ and $Y^2$ are both —O—; and $R^1$ and $R^2$ are each independently H, alkyl, or substituted alkyl.

In another embodiment of the compounds of formula Ia, $X^1$ is alkylene or substituted alkylene; $L^1$ is arylene, substituted arylene, heterocyclylene, substituted heterocyclylene, carbocyclylene, or substituted carbocyclylene; and $X^2$ is a covalent bond, alkylene, or substituted alkylene.

In another embodiment of the compounds of formula IIa, $X^1$ is carbocyclylene, substituted carbocyclylene, heterocyclylene, or substituted heterocyclylene; $L^1$ is a covalent bond; and $X^2$ is a covalent bond, alkylene, or substituted alkylene.

In another embodiment of the compounds of formula Ia, —$X^1$-$L^1$-$X^2$— is

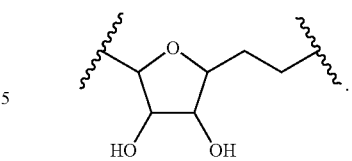

In another embodiment of the compounds of formula Ia, $X^1$ is carbocyclylene, substituted carbocyclylene, heterocyclylene, or substituted heterocyclylene; $L^1$ is a covalent bond; $X^2$ is a covalent bond, alkylene, or substituted alkylene; $Y^1$ and $Y^2$ are both —O—, and $R^1$ and $R^2$ are each independently H, alkyl, or substituted alkyl.

In the above embodiments of the compounds of formula IIa, each $R^3$, $R^4$, and $R^5$ are independently H, alkyl, substituted alkyl, carbocyclyl, substituted carbocyclyl, heterocyclyl, substituted heterocyclyl, alkenyl, substituted alkenyl alkynyl, substituted alkynyl, arylalkyl, substituted arylalkyl, heterocyclylalkyl, or substituted heterocyclylalkyl.

In another embodiment of the compounds of formula Ia, the compound is selected from the group consisting of:

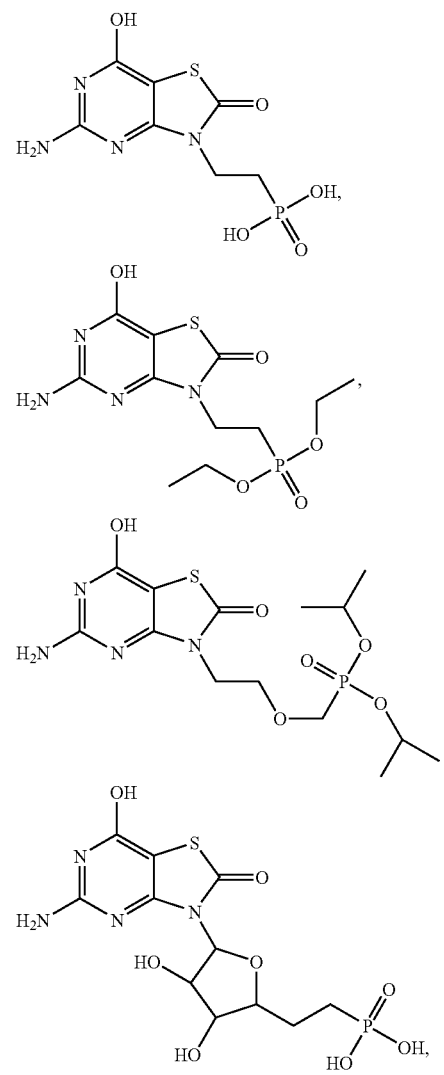

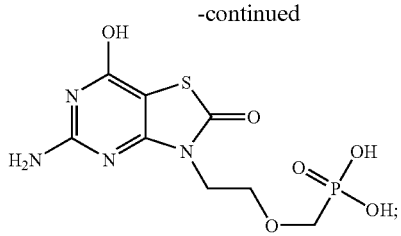

or pharmaceutically acceptable salts, solvates, and/or esters thereof.

In still yet another embodiment, compounds of Formula I or II are named below in tabular format (Table 6) as compounds of general Formula III:

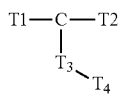

Formula III

Compounds of general Formula I or II are depicted as a "core" structure (C) substituted with four moieties T1, T2, T3 and T4. The core structures C are depicted in Table 1. The points of attachment of T1, T2, T3 and T4 are indicated on each of the core structures depicted in Table 1. Tables 2-5, respectively, show the structures of the T1, T2, T3 and T4 moieties. The point of attachment of the core structure C is indicated in each of the structures of T1, T2, T3 and T4. The core structure C in Table 1, and each substituent T1, T2, T3 and T4 in Tables 2-5 are represented by a "code" comprising a letter and a number. Each structure of a compound of Formula III can be designated in tabular form by combining the "code" representing each structural moiety using the following syntax: T1.T2.T3.T4. Thus, for example, T1A, T2A, T3A and T4A represents the following structure:

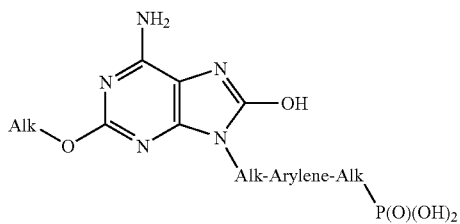

In the structures depicted in Tables 1-5, the term "Alk" means a substituted or unsubstituted alkyl or alkylene group, wherein the terms "alkyl" and "alkylene" are as defined herein. "Alk" means an alkyl group when depicted as monovalent, and an alkylene group when depicted as divalent. "Het" is a substituted or unsubstituted heterocyclyl or heterocyclylene group, wherein the term "heterocyclyl" is as defined herein, and the term "heterocyclylene" means a heterocyclyl group as defined herein, in which a hydrogen atom has been replaced by an open valence (in analogy to alkylene), thereby defining a divalent heterocyclyl. "Het" is a heterocyclyl when depicted as monovalent, and heterocyclylene when depicted as divalent. "Ar" is a substitute or unsubstituted aryl or arylene group, wherein the term "aryl" is as defined herein, and the term "arylene" means an aryl group as defined herein, in which a hydrogen atom has been replaced by an open valence (in analogy to alkylene), thereby defining a divalent aryl. "Ar" is aryl when depicted as monovalent, and arylene when depicted as divalent. When substituted, "Alk", "Het", and "Ar" can be substituted with any of the substituents defined or exemplified herein. For example, substituents of "Alk" can include ether, halogen, —OH, amide, amine, etc., substituents of "Het" can include alkyl, aryl, carbonyl, —OH, halogen, and substituents of "Ar" can include alkyl, aryl, —OH, halogen, etc., with the proviso that the resulting structure is chemically reasonable, and would provide compounds which are sufficiently stable for formulation in a pharmaceutically acceptable composition.

TABLE 1

Core Structure

| Code | Subgenus Structure |
|------|---------------------|
| C1   | (purine core with NH₂, T1, T2, T3, T4 substituents) |

TABLE 2

T1 Structures

| Label | T1 Structure |
|-------|--------------|
| T1A | —O-alkyl |
| T1B | —O-alkylene-O-alkyl |
| T1C | —S-alkyl |
| T1D | —NH-substituted or unsubstituted alkyl |
| T1E | alkyl |

TABLE 3

T2 Structures

| Label | T2 Structure |
|-------|--------------|
| T2A | —OH |
| T2B | —SH |
| T2C | —NH-alkyl |
| T2D | —NH-aryl |
| T2E | —NH₂ |
| T2F | —NH-(heterocyclylalkyl) |

TABLE 4

T3 Structures

| Label | T3 Structure |
|-------|--------------|
| T3A | -alkylene-arylene-alkylene-T4 (substituted or unsubstituted) |
| T3B | -alkylene-O-alkylene-T4 (substituted or unsubstituted) |
| T3C | -alkylene-T4 (substituted or unsubstituted) |
| T3D | -alkylene-arylene-T4 (substituted or unsubstituted) |
| T3E | -alkylene-carbocyclylene-alkylene-T4 (substituted or unsubstituted) |
| T3F | -alkylene-heteroarylene-alkylene-T4 (substituted or unsubstituted) |
| T3G | -alkylene-heteroarylene-T4 (substituted or unsubstituted) |

TABLE 5

T4 Structures

| Label | T4 Structure |
|---|---|
| T4A | —P(O)(OH)$_2$ |
| T4B | —P(O)(O-aryl)(NH-substituted or unsubstituted alkylene-C(O)—O-alkyl) |
| T4C | —P(O)(substituted or unsubstituted alkyl)(OH) |
| T4D | —P(O)(aryl)(O-substituted or unsubstituted alkyl) |
| T4E | —P(O)(NH-substituted or unsubstituted alkylene-C(O)—O-alkyl)$_2$ |
| T4F | —P(O)(arylalkyl)(OH) |

TABLE 6

List of Compound Structure of Formula III with the core structure (C1)

T1A.T2A.T3A.T4A, T1B.T2A.T3A.T4A, T1C.T2A.T3A.T4A,
T1D.T2A.T3A.T4A, T1E.T2A.T3A.T4A, T1A.T2B.T3A.T4A,
T1B.T2B.T3A.T4A, T1C.T2B.T3A.T4A, T1D.T2B.T3A.T4A,
T1E.T2B.T3A.T4A, T1A.T2C.T3A.T4A, T1B.T2C.T3A.T4A,
T1C.T2C.T3A.T4A, T1D.T2C.T3A.T4A, T1E.T2C.T3A.T4A,
T1A.T2D.T3A.T4A, T1B.T2D.T3A.T4A, T1C.T2D.T3A.T4A,
T1D.T2D.T3A.T4A, T1E.T2D.T3A.T4A, T1A.T2E.T3A.T4A,
T1B.T2E.T3A.T4A, T1C.T2E.T3A.T4A, T1D.T2E.T3A.T4A,
T1E.T2E.T3A.T4A, T1A.T2F.T3A.T4A, T1B.T2F.T3A.T4A,
T1C.T2F.T3A.T4A, T1D.T2F.T3A.T4A, T1E.T2F.T3A.T4A,
T1A.T2A.T3B.T4A, T1B.T2A.T3B.T4A, T1C.T2A.T3B.T4A,
T1D.T2A.T3B.T4A, T1E.T2A.T3B.T4A, T1A.T2B.T3B.T4A,
T1B.T2B.T3B.T4A, T1C.T2B.T3B.T4A, T1D.T2B.T3B.T4A,
T1E.T2B.T3B.T4A, T1A.T2C.T3B.T4A, T1B.T2C.T3B.T4A,
T1C.T2C.T3B.T4A, T1D.T2C.T3B.T4A, T1E.T2C.T3B.T4A,
T1A.T2D.T3B.T4A, T1B.T2D.T3B.T4A, T1C.T2D.T3B.T4A,
T1D.T2D.T3B.T4A, T1E.T2D.T3B.T4A, T1A.T2E.T3B.T4A,
T1B.T2E.T3B.T4A, T1C.T2E.T3B.T4A, T1D.T2E.T3B.T4A,
T1E.T2E.T3B.T4A, T1A.T2F.T3B.T4A, T1B.T2F.T3B.T4A,
T1C.T2F.T3B.T4A, T1D.T2F.T3B.T4A, T1E.T2F.T3B.T4A,
T1A.T2A.T3C.T4A, T1B.T2A.T3C.T4A, T1C.T2A.T3C.T4A,
T1D.T2A.T3C.T4A, T1E.T2A.T3C.T4A, T1A.T2B.T3C.T4A,
T1B.T2B.T3C.T4A, T1C.T2B.T3C.T4A, T1D.T2B.T3C.T4A,
T1E.T2B.T3C.T4A, T1A.T2C.T3C.T4A, T1B.T2C.T3C.T4A,
T1C.T2C.T3C.T4A, T1D.T2C.T3C.T4A, T1E.T2C.T3C.T4A,
T1A.T2D.T3C.T4A, T1B.T2D.T3C.T4A, T1C.T2D.T3C.T4A,
T1D.T2D.T3C.T4A, T1E.T2D.T3C.T4A, T1A.T2E.T3C.T4A,
T1B.T2E.T3C.T4A, T1C.T2E.T3C.T4A, T1D.T2E.T3C.T4A,
T1E.T2E.T3C.T4A, T1A.T2F.T3C.T4A, T1B.T2F.T3C.T4A,
T1C.T2F.T3C.T4A, T1D.T2F.T3C.T4A, T1E.T2F.T3C.T4A,
T1A.T2A.T3D.T4A, T1B.T2A.T3D.T4A, T1C.T2A.T3D.T4A,
T1D.T2A.T3D.T4A, T1E.T2A.T3D.T4A, T1A.T2B.T3D.T4A,
T1B.T2B.T3D.T4A, T1C.T2B.T3D.T4A, T1D.T2B.T3D.T4A,
T1E.T2B.T3D.T4A, T1A.T2C.T3D.T4A, T1B.T2C.T3D.T4A,
T1C.T2C.T3D.T4A, T1D.T2C.T3D.T4A, T1E.T2C.T3D.T4A,
T1A.T2D.T3D.T4A, T1B.T2D.T3D.T4A, T1C.T2D.T3D.T4A,
T1D.T2D.T3D.T4A, T1E.T2D.T3D.T4A, T1A.T2E.T3D.T4A,
T1B.T2E.T3D.T4A, T1C.T2E.T3D.T4A, T1D.T2E.T3D.T4A,
T1E.T2E.T3D.T4A, T1A.T2F.T3D.T4A, T1B.T2F.T3D.T4A,
T1C.T2F.T3D.T4A, T1D.T2F.T3D.T4A, T1E.T2F.T3D.T4A,
T1A.T2A.T3E.T4A, T1B.T2A.T3E.T4A, T1C.T2A.T3E.T4A,
T1D.T2A.T3E.T4A, T1E.T2A.T3E.T4A, T1A.T2B.T3E.T4A,
T1B.T2B.T3E.T4A, T1C.T2B.T3E.T4A, T1D.T2B.T3E.T4A,
T1E.T2B.T3E.T4A, T1A.T2C.T3E.T4A, T1B.T2C.T3E.T4A,
T1C.T2C.T3E.T4A, T1D.T2C.T3E.T4A, T1E.T2C.T3E.T4A,
T1A.T2D.T3E.T4A, T1B.T2D.T3E.T4A, T1C.T2D.T3E.T4A,
T1D.T2D.T3E.T4A, T1E.T2D.T3E.T4A, T1A.T2E.T3E.T4A,
T1B.T2E.T3E.T4A, T1C.T2E.T3E.T4A, T1D.T2E.T3E.T4A,
T1E.T2E.T3E.T4A, T1A.T2F.T3E.T4A, T1B.T2F.T3E.T4A,
T1C.T2F.T3E.T4A, T1D.T2F.T3E.T4A, T1E.T2F.T3E.T4A,
T1A.T2A.T3F.T4A, T1B.T2A.T3F.T4A, T1C.T2A.T3F.T4A,
T1D.T2A.T3F.T4A, T1E.T2A.T3F.T4A, T1A.T2B.T3F.T4A,
T1B.T2B.T3F.T4A, T1C.T2B.T3F.T4A, T1D.T2B.T3F.T4A,
T1E.T2B.T3F.T4A, T1A.T2C.T3F.T4A, T1B.T2C.T3F.T4A,
T1C.T2C.T3F.T4A, T1D.T2C.T3F.T4A, T1E.T2C.T3F.T4A,
T1A.T2D.T3F.T4A, T1B.T2D.T3F.T4A, T1C.T2D.T3F.T4A,
T1D.T2D.T3F.T4A, T1E.T2D.T3F.T4A, T1A.T2E.T3F.T4A,
T1B.T2E.T3F.T4A, T1C.T2E.T3F.T4A, T1D.T2E.T3F.T4A,
T1E.T2E.T3F.T4A, T1A.T2F.T3F.T4A, T1B.T2F.T3F.T4A,
T1C.T2F.T3F.T4A, T1D.T2F.T3F.T4A, T1E.T2F.T3F.T4A,
T1A.T2A.T3G.T4A, T1B.T2A.T3G.T4A, T1C.T2A.T3G.T4A,
T1D.T2A.T3G.T4A, T1E.T2A.T3G.T4A, T1A.T2B.T3G.T4A,
T1B.T2B.T3G.T4A, T1C.T2B.T3G.T4A, T1D.T2B.T3G.T4A,
T1E.T2B.T3G.T4A, T1A.T2C.T3G.T4A, T1B.T2C.T3G.T4A,
T1C.T2C.T3G.T4A, T1D.T2C.T3G.T4A, T1E.T2C.T3G.T4A,
T1A.T2D.T3G.T4A, T1B.T2D.T3G.T4A, T1C.T2D.T3G.T4A,
T1D.T2D.T3G.T4A, T1E.T2D.T3G.T4A, T1A.T2E.T3G.T4A,
T1B.T2E.T3G.T4A, T1C.T2E.T3G.T4A, T1D.T2E.T3G.T4A,
T1E.T2E.T3G.T4A, T1A.T2F.T3G.T4A, T1B.T2F.T3G.T4A,
T1C.T2F.T3G.T4A, T1D.T2F.T3G.T4A, T1E.T2F.T3G.T4A,
T1A.T2A.T3A.T4B, T1B.T2A.T3A.T4B, T1C.T2A.T3A.T4B,
T1D.T2A.T3A.T4B, T1E.T2A.T3A.T4B, T1A.T2B.T3A.T4B,
T1B.T2B.T3A.T4B, T1C.T2B.T3A.T4B, T1D.T2B.T3A.T4B,
T1E.T2B.T3A.T4B, T1A.T2C.T3A.T4B, T1B.T2C.T3A.T4B,
T1C.T2C.T3A.T4B, T1D.T2C.T3A.T4B, T1E.T2C.T3A.T4B,
T1A.T2D.T3A.T4B, T1B.T2D.T3A.T4B, T1C.T2D.T3A.T4B,
T1D.T2D.T3A.T4B, T1E.T2D.T3A.T4B, T1A.T2E.T3A.T4B,
T1B.T2E.T3A.T4B, T1C.T2E.T3A.T4B, T1D.T2E.T3A.T4B,
T1E.T2E.T3A.T4B, T1A.T2F.T3A.T4B, T1B.T2F.T3A.T4B,
T1C.T2F.T3A.T4B, T1D.T2F.T3A.T4B, T1E.T2F.T3A.T4B,
T1A.T2A.T3B.T4B, T1B.T2A.T3B.T4B, T1C.T2A.T3B.T4B,
T1D.T2A.T3B.T4B, T1E.T2A.T3B.T4B, T1A.T2B.T3B.T4B,
T1B.T2B.T3B.T4B, T1C.T2B.T3B.T4B, T1D.T2B.T3B.T4B,
T1E.T2B.T3B.T4B, T1A.T2C.T3B.T4B, T1B.T2C.T3B.T4B,
T1C.T2C.T3B.T4B, T1D.T2C.T3B.T4B, T1E.T2C.T3B.T4B,
T1A.T2D.T3B.T4B, T1B.T2D.T3B.T4B, T1C.T2D.T3B.T4B,
T1D.T2D.T3B.T4B, T1E.T2D.T3B.T4B, T1A.T2E.T3B.T4B,
T1B.T2E.T3B.T4B, T1C.T2E.T3B.T4B, T1D.T2E.T3B.T4B,
T1E.T2E.T3B.T4B, T1A.T2F.T3B.T4B, T1B.T2F.T3B.T4B,
T1C.T2F.T3B.T4B, T1D.T2F.T3B.T4B, T1E.T2F.T3B.T4B,
T1A.T2A.T3C.T4B, T1B.T2A.T3C.T4B, T1C.T2A.T3C.T4B,
T1D.T2A.T3C.T4B, T1E.T2A.T3C.T4B, T1A.T2B.T3C.T4B,
T1B.T2B.T3C.T4B, T1C.T2B.T3C.T4B, T1D.T2B.T3C.T4B,
T1E.T2B.T3C.T4B, T1A.T2C.T3C.T4B, T1B.T2C.T3C.T4B,
T1C.T2C.T3C.T4B, T1D.T2C.T3C.T4B, T1E.T2C.T3C.T4B,
T1A.T2D.T3C.T4B, T1B.T2D.T3C.T4B, T1C.T2D.T3C.T4B,
T1D.T2D.T3C.T4B, T1E.T2D.T3C.T4B, T1A.T2E.T3C.T4B,
T1B.T2E.T3C.T4B, T1C.T2E.T3C.T4B, T1D.T2E.T3C.T4B,
T1E.T2E.T3C.T4B, T1A.T2F.T3C.T4B, T1B.T2F.T3C.T4B,
T1C.T2F.T3C.T4B, T1D.T2F.T3C.T4B, T1E.T2F.T3C.T4B,
T1A.T2A.T3D.T4B, T1B.T2A.T3D.T4B, T1C.T2A.T3D.T4B,
T1D.T2A.T3D.T4B, T1E.T2A.T3D.T4B, T1A.T2B.T3D.T4B,
T1B.T2B.T3D.T4B, T1C.T2B.T3D.T4B, T1D.T2B.T3D.T4B,
T1E.T2B.T3D.T4B, T1A.T2C.T3D.T4B, T1B.T2C.T3D.T4B,
T1C.T2C.T3D.T4B, T1D.T2C.T3D.T4B, T1E.T2C.T3D.T4B,
T1A.T2D.T3D.T4B, T1B.T2D.T3D.T4B, T1C.T2D.T3D.T4B,
T1D.T2D.T3D.T4B, T1E.T2D.T3D.T4B, T1A.T2E.T3D.T4B,
T1B.T2E.T3D.T4B, T1C.T2E.T3D.T4B, T1D.T2E.T3D.T4B,
T1E.T2E.T3D.T4B, T1A.T2F.T3D.T4B, T1B.T2F.T3D.T4B,
T1C.T2F.T3D.T4B, T1D.T2F.T3D.T4B, T1E.T2F.T3D.T4B,
T1A.T2A.T3E.T4B, T1B.T2A.T3E.T4B, T1C.T2A.T3E.T4B,
T1D.T2A.T3E.T4B, T1E.T2A.T3E.T4B, T1A.T2B.T3E.T4B,
T1B.T2B.T3E.T4B, T1C.T2B.T3E.T4B, T1D.T2B.T3E.T4B,
T1E.T2B.T3E.T4B, T1A.T2C.T3E.T4B, T1B.T2C.T3E.T4B,
T1C.T2C.T3E.T4B, T1D.T2C.T3E.T4B, T1E.T2C.T3E.T4B,
T1A.T2D.T3E.T4B, T1B.T2D.T3E.T4B, T1C.T2D.T3E.T4B,
T1D.T2D.T3E.T4B, T1E.T2D.T3E.T4B, T1A.T2E.T3E.T4B,
T1B.T2E.T3E.T4B, T1C.T2E.T3E.T4B, T1D.T2E.T3E.T4B,
T1E.T2E.T3E.T4B, T1A.T2F.T3E.T4B, T1B.T2F.T3E.T4B,
T1C.T2F.T3E.T4B, T1D.T2F.T3E.T4B, T1E.T2F.T3E.T4B,
T1A.T2A.T3F.T4B, T1B.T2A.T3F.T4B, T1C.T2A.T3F.T4B,
T1D.T2A.T3F.T4B, T1E.T2A.T3F.T4B, T1A.T2B.T3F.T4B,
T1B.T2B.T3F.T4B, T1C.T2B.T3F.T4B, T1D.T2B.T3F.T4B,
T1E.T2B.T3F.T4B, T1A.T2C.T3F.T4B, T1B.T2C.T3F.T4B,
T1C.T2C.T3F.T4B, T1D.T2C.T3F.T4B, T1E.T2C.T3F.T4B,
T1A.T2D.T3F.T4B, T1B.T2D.T3F.T4B, T1C.T2D.T3F.T4B,
T1D.T2D.T3F.T4B, T1E.T2D.T3F.T4B, T1A.T2E.T3F.T4B,
T1B.T2E.T3F.T4B, T1C.T2E.T3F.T4B, T1D.T2E.T3F.T4B,
T1E.T2E.T3F.T4B, T1A.T2F.T3F.T4B, T1B.T2F.T3F.T4B,
T1C.T2F.T3F.T4B, T1D.T2F.T3F.T4B, T1E.T2F.T3F.T4B,
T1A.T2A.T3G.T4B, T1B.T2A.T3G.T4B, T1C.T2A.T3G.T4B,
T1D.T2A.T3G.T4B, T1E.T2A.T3G.T4B, T1A.T2B.T3G.T4B,
T1B.T2B.T3G.T4B, T1C.T2B.T3G.T4B, T1D.T2B.T3G.T4B,
T1E.T2B.T3G.T4B, T1A.T2C.T3G.T4B, T1B.T2C.T3G.T4B,
T1C.T2C.T3G.T4B, T1D.T2C.T3G.T4B, T1E.T2C.T3G.T4B,
T1A.T2D.T3G.T4B, T1B.T2D.T3G.T4B, T1C.T2D.T3G.T4B,

TABLE 6-continued

List of Compound Structure of Formula III with the core structure (C1)

T1D.T2D.T3G.T4B, T1E.T2D.T3G.T4B, T1A.T2E.T3G.T4B,
T1B.T2E.T3G.T4B, T1C.T2E.T3G.T4B, T1D.T2E.T3G.T4B,
T1E.T2E.T3G.T4B, T1A.T2F.T3G.T4B, T1B.T2F.T3G.T4B,
T1C.T2F.T3G.T4B, T1D.T2F.T3G.T4B, T1E.T2F.T3G.T4B,
T1A.T2A.T3A.T4C, T1B.T2A.T3A.T4C, T1C.T2A.T3A.T4C,
T1D.T2A.T3A.T4C, T1E.T2A.T3A.T4C, T1A.T2B.T3A.T4C,
T1B.T2B.T3A.T4C, T1C.T2B.T3A.T4C, T1D.T2B.T3A.T4C,
T1E.T2B.T3A.T4C, T1A.T2C.T3A.T4C, T1B.T2C.T3A.T4C,
T1C.T2C.T3A.T4C, T1D.T2C.T3A.T4C, T1E.T2C.T3A.T4C,
T1A.T2D.T3A.T4C, T1B.T2D.T3A.T4C, T1C.T2D.T3A.T4C,
T1D.T2D.T3A.T4C, T1E.T2D.T3A.T4C, T1A.T2E.T3A.T4C,
T1B.T2E.T3A.T4C, T1C.T2E.T3A.T4C, T1D.T2E.T3A.T4C,
T1E.T2E.T3A.T4C, T1A.T2F.T3A.T4C, T1B.T2F.T3A.T4C,
T1C.T2F.T3A.T4C, T1D.T2F.T3A.T4C, T1E.T2F.T3A.T4C,
T1A.T2A.T3B.T4C, T1B.T2A.T3B.T4C, T1C.T2A.T3B.T4C,
T1D.T2A.T3B.T4C, T1E.T2A.T3B.T4C, T1A.T2B.T3B.T4C,
T1B.T2B.T3B.T4C, T1C.T2B.T3B.T4C, T1D.T2B.T3B.T4C,
T1E.T2B.T3B.T4C, T1A.T2C.T3B.T4C, T1B.T2C.T3B.T4C,
T1C.T2C.T3B.T4C, T1D.T2C.T3B.T4C, T1E.T2C.T3B.T4C,
T1A.T2D.T3B.T4C, T1B.T2D.T3B.T4C, T1C.T2D.T3B.T4C,
T1D.T2D.T3B.T4C, T1E.T2D.T3B.T4C, T1A.T2E.T3B.T4C,
T1B.T2E.T3B.T4C, T1C.T2E.T3B.T4C, T1D.T2E.T3B.T4C,
T1E.T2E.T3B.T4C, T1A.T2F.T3B.T4C, T1B.T2F.T3B.T4C,
T1C.T2F.T3B.T4C, T1D.T2F.T3B.T4C, T1E.T2F.T3B.T4C,
T1A.T2A.T3C.T4C, T1B.T2A.T3C.T4C, T1C.T2A.T3C.T4C,
T1D.T2A.T3C.T4C, T1E.T2A.T3C.T4C, T1A.T2B.T3C.T4C,
T1B.T2B.T3C.T4C, T1C.T2B.T3C.T4C, T1D.T2B.T3C.T4C,
T1E.T2B.T3C.T4C, T1A.T2C.T3C.T4C, T1B.T2C.T3C.T4C,
T1C.T2C.T3C.T4C, T1D.T2C.T3C.T4C, T1E.T2C.T3C.T4C,
T1A.T2D.T3C.T4C, T1B.T2D.T3C.T4C, T1C.T2D.T3C.T4C,
T1D.T2D.T3C.T4C, T1E.T2D.T3C.T4C, T1A.T2E.T3C.T4C,
T1B.T2E.T3C.T4C, T1C.T2E.T3C.T4C, T1D.T2E.T3C.T4C,
T1E.T2E.T3C.T4C, T1A.T2F.T3C.T4C, T1B.T2F.T3C.T4C,
T1C.T2F.T3C.T4C, T1D.T2F.T3C.T4C, T1E.T2F.T3C.T4C,
T1A.T2A.T3D.T4C, T1B.T2A.T3D.T4C, T1C.T2A.T3D.T4C,
T1D.T2A.T3D.T4C, T1E.T2A.T3D.T4C, T1A.T2B.T3D.T4C,
T1B.T2B.T3D.T4C, T1C.T2B.T3D.T4C, T1D.T2B.T3D.T4C,
T1E.T2B.T3D.T4C, T1A.T2C.T3D.T4C, T1B.T2C.T3D.T4C,
T1C.T2C.T3D.T4C, T1D.T2C.T3D.T4C, T1E.T2C.T3D.T4C,
T1A.T2D.T3D.T4C, T1B.T2D.T3D.T4C, T1C.T2D.T3D.T4C,
T1D.T2D.T3D.T4C, T1E.T2D.T3D.T4C, T1A.T2E.T3D.T4C,
T1B.T2E.T3D.T4C, T1C.T2E.T3D.T4C, T1D.T2E.T3D.T4C,
T1E.T2E.T3D.T4C, T1A.T2F.T3D.T4C, T1B.T2F.T3D.T4C,
T1C.T2F.T3D.T4C, T1D.T2F.T3D.T4C, T1E.T2F.T3D.T4C,
T1A.T2A.T3E.T4C, T1B.T2A.T3E.T4C, T1C.T2A.T3E.T4C,
T1D.T2A.T3E.T4C, T1E.T2A.T3E.T4C, T1A.T2B.T3E.T4C,
T1B.T2B.T3E.T4C, T1C.T2B.T3E.T4C, T1D.T2B.T3E.T4C,
T1E.T2B.T3E.T4C, T1A.T2C.T3E.T4C, T1B.T2C.T3E.T4C,
T1C.T2C.T3E.T4C, T1D.T2C.T3E.T4C, T1E.T2C.T3E.T4C,
T1A.T2D.T3E.T4C, T1B.T2D.T3E.T4C, T1C.T2D.T3E.T4C,
T1D.T2D.T3E.T4C, T1E.T2D.T3E.T4C, T1A.T2E.T3E.T4C,
T1B.T2E.T3E.T4C, T1C.T2E.T3E.T4C, T1D.T2E.T3E.T4C,
T1E.T2E.T3E.T4C, T1A.T2F.T3E.T4C, T1B.T2F.T3E.T4C,
T1C.T2F.T3E.T4C, T1D.T2F.T3E.T4C, T1E.T2F.T3E.T4C,
T1A.T2A.T3F.T4C, T1B.T2A.T3F.T4C, T1C.T2A.T3F.T4C,
T1D.T2A.T3F.T4C, T1E.T2A.T3F.T4C, T1A.T2B.T3F.T4C,
T1B.T2B.T3F.T4C, T1C.T2B.T3F.T4C, T1D.T2B.T3F.T4C,
T1E.T2B.T3F.T4C, T1A.T2C.T3F.T4C, T1B.T2C.T3F.T4C,
T1C.T2C.T3F.T4C, T1D.T2C.T3F.T4C, T1E.T2C.T3F.T4C,
T1A.T2D.T3F.T4C, T1B.T2D.T3F.T4C, T1C.T2D.T3F.T4C,
T1D.T2D.T3F.T4C, T1E.T2D.T3F.T4C, T1A.T2E.T3F.T4C,
T1B.T2E.T3F.T4C, T1C.T2E.T3F.T4C, T1D.T2E.T3F.T4C,
T1E.T2E.T3F.T4C, T1A.T2F.T3F.T4C, T1B.T2F.T3F.T4C,
T1C.T2F.T3F.T4C, T1D.T2F.T3F.T4C, T1E.T2F.T3F.T4C,
T1A.T2A.T3G.T4C, T1B.T2A.T3G.T4C, T1C.T2A.T3G.T4C,
T1D.T2A.T3G.T4C, T1E.T2A.T3G.T4C, T1A.T2B.T3G.T4C,
T1B.T2B.T3G.T4C, T1C.T2B.T3G.T4C, T1D.T2B.T3G.T4C,
T1E.T2B.T3G.T4C, T1A.T2C.T3G.T4C, T1B.T2C.T3G.T4C,
T1C.T2C.T3G.T4C, T1D.T2C.T3G.T4C, T1E.T2C.T3G.T4C,
T1A.T2D.T3G.T4C, T1B.T2D.T3G.T4C, T1C.T2D.T3G.T4C,
T1D.T2D.T3G.T4C, T1E.T2D.T3G.T4C, T1A.T2E.T3G.T4C,
T1B.T2E.T3G.T4C, T1C.T2E.T3G.T4C, T1D.T2E.T3G.T4C,
T1E.T2E.T3G.T4C, T1A.T2F.T3G.T4C, T1B.T2F.T3G.T4C,
T1C.T2F.T3G.T4C, T1D.T2F.T3G.T4C, T1E.T2F.T3G.T4C,
T1A.T2A.T3A.T4D, T1B.T2A.T3A.T4D, T1C.T2A.T3A.T4D,
T1D.T2A.T3A.T4D, T1E.T2A.T3A.T4D, T1A.T2B.T3A.T4D,
T1B.T2B.T3A.T4D, T1C.T2B.T3A.T4D, T1D.T2B.T3A.T4D,
T1E.T2B.T3A.T4D, T1A.T2C.T3A.T4D, T1B.T2C.T3A.T4D,
T1C.T2C.T3A.T4D, T1D.T2C.T3A.T4D, T1E.T2C.T3A.T4D,
T1A.T2D.T3A.T4D, T1B.T2D.T3A.T4D, T1C.T2D.T3A.T4D,
T1D.T2D.T3A.T4D, T1E.T2D.T3A.T4D, T1A.T2E.T3A.T4D,
T1B.T2E.T3A.T4D, T1C.T2E.T3A.T4D, T1D.T2E.T3A.T4D,
T1E.T2E.T3A.T4D, T1A.T2F.T3A.T4D, T1B.T2F.T3A.T4D,
T1C.T2F.T3A.T4D, T1D.T2F.T3A.T4D, T1E.T2F.T3A.T4D,
T1A.T2A.T3B.T4D, T1B.T2A.T3B.T4D, T1C.T2A.T3B.T4D,
T1D.T2A.T3B.T4D, T1E.T2A.T3B.T4D, T1A.T2B.T3B.T4D,
T1B.T2B.T3B.T4D, T1C.T2B.T3B.T4D, T1D.T2B.T3B.T4D,
T1E.T2B.T3B.T4D, T1A.T2C.T3B.T4D, T1B.T2C.T3B.T4D,
T1C.T2C.T3B.T4D, T1D.T2C.T3B.T4D, T1E.T2C.T3B.T4D,
T1A.T2D.T3B.T4D, T1B.T2D.T3B.T4D, T1C.T2D.T3B.T4D,
T1D.T2D.T3B.T4D, T1E.T2D.T3B.T4D, T1A.T2E.T3B.T4D,
T1B.T2E.T3B.T4D, T1C.T2E.T3B.T4D, T1D.T2E.T3B.T4D,
T1E.T2E.T3B.T4D, T1A.T2F.T3B.T4D, T1B.T2F.T3B.T4D,
T1C.T2F.T3B.T4D, T1D.T2F.T3B.T4D, T1E.T2F.T3B.T4D,
T1A.T2A.T3C.T4D, T1B.T2A.T3C.T4D, T1C.T2A.T3C.T4D,
T1D.T2A.T3C.T4D, T1E.T2A.T3C.T4D, T1A.T2B.T3C.T4D,
T1B.T2B.T3C.T4D, T1C.T2B.T3C.T4D, T1D.T2B.T3C.T4D,
T1E.T2B.T3C.T4D, T1A.T2C.T3C.T4D, T1B.T2C.T3C.T4D,
T1C.T2C.T3C.T4D, T1D.T2C.T3C.T4D, T1E.T2C.T3C.T4D,
T1A.T2D.T3C.T4D, T1B.T2D.T3C.T4D, T1C.T2D.T3C.T4D,
T1D.T2D.T3C.T4D, T1E.T2D.T3C.T4D, T1A.T2E.T3C.T4D,
T1B.T2E.T3C.T4D, T1C.T2E.T3C.T4D, T1D.T2E.T3C.T4D,
T1E.T2E.T3C.T4D, T1A.T2F.T3C.T4D, T1B.T2F.T3C.T4D,
T1C.T2F.T3C.T4D, T1D.T2F.T3C.T4D, T1E.T2F.T3C.T4D,
T1A.T2A.T3D.T4D, T1B.T2A.T3D.T4D, T1C.T2A.T3D.T4D,
T1D.T2A.T3D.T4D, T1E.T2A.T3D.T4D, T1A.T2B.T3D.T4D,
T1B.T2B.T3D.T4D, T1C.T2B.T3D.T4D, T1D.T2B.T3D.T4D,
T1E.T2B.T3D.T4D, T1A.T2C.T3D.T4D, T1B.T2C.T3D.T4D,
T1C.T2C.T3D.T4D, T1D.T2C.T3D.T4D, T1E.T2C.T3D.T4D,
T1A.T2D.T3D.T4D, T1B.T2D.T3D.T4D, T1C.T2D.T3D.T4D,
T1D.T2D.T3D.T4D, T1E.T2D.T3D.T4D, T1A.T2E.T3D.T4D,
T1B.T2E.T3D.T4D, T1C.T2E.T3D.T4D, T1D.T2E.T3D.T4D,
T1E.T2E.T3D.T4D, T1A.T2F.T3D.T4D, T1B.T2F.T3D.T4D,
T1C.T2F.T3D.T4D, T1D.T2F.T3D.T4D, T1E.T2F.T3D.T4D,
T1A.T2A.T3E.T4D, T1B.T2A.T3E.T4D, T1C.T2A.T3E.T4D,
T1D.T2A.T3E.T4D, T1E.T2A.T3E.T4D, T1A.T2B.T3E.T4D,
T1B.T2B.T3E.T4D, T1C.T2B.T3E.T4D, T1D.T2B.T3E.T4D,
T1E.T2B.T3E.T4D, T1A.T2C.T3E.T4D, T1B.T2C.T3E.T4D,
T1C.T2C.T3E.T4D, T1D.T2C.T3E.T4D, T1E.T2C.T3E.T4D,
T1A.T2D.T3E.T4D, T1B.T2D.T3E.T4D, T1C.T2D.T3E.T4D,
T1D.T2D.T3E.T4D, T1E.T2D.T3E.T4D, T1A.T2E.T3E.T4D,
T1B.T2E.T3E.T4D, T1C.T2E.T3E.T4D, T1D.T2E.T3E.T4D,
T1E.T2E.T3E.T4D, T1A.T2F.T3E.T4D, T1B.T2F.T3E.T4D,
T1C.T2F.T3E.T4D, T1D.T2F.T3E.T4D, T1E.T2F.T3E.T4D,
T1A.T2A.T3F.T4D, T1B.T2A.T3F.T4D, T1C.T2A.T3F.T4D,
T1D.T2A.T3F.T4D, T1E.T2A.T3F.T4D, T1A.T2B.T3F.T4D,
T1B.T2B.T3F.T4D, T1C.T2B.T3F.T4D, T1D.T2B.T3F.T4D,
T1E.T2B.T3F.T4D, T1A.T2C.T3F.T4D, T1B.T2C.T3F.T4D,
T1C.T2C.T3F.T4D, T1D.T2C.T3F.T4D, T1E.T2C.T3F.T4D,
T1A.T2D.T3F.T4D, T1B.T2D.T3F.T4D, T1C.T2D.T3F.T4D,
T1D.T2D.T3F.T4D, T1E.T2D.T3F.T4D, T1A.T2E.T3F.T4D,
T1B.T2E.T3F.T4D, T1C.T2E.T3F.T4D, T1D.T2E.T3F.T4D,
T1E.T2E.T3F.T4D, T1A.T2F.T3F.T4D, T1B.T2F.T3F.T4D,
T1C.T2F.T3F.T4D, T1D.T2F.T3F.T4D, T1E.T2F.T3F.T4D,
T1A.T2A.T3G.T4D, T1B.T2A.T3G.T4D, T1C.T2A.T3G.T4D,
T1D.T2A.T3G.T4D, T1E.T2A.T3G.T4D, T1A.T2B.T3G.T4D,
T1B.T2B.T3G.T4D, T1C.T2B.T3G.T4D, T1D.T2B.T3G.T4D,
T1E.T2B.T3G.T4D, T1A.T2C.T3G.T4D, T1B.T2C.T3G.T4D,
T1C.T2C.T3G.T4D, T1D.T2C.T3G.T4D, T1E.T2C.T3G.T4D,
T1A.T2D.T3G.T4D, T1B.T2D.T3G.T4D, T1C.T2D.T3G.T4D,
T1D.T2D.T3G.T4D, T1E.T2D.T3G.T4D, T1A.T2E.T3G.T4D,
T1B.T2E.T3G.T4D, T1C.T2E.T3G.T4D, T1D.T2E.T3G.T4D,
T1E.T2E.T3G.T4D, T1A.T2F.T3G.T4D, T1B.T2F.T3G.T4D,
T1C.T2F.T3G.T4D, T1D.T2F.T3G.T4D, T1E.T2F.T3G.T4D,
T1A.T2A.T3A.T4E, T1B.T2A.T3A.T4E, T1C.T2A.T3A.T4E,
T1D.T2A.T3A.T4E, T1E.T2A.T3A.T4E, T1A.T2B.T3A.T4E,
T1B.T2B.T3A.T4E, T1C.T2B.T3A.T4E, T1D.T2B.T3A.T4E,
T1E.T2B.T3A.T4E, T1A.T2C.T3A.T4E, T1B.T2C.T3A.T4E,
T1C.T2C.T3A.T4E, T1D.T2C.T3A.T4E, T1E.T2C.T3A.T4E,
T1A.T2D.T3A.T4E, T1B.T2D.T3A.T4E, T1C.T2D.T3A.T4E,
T1D.T2D.T3A.T4E, T1E.T2D.T3A.T4E, T1A.T2E.T3A.T4E,
T1B.T2E.T3A.T4E, T1C.T2E.T3A.T4E, T1D.T2E.T3A.T4E,
T1E.T2E.T3A.T4E, T1A.T2F.T3A.T4E, T1B.T2F.T3A.T4E,
T1C.T2F.T3A.T4E, T1D.T2F.T3A.T4E, T1E.T2F.T3A.T4E,
T1A.T2A.T3B.T4E, T1B.T2A.T3B.T4E, T1C.T2A.T3B.T4E,
T1D.T2A.T3B.T4E, T1E.T2A.T3B.T4E, T1A.T2B.T3B.T4E,

TABLE 6-continued

List of Compound Structure of Formula III with the core structure (C1)

T1B.T2B.T3B.T4E, T1C.T2B.T3B.T4E, T1D.T2B.T3B.T4E,
T1E.T2B.T3B.T4E, T1A.T2C.T3B.T4E, T1B.T2C.T3B.T4E,
T1C.T2C.T3B.T4E, T1D.T2C.T3B.T4E, T1E.T2C.T3B.T4E,
T1A.T2D.T3B.T4E, T1B.T2D.T3B.T4E, T1C.T2D.T3B.T4E,
T1D.T2D.T3B.T4E, T1E.T2D.T3B.T4E, T1A.T2E.T3B.T4E,
T1B.T2E.T3B.T4E, T1C.T2E.T3B.T4E, T1D.T2E.T3B.T4E,
T1E.T2E.T3B.T4E, T1A.T2F.T3B.T4E, T1B.T2F.T3B.T4E,
T1C.T2F.T3B.T4E, T1D.T2F.T3B.T4E, T1E.T2F.T3B.T4E,
T1A.T2A.T3C.T4E, T1B.T2A.T3C.T4E, T1C.T2A.T3C.T4E,
T1D.T2A.T3C.T4E, T1E.T2A.T3C.T4E, T1A.T2B.T3C.T4E,
T1B.T2B.T3C.T4E, T1C.T2B.T3C.T4E, T1D.T2B.T3C.T4E,
T1E.T2B.T3C.T4E, T1A.T2C.T3C.T4E, T1B.T2C.T3C.T4E,
T1C.T2C.T3C.T4E, T1D.T2C.T3C.T4E, T1E.T2C.T3C.T4E,
T1A.T2D.T3C.T4E, T1B.T2D.T3C.T4E, T1C.T2D.T3C.T4E,
T1D.T2D.T3C.T4E, T1E.T2D.T3C.T4E, T1A.T2E.T3C.T4E,
T1B.T2E.T3C.T4E, T1C.T2E.T3C.T4E, T1D.T2E.T3C.T4E,
T1E.T2E.T3C.T4E, T1A.T2F.T3C.T4E, T1B.T2F.T3C.T4E,
T1C.T2F.T3C.T4E, T1D.T2F.T3C.T4E, T1E.T2F.T3C.T4E,
T1A.T2A.T3D.T4E, T1B.T2A.T3D.T4E, T1C.T2A.T3D.T4E,
T1D.T2A.T3D.T4E, T1E.T2A.T3D.T4E, T1A.T2B.T3D.T4E,
T1B.T2B.T3D.T4E, T1C.T2B.T3D.T4E, T1D.T2B.T3D.T4E,
T1E.T2B.T3D.T4E, T1A.T2C.T3D.T4E, T1B.T2C.T3D.T4E,
T1C.T2C.T3D.T4E, T1D.T2C.T3D.T4E, T1E.T2C.T3D.T4E,
T1A.T2D.T3D.T4E, T1B.T2D.T3D.T4E, T1C.T2D.T3D.T4E,
T1D.T2D.T3D.T4E, T1E.T2D.T3D.T4E, T1A.T2E.T3D.T4E,
T1B.T2E.T3D.T4E, T1C.T2E.T3D.T4E, T1D.T2E.T3D.T4E,
T1E.T2E.T3D.T4E, T1A.T2F.T3D.T4E, T1B.T2F.T3D.T4E,
T1C.T2F.T3D.T4E, T1D.T2F.T3D.T4E, T1E.T2F.T3D.T4E,
T1A.T2A.T3E.T4E, T1B.T2A.T3E.T4E, T1C.T2A.T3E.T4E,
T1D.T2A.T3E.T4E, T1E.T2A.T3E.T4E, T1A.T2B.T3E.T4E,
T1B.T2B.T3E.T4E, T1C.T2B.T3E.T4E, T1D.T2B.T3E.T4E,
T1E.T2B.T3E.T4E, T1A.T2C.T3E.T4E, T1B.T2C.T3E.T4E,
T1C.T2C.T3E.T4E, T1D.T2C.T3E.T4E, T1E.T2C.T3E.T4E,
T1A.T2D.T3E.T4E, T1B.T2D.T3E.T4E, T1C.T2D.T3E.T4E,
T1D.T2D.T3E.T4E, T1E.T2D.T3E.T4E, T1A.T2E.T3E.T4E,
T1B.T2E.T3E.T4E, T1C.T2E.T3E.T4E, T1D.T2E.T3E.T4E,
T1E.T2E.T3E.T4E, T1A.T2F.T3E.T4E, T1B.T2F.T3E.T4E,
T1C.T2F.T3E.T4E, T1D.T2F.T3E.T4E, T1E.T2F.T3E.T4E,
T1A.T2A.T3F.T4E, T1B.T2A.T3F.T4E, T1C.T2A.T3F.T4E,
T1D.T2A.T3F.T4E, T1E.T2A.T3F.T4E, T1A.T2B.T3F.T4E,
T1B.T2B.T3F.T4E, T1C.T2B.T3F.T4E, T1D.T2B.T3F.T4E,
T1E.T2B.T3F.T4E, T1A.T2C.T3F.T4E, T1B.T2C.T3F.T4E,
T1C.T2C.T3F.T4E, T1D.T2C.T3F.T4E, T1E.T2C.T3F.T4E,
T1A.T2D.T3F.T4E, T1B.T2D.T3F.T4E, T1C.T2D.T3F.T4E,
T1D.T2D.T3F.T4E, T1E.T2D.T3F.T4E, T1A.T2E.T3F.T4E,
T1B.T2E.T3F.T4E, T1C.T2E.T3F.T4E, T1D.T2E.T3F.T4E,
T1E.T2E.T3F.T4E, T1A.T2F.T3F.T4E, T1B.T2F.T3F.T4E,
T1C.T2F.T3F.T4E, T1D.T2F.T3F.T4E, T1E.T2F.T3F.T4E,
T1A.T2A.T3G.T4E, T1B.T2A.T3G.T4E, T1C.T2A.T3G.T4E,
T1D.T2A.T3G.T4E, T1E.T2A.T3G.T4E, T1A.T2B.T3G.T4E,
T1B.T2B.T3G.T4E, T1C.T2B.T3G.T4E, T1D.T2B.T3G.T4E,
T1E.T2B.T3G.T4E, T1A.T2C.T3G.T4E, T1B.T2C.T3G.T4E,
T1C.T2C.T3G.T4E, T1D.T2C.T3G.T4E, T1E.T2C.T3G.T4E,
T1A.T2D.T3G.T4E, T1B.T2D.T3G.T4E, T1C.T2D.T3G.T4E,
T1D.T2D.T3G.T4E, T1E.T2D.T3G.T4E, T1A.T2E.T3G.T4E,
T1B.T2E.T3G.T4E, T1C.T2E.T3G.T4E, T1D.T2E.T3G.T4E,
T1E.T2E.T3G.T4E, T1A.T2F.T3G.T4E, T1B.T2F.T3G.T4E,
T1C.T2F.T3G.T4E, T1D.T2F.T3G.T4E, T1E.T2F.T3G.T4E,
T1A.T2A.T3A.T4F, T1B.T2A.T3A.T4F, T1C.T2A.T3A.T4F,
T1D.T2A.T3A.T4F, T1E.T2A.T3A.T4F, T1A.T2B.T3A.T4F,
T1B.T2B.T3A.T4F, T1C.T2B.T3A.T4F, T1D.T2B.T3A.T4F,
T1E.T2B.T3A.T4F, T1A.T2C.T3A.T4F, T1B.T2C.T3A.T4F,
T1C.T2C.T3A.T4F, T1D.T2C.T3A.T4F, T1E.T2C.T3A.T4F,
T1A.T2D.T3A.T4F, T1B.T2D.T3A.T4F, T1C.T2D.T3A.T4F,
T1D.T2D.T3A.T4F, T1E.T2D.T3A.T4F, T1A.T2E.T3A.T4F,
T1B.T2E.T3A.T4F, T1C.T2E.T3A.T4F, T1D.T2E.T3A.T4F,
T1E.T2E.T3A.T4F, T1A.T2F.T3A.T4F, T1B.T2F.T3A.T4F,
T1C.T2F.T3A.T4F, T1D.T2F.T3A.T4F, T1E.T2F.T3A.T4F,
T1A.T2A.T3B.T4F, T1B.T2A.T3B.T4F, T1C.T2A.T3B.T4F,
T1D.T2A.T3B.T4F, T1E.T2A.T3B.T4F, T1A.T2B.T3B.T4F,
T1B.T2B.T3B.T4F, T1C.T2B.T3B.T4F, T1D.T2B.T3B.T4F,
T1E.T2B.T3B.T4F, T1A.T2C.T3B.T4F, T1B.T2C.T3B.T4F,
T1C.T2C.T3B.T4F, T1D.T2C.T3B.T4F, T1E.T2C.T3B.T4F,
T1A.T2D.T3B.T4F, T1B.T2D.T3B.T4F, T1C.T2D.T3B.T4F,
T1D.T2D.T3B.T4F, T1E.T2D.T3B.T4F, T1A.T2E.T3B.T4F,
T1B.T2E.T3B.T4F, T1C.T2E.T3B.T4F, T1D.T2E.T3B.T4F,
T1E.T2E.T3B.T4F, T1A.T2F.T3B.T4F, T1B.T2F.T3B.T4F,
T1C.T2F.T3B.T4F, T1D.T2F.T3B.T4F, T1E.T2F.T3B.T4F,
T1A.T2A.T3C.T4F, T1B.T2A.T3C.T4F, T1C.T2A.T3C.T4F,
T1D.T2A.T3C.T4F, T1E.T2A.T3C.T4F, T1A.T2B.T3C.T4F,
T1B.T2B.T3C.T4F, T1C.T2B.T3C.T4F, T1D.T2B.T3C.T4F,
T1E.T2B.T3C.T4F, T1A.T2C.T3C.T4F, T1B.T2C.T3C.T4F,
T1C.T2C.T3C.T4F, T1D.T2C.T3C.T4F, T1E.T2C.T3C.T4F,
T1A.T2D.T3C.T4F, T1B.T2D.T3C.T4F, T1C.T2D.T3C.T4F,
T1D.T2D.T3C.T4F, T1E.T2D.T3C.T4F, T1A.T2E.T3C.T4F,
T1B.T2E.T3C.T4F, T1C.T2E.T3C.T4F, T1D.T2E.T3C.T4F,
T1E.T2E.T3C.T4F, T1A.T2F.T3C.T4F, T1B.T2F.T3C.T4F,
T1C.T2F.T3C.T4F, T1D.T2F.T3C.T4F, T1E.T2F.T3C.T4F,
T1A.T2A.T3D.T4F, T1B.T2A.T3D.T4F, T1C.T2A.T3D.T4F,
T1D.T2A.T3D.T4F, T1E.T2A.T3D.T4F, T1A.T2B.T3D.T4F,
T1B.T2B.T3D.T4F, T1C.T2B.T3D.T4F, T1D.T2B.T3D.T4F,
T1E.T2B.T3D.T4F, T1A.T2C.T3D.T4F, T1B.T2C.T3D.T4F,
T1C.T2C.T3D.T4F, T1D.T2C.T3D.T4F, T1E.T2C.T3D.T4F,
T1A.T2D.T3D.T4F, T1B.T2D.T3D.T4F, T1C.T2D.T3D.T4F,
T1D.T2D.T3D.T4F, T1E.T2D.T3D.T4F, T1A.T2E.T3D.T4F,
T1B.T2E.T3D.T4F, T1C.T2E.T3D.T4F, T1D.T2E.T3D.T4F,
T1E.T2E.T3D.T4F, T1A.T2F.T3D.T4F, T1B.T2F.T3D.T4F,
T1C.T2F.T3D.T4F, T1D.T2F.T3D.T4F, T1E.T2F.T3D.T4F,
T1A.T2A.T3E.T4F, T1B.T2A.T3E.T4F, T1C.T2A.T3E.T4F,
T1D.T2A.T3E.T4F, T1E.T2A.T3E.T4F, T1A.T2B.T3E.T4F,
T1B.T2B.T3E.T4F, T1C.T2B.T3E.T4F, T1D.T2B.T3E.T4F,
T1E.T2B.T3E.T4F, T1A.T2C.T3E.T4F, T1B.T2C.T3E.T4F,
T1C.T2C.T3E.T4F, T1D.T2C.T3E.T4F, T1E.T2C.T3E.T4F,
T1A.T2D.T3E.T4F, T1B.T2D.T3E.T4F, T1C.T2D.T3E.T4F,
T1D.T2D.T3E.T4F, T1E.T2D.T3E.T4F, T1A.T2E.T3E.T4F,
T1B.T2E.T3E.T4F, T1C.T2E.T3E.T4F, T1D.T2E.T3E.T4F,
T1E.T2E.T3E.T4F, T1A.T2F.T3E.T4F, T1B.T2F.T3E.T4F,
T1C.T2F.T3E.T4F, T1D.T2F.T3E.T4F, T1E.T2F.T3E.T4F,
T1A.T2A.T3F.T4F, T1B.T2A.T3F.T4F, T1C.T2A.T3F.T4F,
T1D.T2A.T3F.T4F, T1E.T2A.T3F.T4F, T1A.T2B.T3F.T4F,
T1B.T2B.T3F.T4F, T1C.T2B.T3F.T4F, T1D.T2B.T3F.T4F,
T1E.T2B.T3F.T4F, T1A.T2C.T3F.T4F, T1B.T2C.T3F.T4F,
T1C.T2C.T3F.T4F, T1D.T2C.T3F.T4F, T1E.T2C.T3F.T4F,
T1A.T2D.T3F.T4F, T1B.T2D.T3F.T4F, T1C.T2D.T3F.T4F,
T1D.T2D.T3F.T4F, T1E.T2D.T3F.T4F, T1A.T2E.T3F.T4F,
T1B.T2E.T3F.T4F, T1C.T2E.T3F.T4F, T1D.T2E.T3F.T4F,
T1E.T2E.T3F.T4F, T1A.T2F.T3F.T4F, T1B.T2F.T3F.T4F,
T1C.T2F.T3F.T4F, T1D.T2F.T3F.T4F, T1E.T2F.T3F.T4F,
T1A.T2A.T3G.T4F, T1B.T2A.T3G.T4F, T1C.T2A.T3G.T4F,
T1D.T2A.T3G.T4F, T1E.T2A.T3G.T4F, T1A.T2B.T3G.T4F,
T1B.T2B.T3G.T4F, T1C.T2B.T3G.T4F, T1D.T2B.T3G.T4F,
T1E.T2B.T3G.T4F, T1A.T2C.T3G.T4F, T1B.T2C.T3G.T4F,
T1C.T2C.T3G.T4F, T1D.T2C.T3G.T4F, T1E.T2C.T3G.T4F,
T1A.T2D.T3G.T4F, T1B.T2D.T3G.T4F, T1C.T2D.T3G.T4F,
T1D.T2D.T3G.T4F, T1E.T2D.T3G.T4F, T1A.T2E.T3G.T4F,
T1B.T2E.T3G.T4F, T1C.T2E.T3G.T4F, T1D.T2E.T3G.T4F,
T1E.T2E.T3G.T4F, T1A.T2F.T3G.T4F, T1B.T2F.T3G.T4F,
T1C.T2F.T3G.T4F, T1D.T2F.T3G.T4F, T1E.T2F.T3G.T4F,
T1A.T2A.T3A.T4G, T1B.T2A.T3A.T4G, T1C.T2A.T3A.T4G,
T1D.T2A.T3A.T4G, T1E.T2A.T3A.T4G, T1A.T2B.T3A.T4G,
T1B.T2B.T3A.T4G, T1C.T2B.T3A.T4G, T1D.T2B.T3A.T4G,
T1E.T2B.T3A.T4G, T1A.T2C.T3A.T4G, T1B.T2C.T3A.T4G,
T1C.T2C.T3A.T4G, T1D.T2C.T3A.T4G, T1E.T2C.T3A.T4G,
T1A.T2D.T3A.T4G, T1B.T2D.T3A.T4G, T1C.T2D.T3A.T4G,
T1D.T2D.T3A.T4G, T1E.T2D.T3A.T4G, T1A.T2E.T3A.T4G,
T1B.T2E.T3A.T4G, T1C.T2E.T3A.T4G, T1D.T2E.T3A.T4G,
T1E.T2E.T3A.T4G, T1A.T2F.T3A.T4G, T1B.T2F.T3A.T4G,
T1C.T2F.T3A.T4G, T1D.T2F.T3A.T4G, T1E.T2F.T3A.T4G,
T1A.T2A.T3B.T4G, T1B.T2A.T3B.T4G, T1C.T2A.T3B.T4G,
T1D.T2A.T3B.T4G, T1E.T2A.T3B.T4G, T1A.T2B.T3B.T4G,
T1B.T2B.T3B.T4G, T1C.T2B.T3B.T4G, T1D.T2B.T3B.T4G,
T1E.T2B.T3B.T4G, T1A.T2C.T3B.T4G, T1B.T2C.T3B.T4G,
T1C.T2C.T3B.T4G, T1D.T2C.T3B.T4G, T1E.T2C.T3B.T4G,
T1A.T2D.T3B.T4G, T1B.T2D.T3B.T4G, T1C.T2D.T3B.T4G,
T1D.T2D.T3B.T4G, T1E.T2D.T3B.T4G, T1A.T2E.T3B.T4G,
T1B.T2E.T3B.T4G, T1C.T2E.T3B.T4G, T1D.T2E.T3B.T4G,
T1E.T2E.T3B.T4G, T1A.T2F.T3B.T4G, T1B.T2F.T3B.T4G,
T1C.T2F.T3B.T4G, T1D.T2F.T3B.T4G, T1E.T2F.T3B.T4G,
T1A.T2A.T3C.T4G, T1B.T2A.T3C.T4G, T1C.T2A.T3C.T4G,
T1D.T2A.T3C.T4G, T1E.T2A.T3C.T4G, T1A.T2B.T3C.T4G,
T1B.T2B.T3C.T4G, T1C.T2B.T3C.T4G, T1D.T2B.T3C.T4G,
T1E.T2B.T3C.T4G, T1A.T2C.T3C.T4G, T1B.T2C.T3C.T4G,
T1C.T2C.T3C.T4G, T1D.T2C.T3C.T4G, T1E.T2C.T3C.T4G,
T1A.T2D.T3C.T4G, T1B.T2D.T3C.T4G, T1C.T2D.T3C.T4G,
T1D.T2D.T3C.T4G, T1E.T2D.T3C.T4G, T1A.T2E.T3C.T4G,
T1B.T2E.T3C.T4G, T1C.T2E.T3C.T4G, T1D.T2E.T3C.T4G,

TABLE 6-continued

List of Compound Structure of Formula III with the core structure (C1)

T1E.T2E.T3C.T4G, T1A.T2F.T3C.T4G, T1B.T2F.T3C.T4G,
T1C.T2F.T3C.T4G, T1D.T2F.T3C.T4G, T1E.T2F.T3C.T4G,
T1A.T2A.T3D.T4G, T1B.T2A.T3D.T4G, T1C.T2A.T3D.T4G,
T1D.T2A.T3D.T4G, T1E.T2A.T3D.T4G, T1A.T2B.T3D.T4G,
T1B.T2B.T3D.T4G, T1C.T2B.T3D.T4G, T1D.T2B.T3D.T4G,
T1E.T2B.T3D.T4G, T1A.T2C.T3D.T4G, T1B.T2C.T3D.T4G,
T1C.T2C.T3D.T4G, T1D.T2C.T3D.T4G, T1E.T2C.T3D.T4G,
T1A.T2D.T3D.T4G, T1B.T2D.T3D.T4G, T1C.T2D.T3D.T4G,
T1D.T2D.T3D.T4G, T1E.T2D.T3D.T4G, T1A.T2E.T3D.T4G,
T1B.T2E.T3D.T4G, T1C.T2E.T3D.T4G, T1D.T2E.T3D.T4G,
T1E.T2E.T3D.T4G, T1A.T2F.T3D.T4G, T1B.T2F.T3D.T4G,
T1C.T2F.T3D.T4G, T1D.T2F.T3D.T4G, T1E.T2F.T3D.T4G,
T1A.T2A.T3E.T4G, T1B.T2A.T3E.T4G, T1C.T2A.T3E.T4G,
T1D.T2A.T3E.T4G, T1E.T2A.T3E.T4G, T1A.T2B.T3E.T4G,
T1B.T2B.T3E.T4G, T1C.T2B.T3E.T4G, T1D.T2B.T3E.T4G,
T1E.T2B.T3E.T4G, T1A.T2C.T3E.T4G, T1B.T2C.T3E.T4G,
T1C.T2C.T3E.T4G, T1D.T2C.T3E.T4G, T1E.T2C.T3E.T4G,
T1A.T2D.T3E.T4G, T1B.T2D.T3E.T4G, T1C.T2D.T3E.T4G,
T1D.T2D.T3E.T4G, T1E.T2D.T3E.T4G, T1A.T2E.T3E.T4G,
T1B.T2E.T3E.T4G, T1C.T2E.T3E.T4G, T1D.T2E.T3E.T4G,
T1E.T2E.T3E.T4G, T1A.T2F.T3E.T4G, T1B.T2F.T3E.T4G,
T1C.T2F.T3E.T4G, T1D.T2F.T3E.T4G, T1E.T2F.T3E.T4G,
T1A.T2A.T3F.T4G, T1B.T2A.T3F.T4G, T1C.T2A.T3F.T4G,
T1D.T2A.T3F.T4G, T1E.T2A.T3F.T4G, T1A.T2B.T3F.T4G,
T1B.T2B.T3F.T4G, T1C.T2B.T3F.T4G, T1D.T2B.T3F.T4G,
T1E.T2B.T3F.T4G, T1A.T2C.T3F.T4G, T1B.T2C.T3F.T4G,
T1C.T2C.T3F.T4G, T1D.T2C.T3F.T4G, T1E.T2C.T3F.T4G,
T1A.T2D.T3F.T4G, T1B.T2D.T3F.T4G, T1C.T2D.T3F.T4G,
T1D.T2D.T3F.T4G, T1E.T2D.T3F.T4G, T1A.T2E.T3F.T4G,
T1B.T2E.T3F.T4G, T1C.T2E.T3F.T4G, T1D.T2E.T3F.T4G,
T1E.T2E.T3F.T4G, T1A.T2F.T3F.T4G, T1B.T2F.T3F.T4G,
T1C.T2F.T3F.T4G, T1D.T2F.T3F.T4G, T1E.T2F.T3F.T4G,
T1A.T2A.T3G.T4G, T1B.T2A.T3G.T4G, T1C.T2A.T3G.T4G,
T1D.T2A.T3G.T4G, T1E.T2A.T3G.T4G, T1A.T2B.T3G.T4G,
T1B.T2B.T3G.T4G, T1C.T2B.T3G.T4G, T1D.T2B.T3G.T4G,
T1E.T2B.T3G.T4G, T1A.T2C.T3G.T4G, T1B.T2C.T3G.T4G,
T1C.T2C.T3G.T4G, T1D.T2C.T3G.T4G, T1E.T2C.T3G.T4G,
T1A.T2D.T3G.T4G, T1B.T2D.T3G.T4G, T1C.T2D.T3G.T4G,
T1D.T2D.T3G.T4G, T1E.T2D.T3G.T4G, T1A.T2E.T3G.T4G,
T1B.T2E.T3G.T4G, T1C.T2E.T3G.T4G, T1D.T2E.T3G.T4G,
T1E.T2E.T3G.T4G, T1A.T2F.T3G.T4G, T1B.T2F.T3G.T4G,
T1C.T2F.T3G.T4G, T1D.T2F.T3G.T4G, T1E.T2F.T3G.T4G.

Phosphonate Embodiments of Compounds of Formula I

In another embodiment, the compounds of the present invention can have one of the structures shown in Table 1.1, wherein M represents alkyl, substituted alkyl heteroalkyl, substituted heteroalkyl, alkenyl, substituted alkenyl, aryl, substituted aryl, arylalkyl, substituted arylalkyl, heterocyclyl, substituted heterocyclyl, heterocyclylalkyl, or substituted heterocyclylalkyl; and Z represents halo, alkyl, haloalkyl, or alkoxy.

$Pd^1$ and $Pd^2$ are each independently selected from species in Tables 20.1 to 20.37. The variables used in Tables 20.1 to 20.37 (e.g., $W^3$, $R^1$, etc.) pertain only to Tables 20.1-20.37, unless otherwise indicated. Additional phosphonate groups are disclosed in U.S. patent publication No. 2004/100960, the entirety of which is incorporated herein by reference.

The variables used in Tables 20.1 to 20.37 have the following definitions:

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, N3 or —NO$_2$;

$R^{3b}$ is $Y^1$;

$R^{3c}$ is —$R^x$, —N($R^x$)($R^x$), —S$R^x$, —S(O)$R^x$, —S(O)$_2R^x$, —S(O)(O$R^x$), —S(O)$_2$(O$R^x$), —OC($Y^1$)$R^x$, —OC($Y^1$)O$R^x$, —OC($Y^1$)(N($R^x$)($R^x$)), —SC($Y^1$)$R^x$, —SC($Y^1$)O$R^x$, —SC($Y^1$)(N($R^x$)($R^x$)), —N($R^x$)C($Y^1$)$R^x$, —N($R^x$)C($Y^1$)O$R^x$, or —N($R^x$)C($Y^1$)(N($R^x$)($R^x$));

$R^{3d}$ is —C($Y^1$)$R^x$, —C($Y^1$)O$R^x$ or —C($Y^1$)(N($R^x$)($R^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —C($Y^1$)$R^5$, —C($Y^1$)$W^5$, —SO$_2R^5$, or —SO$_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

TABLE 1.1

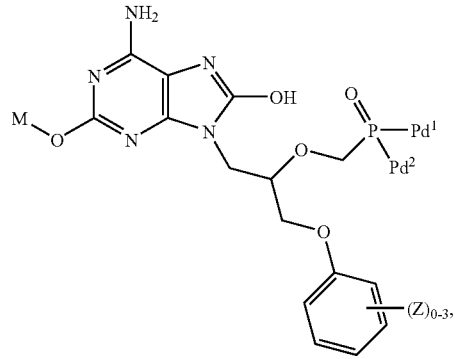

A

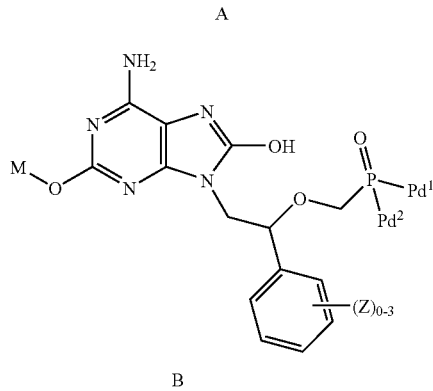

B

TABLE 1.1-continued
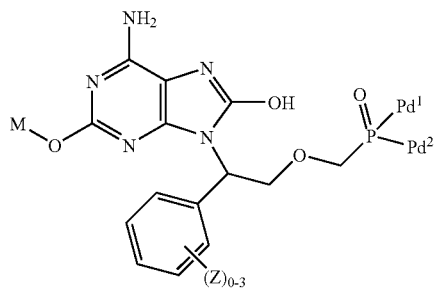
C
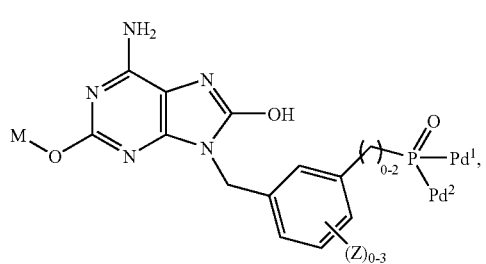
D
TABLE 20.1
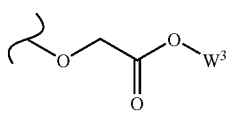
1
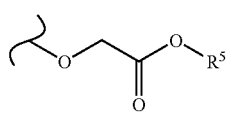
2
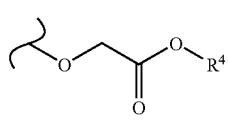
3
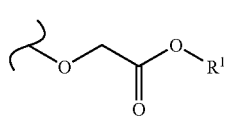
4
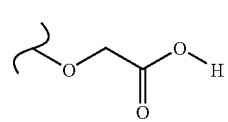
5
TABLE 20.1-continued
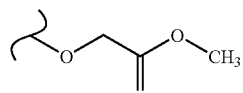
6
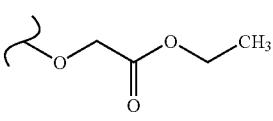
7
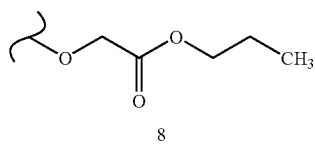
8
TABLE 20.2
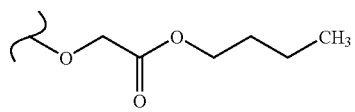
9
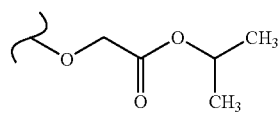
10
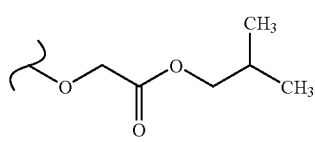
11
TABLE 20.3
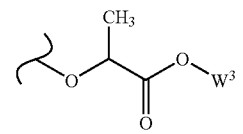
12
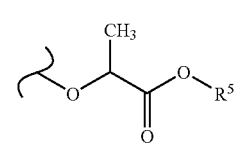
13

TABLE 20.3-continued
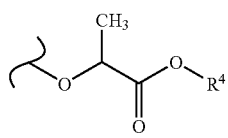
14
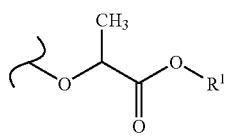
15
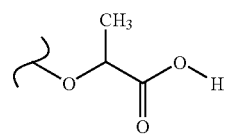
16
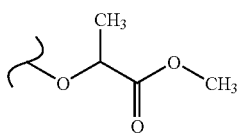
17
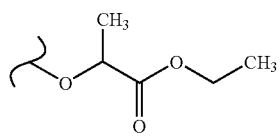
18
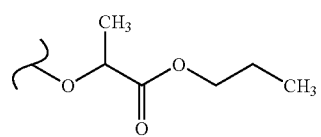
19
TABLE 20.4
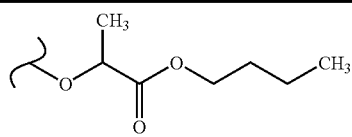
20
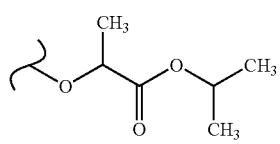
21
TABLE 20.4-continued
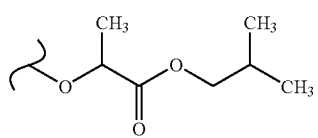
22
TABLE 20.5
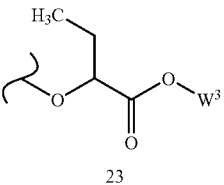
23
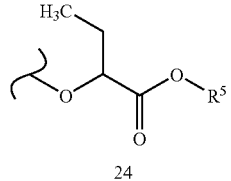
24
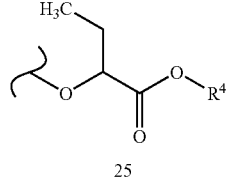
25
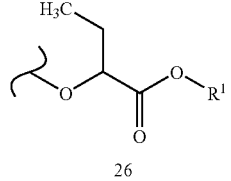
26
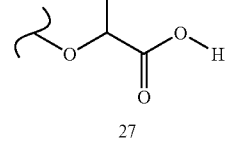
27
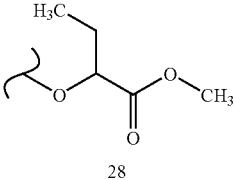
28

TABLE 20.5-continued
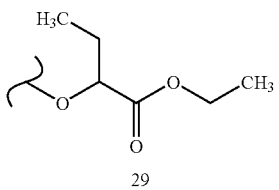
29
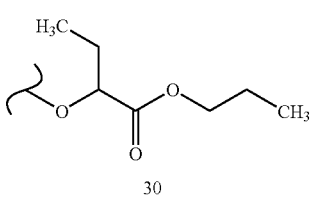
30
TABLE 20.6
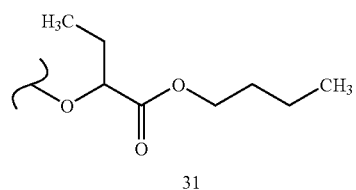
31
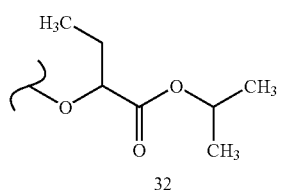
32
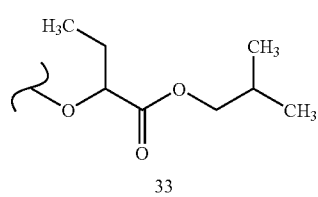
33
TABLE 20.7
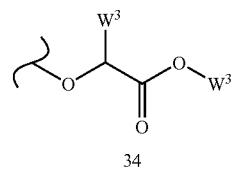
34
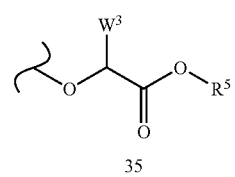
35
TABLE 20.7-continued
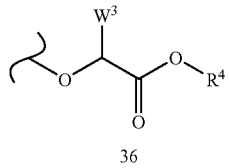
36
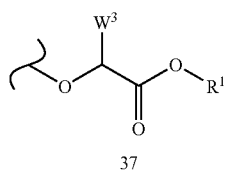
37
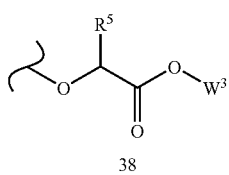
38
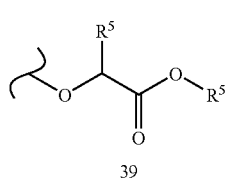
39
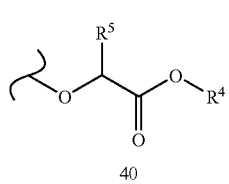
40
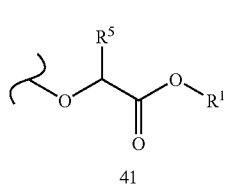
41
TABLE 20.8
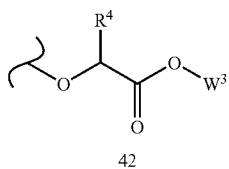
42
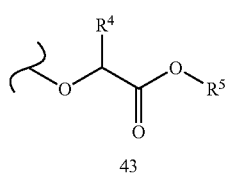
43

TABLE 20.8-continued
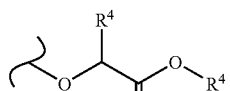
44
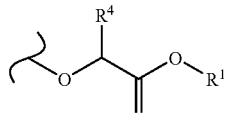
45
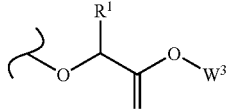
46
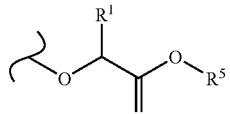
47
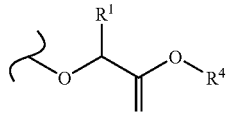
48
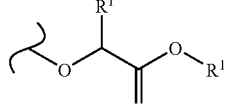
49
TABLE 20.9
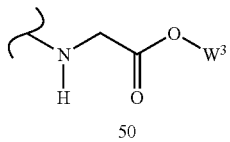
50
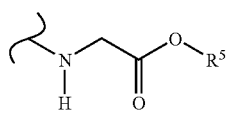
51
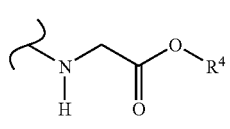
52
TABLE 20.9-continued
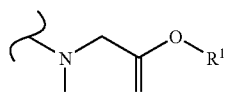
53
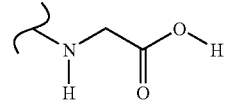
54
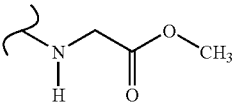
55
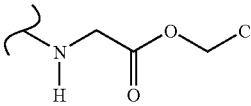
56
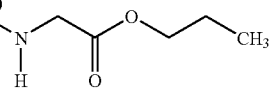
57
TABLE 20.10
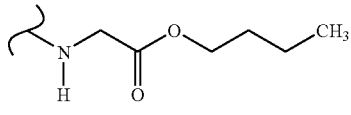
58
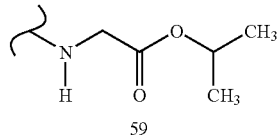
59
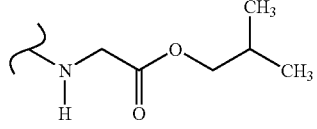
60
TABLE 20.11
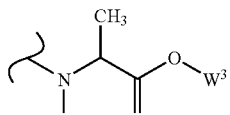
61

TABLE 20.11-continued
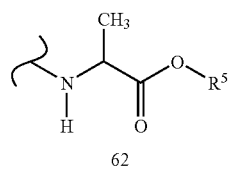
62
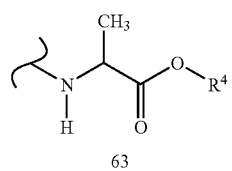
63
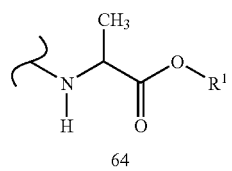
64
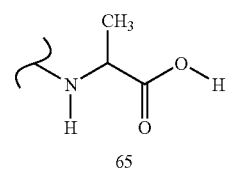
65
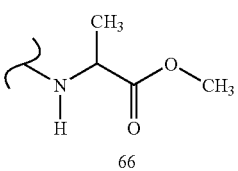
66
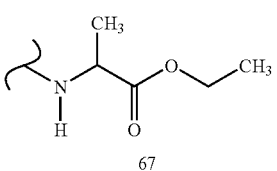
67
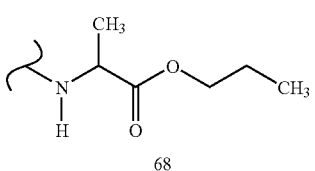
68
TABLE 20.12
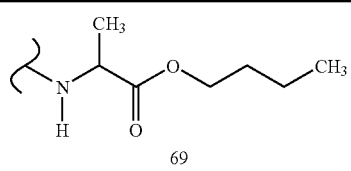
69
TABLE 20.12-continued
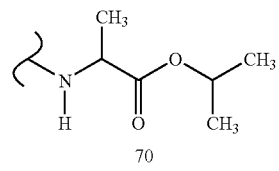
70
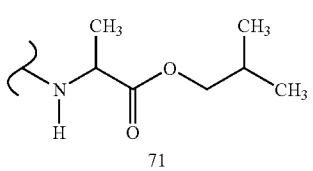
71
TABLE 20.13
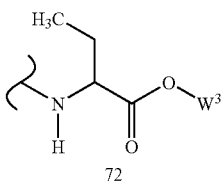
72
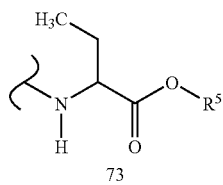
73
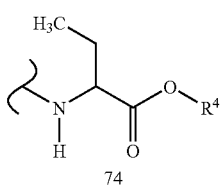
74
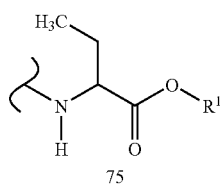
75
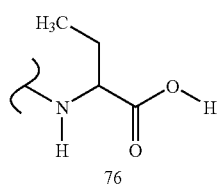
76
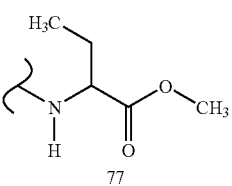
77
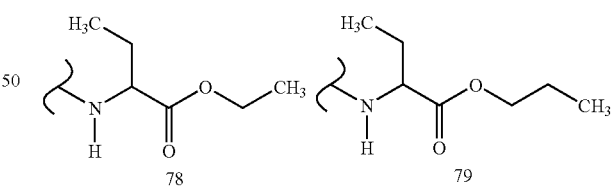
78
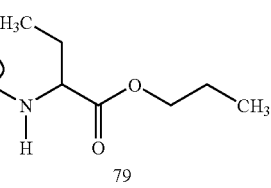
79
TABLE 20.14
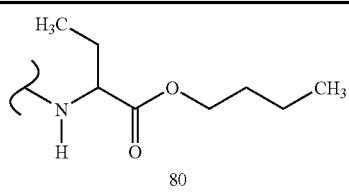
80

TABLE 20.14-continued
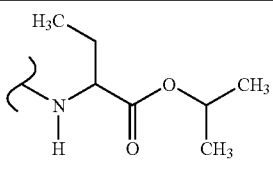
81
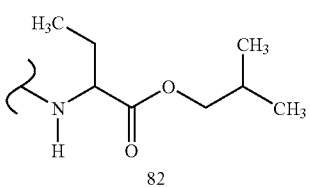
82
TABLE 20.15
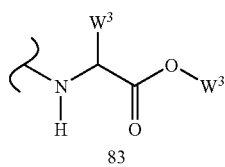 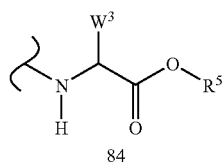
83 84
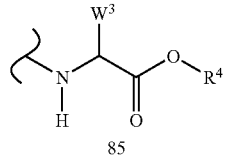 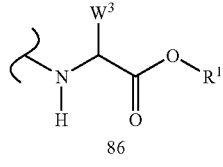
85 86
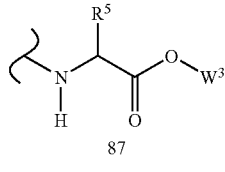 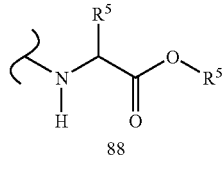
87 88
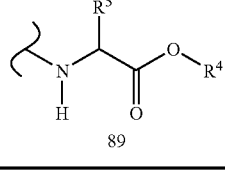 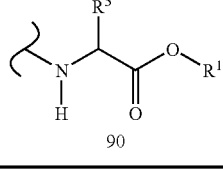
89 90
TABLE 20.16
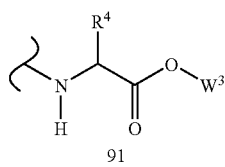 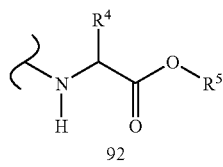
91 92
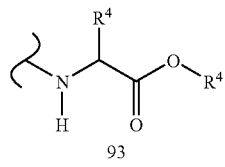 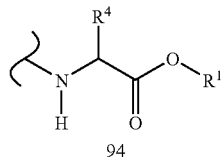
93 94
TABLE 20.16-continued
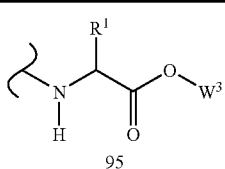 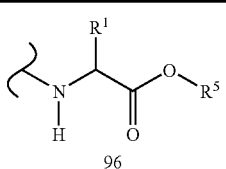
95 96
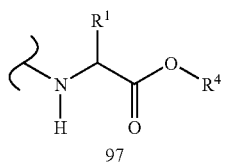 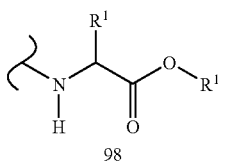
97 98
TABLE 20.17
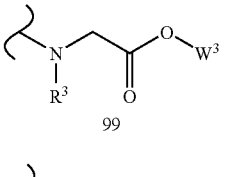 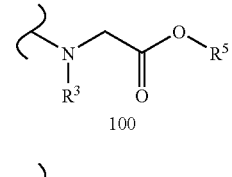
99 100
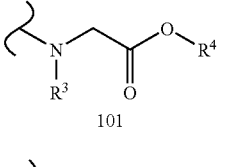 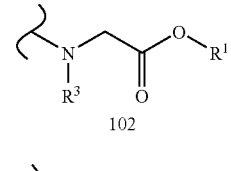
101 102
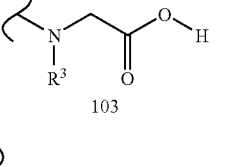 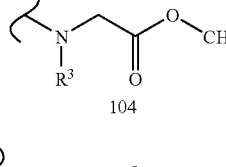
103 104
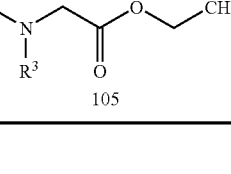 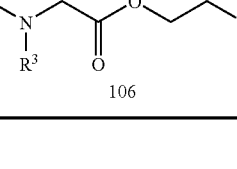
105 106
TABLE 20.18
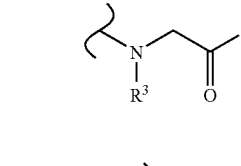
107
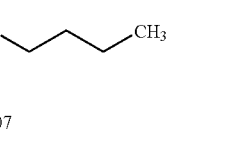
108
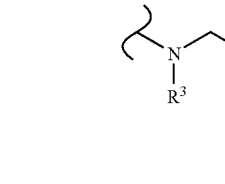
109

TABLE 20.19
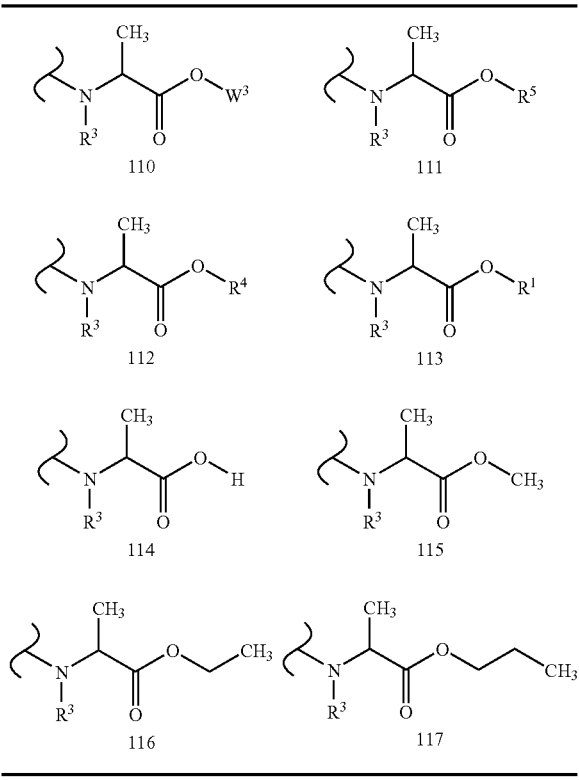
TABLE 20.20
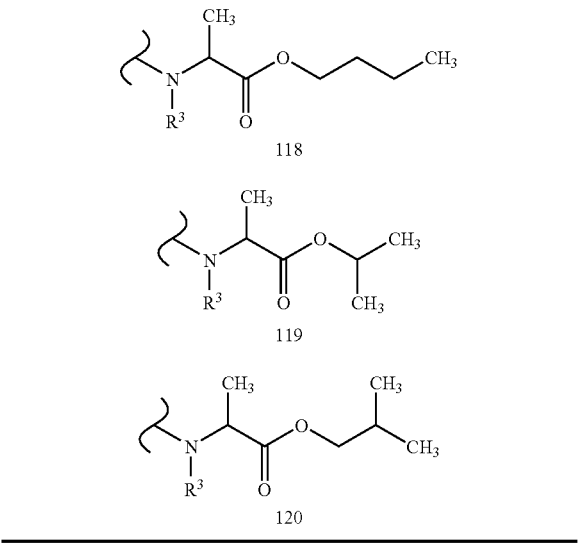
TABLE 20.21
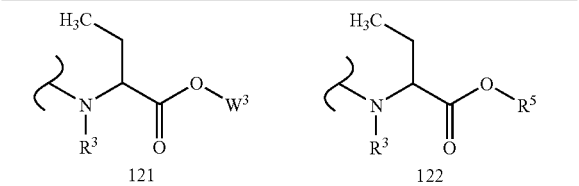
TABLE 20.21-continued
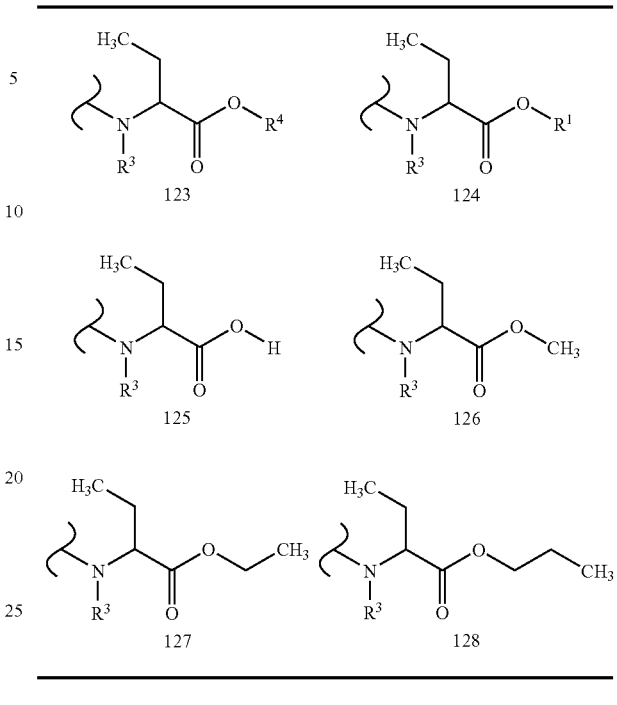
TABLE 20.22
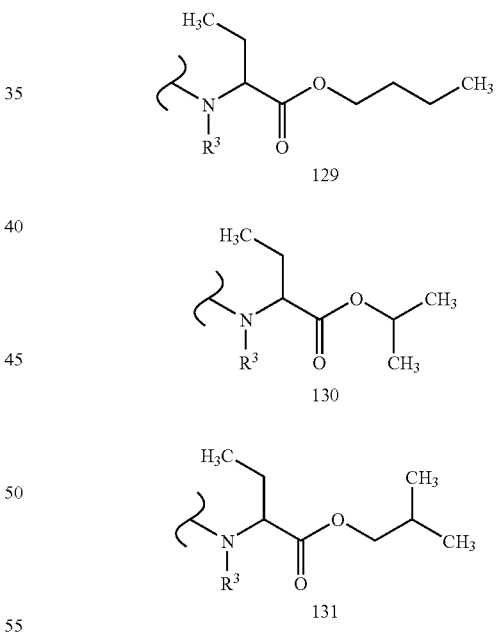
TABLE 20.23
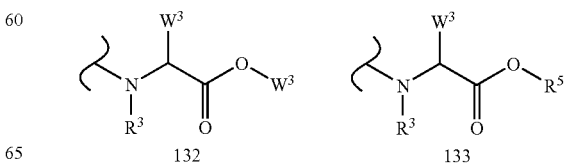

TABLE 20.23-continued
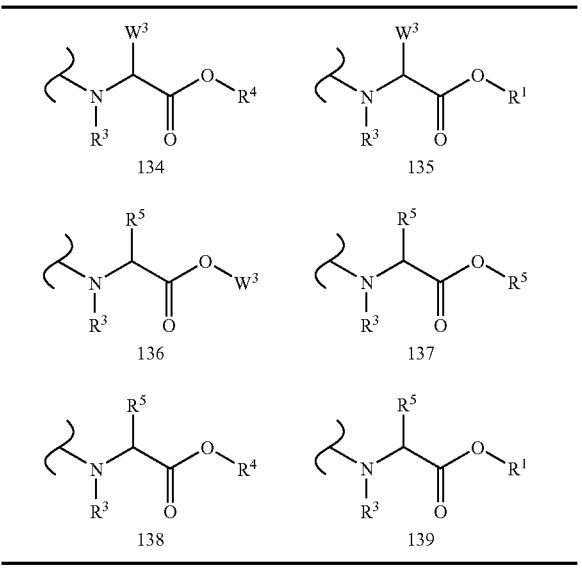
TABLE 20.24
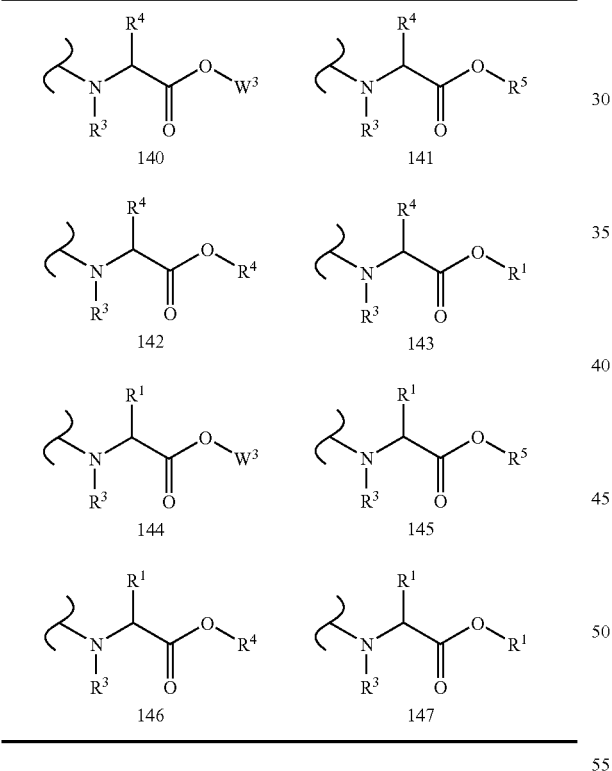
TABLE 20.25
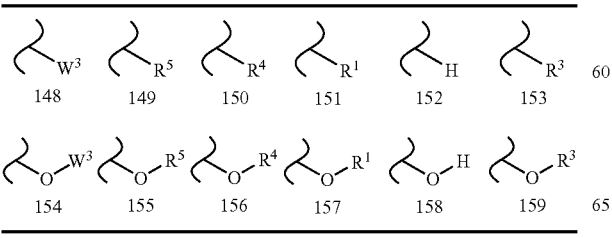
TABLE 20.26
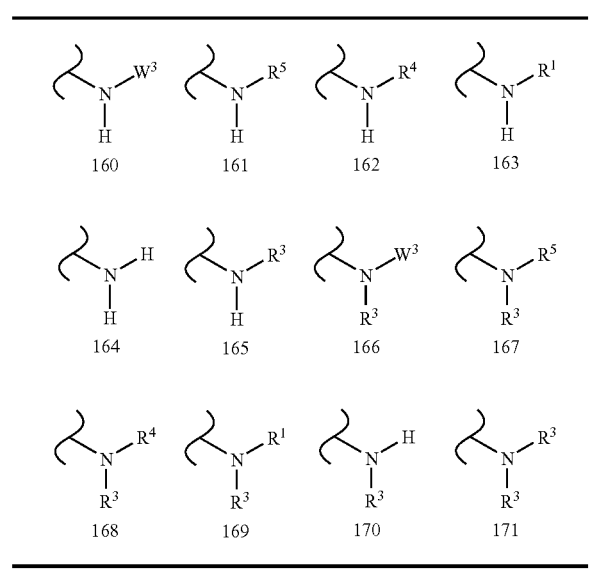
TABLE 20.27
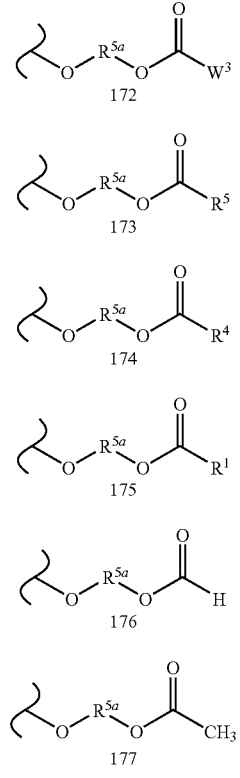
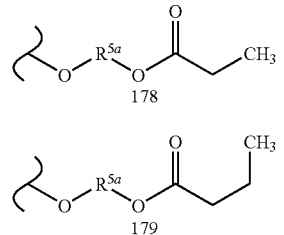

TABLE 20.28
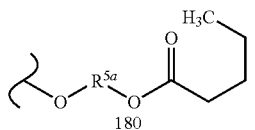
180
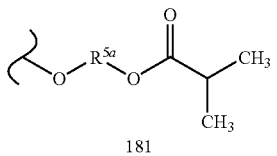
181
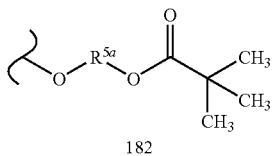
182
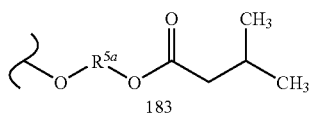
183
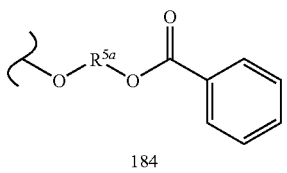
184
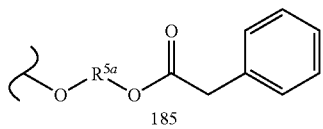
185
TABLE 20.29
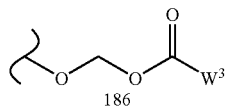
186
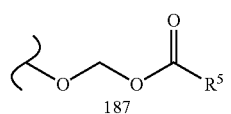
187
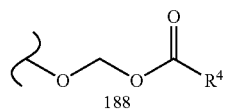
188
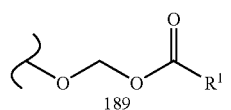
189
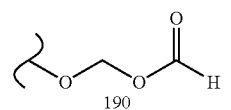
190
TABLE 20.29-continued
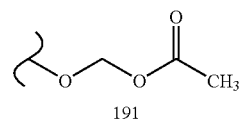
191
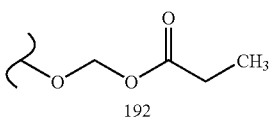
192
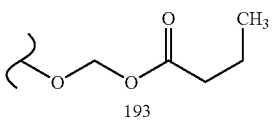
193
TABLE 20.30
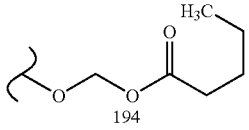
194
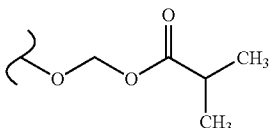
195
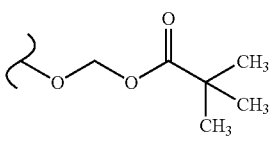
196
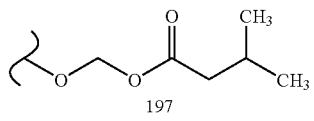
197
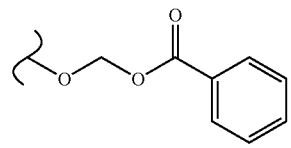
198
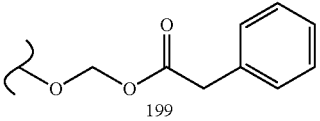
199
TABLE 20.31
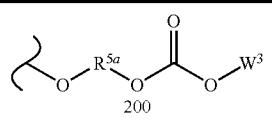
200

TABLE 20.31-continued
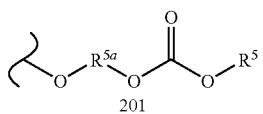
201
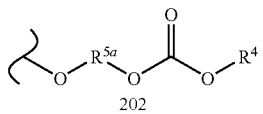
202
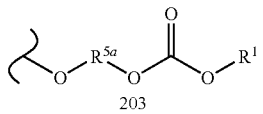
203
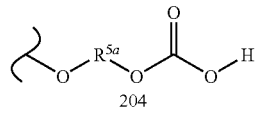
204
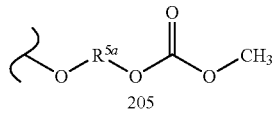
205
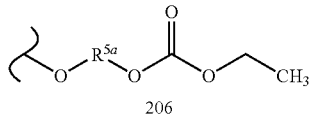
206
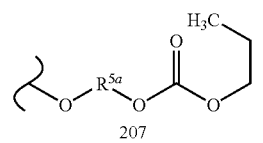
207
TABLE 20.32
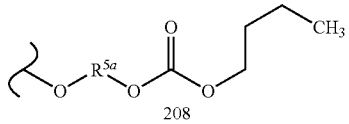
208
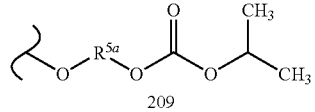
209
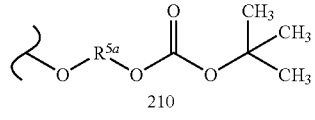
210
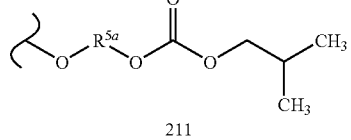
211
TABLE 20.32-continued
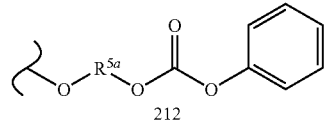
212
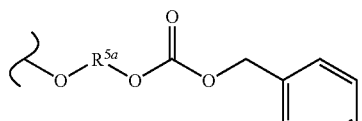
213
TABLE 20.33
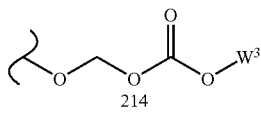
214
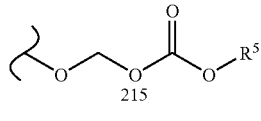
215
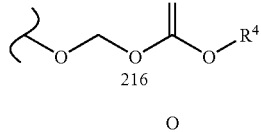
216
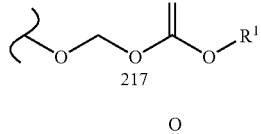
217
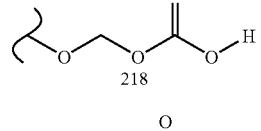
218
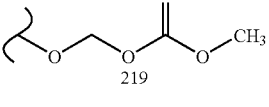
219
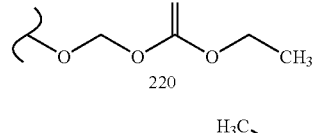
220
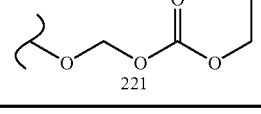
221
TABLE 20.34
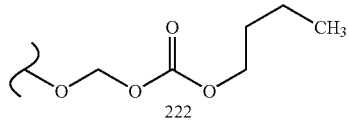
222

TABLE 20.34-continued
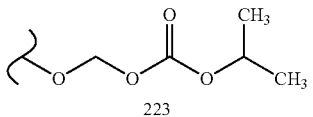
223
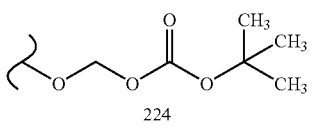
224
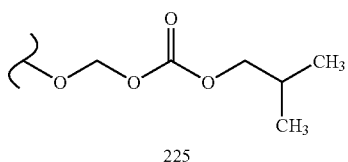
225
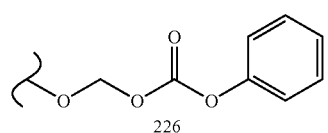
226
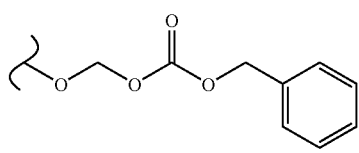
227
TABLE 20.35
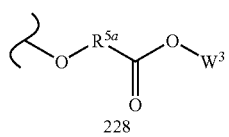
228
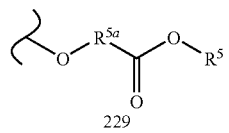
229
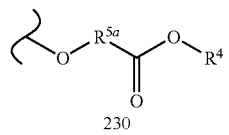
230
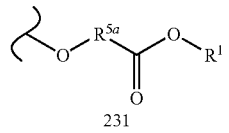
231
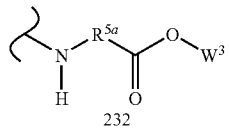
232
TABLE 20.35-continued
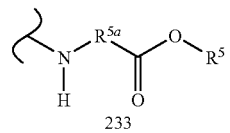
233
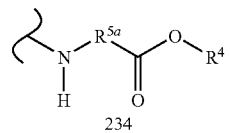
234
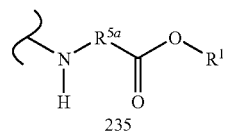
235
TABLE 20.36
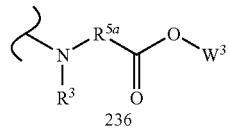
236
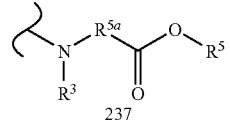
237
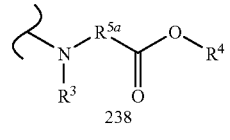
238
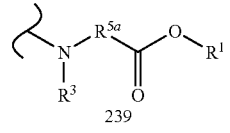
239
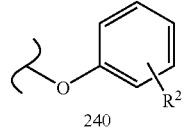
240
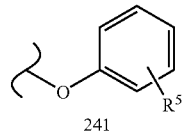
241
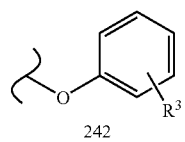
242
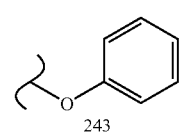
243

TABLE 20.37

244: [structure with R²]

245: [structure with R⁵]

246: [structure with R³]

247: [structure, unsubstituted]

In the following embodiments, the term "Sc" refers to one of the structures of Table 1.1.

In one embodiment of the compounds of Formula I, Sc is Formula A; Pd¹ is —O-Ph; Pd² is —NH—CH(CH₃)—C(O)—O—CH₂CH₃.

In another embodiment of the compounds of Formula I, Sc is Formula A; Pd¹ is —O-Ph; Pd² is —NH—CH(CH₃)—C(O)—O—CH₂CH₂CH₂CH₃.

In another embodiment of the compounds of Formula I, Sc is Formula A; Pd¹ is —O-Ph; Pd² is —NH—CH(benzyl)-C(O)—O—CH₂CH₃.

In another embodiment of the compounds of Formula I, Sc is Formula A; Pd¹ is —O-Ph; Pd² is —NH—CH(benzyl)-C(O)—O—CH₂CH₂CH₂CH₃.

In another embodiment of the compounds of Formula I, Sc is Formula A; Pd¹ is —NH—CH(CH₃)—C(O)—O—CH₂CH₃; Pd² is —NH—CH(CH₃)—C(O)—O—CH₂CH₃.

In another embodiment of the compounds of Formula I, Sc is Formula A; Pd¹ is —NH—CH(CH₃)—C(O)—O—CH₂CH₂CH₂CH₃; Pd² is —NH—CH(CH₃)—C(O)—O—CH₂CH₂CH₂CH₃.

In another embodiment of the compounds of Formula I, Sc is Formula A; Pd¹ is —NH—CH(CH₃)—C(O)—O—CH₂CH₃; Pd² is —NH—CH(CH₃)—C(O)—O—CH₂CH₂CH₂CH₃.

In another embodiment of the compounds of Formula I, Sc is Formula A; Pd¹ is —NH—CH(benzyl)-C(O)—O—CH₂CH₃; Pd² is —NH—CH(benzyl)-C(O)—O—CH₂CH₃.

In another embodiment of the compounds of Formula I, Sc is Formula A; Pd¹ is —NH—CH(benzyl)-C(O)—O—CH₂CH₂CH₂CH₃, Pd² is —NH—CH(benzyl)-C(O)—O—CH₂CH₂CH₂CH₃.

In another embodiment of the compounds of Formula I, Sc is Formula A; Pd¹ is —NH—CH(benzyl)-C(O)—O—CH₂CH₃; Pd² is —NH—CH(benzyl)-C(O)—O—CH₂CH₂CH₂CH₃.

In another embodiment of the compounds of Formula I, Sc is Formula A; Pd¹ is —O—CH₂—O—C(O)—O—CH(CH₃)₂, Pd² is —O—CH₂—O—C(O)—O—CH(CH₃)₂.

In another embodiment of the compounds of Formula I, Sc is Formula A; Pd¹ is —O—CH₂—O—C(O)—O—CH₂CH₃, Pd² is —O—CH₂—O—C(O)—O—CH₂CH₃.

In another embodiment of the compounds of Formula I, Sc is Formula A; Pd¹ is —O—CH—O—C(O)—C(CH₃)₃, Pd² is —O—CH₂—O—C(O)—C(CH₃)₃.

In one embodiment of the compounds of Formula I, Sc is Formula B; Pd¹ is —O-Ph; Pd² is —NH—CH(CH₃)—C(O)—O—CH₂CH₃.

In another embodiment of the compounds of Formula I, Sc is Formula B; Pd¹ is —O-Ph; Pd² is —NH—CH(CH₃)—C(O)—O—CH₂CH₂CH₂CH₃.

In another embodiment of the compounds of Formula I, Sc is Formula B; Pd¹ is —O-Ph; Pd² is —NH—CH(benzyl)-C(O)—O—CH₂CH₃.

In another embodiment of the compounds of Formula I, Sc is Formula B; Pd¹ is —O-Ph; Pd² is —NH—CH(benzyl)-C(O)—O—CH₂CH₂CH₂CH₃.

In another embodiment of the compounds of Formula I, Sc is Formula B; Pd¹ is —NH—CH(CH₃)—C(O)—O—CH₂CH₃; Pd² is —NH—CH(CH₃)—C(O)—O—CH₂CH₃.

In another embodiment of the compounds of Formula I, Sc is Formula B; Pd¹ is —NH—CH(CH₃)—C(O)—O—CH₂CH₂CH₂CH₃; Pd² is —NH—CH(CH₃)—C(O)—O—CH₂CH₂CH₂CH₃.

In another embodiment of the compounds of Formula I, Sc is Formula B; Pd¹ is —NH—CH(CH₃)—C(O)—O—CH₂CH₃; Pd² is —NH—CH(CH₃)—C(O)—O—CH₂CH₂CH₂CH₃.

In another embodiment of the compounds of Formula I, Sc is Formula B; Pd¹ is —NH—CH(benzyl)-C(O)—O—CH₂CH₃; Pd² is —NH—CH(benzyl)-C(O)—O—CH₂CH₃.

In another embodiment of the compounds of Formula I, Sc is Formula B; Pd¹ is —NH—CH(benzyl)-C(O)—O—CH₂CH₂CH₂CH₃; Pd² is —NH—CH(benzyl)-C(O)—O—CH₂CH₂CH₂CH₃.

In another embodiment of the compounds of Formula I, Sc is Formula B; Pd¹ is —NH—CH(benzyl)-C(O)—O—CH₂CH₃; Pd² is —NH—CH(benzyl)-C(O)—O—CH₂CH₂CH₂CH₃.

In another embodiment of the compounds of Formula I, Sc is Formula B; Pd¹ is —O—CH₂—O—C(O)—O—CH(CH₂)₂, Pd² is —O—CH₂—O—C(O)—O—CH(CH₃)₂.

In another embodiment of the compounds of Formula I, Sc is Formula B; Pd¹ is —O—CH₂—O—C(O)—O—CH₂CH₃, Pd² is —O—CH₂—O—C(O)—O—CH₂CH₃.

In another embodiment of the compounds of Formula I, Sc is Formula B; Pd¹ is —O—CH₂—O—C(O)—C(CH₃)₃, Pd² is —O—CH₂—O—C(O)—C(CH₃)₃.

In one embodiment of the compounds of Formula I, Sc is Formula C; Pd¹ is —O-Ph; Pd² is —NH—CH(CH₃)—C(O)—O—CH₂CH₃.

In another embodiment of the compounds of Formula I, Sc is Formula C; Pd¹ is —O-Ph; Pd² is —NH—CH(CH₃)—C(O)—O—CH₂CH₂CH₂CH₃.

In another embodiment of the compounds of Formula I, Sc is Formula C; Pd¹ is —O-Ph; Pd² is —NH—CH(benzyl)-C(O)—O—CH₂CH₃.

In another embodiment of the compounds of Formula I, Sc is Formula C; Pd¹ is —O-Ph; Pd² is —NH—CH(benzyl)-C(O)—O—CH₂CH₂CH₂CH₃.

In another embodiment of the compounds of Formula I, Sc is Formula C; Pd¹ is —NH—CH(CH₃)—C(O)—O—CH₂CH₃; Pd² is —NH—CH(CH₃)—C(O)—O—CH₂CH₃.

In another embodiment of the compounds of Formula I, Sc is Formula C; Pd¹ is —NH—CH(CH₃)—C(O)—O—CH₂CH₂CH₂CH₃; Pd² is —NH—CH(CH₃)—C(O)—O—CH₂CH₂CH₂CH₃.

In another embodiment of the compounds of Formula I, Sc is Formula C; Pd¹ is —NH—CH(CH₃)—C(O)—O—CH₂CH₃; Pd² is —NH—CH(CH₃)—C(O)—O—CH₂CH₂CH₂CH₃.

In another embodiment of the compounds of Formula I, Sc is Formula C; Pd¹ is —NH—CH(benzyl)-C(O)—O—CH₂CH₃; Pd² is —NH—CH(benzyl)-C(O)—O—CH₂CH₃.

In another embodiment of the compounds of Formula I, Sc is Formula C; Pd¹ is —NH—CH(benzyl)-C(O)—O—CH₂CH₂CH₂CH₃; Pd² is —NH—CH(benzyl)-C(O)—O—CH₂CH₂CH₂CH₃.

In another embodiment of the compounds of Formula I, Sc is Formula C; Pd¹ is —NH—CH(benzyl)-C(O)—O—CH₂CH₃; Pd² is —NH—CH(benzyl)-C(O)—O—CH₂CH₂CH₂CH₃.

In another embodiment of the compounds of Formula I, Sc is Formula C; Pd¹ is —O—CH₂—O—C(O)—O—CH(CH₃)₂, Pd² is O—CH—O—C(O)—O—CH(CH₃)₂.

In another embodiment of the compounds of Formula I, Sc is Formula C; Pd¹ is —O—CH₂—O—C(O)—O—CH₂CH₂, Pd² is —O—CH₂—O—C(O)—O—CH₂CH₃.

In another embodiment of the compounds of Formula I, Sc is Formula C; Pd¹ is —O—CH₂—O—C(O)—C(CH₃)₃, Pd² is —O—CH₂—O—C(O)—C(CH₃)₃.

In one embodiment of the compounds of Formula I, Sc is Formula D; Pd¹ is —O-Ph; Pd² is —NH—CH(CH₃)—C(O)—O—CH₂CH₃.

In another embodiment of the compounds of Formula I, Sc is Formula D; Pd¹ is —O-Ph; Pd² is —NH—CH(CH₃)—C(O)—O—CH₂CH₂CH₂CH₃.

In another embodiment of the compounds of Formula I, Sc is Formula D; Pd¹ is —O-Ph; Pd² is —NH—CH(benzyl)-C(O)—O—CH₂CH₃.

In another embodiment of the compounds of Formula I, Sc is Formula D; Pd¹ is —O-Ph; Pd² is —NH—CH(benzyl)-C(O)—O—CH₂CH₂CH₂CH₃.

In another embodiment of the compounds of Formula I, Sc is Formula D; Pd¹ is —NH—CH(CH₃)—C(O)—O—CH₂CH₃; Pd² is —NH—CH(CH₃)—C(O)—O—CH₂CH₃.

In another embodiment of the compounds of Formula I, Sc is Formula D; Pd¹ is —NH—CH(CH₃)—C(O)—O—CH₂CH₂CH₂CH₃; Pd² is —NH—CH(CH₃)—C(O)—O—CH₂CH₂CH₂CH₃. In another embodiment of the compounds of Formula I, Sc is Formula D; Pd¹ is —NH—CH(CH₃)—C(O)—O—CH₂CH₃; Pd² is —NH—CH(CH₃)—C(O)—O—CH₂CH₂CH₂CH₃.

In another embodiment of the compounds of Formula I, Sc is Formula D; Pd¹ is —NH—CH(benzyl)-C(O)—O—CH₂CH₃; Pd² is —NH—CH(benzyl)-C(O)—O—CH₂CH₃.

In another embodiment of the compounds of Formula I, Sc is Formula D; Pd¹ is —NH—CH(benzyl)-C(O)—O—CH₂CH₂CH₂CH₃; Pd² is —NH—CH(benzyl)-C(O)—O—CH₂CH₂CH₂CH₃.

In another embodiment of the compounds of Formula I, Sc is Formula D; Pd¹ is —NH—CH(benzyl)-C(O)—O—CH₂CH₃; Pd² is —NH—CH(benzyl)-C(O)—O—CH₂CH₂CH₂CH₃. In another embodiment of the compounds of Formula I, Sc is Formula D; Pd¹ is —O—CH—O—C(O)—O—CH(CH₃)₂, Pd² is —O—CH₂—O—C(O)—O—CH(CH₃)₂.

In another embodiment of the compounds of Formula I, Sc is Formula D; Pd¹ is —O—CH₂—O—C(O)—O—CH₂CH₃, Pd² is —O—CH₂—O—C(O)—O—CH₂CH₃.

In another embodiment of the compounds of Formula I, Sc is Formula D; Pd¹ is —O—CH₂—O—C(O)—C(C₁₋₃)₃, Pd² is —O—CH₂—O—C(O)—C(CH₁₃)₃.

In still another embodiment, selected compounds of Formula I are named below in tabular format (Table 11) as compounds of general Formula IV (below):

X-A-Y—Z    Formula IV where A, X, Y and Z are defined in Tables 7-10, below. Each compound is designated in tabular form by combining the "code" representing each structural moiety using the following syntax: A.X.Y.Z. Thus, for example, A1.X1.Y1.Z1. represents the following structure:

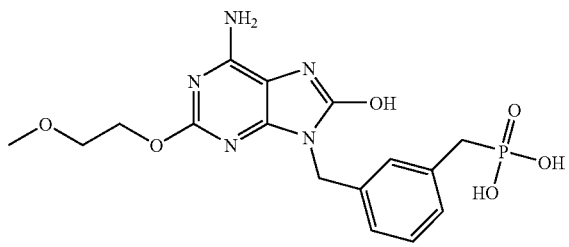

TABLE 7

| Code | "A" Structures "A" Structure |
|---|---|
| A1 | ![structure with NH₂, OH, X, Y-Z] |
| A2 | ![structure with NH₂, NH-butyl, X, Y-Z] |
| A3 | ![structure with NH₂, SH, X, Y-Z] |
| A4 | ![structure with OH, S, =O, X, Y-Z] |

TABLE 7-continued
"A" Structures
| Code | "A" Structure |
|---|---|
| A5 | 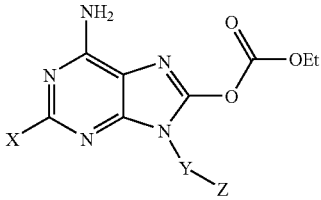 |
TABLE 8
"X" Structures
| Code | "X" Structure |
|---|---|
| X1 | 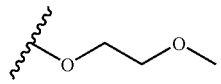 |
| X2 | 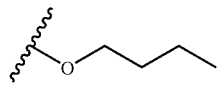 |
| X3 | 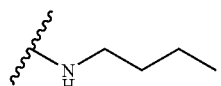 |
| X4 | 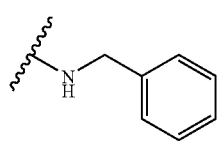 |
| X5 | —NH$_2$ |
TABLE 9
"Y" Structures
| Code | "Y" Structure |
|---|---|
| Y1 | 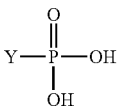 |
| Y2 | 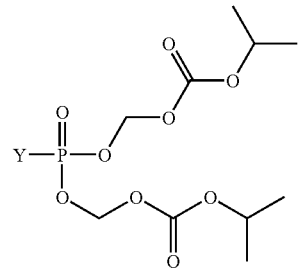 |
| Y3 | 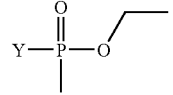 |
TABLE 9-continued
"Y" Structures
| Code | "Y" Structure |
|---|---|
| Y4 | 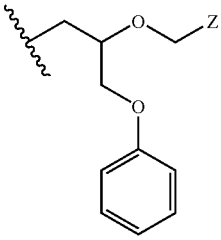 |
| Y5 | —N(CH$_3$)-(3-pyridyl) |
TABLE 10
"Z" Structures
| Code | "Z" Structure |
|---|---|
| Z1 | 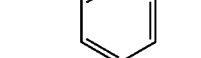 |
| Z2 | 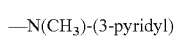 |
| Z3 | 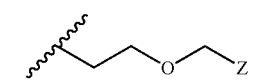 |
| Z4 | 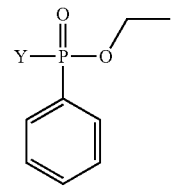 |
| Z5 | 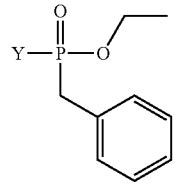 |

TABLE 10-continued

"Z" Structures

| Code | "Z" Structure |
|---|---|
| Z6 | (phosphoramidate with alanine ethyl ester and phenoxy) |
| Z7 | (phosphoramidate with alanine isopropyl ester and acetoxime O-linkage) |
| Z8 | (phosphoramidate with alanine isopropyl ester and phenoxy) |
| Z9 | (bis-phosphoramidate with two alanine ethyl esters) |
| Z10 | (bis-phosphoramidate with two alanine isopropyl esters) |
| Z11 | (bis-phosphoramidate with two alanine tert-butyl esters) |
| Z12 | (phosphoramidate with 2-(methoxymethyl)pyrrolidine and alanine isopropyl ester) |
| Z13 | (phosphoramidate with morpholine and alanine isopropyl ester) |
| Z14 | (bis-phosphoramidate with two phenylalanine ethyl esters) |

TABLE 11

A1.X1.Y1.Z1, A1.X1.Y1.Z2, A1.X1.Y1.Z3, A1.X1.Y1.Z4, A1.X1.Y1.Z5,
A1.X1.Y1.Z6, A1.X1.Y1.Z7, A1.X1.Y1.Z8, A1.X1.Y1.Z9,
A1.X1.Y1.Z10, A1.X1.Y1.Z11, A1.X1.Y1.Z12, A1.X1.Y1.Z13,
A1.X1.Y1.Z14, A1.X1.Y2.Z1, A1.X1.Y2.Z2, A1.X1.Y2.Z3,
A1.X1.Y2.Z4, A1.X1.Y2.Z5, A1.X1.Y2.Z6, A1.X1.Y2.Z7, A1.X1.Y2.Z8,
A1.X1.Y2.Z9, A1.X1.Y2.Z10, A1.X1.Y2.Z11, A1.X1.Y2.Z12,
A1.X1.Y2.Z13, A1.X1.Y2.Z14, A1.X1.Y3.Z1, A1.X1.Y3.Z2,
A1.X1.Y3.Z3, A1.X1.Y3.Z4, A1.X1.Y3.Z5, A1.X1.Y3.Z6, A1.X1.Y3.Z7,
A1.X1.Y3.Z8, A1.X1.Y3.Z9, A1.X1.Y3.Z10, A1.X1.Y3.Z11,
A1.X1.Y3.Z12, A1.X1.Y3.Z13, A1.X1.Y3.Z14, A1.X1.Y4.Z1,
A1.X1.Y4.Z2, A1.X1.Y4.Z3, A1.X1.Y4.Z4, A1.X1.Y4.Z5, A1.X1.Y4.Z6,
A1.X1.Y4.Z7, A1.X1.Y4.Z8, A1.X1.Y4.Z9, A1.X1.Y4.Z10,
A1.X1.Y4.Z11, A1.X1.Y4.Z12, A1.X1.Y4.Z13, A1.X1.Y4.Z14,
A1.X1.Y5.Z1, A1.X1.Y5.Z2, A1.X1.Y5.Z3, A1.X1.Y5.Z4, A1.X1.Y5.Z5,
A1.X1.Y5.Z6, A1.X1.Y5.Z7, A1.X1.Y5.Z8, A1.X1.Y5.Z9,

TABLE 11-continued

A1.X1.Y5.Z10, A1.X1.Y5.Z11, A1.X1.Y5.Z12, A1.X1.Y5.Z13,
A1.X1.Y5.Z14, A1.X2.Y1.Z1, A1.X2.Y1.Z2, A1.X2.Y1.Z3,
A1.X2.Y1.Z4, A1.X2.Y1.Z5, A1.X2.Y1.Z6, A1.X2.Y1.Z7,
A1.X2.Y1.Z8, A1.X2.Y1.Z9, A1.X2.Y1.Z10, A1.X2.Y1.Z11,
A1.X2.Y1.Z12, A1.X2.Y1.Z13, A1.X2.Y1.Z14, A1.X2.Y2.Z1,
A1.X2.Y2.Z2, A1.X2.Y2.Z3, A1.X2.Y2.Z4, A1.X2.Y2.Z5, A1.X2.Y2.Z6,
A1.X2.Y2.Z7, A1.X2.Y2.Z8, A1.X2.Y2.Z9, A1.X2.Y2.Z10,
A1.X2.Y2.Z11, A1.X2.Y2.Z12, A1.X2.Y2.Z13, A1.X2.Y2.Z14,
A1.X2.Y3.Z1, A1.X2.Y3.Z2, A1.X2.Y3.Z3, A1.X2.Y3.Z4, A1.X2.Y3.Z5,
A1.X2.Y3.Z6, A1.X2.Y3.Z7, A1.X2.Y3.Z8, A1.X2.Y3.Z9,
A1.X2.Y3.Z10, A1.X2.Y3.Z11, A1.X2.Y3.Z12, A1.X2.Y3.Z13,
A1.X2.Y3.Z14, A1.X2.Y4.Z1, A1.X2.Y4.Z2, A1.X2.Y4.Z3,
A1.X2.Y4.Z4, A1.X2.Y4.Z5, A1.X2.Y4.Z6, A1.X2.Y4.Z7, A1.X2.Y4.Z8,
A1.X2.Y4.Z9, A1.X2.Y4.Z10, A1.X2.Y4.Z11, A1.X2.Y4.Z12,
A1.X2.Y4.Z13, A1.X2.Y4.Z14, A1.X2.Y5.Z1, A1.X2.Y5.Z2,
A1.X2.Y5.Z3, A1.X2.Y5.Z4, A1.X2.Y5.Z5, A1.X2.Y5.Z6, A1.X2.Y5.Z7,
A1.X2.Y5.Z8, A1.X2.Y5.Z9, A1.X2.Y5.Z10, A1.X2.Y5.Z11,
A1.X2.Y5.Z12, A1.X2.Y5.Z13, A1.X2.Y5.Z14, A1.X3.Y1.Z1,
A1.X3.Y1.Z2, A1.X3.Y1.Z3, A1.X3.Y1.Z4, A1.X3.Y1.Z5, A1.X3.Y1.Z6,
A1.X3.Y1.Z7, A1.X3.Y1.Z8, A1.X3.Y1.Z9, A1.X3.Y1.Z10,
A1.X3.Y1.Z11, A1.X3.Y1.Z12, A1.X3.Y1.Z13, A1.X3.Y1.Z14,
A1.X3.Y2.Z1, A1.X3.Y2.Z2, A1.X3.Y2.Z3, A1.X3.Y2.Z4, A1.X3.Y2.Z5,
A1.X3.Y2.Z6, A1.X3.Y2.Z7, A1.X3.Y2.Z8, A1.X3.Y2.Z9,
A1.X3.Y2.Z10, A1.X3.Y2.Z11, A1.X3.Y2.Z12, A1.X3.Y2.Z13,
A1.X3.Y2.Z14, A1.X3.Y3.Z1, A1.X3.Y3.Z2, A1.X3.Y3.Z3,
A1.X3.Y3.Z4, A1.X3.Y3.Z5, A1.X3.Y3.Z6, A1.X3.Y3.Z7, A1.X3.Y3.Z8,
A1.X3.Y3.Z9, A1.X3.Y3.Z10, A1.X3.Y3.Z11, A1.X3.Y3.Z12,
A1.X3.Y3.Z13, A1.X3.Y3.Z14, A1.X3.Y4.Z1, A1.X3.Y4.Z2,
A1.X3.Y4.Z3, A1.X3.Y4.Z4, A1.X3.Y4.Z5, A1.X3.Y4.Z6, A1.X3.Y4.Z7,
A1.X3.Y4.Z8, A1.X3.Y4.Z9, A1.X3.Y4.Z10, A1.X3.Y4.Z11,
A1.X3.Y4.Z12, A1.X3.Y4.Z13, A1.X3.Y4.Z14, A1.X3.Y5.Z1,
A1.X3.Y5.Z2, A1.X3.Y5.Z3, A1.X3.Y5.Z4, A1.X3.Y5.Z5, A1.X3.Y5.Z6,
A1.X3.Y5.Z7, A1.X3.Y5.Z8, A1.X3.Y5.Z9, A1.X3.Y5.Z10,
A1.X3.Y5.Z11, A1.X3.Y5.Z12, A1.X3.Y5.Z13, A1.X3.Y5.Z14,
A1.X4.Y1.Z1, A1.X4.Y1.Z2, A1.X4.Y1.Z3, A1.X4.Y1.Z4, A1.X4.Y1.Z5,
A1.X4.Y1.Z6, A1.X4.Y1.Z7, A1.X4.Y1.Z8, A1.X4.Y1.Z9,
A1.X4.Y1.Z10, A1.X4.Y1.Z11, A1.X4.Y1.Z12, A1.X4.Y1.Z13,
A1.X4.Y1.Z14, A1.X4.Y2.Z1, A1.X4.Y2.Z2, A1.X4.Y2.Z3,
A1.X4.Y2.Z4, A1.X4.Y2.Z5, A1.X4.Y2.Z6, A1.X4.Y2.Z7, A1.X4.Y2.Z8,
A1.X4.Y2.Z9, A1.X4.Y2.Z10, A1.X4.Y2.Z11, A1.X4.Y2.Z12,
A1.X4.Y2.Z13, A1.X4.Y2.Z14, A1.X4.Y3.Z1, A1.X4.Y3.Z2,
A1.X4.Y3.Z3, A1.X4.Y3.Z4, A1.X4.Y3.Z5, A1.X4.Y3.Z6, A1.X4.Y3.Z7,
A1.X4.Y3.Z8, A1.X4.Y3.Z9, A1.X4.Y3.Z10, A1.X4.Y3.Z11,
A1.X4.Y3.Z12, A1.X4.Y3.Z13, A1.X4.Y3.Z14, A1.X4.Y4.Z1,
A1.X4.Y4.Z2, A1.X4.Y4.Z3, A1.X4.Y4.Z4, A1.X4.Y4.Z5, A1.X4.Y4.Z6,
A1.X4.Y4.Z7, A1.X4.Y4.Z8, A1.X4.Y4.Z9, A1.X4.Y4.Z10,
A1.X4.Y4.Z11, A1.X4.Y4.Z12, A1.X4.Y4.Z13, A1.X4.Y4.Z14,
A1.X4.Y5.Z1, A1.X4.Y5.Z2, A1.X4.Y5.Z3, A1.X4.Y5.Z4, A1.X4.Y5.Z5,
A1.X4.Y5.Z6, A1.X4.Y5.Z7, A1.X4.Y5.Z8, A1.X4.Y5.Z9,
A1.X4.Y5.Z10, A1.X4.Y5.Z11, A1.X4.Y5.Z12, A1.X4.Y5.Z13,
A1.X4.Y5.Z14, A1.X5.Y1.Z1, A1.X5.Y1.Z2, A1.X5.Y1.Z3,
A1.X5.Y1.Z4, A1.X5.Y1.Z5, A1.X5.Y1.Z6, A1.X5.Y1.Z7, A1.X5.Y1.Z8,
A1.X5.Y1.Z9, A1.X5.Y1.Z10, A1.X5.Y1.Z11, A1.X5.Y1.Z12,
A1.X5.Y1.Z13, A1.X5.Y1.Z14, A1.X5.Y2.Z1, A1.X5.Y2.Z2,
A1.X5.Y2.Z3, A1.X5.Y2.Z4, A1.X5.Y2.Z5, A1.X5.Y2.Z6, A1.X5.Y2.Z7,
A1.X5.Y2.Z8, A1.X5.Y2.Z9, A1.X5.Y2.Z10, A1.X5.Y2.Z11,
A1.X5.Y2.Z12, A1.X5.Y2.Z13, A1.X5.Y2.Z14, A1.X5.Y3.Z1,
A1.X5.Y3.Z2, A1.X5.Y3.Z3, A1.X5.Y3.Z4, A1.X5.Y3.Z5, A1.X5.Y3.Z6,
A1.X5.Y3.Z7, A1.X5.Y3.Z8, A1.X5.Y3.Z9, A1.X5.Y3.Z10,
A1.X5.Y3.Z11, A1.X5.Y3.Z12, A1.X5.Y3.Z13, A1.X5.Y3.Z14,
A1.X5.Y4.Z1, A1.X5.Y4.Z2, A1.X5.Y4.Z3, A1.X5.Y4.Z4, A1.X5.Y4.Z5,
A1.X5.Y4.Z6, A1.X5.Y4.Z7, A1.X5.Y4.Z8, A1.X5.Y4.Z9,
A1.X5.Y4.Z10, A1.X5.Y4.Z11, A1.X5.Y4.Z12, A1.X5.Y4.Z13,
A1.X5.Y4.Z14, A1.X5.Y5.Z1, A1.X5.Y5.Z2, A1.X5.Y5.Z3,
A1.X5.Y5.Z4, A1.X5.Y5.Z5, A1.X5.Y5.Z6, A1.X5.Y5.Z7, A1.X5.Y5.Z8,
A1.X5.Y5.Z9, A1.X5.Y5.Z10, A1.X5.Y5.Z11, A1.X5.Y5.Z12,
A1.X5.Y5.Z13, A1.X5.Y5.Z14, A2.X1.Y1.Z1, A2.X1.Y1.Z2,
A2.X1.Y1.Z3, A2.X1.Y1.Z4, A2.X1.Y1.Z5, A2.X1.Y1.Z6, A2.X1.Y1.Z7,
A2.X1.Y1.Z8, A2.X1.Y1.Z9, A2.X1.Y1.Z10, A2.X1.Y1.Z11,
A2.X1.Y1.Z12, A2.X1.Y1.Z13, A2.X1.Y1.Z14, A2.X1.Y2.Z1,
A2.X1.Y2.Z2, A2.X1.Y2.Z3, A2.X1.Y2.Z4, A2.X1.Y2.Z5,
A2.X1.Y2.Z6, A2.X1.Y2.Z7, A2.X1.Y2.Z8, A2.X1.Y2.Z9,
A2.X1.Y2.Z10, A2.X1.Y2.Z11, A2.X1.Y2.Z12, A2.X1.Y2.Z13,
A2.X1.Y2.Z14, A2.X1.Y3.Z1, A2.X1.Y3.Z2, A2.X1.Y3.Z3,
A2.X1.Y3.Z4, A2.X1.Y3.Z5, A2.X1.Y3.Z6, A2.X1.Y3.Z7, A2.X1.Y3.Z8,
A2.X1.Y3.Z9, A2.X1.Y3.Z10, A2.X1.Y3.Z11, A2.X1.Y3.Z12,
A2.X1.Y3.Z13, A2.X1.Y3.Z14, A2.X1.Y4.Z1, A2.X1.Y4.Z2,
A2.X1.Y4.Z3, A2.X1.Y4.Z4, A2.X1.Y4.Z5, A2.X1.Y4.Z6, A2.X1.Y4.Z7,
A2.X1.Y4.Z8, A2.X1.Y4.Z9, A2.X1.Y4.Z10, A2.X1.Y4.Z11,
A2.X1.Y4.Z12, A2.X1.Y4.Z13, A2.X1.Y4.Z14, A2.X1.Y5.Z1,
A2.X1.Y5.Z2, A2.X1.Y5.Z3, A2.X1.Y5.Z4, A2.X1.Y5.Z5, A2.X1.Y5.Z6,
A2.X1.Y5.Z7, A2.X1.Y5.Z8, A2.X1.Y5.Z9, A2.X1.Y5.Z10,
A2.X1.Y5.Z11, A2.X1.Y5.Z12, A2.X1.Y5.Z13, A2.X1.Y5.Z14,
A2.X2.Y1.Z1, A2.X2.Y1.Z2, A2.X2.Y1.Z3, A2.X2.Y1.Z4, A2.X2.Y1.Z5,
A2.X2.Y1.Z6, A2.X2.Y1.Z7, A2.X2.Y1.Z8, A2.X2.Y1.Z9,
A2.X2.Y1.Z10, A2.X2.Y1.Z11, A2.X2.Y1.Z12, A2.X2.Y1.Z13,
A2.X2.Y1.Z14, A2.X2.Y2.Z1, A2.X2.Y2.Z2, A2.X2.Y2.Z3,
A2.X2.Y2.Z4, A2.X2.Y2.Z5, A2.X2.Y2.Z6, A2.X2.Y2.Z7, A2.X2.Y2.Z8,
A2.X2.Y2.Z9, A2.X2.Y2.Z10, A2.X2.Y2.Z11, A2.X2.Y2.Z12,
A2.X2.Y2.Z13, A2.X2.Y2.Z14, A2.X2.Y3.Z1, A2.X2.Y3.Z2,
A2.X2.Y3.Z3, A2.X2.Y3.Z4, A2.X2.Y3.Z5, A2.X2.Y3.Z6, A2.X2.Y3.Z7,
A2.X2.Y3.Z8, A2.X2.Y3.Z9, A2.X2.Y3.Z10, A2.X2.Y3.Z11,
A2.X2.Y3.Z12, A2.X2.Y3.Z13, A2.X2.Y3.Z14, A2.X2.Y4.Z1,
A2.X2.Y4.Z2, A2.X2.Y4.Z3, A2.X2.Y4.Z4, A2.X2.Y4.Z5, A2.X2.Y4.Z6,
A2.X2.Y4.Z7, A2.X2.Y4.Z8, A2.X2.Y4.Z9, A2.X2.Y4.Z10,
A2.X2.Y4.Z11, A2.X2.Y4.Z12, A2.X2.Y4.Z13, A2.X2.Y4.Z14,
A2.X2.Y5.Z1, A2.X2.Y5.Z2, A2.X2.Y5.Z3, A2.X2.Y5.Z4, A2.X2.Y5.Z5,
A2.X2.Y5.Z6, A2.X2.Y5.Z7, A2.X2.Y5.Z8, A2.X2.Y5.Z9,
A2.X2.Y5.Z10, A2.X2.Y5.Z11, A2.X2.Y5.Z12, A2.X2.Y5.Z13,
A2.X2.Y5.Z14, A2.X3.Y1.Z1, A2.X3.Y1.Z2, A2.X3.Y1.Z3,
A2.X3.Y1.Z4, A2.X3.Y1.Z5, A2.X3.Y1.Z6, A2.X3.Y1.Z7, A2.X3.Y1.Z8,
A2.X3.Y1.Z9, A2.X3.Y1.Z10, A2.X3.Y1.Z11, A2.X3.Y1.Z12,
A2.X3.Y1.Z13, A2.X3.Y1.Z14, A2.X3.Y2.Z1, A2.X3.Y2.Z2,
A2.X3.Y2.Z3, A2.X3.Y2.Z4, A2.X3.Y2.Z5, A2.X3.Y2.Z6, A2.X3.Y2.Z7,
A2.X3.Y2.Z8, A2.X3.Y2.Z9, A2.X3.Y2.Z10, A2.X3.Y2.Z11,
A2.X3.Y2.Z12, A2.X3.Y2.Z13, A2.X3.Y2.Z14, A2.X3.Y3.Z1,
A2.X3.Y3.Z2, A2.X3.Y3.Z3, A2.X3.Y3.Z4, A2.X3.Y3.Z5, A2.X3.Y3.Z6,
A2.X3.Y3.Z7, A2.X3.Y3.Z8, A2.X3.Y3.Z9, A2.X3.Y3.Z10,
A2.X3.Y3.Z11, A2.X3.Y3.Z12, A2.X3.Y3.Z13, A2.X3.Y3.Z14,
A2.X3.Y4.Z1, A2.X3.Y4.Z2, A2.X3.Y4.Z3, A2.X3.Y4.Z4, A2.X3.Y4.Z5,
A2.X3.Y4.Z6, A2.X3.Y4.Z7, A2.X3.Y4.Z8, A2.X3.Y4.Z9,
A2.X3.Y4.Z10, A2.X3.Y4.Z11, A2.X3.Y4.Z12, A2.X3.Y4.Z13,
A2.X3.Y4.Z14, A2.X3.Y5.Z1, A2.X3.Y5.Z2, A2.X3.Y5.Z3,
A2.X3.Y5.Z4, A2.X3.Y5.Z5, A2.X3.Y5.Z6, A2.X3.Y5.Z7, A2.X3.Y5.Z8,
A2.X3.Y5.Z9, A2.X3.Y5.Z10, A2.X3.Y5.Z11, A2.X3.Y5.Z12,
A2.X3.Y5.Z13, A2.X3.Y5.Z14, A2.X4.Y1.Z1, A2.X4.Y1.Z2,
A2.X4.Y1.Z3, A2.X4.Y1.Z4, A2.X4.Y1.Z5, A2.X4.Y1.Z6, A2.X4.Y1.Z7,
A2.X4.Y1.Z8, A2.X4.Y1.Z9, A2.X4.Y1.Z10, A2.X4.Y1.Z11,
A2.X4.Y1.Z12, A2.X4.Y1.Z13, A2.X4.Y1.Z14, A2.X4.Y2.Z1,
A2.X4.Y2.Z2, A2.X4.Y2.Z3, A2.X4.Y2.Z4, A2.X4.Y2.Z5, A2.X4.Y2.Z6,
A2.X4.Y2.Z7, A2.X4.Y2.Z8, A2.X4.Y2.Z9, A2.X4.Y2.Z10,
A2.X4.Y2.Z11, A2.X4.Y2.Z12, A2.X4.Y2.Z13, A2.X4.Y2.Z14,
A2.X4.Y3.Z1, A2.X4.Y3.Z2, A2.X4.Y3.Z3, A2.X4.Y3.Z4, A2.X4.Y3.Z5,
A2.X4.Y3.Z6, A2.X4.Y3.Z7, A2.X4.Y3.Z8, A2.X4.Y3.Z9,
A2.X4.Y3.Z10, A2.X4.Y3.Z11, A2.X4.Y3.Z12, A2.X4.Y3.Z13,
A2.X4.Y3.Z14, A2.X4.Y4.Z1, A2.X4.Y4.Z2, A2.X4.Y4.Z3,
A2.X4.Y4.Z4, A2.X4.Y4.Z5, A2.X4.Y4.Z6, A2.X4.Y4.Z7, A2.X4.Y4.Z8,
A2.X4.Y4.Z9, A2.X4.Y4.Z10, A2.X4.Y4.Z11, A2.X4.Y4.Z12,
A2.X4.Y4.Z13, A2.X4.Y4.Z14, A2.X4.Y5.Z1, A2.X4.Y5.Z2,
A2.X4.Y5.Z3, A2.X4.Y5.Z4, A2.X4.Y5.Z5, A2.X4.Y5.Z6, A2.X4.Y5.Z7,
A2.X4.Y5.Z8, A2.X4.Y5.Z9, A2.X4.Y5.Z10, A2.X4.Y5.Z11,
A2.X4.Y5.Z12, A2.X4.Y5.Z13, A2.X4.Y5.Z14, A2.X5.Y1.Z1,
A2.X5.Y1.Z2, A2.X5.Y1.Z3, A2.X5.Y1.Z4, A2.X5.Y1.Z5, A2.X5.Y1.Z6,
A2.X5.Y1.Z7, A2.X5.Y1.Z8, A2.X5.Y1.Z9, A2.X5.Y1.Z10,
A2.X5.Y1.Z11, A2.X5.Y1.Z12, A2.X5.Y1.Z13, A2.X5.Y1.Z14,
A2.X5.Y2.Z1, A2.X5.Y2.Z2, A2.X5.Y2.Z3, A2.X5.Y2.Z4, A2.X5.Y2.Z5,
A2.X5.Y2.Z6, A2.X5.Y2.Z7, A2.X5.Y2.Z8, A2.X5.Y2.Z9,
A2.X5.Y2.Z10, A2.X5.Y2.Z11, A2.X5.Y2.Z12, A2.X5.Y2.Z13,
A2.X5.Y2.Z14, A2.X5.Y3.Z1, A2.X5.Y3.Z2, A2.X5.Y3.Z3,
A2.X5.Y3.Z4, A2.X5.Y3.Z5, A2.X5.Y3.Z6, A2.X5.Y3.Z7, A2.X5.Y3.Z8,
A2.X5.Y3.Z9, A2.X5.Y3.Z10, A2.X5.Y3.Z11, A2.X5.Y3.Z12,
A2.X5.Y3.Z13, A2.X5.Y3.Z14, A2.X5.Y4.Z1, A2.X5.Y4.Z2,
A2.X5.Y4.Z3, A2.X5.Y4.Z4, A2.X5.Y4.Z5, A2.X5.Y4.Z6, A2.X5.Y4.Z7,
A2.X5.Y4.Z8, A2.X5.Y4.Z9, A2.X5.Y4.Z10, A2.X5.Y4.Z11,
A2.X5.Y4.Z12, A2.X5.Y4.Z13, A2.X5.Y4.Z14, A2.X5.Y5.Z1,
A2.X5.Y5.Z2, A2.X5.Y5.Z3, A2.X5.Y5.Z4, A2.X5.Y5.Z5, A2.X5.Y5.Z6,
A2.X5.Y5.Z7, A2.X5.Y5.Z8, A2.X5.Y5.Z9, A2.X5.Y5.Z10,
A2.X5.Y5.Z11, A2.X5.Y5.Z12, A2.X5.Y5.Z13, A2.X5.Y5.Z14,
A3.X1.Y1.Z1, A3.X1.Y1.Z2, A3.X1.Y1.Z3, A3.X1.Y1.Z4, A3.X1.Y1.Z5,
A3.X1.Y1.Z6, A3.X1.Y1.Z7, A3.X1.Y1.Z8, A3.X1.Y1.Z9,
A3.X1.Y1.Z10, A3.X1.Y1.Z11, A3.X1.Y1.Z12, A3.X1.Y1.Z13,
A3.X1.Y1.Z14, A3.X1.Y2.Z1, A3.X1.Y2.Z2, A3.X1.Y2.Z3,
A3.X1.Y2.Z4, A3.X1.Y2.Z5, A3.X1.Y2.Z6, A3.X1.Y2.Z7, A3.X1.Y2.Z8,
A3.X1.Y2.Z9, A3.X1.Y2.Z10, A3.X1.Y2.Z11, A3.X1.Y2.Z12,
A3.X1.Y2.Z13, A3.X1.Y2.Z14, A3.X1.Y3.Z1, A3.X1.Y3.Z2,
A3.X1.Y3.Z3, A3.X1.Y3.Z4, A3.X1.Y3.Z5, A3.X1.Y3.Z6, A3.X1.Y3.Z7,
A3.X1.Y3.Z8, A3.X1.Y3.Z9, A3.X1.Y3.Z10, A3.X1.Y3.Z11,
A3.X1.Y3.Z12, A3.X1.Y3.Z13, A3.X1.Y3.Z14, A3.X1.Y4.Z1,
A3.X1.Y4.Z2, A3.X1.Y4.Z3, A3.X1.Y4.Z4, A3.X1.Y4.Z5, A3.X1.Y4.Z6,
A3.X1.Y4.Z7, A3.X1.Y4.Z8, A3.X1.Y4.Z9, A3.X1.Y4.Z10,

TABLE 11-continued

A3.X1.Y4.Z11, A3.X1.Y4.Z12, A3.X1.Y4.Z13, A3.X1.Y4.Z14,
A3.X1.Y5.Z1, A3.X1.Y5.Z2, A3.X1.Y5.Z3, A3.X1.Y5.Z4, A3.X1.Y5.Z5,
A3.X1.Y5.Z6, A3.X1.Y5.Z7, A3.X1.Y5.Z8, A3.X1.Y5.Z9,
A3.X1.Y5.Z10, A3.X1.Y5.Z11, A3.X1.Y5.Z12, A3.X1.Y5.Z13,
A3.X1.Y5.Z14, A3.X2.Y1.Z1, A3.X2.Y1.Z2, A3.X2.Y1.Z3,
A3.X2.Y1.Z4, A3.X2.Y1.Z5, A3.X2.Y1.Z6, A3.X2.Y1.Z7, A3.X2.Y1.Z8,
A3.X2.Y1.Z9, A3.X2.Y1.Z10, A3.X2.Y1.Z11, A3.X2.Y1.Z12,
A3.X2.Y1.Z13, A3.X2.Y1.Z14, A3.X2.Y2.Z1, A3.X2.Y2.Z2,
A3.X2.Y2.Z3, A3.X2.Y2.Z4, A3.X2.Y2.Z5, A3.X2.Y2.Z6, A3.X2.Y2.Z7,
A3.X2.Y2.Z8, A3.X2.Y2.Z9, A3.X2.Y2.Z10, A3.X2.Y2.Z11,
A3.X2.Y2.Z12, A3.X2.Y2.Z13, A3.X2.Y2.Z14, A3.X2.Y3.Z1,
A3.X2.Y3.Z2, A3.X2.Y3.Z3, A3.X2.Y3.Z4, A3.X2.Y3.Z5, A3.X2.Y3.Z6,
A3.X2.Y3.Z7, A3.X2.Y3.Z8, A3.X2.Y3.Z9, A3.X2.Y3.Z10,
A3.X2.Y3.Z11, A3.X2.Y3.Z12, A3.X2.Y3.Z13, A3.X2.Y3.Z14,
A3.X2.Y4.Z1, A3.X2.Y4.Z2, A3.X2.Y4.Z3, A3.X2.Y4.Z4, A3.X2.Y4.Z5,
A3.X2.Y4.Z6, A3.X2.Y4.Z7, A3.X2.Y4.Z8, A3.X2.Y4.Z9,
A3.X2.Y4.Z10, A3.X2.Y4.Z11, A3.X2.Y4.Z12, A3.X2.Y4.Z13,
A3.X2.Y4.Z14, A3.X2.Y5.Z1, A3.X2.Y5.Z2, A3.X2.Y5.Z3,
A3.X2.Y5.Z4, A3.X2.Y5.Z5, A3.X2.Y5.Z6, A3.X2.Y5.Z7, A3.X2.Y5.Z8,
A3.X2.Y5.Z9, A3.X2.Y5.Z10, A3.X2.Y5.Z11, A3.X2.Y5.Z12,
A3.X2.Y5.Z13, A3.X2.Y5.Z14, A3.X3.Y1.Z1, A3.X3.Y1.Z2,
A3.X3.Y1.Z3, A3.X3.Y1.Z4, A3.X3.Y1.Z5, A3.X3.Y1.Z6, A3.X3.Y1.Z7,
A3.X3.Y1.Z8, A3.X3.Y1.Z9, A3.X3.Y1.Z10, A3.X3.Y1.Z11,
A3.X3.Y1.Z12, A3.X3.Y1.Z13, A3.X3.Y1.Z14, A3.X3.Y2.Z1,
A3.X3.Y2.Z2, A3.X3.Y2.Z3, A3.X3.Y2.Z4, A3.X3.Y2.Z5, A3.X3.Y2.Z6,
A3.X3.Y2.Z7, A3.X3.Y2.Z8, A3.X3.Y2.Z9, A3.X3.Y2.Z10,
A3.X3.Y2.Z11, A3.X3.Y2.Z12, A3.X3.Y2.Z13, A3.X3.Y2.Z14,
A3.X3.Y3.Z1, A3.X3.Y3.Z2, A3.X3.Y3.Z3, A3.X3.Y3.Z4, A3.X3.Y3.Z5,
A3.X3.Y3.Z6, A3.X3.Y3.Z7, A3.X3.Y3.Z8, A3.X3.Y3.Z9,
A3.X3.Y3.Z10, A3.X3.Y3.Z11, A3.X3.Y3.Z12, A3.X3.Y3.Z13,
A3.X3.Y3.Z14, A3.X3.Y4.Z1, A3.X3.Y4.Z2, A3.X3.Y4.Z3,
A3.X3.Y4.Z4, A3.X3.Y4.Z5, A3.X3.Y4.Z6, A3.X3.Y4.Z7, A3.X3.Y4.Z8,
A3.X3.Y4.Z9, A3.X3.Y4.Z10, A3.X3.Y4.Z11, A3.X3.Y4.Z12,
A3.X3.Y4.Z13, A3.X3.Y4.Z14, A3.X3.Y5.Z1, A3.X3.Y5.Z2,
A3.X3.Y5.Z3, A3.X3.Y5.Z4, A3.X3.Y5.Z5, A3.X3.Y5.Z6, A3.X3.Y5.Z7,
A3.X3.Y5.Z8, A3.X3.Y5.Z9, A3.X3.Y5.Z10, A3.X3.Y5.Z11,
A3.X3.Y5.Z12, A3.X3.Y5.Z13, A3.X3.Y5.Z14, A3.X4.Y1.Z1,
A3.X4.Y1.Z2, A3.X4.Y1.Z3, A3.X4.Y1.Z4, A3.X4.Y1.Z5, A3.X4.Y1.Z6,
A3.X4.Y1.Z7, A3.X4.Y1.Z8, A3.X4.Y1.Z9, A3.X4.Y1.Z10,
A3.X4.Y1.Z11, A3.X4.Y1.Z12, A3.X4.Y1.Z13, A3.X4.Y1.Z14,
A3.X4.Y2.Z1, A3.X4.Y2.Z2, A3.X4.Y2.Z3, A3.X4.Y2.Z4, A3.X4.Y2.Z5,
A3.X4.Y2.Z6, A3.X4.Y2.Z7, A3.X4.Y2.Z8, A3.X4.Y2.Z9,
A3.X4.Y2.Z10, A3.X4.Y2.Z11, A3.X4.Y2.Z12, A3.X4.Y2.Z13,
A3.X4.Y2.Z14, A3.X4.Y3.Z1, A3.X4.Y3.Z2, A3.X4.Y3.Z3,
A3.X4.Y3.Z4, A3.X4.Y3.Z5, A3.X4.Y3.Z6, A3.X4.Y3.Z7, A3.X4.Y3.Z8,
A3.X4.Y3.Z9, A3.X4.Y3.Z10, A3.X4.Y3.Z11, A3.X4.Y3.Z12,
A3.X4.Y3.Z13, A3.X4.Y3.Z14, A3.X4.Y4.Z1, A3.X4.Y4.Z2,
A3.X4.Y4.Z3, A3.X4.Y4.Z4, A3.X4.Y4.Z5, A3.X4.Y4.Z6, A3.X4.Y4.Z7,
A3.X4.Y4.Z8, A3.X4.Y4.Z9, A3.X4.Y4.Z10, A3.X4.Y4.Z11,
A3.X4.Y4.Z12, A3.X4.Y4.Z13, A3.X4.Y4.Z14, A3.X4.Y5.Z1,
A3.X4.Y5.Z2, A3.X4.Y5.Z3, A3.X4.Y5.Z4, A3.X4.Y5.Z5, A3.X4.Y5.Z6,
A3.X4.Y5.Z7, A3.X4.Y5.Z8, A3.X4.Y5.Z9, A3.X4.Y5.Z10,
A3.X4.Y5.Z11, A3.X4.Y5.Z12, A3.X4.Y5.Z13, A3.X4.Y5.Z14,
A3.X5.Y1.Z1, A3.X5.Y1.Z2, A3.X5.Y1.Z3, A3.X5.Y1.Z4, A3.X5.Y1.Z5,
A3.X5.Y1.Z6, A3.X5.Y1.Z7, A3.X5.Y1.Z8, A3.X5.Y1.Z9,
A3.X5.Y1.Z10, A3.X5.Y1.Z11, A3.X5.Y1.Z12, A3.X5.Y1.Z13,
A3.X5.Y1.Z14, A3.X5.Y2.Z1, A3.X5.Y2.Z2, A3.X5.Y2.Z3,
A3.X5.Y2.Z4, A3.X5.Y2.Z5, A3.X5.Y2.Z6, A3.X5.Y2.Z7, A3.X5.Y2.Z8,
A3.X5.Y2.Z9, A3.X5.Y2.Z10, A3.X5.Y2.Z11, A3.X5.Y2.Z12,
A3.X5.Y2.Z13, A3.X5.Y2.Z14, A3.X5.Y3.Z1, A3.X5.Y3.Z2,
A3.X5.Y3.Z3, A3.X5.Y3.Z4, A3.X5.Y3.Z5, A3.X5.Y3.Z6, A3.X5.Y3.Z7,
A3.X5.Y3.Z8, A3.X5.Y3.Z9, A3.X5.Y3.Z10, A3.X5.Y3.Z11,
A3.X5.Y3.Z12, A3.X5.Y3.Z13, A3.X5.Y3.Z14, A3.X5.Y4.Z1,
A3.X5.Y4.Z2, A3.X5.Y4.Z3, A3.X5.Y4.Z4, A3.X5.Y4.Z5, A3.X5.Y4.Z6,
A3.X5.Y4.Z7, A3.X5.Y4.Z8, A3.X5.Y4.Z9, A3.X5.Y4.Z10,
A3.X5.Y4.Z11, A3.X5.Y4.Z12, A3.X5.Y4.Z13, A3.X5.Y4.Z14,
A3.X5.Y5.Z1, A3.X5.Y5.Z2, A3.X5.Y5.Z3, A3.X5.Y5.Z4, A3.X5.Y5.Z5,
A3.X5.Y5.Z6, A3.X5.Y5.Z7, A3.X5.Y5.Z8, A3.X5.Y5.Z9,
A3.X5.Y5.Z10, A3.X5.Y5.Z11, A3.X5.Y5.Z12, A3.X5.Y5.Z13,
A3.X5.Y5.Z14, A4.X1.Y1.Z1, A4.X1.Y1.Z2, A4.X1.Y1.Z3,
A4.X1.Y1.Z4, A4.X1.Y1.Z5, A4.X1.Y1.Z6, A4.X1.Y1.Z7, A4.X1.Y1.Z8,
A4.X1.Y1.Z9, A4.X1.Y1.Z10, A4.X1.Y1.Z11, A4.X1.Y1.Z12,
A4.X1.Y1.Z13, A4.X1.Y1.Z14, A4.X1.Y2.Z1, A4.X1.Y2.Z2,
A4.X1.Y2.Z3, A4.X1.Y2.Z4, A4.X1.Y2.Z5, A4.X1.Y2.Z6, A4.X1.Y2.Z7,
A4.X1.Y2.Z8, A4.X1.Y2.Z9, A4.X1.Y2.Z10, A4.X1.Y2.Z11,
A4.X1.Y2.Z12, A4.X1.Y2.Z13, A4.X1.Y2.Z14, A4.X1.Y3.Z1,
A4.X1.Y3.Z2, A4.X1.Y3.Z3, A4.X1.Y3.Z4, A4.X1.Y3.Z5, A4.X1.Y3.Z6,
A4.X1.Y3.Z7, A4.X1.Y3.Z8, A4.X1.Y3.Z9, A4.X1.Y3.Z10,
A4.X1.Y3.Z11, A4.X1.Y3.Z12, A4.X1.Y3.Z13, A4.X1.Y3.Z14,
A4.X1.Y4.Z1, A4.X1.Y4.Z2, A4.X1.Y4.Z3, A4.X1.Y4.Z4,

TABLE 11-continued

A4.X1.Y4.Z5, A4.X1.Y4.Z6, A4.X1.Y4.Z7, A4.X1.Y4.Z8, A4.X1.Y4.Z9,
A4.X1.Y4.Z10, A4.X1.Y4.Z11, A4.X1.Y4.Z12, A4.X1.Y4.Z13,
A4.X1.Y4.Z14, A4.X1.Y5.Z1, A4.X1.Y5.Z2, A4.X1.Y5.Z3,
A4.X1.Y5.Z4, A4.X1.Y5.Z5, A4.X1.Y5.Z6, A4.X1.Y5.Z7, A4.X1.Y5.Z8,
A4.X1.Y5.Z9, A4.X1.Y5.Z10, A4.X1.Y5.Z11, A4.X1.Y5.Z12,
A4.X1.Y5.Z13, A4.X1.Y5.Z14, A4.X2.Y1.Z1, A4.X2.Y1.Z2,
A4.X2.Y1.Z3, A4.X2.Y1.Z4, A4.X2.Y1.Z5, A4.X2.Y1.Z6, A4.X2.Y1.Z7,
A4.X2.Y1.Z8, A4.X2.Y1.Z9, A4.X2.Y1.Z10, A4.X2.Y1.Z11,
A4.X2.Y1.Z12, A4.X2.Y1.Z13, A4.X2.Y1.Z14, A4.X2.Y2.Z1,
A4.X2.Y2.Z2, A4.X2.Y2.Z3, A4.X2.Y2.Z4, A4.X2.Y2.Z5, A4.X2.Y2.Z6,
A4.X2.Y2.Z7, A4.X2.Y2.Z8, A4.X2.Y2.Z9, A4.X2.Y2.Z10,
A4.X2.Y2.Z11, A4.X2.Y2.Z12, A4.X2.Y2.Z13, A4.X2.Y2.Z14,
A4.X2.Y3.Z1, A4.X2.Y3.Z2, A4.X2.Y3.Z3, A4.X2.Y3.Z4, A4.X2.Y3.Z5,
A4.X2.Y3.Z6, A4.X2.Y3.Z7, A4.X2.Y3.Z8, A4.X2.Y3.Z9,
A4.X2.Y3.Z10, A4.X2.Y3.Z11, A4.X2.Y3.Z12, A4.X2.Y3.Z13,
A4.X2.Y3.Z14, A4.X2.Y4.Z1, A4.X2.Y4.Z2, A4.X2.Y4.Z3,
A4.X2.Y4.Z4, A4.X2.Y4.Z5, A4.X2.Y4.Z6, A4.X2.Y4.Z7, A4.X2.Y4.Z8,
A4.X2.Y4.Z9, A4.X2.Y4.Z10, A4.X2.Y4.Z11, A4.X2.Y4.Z12,
A4.X2.Y4.Z13, A4.X2.Y4.Z14, A4.X2.Y5.Z1, A4.X2.Y5.Z2,
A4.X2.Y5.Z3, A4.X2.Y5.Z4, A4.X2.Y5.Z5, A4.X2.Y5.Z6, A4.X2.Y5.Z7,
A4.X2.Y5.Z8, A4.X2.Y5.Z9, A4.X2.Y5.Z10, A4.X2.Y5.Z11,
A4.X2.Y5.Z12, A4.X2.Y5.Z13, A4.X2.Y5.Z14, A4.X3.Y1.Z1,
A4.X3.Y1.Z2, A4.X3.Y1.Z3, A4.X3.Y1.Z4, A4.X3.Y1.Z5, A4.X3.Y1.Z6,
A4.X3.Y1.Z7, A4.X3.Y1.Z8, A4.X3.Y1.Z9, A4.X3.Y1.Z10,
A4.X3.Y1.Z11, A4.X3.Y1.Z12, A4.X3.Y1.Z13, A4.X3.Y1.Z14,
A4.X3.Y2.Z1, A4.X3.Y2.Z2, A4.X3.Y2.Z3, A4.X3.Y2.Z4, A4.X3.Y2.Z5,
A4.X3.Y2.Z6, A4.X3.Y2.Z7, A4.X3.Y2.Z8, A4.X3.Y2.Z9,
A4.X3.Y2.Z10, A4.X3.Y2.Z11, A4.X3.Y2.Z12, A4.X3.Y2.Z13,
A4.X3.Y2.Z14, A4.X3.Y3.Z1, A4.X3.Y3.Z2, A4.X3.Y3.Z3,
A4.X3.Y3.Z4, A4.X3.Y3.Z5, A4.X3.Y3.Z6, A4.X3.Y3.Z7, A4.X3.Y3.Z8,
A4.X3.Y3.Z9, A4.X3.Y3.Z10, A4.X3.Y3.Z11, A4.X3.Y3.Z12,
A4.X3.Y3.Z13, A4.X3.Y3.Z14, A4.X3.Y4.Z1, A4.X3.Y4.Z2,
A4.X3.Y4.Z3, A4.X3.Y4.Z4, A4.X3.Y4.Z5, A4.X3.Y4.Z6, A4.X3.Y4.Z7,
A4.X3.Y4.Z8, A4.X3.Y4.Z9, A4.X3.Y4.Z10, A4.X3.Y4.Z11,
A4.X3.Y4.Z12, A4.X3.Y4.Z13, A4.X3.Y4.Z14, A4.X3.Y5.Z1,
A4.X3.Y5.Z2, A4.X3.Y5.Z3, A4.X3.Y5.Z4, A4.X3.Y5.Z5, A4.X3.Y5.Z6,
A4.X3.Y5.Z7, A4.X3.Y5.Z8, A4.X3.Y5.Z9, A4.X3.Y5.Z10,
A4.X3.Y5.Z11, A4.X3.Y5.Z12, A4.X3.Y5.Z13, A4.X3.Y5.Z14,
A4.X4.Y1.Z1, A4.X4.Y1.Z2, A4.X4.Y1.Z3, A4.X4.Y1.Z4, A4.X4.Y1.Z5,
A4.X4.Y1.Z6, A4.X4.Y1.Z7, A4.X4.Y1.Z8, A4.X4.Y1.Z9,
A4.X4.Y1.Z10, A4.X4.Y1.Z11, A4.X4.Y1.Z12, A4.X4.Y1.Z13,
A4.X4.Y1.Z14, A4.X4.Y2.Z1, A4.X4.Y2.Z2, A4.X4.Y2.Z3,
A4.X4.Y2.Z4, A4.X4.Y2.Z5, A4.X4.Y2.Z6, A4.X4.Y2.Z7,
A4.X4.Y2.Z8, A4.X4.Y2.Z9, A4.X4.Y2.Z10, A4.X4.Y2.Z11,
A4.X4.Y2.Z12, A4.X4.Y2.Z13, A4.X4.Y2.Z14, A4.X4.Y3.Z1,
A4.X4.Y3.Z2, A4.X4.Y3.Z3, A4.X4.Y3.Z4, A4.X4.Y3.Z5, A4.X4.Y3.Z6,
A4.X4.Y3.Z7, A4.X4.Y3.Z8, A4.X4.Y3.Z9, A4.X4.Y3.Z10,
A4.X4.Y3.Z11, A4.X4.Y3.Z12, A4.X4.Y3.Z13, A4.X4.Y3.Z14,
A4.X4.Y4.Z1, A4.X4.Y4.Z2, A4.X4.Y4.Z3, A4.X4.Y4.Z4, A4.X4.Y4.Z5,
A4.X4.Y4.Z6, A4.X4.Y4.Z7, A4.X4.Y4.Z8, A4.X4.Y4.Z9,
A4.X4.Y4.Z10, A4.X4.Y4.Z11, A4.X4.Y4.Z12, A4.X4.Y4.Z13,
A4.X4.Y4.Z14, A4.X4.Y5.Z1, A4.X4.Y5.Z2, A4.X4.Y5.Z3,
A4.X4.Y5.Z4, A4.X4.Y5.Z5, A4.X4.Y5.Z6, A4.X4.Y5.Z7, A4.X4.Y5.Z8,
A4.X4.Y5.Z9, A4.X4.Y5.Z10, A4.X4.Y5.Z11, A4.X4.Y5.Z12,
A4.X4.Y5.Z13, A4.X4.Y5.Z14, A4.X5.Y1.Z1, A4.X5.Y1.Z2,
A4.X5.Y1.Z3, A4.X5.Y1.Z4, A4.X5.Y1.Z5, A4.X5.Y1.Z6, A4.X5.Y1.Z7,
A4.X5.Y1.Z8, A4.X5.Y1.Z9, A4.X5.Y1.Z10, A4.X5.Y1.Z11,
A4.X5.Y1.Z12, A4.X5.Y1.Z13, A4.X5.Y1.Z14, A4.X5.Y2.Z1,
A4.X5.Y2.Z2, A4.X5.Y2.Z3, A4.X5.Y2.Z4, A4.X5.Y2.Z5, A4.X5.Y2.Z6,
A4.X5.Y2.Z7, A4.X5.Y2.Z8, A4.X5.Y2.Z9, A4.X5.Y2.Z10,
A4.X5.Y2.Z11, A4.X5.Y2.Z12, A4.X5.Y2.Z13, A4.X5.Y2.Z14,
A4.X5.Y3.Z1, A4.X5.Y3.Z2, A4.X5.Y3.Z3, A4.X5.Y3.Z4, A4.X5.Y3.Z5,
A4.X5.Y3.Z6, A4.X5.Y3.Z7, A4.X5.Y3.Z8, A4.X5.Y3.Z9,
A4.X5.Y3.Z10, A4.X5.Y3.Z11, A4.X5.Y3.Z12, A4.X5.Y3.Z13,
A4.X5.Y3.Z14, A4.X5.Y4.Z1, A4.X5.Y4.Z2, A4.X5.Y4.Z3,
A4.X5.Y4.Z4, A4.X5.Y4.Z5, A4.X5.Y4.Z6, A4.X5.Y4.Z7, A4.X5.Y4.Z8,
A4.X5.Y4.Z9, A4.X5.Y4.Z10, A4.X5.Y4.Z11, A4.X5.Y4.Z12,
A4.X5.Y4.Z13, A4.X5.Y4.Z14, A4.X5.Y5.Z1, A4.X5.Y5.Z2,
A4.X5.Y5.Z3, A4.X5.Y5.Z4, A4.X5.Y5.Z5, A4.X5.Y5.Z6, A4.X5.Y5.Z7,
A4.X5.Y5.Z8, A4.X5.Y5.Z9, A4.X5.Y5.Z10, A4.X5.Y5.Z11,
A4.X5.Y5.Z12, A4.X5.Y5.Z13, A4.X5.Y5.Z14, A5.X1.Y1.Z1,
A5.X1.Y1.Z2, A5.X1.Y1.Z3, A5.X1.Y1.Z4, A5.X1.Y1.Z5, A5.X1.Y1.Z6,
A5.X1.Y1.Z7, A5.X1.Y1.Z8, A5.X1.Y1.Z9, A5.X1.Y1.Z10,
A5.X1.Y1.Z11, A5.X1.Y1.Z12, A5.X1.Y1.Z13, A5.X1.Y1.Z14,
A5.X1.Y2.Z1, A5.X1.Y2.Z2, A5.X1.Y2.Z3, A5.X1.Y2.Z4, A5.X1.Y2.Z5,
A5.X1.Y2.Z6, A5.X1.Y2.Z7, A5.X1.Y2.Z8, A5.X1.Y2.Z9,
A5.X1.Y2.Z10, A5.X1.Y2.Z11, A5.X1.Y2.Z12, A5.X1.Y2.Z13,
A5.X1.Y2.Z14, A5.X1.Y3.Z1, A5.X1.Y3.Z2, A5.X1.Y3.Z3,
A5.X1.Y3.Z4, A5.X1.Y3.Z5, A5.X1.Y3.Z6, A5.X1.Y3.Z7, A5.X1.Y3.Z8,
A5.X1.Y3.Z9, A5.X1.Y3.Z10, A5.X1.Y3.Z11, A5.X1.Y3.Z12,

TABLE 11-continued

A5.X1.Y3.Z13, A5.X1.Y3.Z14, A5.X1.Y4.Z1, A5.X1.Y4.Z2,
A5.X1.Y4.Z3, A5.X1.Y4.Z4, A5.X1.Y4.Z5, A5.X1.Y4.Z6, A5.X1.Y4.Z7,
A5.X1.Y4.Z8, A5.X1.Y4.Z9, A5.X1.Y4.Z10, A5.X1.Y4.Z11,
A5.X1.Y4.Z12, A5.X1.Y4.Z13, A5.X1.Y4.Z14, A5.X1.Y5.Z1,
A5.X1.Y5.Z2, A5.X1.Y5.Z3, A5.X1.Y5.Z4, A5.X1.Y5.Z5, A5.X1.Y5.Z6,
A5.X1.Y5.Z7, A5.X1.Y5.Z8, A5.X1.Y5.Z9, A5.X1.Y5.Z10,
A5.X1.Y5.Z11, A5.X1.Y5.Z12, A5.X1.Y5.Z13, A5.X1.Y5.Z14,
A5.X2.Y1.Z1, A5.X2.Y1.Z2, A5.X2.Y1.Z3, A5.X2.Y1.Z4, A5.X2.Y1.Z5,
A5.X2.Y1.Z6, A5.X2.Y1.Z7, A5.X2.Y1.Z8, A5.X2.Y1.Z9,
A5.X2.Y1.Z10, A5.X2.Y1.Z11, A5.X2.Y1.Z12, A5.X2.Y1.Z13,
A5.X2.Y1.Z14, A5.X2.Y2.Z1, A5.X2.Y2.Z2, A5.X2.Y2.Z3,
A5.X2.Y2.Z4, A5.X2.Y2.Z5, A5.X2.Y2.Z6, A5.X2.Y2.Z7, A5.X2.Y2.Z8,
A5.X2.Y2.Z9, A5.X2.Y2.Z10, A5.X2.Y2.Z11, A5.X2.Y2.Z12,
A5.X2.Y2.Z13, A5.X2.Y2.Z14, A5.X2.Y3.Z1, A5.X2.Y3.Z2,
A5.X2.Y3.Z3, A5.X2.Y3.Z4, A5.X2.Y3.Z5, A5.X2.Y3.Z6, A5.X2.Y3.Z7,
A5.X2.Y3.Z8, A5.X2.Y3.Z9, A5.X2.Y3.Z10, A5.X2.Y3.Z11,
A5.X2.Y3.Z12, A5.X2.Y3.Z13, A5.X2.Y3.Z14, A5.X2.Y4.Z1,
A5.X2.Y4.Z2, A5.X2.Y4.Z3, A5.X2.Y4.Z4, A5.X2.Y4.Z5, A5.X2.Y4.Z6,
A5.X2.Y4.Z7, A5.X2.Y4.Z8, A5.X2.Y4.Z9, A5.X2.Y4.Z10,
A5.X2.Y4.Z11, A5.X2.Y4.Z12, A5.X2.Y4.Z13, A5.X2.Y4.Z14,
A5.X2.Y5.Z1, A5.X2.Y5.Z2, A5.X2.Y5.Z3, A5.X2.Y5.Z4, A5.X2.Y5.Z5,
A5.X2.Y5.Z6, A5.X2.Y5.Z7, A5.X2.Y5.Z8, A5.X2.Y5.Z9,
A5.X2.Y5.Z10, A5.X2.Y5.Z11, A5.X2.Y5.Z12, A5.X2.Y5.Z13,
A5.X2.Y5.Z14, A5.X3.Y1.Z1, A5.X3.Y1.Z2, A5.X3.Y1.Z3,
A5.X3.Y1.Z4, A5.X3.Y1.Z5, A5.X3.Y1.Z6, A5.X3.Y1.Z7, A5.X3.Y1.Z8,
A5.X3.Y1.Z9, A5.X3.Y1.Z10, A5.X3.Y1.Z11, A5.X3.Y1.Z12,
A5.X3.Y1.Z13, A5.X3.Y1.Z14, A5.X3.Y2.Z1, A5.X3.Y2.Z2,
A5.X3.Y2.Z3, A5.X3.Y2.Z4, A5.X3.Y2.Z5, A5.X3.Y2.Z6, A5.X3.Y2.Z7,
A5.X3.Y2.Z8, A5.X3.Y2.Z9, A5.X3.Y2.Z10, A5.X3.Y2.Z11,
A5.X3.Y2.Z12, A5.X3.Y2.Z13, A5.X3.Y2.Z14, A5.X3.Y3.Z1,
A5.X3.Y3.Z2, A5.X3.Y3.Z3, A5.X3.Y3.Z4, A5.X3.Y3.Z5, A5.X3.Y3.Z6,
A5.X3.Y3.Z7, A5.X3.Y3.Z8, A5.X3.Y3.Z9, A5.X3.Y3.Z10,
A5.X3.Y3.Z11, A5.X3.Y3.Z12, A5.X3.Y3.Z13, A5.X3.Y3.Z14,
A5.X3.Y4.Z1, A5.X3.Y4.Z2, A5.X3.Y4.Z3, A5.X3.Y4.Z4, A5.X3.Y4.Z5,
A5.X3.Y4.Z6, A5.X3.Y4.Z7, A5.X3.Y4.Z8, A5.X3.Y4.Z9,
A5.X3.Y4.Z10, A5.X3.Y4.Z11, A5.X3.Y4.Z12, A5.X3.Y4.Z13,
A5.X3.Y4.Z14, A5.X3.Y5.Z1, A5.X3.Y5.Z2, A5.X3.Y5.Z3,
A5.X3.Y5.Z4, A5.X3.Y5.Z5, A5.X3.Y5.Z6, A5.X3.Y5.Z7, A5.X3.Y5.Z8,
A5.X3.Y5.Z9, A5.X3.Y5.Z10, A5.X3.Y5.Z11, A5.X3.Y5.Z12,
A5.X3.Y5.Z13, A5.X3.Y5.Z14, A5.X4.Y1.Z1, A5.X4.Y1.Z2,
A5.X4.Y1.Z3, A5.X4.Y1.Z4, A5.X4.Y1.Z5, A5.X4.Y1.Z6, A5.X4.Y1.Z7,
A5.X4.Y1.Z8, A5.X4.Y1.Z9, A5.X4.Y1.Z10, A5.X4.Y1.Z11,
A5.X4.Y1.Z12, A5.X4.Y1.Z13, A5.X4.Y1.Z14, A5.X4.Y2.Z1,
A5.X4.Y2.Z2, A5.X4.Y2.Z3, A5.X4.Y2.Z4, A5.X4.Y2.Z5, A5.X4.Y2.Z6,
A5.X4.Y2.Z7, A5.X4.Y2.Z8, A5.X4.Y2.Z9, A5.X4.Y2.Z10,
A5.X4.Y2.Z11, A5.X4.Y2.Z12, A5.X4.Y2.Z13, A5.X4.Y2.Z14,
A5.X4.Y3.Z1, A5.X4.Y3.Z2, A5.X4.Y3.Z3, A5.X4.Y3.Z4, A5.X4.Y3.Z5,
A5.X4.Y3.Z6, A5.X4.Y3.Z7, A5.X4.Y3.Z8, A5.X4.Y3.Z9,
A5.X4.Y3.Z10, A5.X4.Y3.Z11, A5.X4.Y3.Z12, A5.X4.Y3.Z13,
A5.X4.Y3.Z14, A5.X4.Y4.Z1, A5.X4.Y4.Z2, A5.X4.Y4.Z3,
A5.X4.Y4.Z4, A5.X4.Y4.Z5, A5.X4.Y4.Z6, A5.X4.Y4.Z7, A5.X4.Y4.Z8,
A5.X4.Y4.Z9, A5.X4.Y4.Z10, A5.X4.Y4.Z11, A5.X4.Y4.Z12,
A5.X4.Y4.Z13, A5.X4.Y4.Z14, A5.X4.Y5.Z1, A5.X4.Y5.Z2,
A5.X4.Y5.Z3, A5.X4.Y5.Z4, A5.X4.Y5.Z5, A5.X4.Y5.Z6, A5.X4.Y5.Z7,
A5.X4.Y5.Z8, A5.X4.Y5.Z9, A5.X4.Y5.Z10, A5.X4.Y5.Z11,
A5.X4.Y5.Z12, A5.X4.Y5.Z13, A5.X4.Y5.Z14, A5.X5.Y1.Z1,
A5.X5.Y1.Z2, A5.X5.Y1.Z3, A5.X5.Y1.Z4, A5.X5.Y1.Z5, A5.X5.Y1.Z6,
A5.X5.Y1.Z7, A5.X5.Y1.Z8, A5.X5.Y1.Z9, A5.X5.Y1.Z10,
A5.X5.Y1.Z11, A5.X5.Y1.Z12, A5.X5.Y1.Z13, A5.X5.Y1.Z14,
A5.X5.Y2.Z1, A5.X5.Y2.Z2, A5.X5.Y2.Z3, A5.X5.Y2.Z4, A5.X5.Y2.Z5,
A5.X5.Y2.Z6, A5.X5.Y2.Z7, A5.X5.Y2.Z8, A5.X5.Y2.Z9,
A5.X5.Y2.Z10, A5.X5.Y2.Z11, A5.X5.Y2.Z12, A5.X5.Y2.Z13,
A5.X5.Y2.Z14, A5.X5.Y3.Z1, A5.X5.Y3.Z2, A5.X5.Y3.Z3,
A5.X5.Y3.Z4, A5.X5.Y3.Z5, A5.X5.Y3.Z6, A5.X5.Y3.Z7, A5.X5.Y3.Z8,
A5.X5.Y3.Z9, A5.X5.Y3.Z10, A5.X5.Y3.Z11, A5.X5.Y3.Z12,
A5.X5.Y3.Z13, A5.X5.Y3.Z14, A5.X5.Y4.Z1, A5.X5.Y4.Z2,
A5.X5.Y4.Z3, A5.X5.Y4.Z4, A5.X5.Y4.Z5, A5.X5.Y4.Z6, A5.X5.Y4.Z7,
A5.X5.Y4.Z8, A5.X5.Y4.Z9, A5.X5.Y4.Z10, A5.X5.Y4.Z11,
A5.X5.Y4.Z12, A5.X5.Y4.Z13, A5.X5.Y4.Z14, A5.X5.Y5.Z1,
A5.X5.Y5.Z2, A5.X5.Y5.Z3, A5.X5.Y5.Z4, A5.X5.Y5.Z5, A5.X5.Y5.Z6,
A5.X5.Y5.Z7, A5.X5.Y5.Z8, A5.X5.Y5.Z9, A5.X5.Y5.Z10,
A5.X5.Y5.Z11, A5.X5.Y5.Z12, A5.X5.Y5.Z13, A5.X5.Y5.Z14

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In yet another embodiment, the present application discloses pharmaceutical compositions comprising a compound of Formula I or II, or a pharmaceutically acceptable salt, solvate, and/or ester thereof, and a pharmaceutically acceptable carrier or excipient.

In yet another embodiment, the present application discloses pharmaceutical compositions comprising a compound of Formula I or II, or a pharmaceutically acceptable salt, solvate, and/or ester thereof, in combination with at least one additional active agent, and a pharmaceutically acceptable carrier or excipient.

In yet another embodiment, the present application discloses pharmaceutical compositions comprising a compound of Formula I or II, or a pharmaceutically acceptable salt, solvate, and/or ester thereof, in combination with at least one additional active agent, and a pharmaceutically acceptable carrier or excipient, wherein the additional active agent is selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta;

Examples of the ribavirin analogs include, but are not limited to rebetol, copegus, and viramidine (taribavirin);

Examples of the NS5b polymerase inhibitors include, but are not limited to NM-283, valopicitabine, R1626, PSI-6130 (R1656), HCV-796, BILB 1941, XTL-2125, MK-0608, NM-107, R7128 (R4048), VCH-759, PF-868554, and GSK625433;

Examples of the HCV NS3 protease inhibitors include, but are not limited to SCH-503034 (SCH-7), VX-950 (telaprevir), BILN-2065, BMS-605339, and ITMN-191;

Examples of the alpha-glucosidase 1 inhibitors include, but are not limited to MX-3253 (celgosivir) and UT-231B;

Examples of the hepatoprotectants include, but are not limited to IDN-6556, ME 3738, LB-84451, and MitoQ;

Examples of the non-nucleoside inhibitors of HCV include, but are not limited to benzimidazole derivatives, benzo-1,2,4-thiadiazine derivatives, phenylalanine derivatives, GS-9190, A-831, and A-689; and Examples of the other drugs for treating HCV include, but are not limited to zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides a combination pharmaceutical agent comprising:

a) a first pharmaceutical composition comprising a compound of Formula I or II, or a pharmaceutically acceptable salt, solvate, or ester thereof; and b) a second pharmaceutical composition comprising at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention are used in combination with other active therapeutic ingredients or agents. Combinations of the compounds of Formula I or II and additional active agents may be selected to treat patients with a viral infection, e.g., HBV, HCV, or HIV infection.

Preferably, the other active therapeutic ingredients or agents are interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

Combinations of the compounds of Formula I or II are typically selected based on the condition to be treated, cross-reactivities of ingredients and pharmaco-properties of the combination. For example, when treating an infection (e.g., HCV), the compositions of the invention are combined with other active agents (such as those described herein).

Suitable active therapeutic agents or ingredients which can be combined with the compounds of formula I or II can include interferons, e.g., pegylated rIFN-apha 2b, pegylated rIFN-alpha 2a, rIFN-alpha 2b, rIFN-alpha 2a, consensus IFN alpha, Infergen® (Three Rivers Pharmaceuticals, LLC brand of interferon alfacon-1), Feron® (Schering-Plough brand of interferon-β), Roferon® (Roche brand of interferon α2), IntermaxAlpha® (LG Life Sciences brand of interferon α2), r-INF-beta, Infergen®+Actimmmune® (InterMune brand of interferon γ), IFN-omega with DUROS® (Durect Corporation brand of pharmaceutical delivery system), -Albuferon® (Novartis/Human Genome Sciences brand of interferon α human albumin fusion protein); Locteron® (Biolex Therapeutics brand of controlled release interferon alpha 2b), Rebif® (Merck Serono/Pfizer brand of interferon β-1a), oral interferon alpha, IFN-alpha 2b XL® (Flamel Technologies brand of controlled delivery IFN alpha-2b), AVI-005, PEG-Infergen® (Three Rivers Pharmaceuticals, LLC brand of interferon alfacon-1), and pegylated IFN-beta; ribavirin analogs, e.g. Rebetol® (Schering brand of ribavirin), Copegus® (Genentech brand of ribavirin), and viramidine (taribavirin); NS5b polymerase inhibitors, e.g. NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-0.950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application discloses pharmaceutical compositions comprising a compound of the present invention, or a pharmaceutically acceptable salt, solvate, and/or ester thereof, in combination with at least one additional active agent, and a pharmaceutically acceptable carrier or excipient.

According to the present invention, the active agent used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In another embodiment, the present application provides pharmaceutical compositions comprising a compound of the present invention, or a pharmaceutically acceptable salt, solvate, and/or ester thereof, in combination with at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides a combination pharmaceutical agent comprising:
a) a first pharmaceutical composition comprising a compound of the present invention, or a pharmaceutically acceptable salt, solvate, or ester thereof; and
b) a second pharmaceutical composition comprising at least one additional active agent selected from the group consisting of interferons, ribavirin analogs, HCV-NS3 protease inhibitors, alpha-glucosidase 1 inhibitors, hepatoprotectants, non-nucleoside inhibitors of HCV, and other drugs for treating HCV, or mixtures thereof.

More specifically, one or more compounds of the present invention may be combined with one or more compounds selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

It is also possible to combine any compound of the invention with one or more other active agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active agents generally refers to simultaneous or sequential administration of a compound of the invention and one or more other active agents, such that therapeutically effective amounts of the compound of the invention and one or more other active agents are both present in the body of the patient.

Co-administration includes administration of unit dosages of the compounds of the invention before or after administration of unit dosages of one or more other active agents, for example, administration of the compounds of the invention within seconds, minutes, or hours of the administration of one or more other active agents. For example, a unit dose of a compound of the invention can be administered first, followed within seconds or minutes by administration of a unit dose of one or more other active agents. Alternatively, a unit dose of one or more other active agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active agents. In other cases, it may be desirable to administer a unit dose of one or more other active agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In still yet another embodiment, the present application provides for methods of inhibiting HCV polymerase in a cell, comprising: contacting a cell infected with HCV with an effective amount of a compound of Formula I or II, or a pharmaceutically acceptable salt, solvate, and/or ester thereof, whereby HCV polymerase is inhibited.

In still yet another embodiment, the present application provides for methods of inhibiting HCV polymerase in a cell, comprising: contacting a cell infected with HCV with an effective amount of a compound of Formula I or II, or a pharmaceutically acceptable salt, solvate, and/or ester thereof, and at least one additional active agent, whereby HCV polymerase is inhibited.

In still yet another embodiment, the present application provides for methods of inhibiting HCV polymerase in a cell, comprising: contacting a cell infected with HCV with an effective amount of a compound of Formula I or II, or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV.

In still yet another embodiment, the present application provides for methods of treating a viral infection in a patient, comprising: administering to the patient a therapeutically effective amount of a compound of Formula I or II, or a pharmaceutically acceptable salt, solvate, and/or ester thereof.

In still yet another embodiment, the present application provides for methods of treating a viral infection in a patient, comprising: administering to the patient a therapeutically effective amount of a compound of Formula I or II, or a pharmaceutically acceptable salt, solvate, and/or ester thereof, and at least one additional active agent.

In still yet another embodiment, the present application provides for methods of treating HCV in a patient, comprising: administering to the patient a therapeutically effective amount of a compound of Formula I or II, or a pharmaceutically acceptable salt, solvate, and/or ester thereof.

In still yet another embodiment, the present application provides for methods of treating HCV in a patient, comprising: administering to the patient a therapeutically effective amount of a compound of Formula I or II, or a pharmaceutically acceptable salt, solvate, and/or ester thereof, and at least one additional active agent, whereby HCV polymerase is inhibited.

In still yet another embodiment, the present application provides for methods of treating HCV in a patient, comprising: administering to the patient a therapeutically effective amount of a compound of Formula I or II, or a pharmaceutically acceptable salt, solvate, and/or ester thereof, and at least one additional active agent selected from the group consisting of interferons, ribavirin analogs, HCV NS3 protease inhibitors, alpha-glucosidase 1 inhibitors, hepatoprotectants, non-nucleoside inhibitors of HCV, and other drugs for treating HCV, or mixtures thereof.

In still yet another embodiment, the present application provides for the use of a compound of the present invention, or a pharmaceutically acceptable salt, solvate, and/or ester thereof, for the preparation of a medicament for treating a viral infection, e.g., an HBV/HCV infection.

In yet another embodiment, the present application provides a method for treating or preventing a viral infection comprising co-administering, to a patient in need thereof, a therapeutically effective amount of at least one compound of Formula I or II and at least one additional active agent selected from the group consisting of interferons, e.g., pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen+actimmune, IFN-omega with DUROS, albuferon, locteron, Albuferon, Rebif, Oral interferon alpha, IFNalpha-2b XL, AVI-005, PEG-Infergen, and Pegylated IFN-beta; ribavirin analogs, e.g., rebetol, copegus, and viramidine (taribavirin); NS5b polymerase inhibitors, e.g., NM-283, valopicitabine, R1626, PSI-6130 (R1656), HCV-796, BILB 1941, XTL-2125, MK-0608, NM-107, R7128 (R4048), VCH-759, PF-868554, and GSK625433; HCV NS3 protease inhibitors, e.g., SCH-503034 (SCH-7), VX-950 (telaprevir), BILN-2065, BMS-605339, and ITMN-191; alpha-glucosidase 1 inhibitors, e.g., MX-3253 (celgosivir) and UT-231B; hepatoprotectants, e.g., IDN-6556, ME 3738, LB-84451, and MitoQ; non-nucleoside inhibitors of HCV, e.g., benzimidazole derivatives, benzo-1,2,4-thiadiazine derivatives, phenylalanine derivatives, GS-9190, A-831, and A-689; and other drugs for treating HCV, e.g., zadaxin, nitazoxanide (alinea), BIVN-401 (virostat), PYN-17 (altirex), KPE02003002, actilon (CPG-10101), KRN-7000, civacir, GI-5005, ANA-975, XTL-6865, ANA 971, NOV-205, tarvacin, EHC-18, NIM811, DEBIO-025, VGX-410C, EMZ-702, AVI 4065, Bavituximab, Oglufanide, and VX-497 (merimepodib).

In yet another embodiment, the present application provides a method for antagonizing toll-like receptor 7, comprising contacting a cell having a toll-like receptor 7 with an effective amount of a compound of claim 1, or a pharmaceutically acceptable salt, solvate, and/or ester thereof.

EXAMPLES

Example A

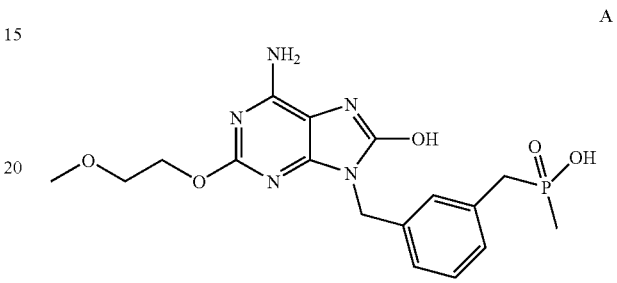

Scheme 1

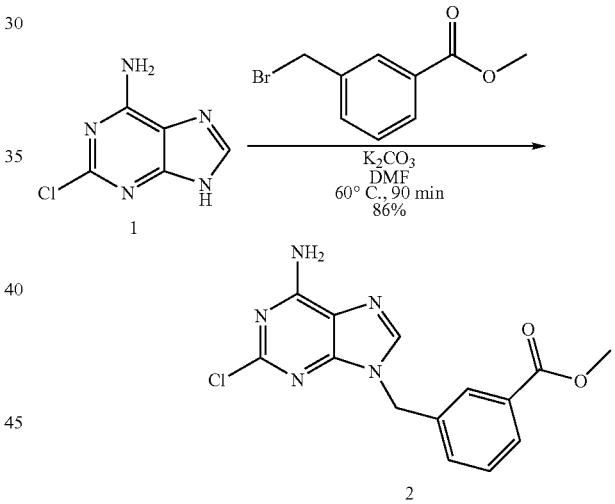

Synthesis of Methyl 3-((6-amino-2-chloro-9H-purin-9-yl)methyl)benzoate (2)

To a solution of 2-chloro-6-aminopurine (1) (10 g, 58.97 mmol) and potassium carbonate (10 g, 744 mmol) in DMF (100 mL) was added methyl 3-(bromomethyl)benzoate (13.5 g, 58.93 mmol). The reaction mixture was heated to 60° C. for 90 minutes at which time the reaction was quenched by adding water. The quenched reaction mixture was extracted with ethyl acetate (3×50 mL) giving 16 g (86%) of Compound (2) as a white solid, which was used in the next step without further purification. $^1$H NMR (300 MHz, DMSO) δ 3.83 (s, 3H), 5.42 (s, 2H), 7.53 (m, 2H), 7.89 (m, 2H), 8.29 (s, 1H). LCMS: m/z for $C_{14}H_{12}ClN_5O_2^+$+H observed 318.1 at 1.99 minutes of a 3.5 minute run, gradient 5-95% $CH_3CN$ in $H_2O$ (C18 column).

Scheme 2

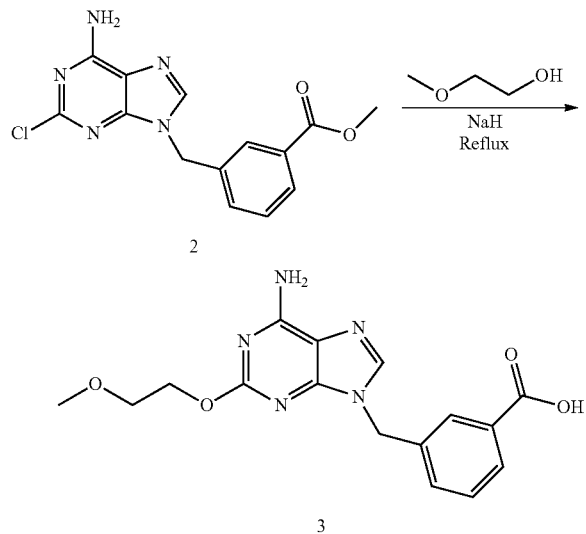

Synthesis of Methyl 3-((6-amino-2-chloro-9H-purin-9-yl)methyl)benzoate (3)

A suspension of Compound (2) (10.3 g, 31.64 mmol) in 2-methoxyethanol (50 mL) was treated with sodium hydride (759 mg, 31.64 mmol) and heated to reflux for 90 minutes. The remaining hydride was quenched with 1N HCl, the solvent removed by rotary evaporation to give 13.69 g (126%) of Compound (3) as a white solid, which was used in the next step without further purification. $^1$H NMR (300 MHz, DMSO) δ 3.26 (s, 3H), 3.59 (t, J=5.1, 9.6 Hz, 2H), 4.32 (t, J=4.5, 9.3 Hz, 2H), 7.46 (t, J=5.4, 9.5 Hz, 1H), 7.56 (d, J=9.3 Hz, 1H), 7.85 (d, J=9.3 Hz, 1H), 8.09 (s, 1H). LCMS: m/z for $C_{17}H_{19}N_5O_4^+$+H observed 358.1 at 3.62 minutes of a 6 minute run, gradient 5-95% $CH_3CN$ in $H_2O$. LCMS: m/z for $C_{16}H_{17}N_5O_4^+$+H observed 344.1 at 1.70 minutes of a 3.5 minute run, gradient 5-95% $CH_3CN$ in $H_2O$ (C18 column).

Scheme 3

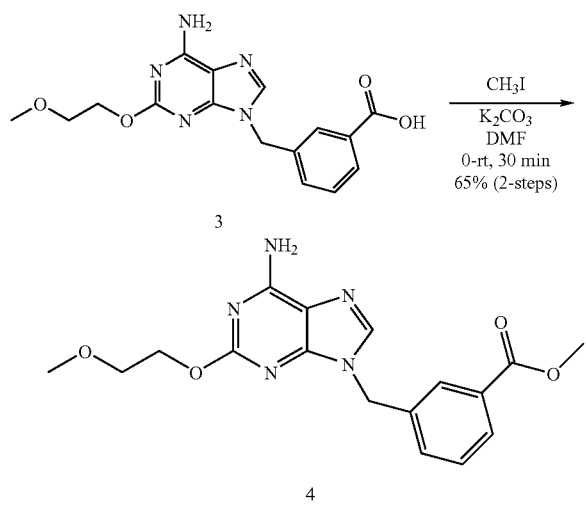

Synthesis of Methyl 3-((6-amino-2-(2-methoxyethoxy)-9H-purin-9-yl)methyl)benzoate (4)

A solution of Compound (3) (13.69 g) and potassium carbonate (8.75 g, 63.28 mmol) in DMF ("dimethylformamide") (20 mL) was cooled to 0° C. Iodomethane (6.74 g, 47.46 mmol) was added to the solution and the mixture was allowed to warm to room temperature. After 30 minutes, the reaction was complete and was quenched with acetic acid. The quenched reaction mixture was extracted with ethyl acetate to give Compound (4) (7.36 g, 65% over two steps). $^1$H NMR (300 MHz, CDCl$_3$) δ 3.43 (s, 3H), 3.77 (t, J=5.4, 10.2 Hz, 2H), 3.92 (s, 3H), 4.51 (t, J=4.8, 9.9 Hz, 2H), 5.32 (s, 2H), 7.45 (m, 3H), 7.65 (s, 1H), 8.03 (s, 1H). LCMS: m/z for $C_{17}H_{19}N_5O_4^+$+H observed 358.1 at 3.62 minutes of a 6 minute run, gradient 5-95% $CH_3CN$ in $H_2O$. LCMS: m/z for $C_{17}H_{19}N_5O_4^+$+H observed 358.1 at 1.93 minutes of a 3.5 minute run, gradient 5-95% $CH_3CN$ in $H_2O$ (C18 column).

Scheme 4

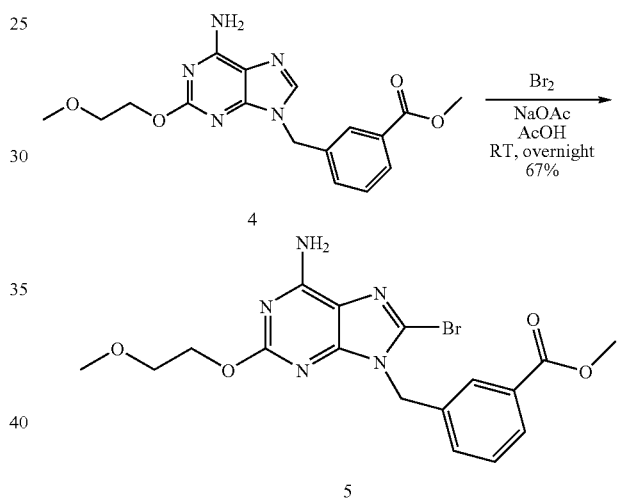

Synthesis of Methyl 3-((6-amino-8-bromo-2-(2-methoxyethoxy)-9H-purin-9-yl)methyl)benzoate (5)

A solution of Compound (4) (4.09 g, 11.45 mmol) and sodium acetate (14.26 g, 171.84 mmol) in acetic acid (50 mL) was cooled to 0° C. in an ice bath. Bromine (23.8 g, 148.93 mmol) was added dropwise by syringe. The reaction mixture was allowed to warm to room temperature and stirred overnight (16 hr), and subsequently quenched with saturated sodium sulfite solution. The quenched reaction mixture was extracted with dichloromethane (3×50 mL), dried over sodium sulfate and solvent evaporated to give Compound (5) as a yellow solid (3.35 g, 67% yield). $^1$H NMR (300 MHz, CDCl$_3$) δ 3.44 (s, 3H), 3.77 (t, J=5.1, 9.9 Hz, 2H), 3.92 (s, 3H), 4.52 (t, J=4.8, 9.9 Hz, 2H), 5.35 (s, 2H), 7.41 (t, J=7.5, 13.5, Hz, 1H), 7.49 (d, J=7.8 Hz, 1H), 7.98 (d, J=7.8 Hz, 1H), 8.09 (s, 1H). LCMS: m/z for $C_{17}H_{18}BrN_5O_4^+$+H observed 437.0 and 438.0 at 3.62 minutes of a 6 minute run, gradient 5-95% $CH_3CN$ in $H_2O$ (C18 column).

Scheme 5

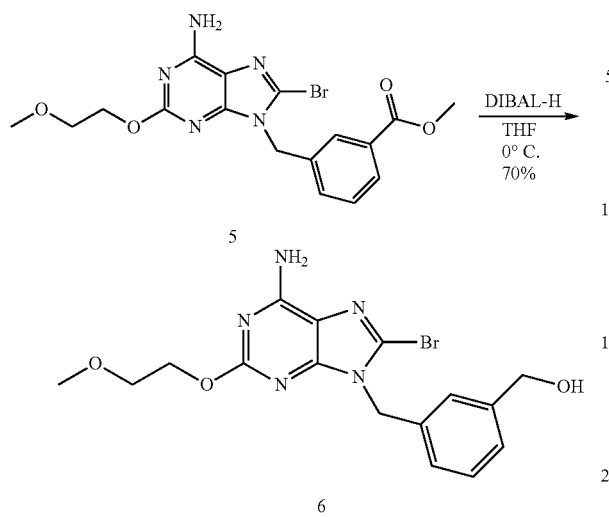

Scheme 6

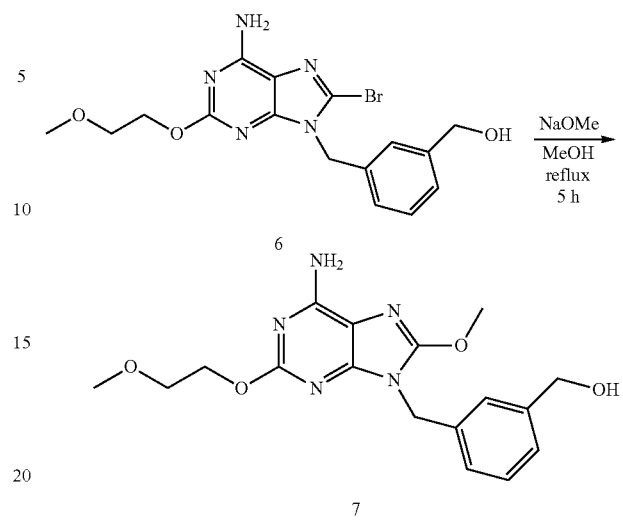

Synthesis of (3-((6-amino-8-bromo-2-(2-methoxyethoxy)-9H-purin-9-yl)methyl)phenyl)methanol (6)

To a solution of Compound (5) (3.35 g, 7.67 mmol) in THF ("tetrahydrofuran") (20 mL) cooled to 0° C. was added a 1 M solution of DIBAL-H (34.5 mL, 34.52 mmol) in toluene. The reaction temperature was maintained at 0° C. for 2 h but little progress in the reaction was observed. Additional equivalents (7.6 mL) of DIBAL-H were added at 2 and 4 hours respectively. The DIBAL-H reagent was quenched with 1N HCl, and the quenched reaction mixture was extracted with dichloromethane (3×50 mL) and dried over $Na_2SO_3$. Evaporation of the solvent gave 38 g (70%) of Compound (6) as a yellow solid. $^1$H NMR (300 MHz, $CDCl_3$) δ 3.42 (s, 3H), 3.74 (t, J=5.1, 9.9 Hz, 2H), 4.49 (t, J=4.8, 10.2 Hz, 2H), 4.67 (s, 2H), 5.29 (s, 2H), 7.29 (m, 3H), 7.39 (s, 1H). LCMS: m/z for $C_{16}H_{18}BrN_5O_3^+$+H observed 408.1 and 410.0 at 1.85 minutes of a 3.5 minute run, eluting 5-95% $CH_3CN$ in $H_2O$ (C18 column).

Synthesis of (3-((6-amino-8-methoxy-2-(2-methoxyethoxy)-9H-purin-9-yl)methyl)phenyl)methanol (7)

To a solution of Compound (6) (1.53 g, 3.74 mmol) in methanol (40 mL) was slowly added sodium methoxide (4.04 g, 74.85 mmol). The reaction mixture was heated to 70° C. for 5 hours, at which time Dowex ($H^+$) resin was added to quench any remaining methoxide. The resin was filtered off and the solvent was evaporated. Salts were removed by partition between water and dichloromethane, and the combined organic layers were dried over magnesium sulfate and evaporated to dryness giving 1.03 g (76%) of Compound (7) as a white solid, which was used in the next step without further purification. $^1$H NMR (300 MHz, $CDCl_3$) δ 3.39 (s, 3H), 3.73 (t, J=4.8, 9.6 Hz, 2H), 4.12 (s, 3H), 4.45 (t, J=4.5, 9.3 Hz, 2H), 4.56 (s, 2H), 5.12 (s, 2H), 7.28 (m, 4H). LCMS: m/z for $C_{17}H_{21}N_5O_4^+$+H observed 360.1 at 1.87 minutes of a 3.5 minute run, eluting 5-95% $CH_3CN$ in $H_2O$ (C18 column).

Scheme 7

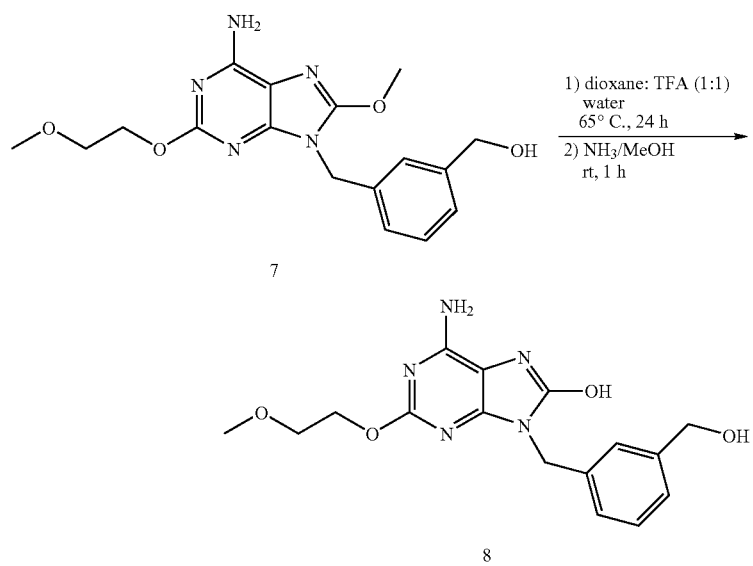

Synthesis of 9-(3-(hydroxymethyl)benzyl)-6-amino-2-(2-methoxyethoxy)-9H-purin-8-ol (8)

A solution of Compound (7) (371.2 mg, 1.03 mmol) in a 1:1 p-dioxane:TFA ("trifluoroacetic acid") mixture, and a catalytic amount of water was heated to 65° C. for 24 hrs. Evaporation of the solvent showed that a trifluoroacetyl adduct had formed. The adduct was converted to the desired diol by stirring in a saturated ammonia in methanol solution. Evaporation of the methanol gave Compound (8) (757.3 mg, 213%) as a white solid. (The large excess in recovery is most likely due to the presence of salts remaining in the mixture.) $^1$H NMR (300 MHz, DMSO) δ 3.26 (s, 3H), 3.57 (t, J=4.8, 9.3 Hz), 4.25 (t, J=4.8, 9.6 Hz, 2H), 4.43 (d, J=5.1, 2H), 7.32 (m, 4H). LCMS: m/z for $C_{16}H_{19}N_5O_4^+$+H observed 346.1 at 1.69 minutes of a 3.5 minute run, gradient 5-95% $CH_3CN$ in $H_2O$ (C18 column).

Synthesis of 9-(3-(bromomethyl)benzyl)-6-amino-2-(2-methoxyethoxy)-9H-purin-8-ol (9)

To a solution of Compound (8) (51.4 mg, 0.148 mmol) in THF (2 mL) was added phosphorus tribromide (0.2 mL). The reaction mixture was allowed to stir at room temperature for 5 minutes then quenched with saturated sodium bicarbonate solution and extracted with dichloromethane. The combined organic layers were dried over $NaSO_3$ and evaporated to give Compound (9) as a white solid. The crude mixture was used in the next step without further purification. The identity of the product was verified by LCMS. LCMS: m/z for $C_{16}H_{19}N_5O_4^+$+H observed 346.1 at 1.69 minutes of a 3.5 minute run, gradient 5-95% $CH_3CN$ in $H_2O$. LCMS: m/z for $C_{16}H_{18}BrN_5O_3^+$+H observed 408.0 and 410.1 at 2.03 minutes of a 3.5 minute run, gradient 5-95% $CH_3CN$ in $H_2O$ (C18 column).

Scheme 9

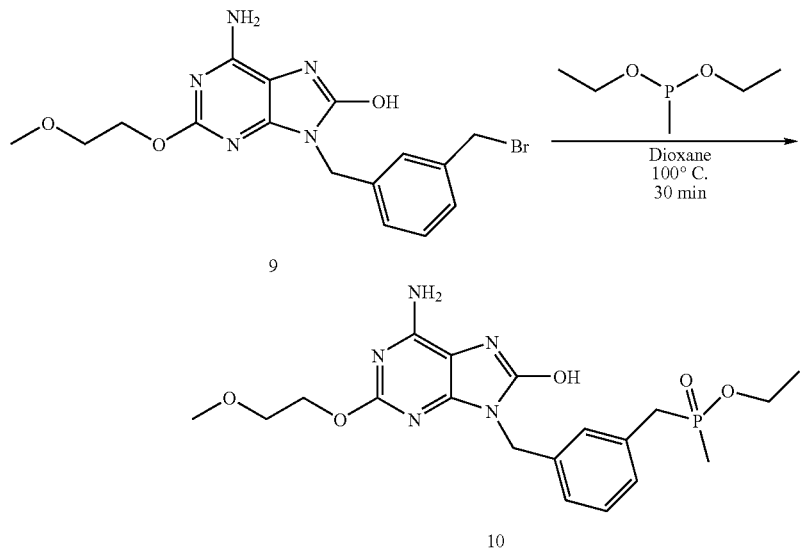

Synthesis of Ethyl (3-((6-amino-8-hydroxy-2-(2-methoxyethoxy)-9H-purin-9-yl)methyl)phenyl)methyl(methyl)phosphinate (10)

A solution of Compound (9) (0.148 mmol) and diethylmethylphosphonite (1 mL) in dioxane (2.5 mL) was placed in an oil bath preheated to 100° C. for 30 minutes. The progress of the reaction was monitored by LCMS at 10 minute intervals. Once the reaction was observed to be complete, all of the solvent and phosphonite reagent were evaporated under high vacuum, and the remaining product was purified by HPLC. Lyophylization of the crude product gave Compound (10) (8.9 mg, 14%) as a white powder. $^1$H NMR (300 MHz, $CD_3OD$) δ 1.22 (t, J=6.9, 14.1 Hz, 2H), 1.36 (d, J=14.1 Hz, 3H), 3.20 (d, J=17.7 Hz, 2H), 3.38 (s, 3H), 3.69 (t, J=4.8, 9.6 Hz, 2H), 3.95 (m, 3H), 4.39 (t, J=4.8, 9.6 Hz, 2H), 4.97 (s, 2H), 7.24 (s, 1H), 7.31 (m, 3H). LCMS: m/z for $C_{19}H_{26}N_5O_5P^+$+H observed 436.1 at 1.29 minutes of a 3.5 minute run, gradient 5-95% $CH_3CN$ in $H_2O$ (C18 column).

Scheme 8

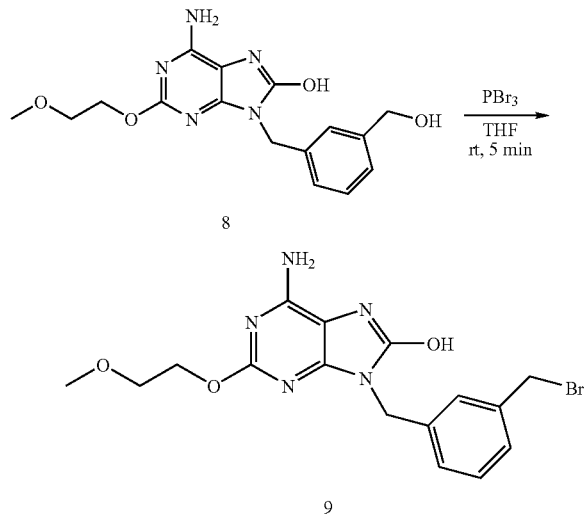

Scheme 10

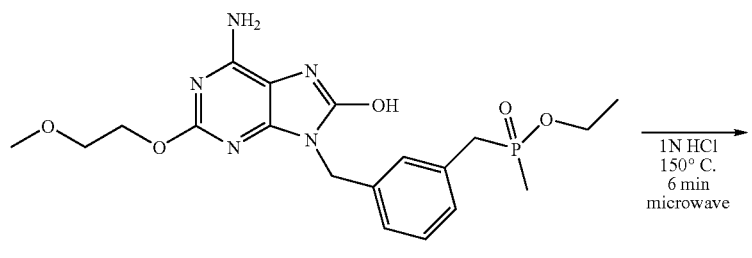

10

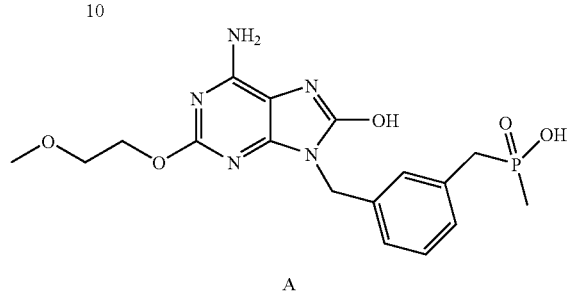

A

Synthesis of (3-(((6-amino-8-hydroxy-2-(2-methoxyethoxy)-9H-purin-9-yl)methyl)phenyl)methyl(methyl)phosphinic acid (Example A)

A solution of Compound (10) (8.9 mg, 0.02 mmol) in 1N HCl (1 mL) was heated to 150° C. in a microwave for 2 minute periods. After 6 minutes of heating the reaction, was complete as determined by LCMS. The solvent was evaporated and the product purified by Prep-HPLC on a 50×21 mm C18 column (mobile phase gradient 2-40% $CH_3CN$ in $H_2O$) giving Example A (1.1 mg) as a white solid. $^1$H NMR (300 MHz, $CD_3OD$) δ 1.33 (d, J=14.1 Hz, 3H), 3.13 (d, J=17.7 Hz, 2H), 3.39 (s, 3H), 3.75 (m, 2H), 4.65 (m, 2H), 5.05 (s, 2H), 7.31 (m, 4H). LCMS: m/z for $C_{17}H_{22}N_5O_5P^+$+H observed 408.1 at 1.13 minutes of a 3.5 minute run, gradient 5-95% $CH_3CN$ in $H_2O$ (C18 column).

Example B

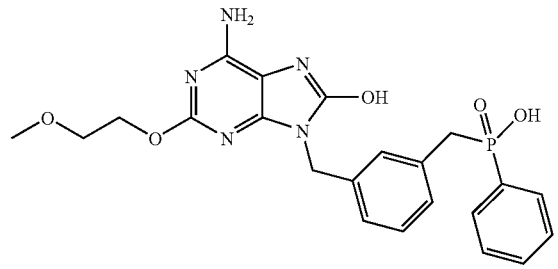

B

Scheme 11

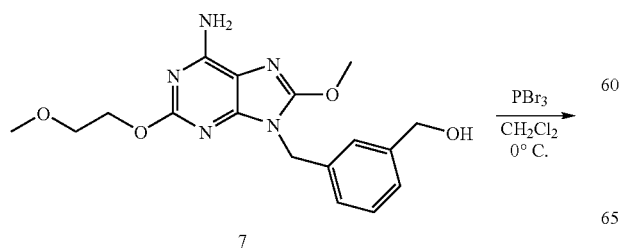

7

-continued

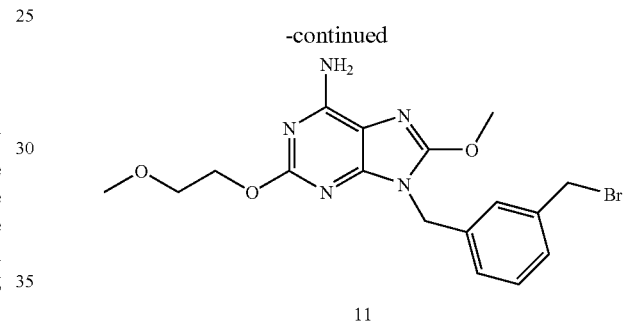

11

Synthesis of 9-(3-(bromomethyl)benzyl)-8-methoxy-2-(2-methoxyethoxy)-9H-purin-6-amine (11)

A solution of Compound 7 (65 mg, 0.18 mmol) in dichloromethane (2 mL) was cooled to 0° C. and phosphorus tribromide (17 μL, 48.9 mg, 0.18 mmol) was added by syringe. The reaction mixture was stirred at 0° C. and the progress of the reaction was monitored by TLC (silica gel, eluting 10% methanol in ethyl acetate). After 20 minutes, the reaction mixture was quenched with saturated sodium bicarbonate solution, washed with water, and the combined organic layers were dried over sodium sulfate and evaporated to dryness. The crude mixture containing Compound (11) was used in the next step without further purification. LCMS: m/z for $C_{17}H_{20}BrN_5O_3^+$+H observed 423 and 424.1 at 1.42 minutes of a 3.0 minute run, eluting 5-95% $CH_3CN$ in $H_2O$ (C18 column).

Scheme 12

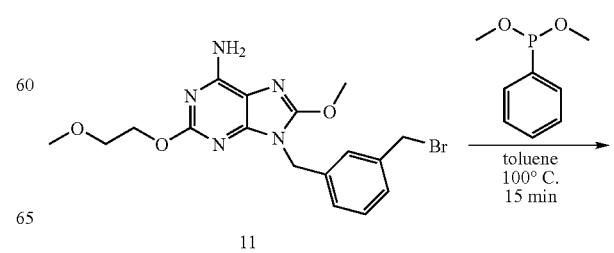

11

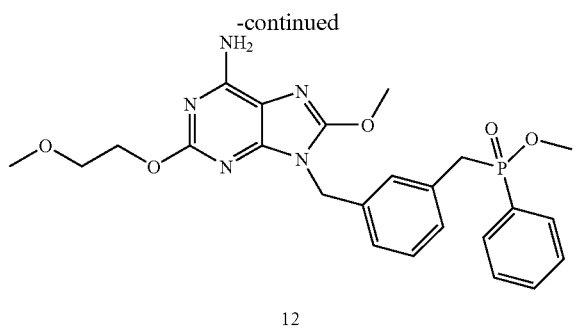

12

Synthesis of Methyl (3-((6-amino-8-methoxy-2-(2-methoxyethoxy)-9H-purin-9-yl)methyl)phenyl)methyl(phenyl)phosphinate (12)

A suspension of Compound (11) (73.4 mg, 0.18 mmol) was combined with dimethyl phenylphosphonite (0.57 mL, 621.5 mg, 3.6 mmol) in a round bottom flask, which was placed in an oil bath preheated to 100° C. The progress of the reaction was monitored by TLC (silica gel, eluting 10% methanol in ethyl acetate). After 15 minutes, the reaction was observed to be complete and the solvent was evaporated. The resulting residue was purified by column chromatography (silica gel, eluting a gradient of 0-25% methanol in ethyl acetate), giving 4.7 mg (5%) of Example (B) as a white solid. $^1$H NMR (300 MHz, CD$_3$OD) δ 3.35 (s, 3H), 3.39 (q, J=4.2, 7.8, 11.4, 3H), 3.58 (dd, J=3.4, 11.4, 2H), 3.72 (m, 2H), 4.10 (s, 3H), 4.42 (m, 2H), 4.99 (d, J=5.4, 2H), 7.20 (m, 2H), 7.31 (m, 5H), 7.46 (m, 2H). LCMS: m/z for C$_{23}$H$_{26}$N$_5$O$_5$P$^+$+H observed 484.1 at 1.84 minutes of a 3.5 minute run, eluting 5-95% CH$_3$CN in H$_2$O (C18 column).

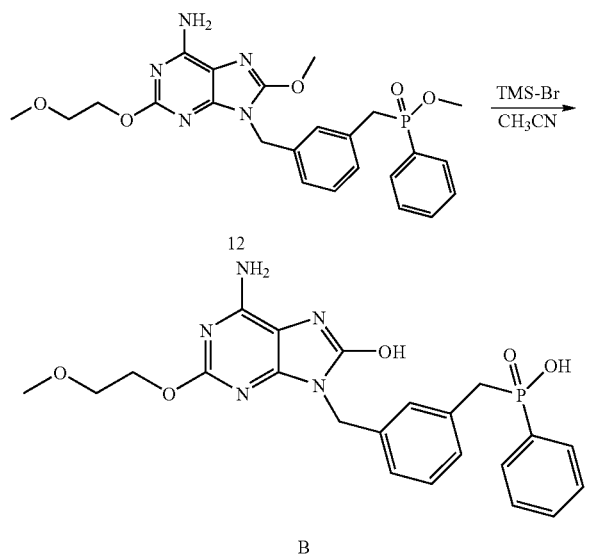

Synthesis of (3-((6-amino-8-hydroxy-2-(2-methoxyethoxy)-9H-purin-9-yl)methyl)phenyl)methyl(phenyl)phosphinic acid (Example B)

A solution of Compound (12) (4.7 mg, 0.01 mmol) in acetonitrile (1 mL) was cooled to 0° C. under nitrogen in an ice bath. Bromotrimethylsilane (100 μL) was added via syringe. The reaction was stirred at 0° C. for 50 minutes, then warmed to room temperature for 1 hr. No reaction was observed, so an additional 200 μL bromotrimethylsilane was added along with an additional 2 mL of acetonitrile. The reaction was observed to be complete 1 hour after the addition of the bromotrimethylsilane. The crude reaction mixture was purified by HPLC on a 50×21 mm C18 column (eluting 15-80% CH$_3$CN in H$_2$O) and lyophilized to give 1.1 mg of Example (B) as a white powder. $^1$H NMR (300 MHz, CD$_3$OD) δ 3.31 (m, 2H), 3.40 (s, 3H), 3.73 (m, 2H), 4.44 (m, 2H), 4.86 (s, 2H), 6.97 (m, 1H), 7.72-7.58 (m, 8H). (LCMS: m/z for C$_{22}$H$_{24}$N$_5$O$_5$P$^+$+H observed 470.2 at 1.62 minutes of a 3.5 minute run, eluting 5-95% CH$_3$CN in H$_2$O (C18 column).

Example C

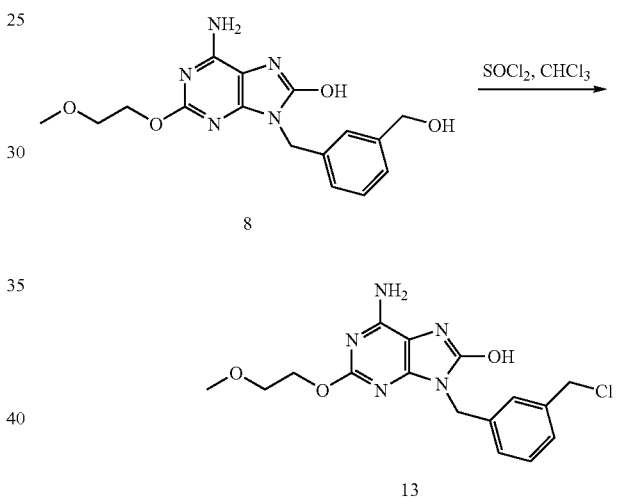

Compound (8) (18 mg, 0.05 mmol) and 100 μl of thionyl chloride in 5 ml of CHCl$_3$ was heated to 80° C. for 5 minutes in a Emzys optimizer. The reaction solution was concentrated and purified using a Gilson HPLC on a C18 column (eluting 2-98% CH$_3$CN in H$_2$O) to afford Compound (13) (18.3 mg, 97%) as a white solid. $^1$H NMR (300 MHz, CD$_3$OD): δ 7.77 (s, 1H), 7.42 (s, 1H), 7.27 (m, 2H), 4.96 (s, 2H), 4.55 (s, 2H), 4.42 (m, 2H), 3.67 (m, 2H), 3.27 (s, 3H). (M$^+$+1): 364.1

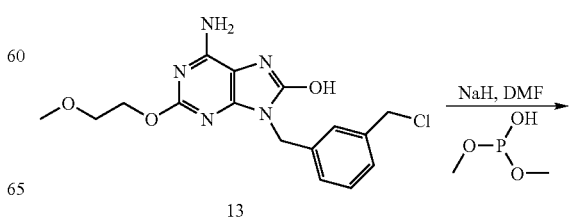

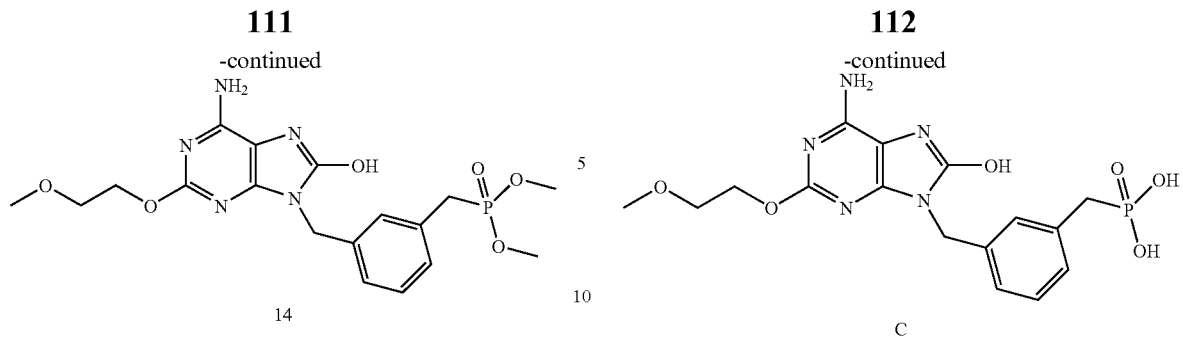

14

NaH (40 mg, 0.85 mmol) was added to a solution of dimethylphosphite (92 ml, 1.00 mmol) in 2 ml of DMF at 0° C. The reaction solution was stirred for 1 hour and then a solution of Compound (13) (18.3 mg, 0.05 mmol) in 1 ml of DMF was added at 0° C. The reaction solution was stirred for 1 hour at room temperature and was quenched with 1N HCl and concentrated. The concentrated material was purified using a Gilson HPLC on a C18 column (eluting 3-95% CH$_3$CN in H$_2$O) to afford Compound (14) (6.5 mg, 31%) as a white solid. $^1$H NMR (300 MHz, DMSO): δ 7.19 (m, 4H), 4.82 (s, 2H), 4.25 (m, 3H), 3.58 (m, 2H), 3.55 (s, 3H), 3.52 (s, 3H), 3.25 (s, 3H). (M$^+$+1): 438.0

Compound (13) (36 mg, 0.08 mmol) was dissolved in 1 ml of CH$_3$CN and TMSBr ("bromotrimethylsilane") (106 μL, 0.80 mmol) was added. The reaction mixture was stirred at room temperature for one hour. The reaction mixture was quenched with MeOH and concentrated. The resulting crude material was purified using a Gilson HPLC on a C18 column (eluting 5-95% CH$_3$CN in H$_2$O) to afford Example (C) (32 mg, 100%) as a white solid. $^1$H NMR (300 MHz, DMSO+CD$_3$OD): δ 7.32 (s, 1H), 7.21 (s, 3H), 4.94 (s, 2H), 4.40 (m, 2H), 3.67 (m, 2H), 3.26 (s, 3H), 3.09 (s, 1H), 3.01 (s, 1H). (M$^+$+1): 410.0

Example D

Scheme 17

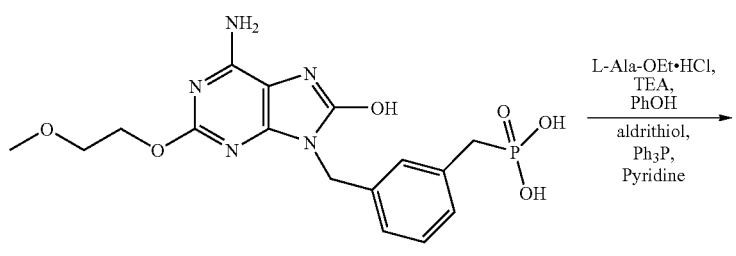

C

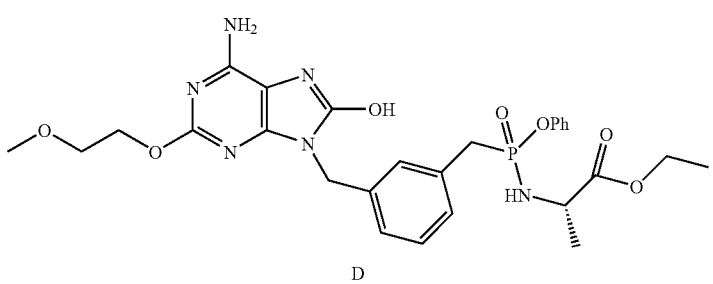

D

Scheme 16

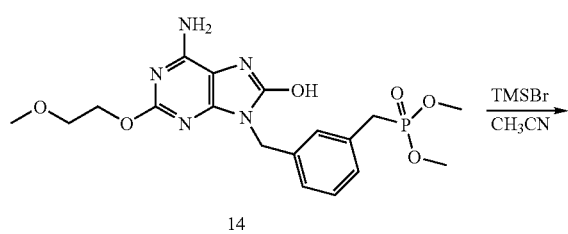

14

Example (C) (28 mg, 0.68 mmol), triethylamine (114 μL, 0.82 mmol), L-Ala-OEt.HCl (21 mg, 0.14 mmol), phenol (32 mg, 0.34 mmol), aldrithiol (105 mg, 0.47 mmol) and triphenylphosphine (126 mg, 0.47 mmol) was heated at 60° C. in 1 ml of pyridine for 7 hours. The solution was concentrated and purified by HPLC to afford Example (D) (10.5 mg, 26%) as a white solid. $^1$H NMR (300 MHz, DMSO+CD$_3$OD): δ 7.32 (m, 6H), 7.10 (m, 3H), 5.58 (m, 1H), 4.83 (s, 2H), 4.23 (m, 2H), 3.98 (m, 2H), 3.58 (m, 2H), 3.22 (s, 5H), 1.15 (m, 3H), 0.98 (m, 3H). (M$^+$+1): 585.2

Example E

Scheme 18

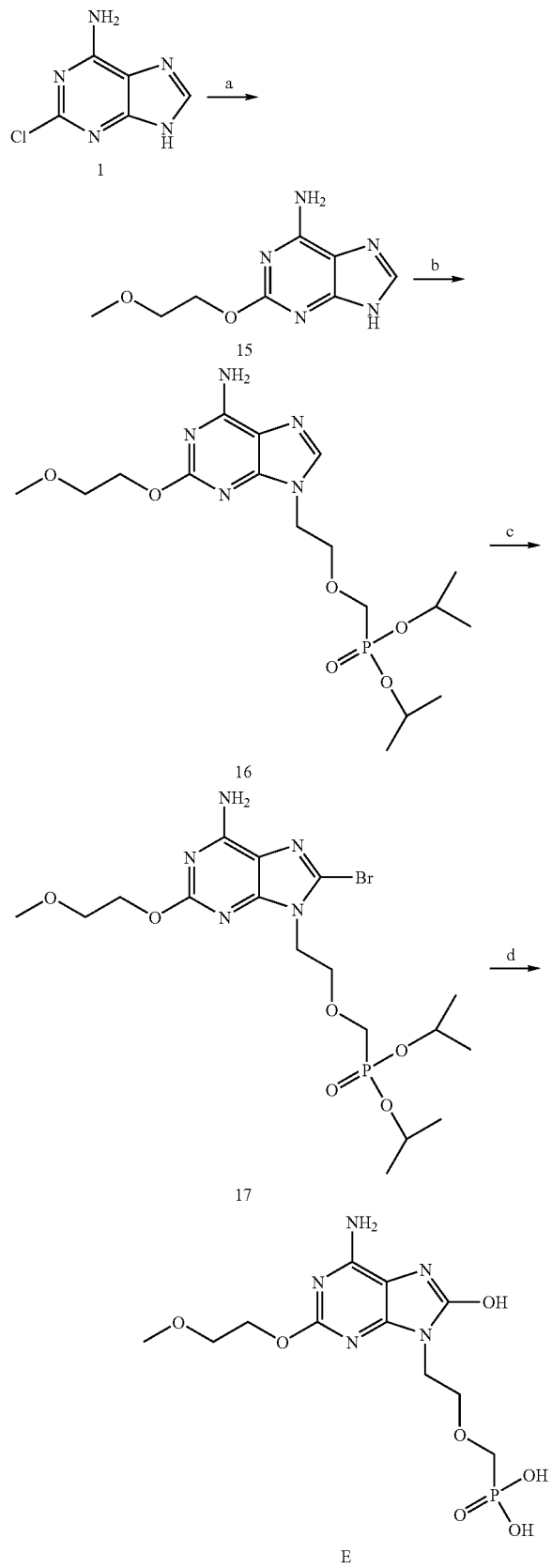

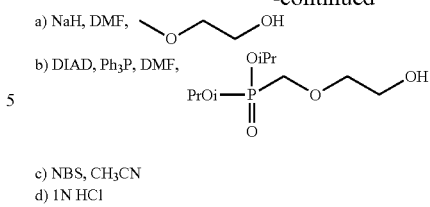

a) NaH, DMF,
b) DIAD, Ph₃P, DMF,
c) NBS, CH₃CN
d) 1N HCl

Step 1: Preparation of 2-(2-methoxyethoxy)adenine (15)

To a flask with 150 ml 2-methoxyethanol, was added NaH (13 g, 60% dispersion in mineral oil). The mixture was allowed to stir at room temperature for 10 min. Then 6-amino-2-chloroadenine (Compound (1)) (25 g, 0.15 mol) was added. The reaction was refluxed for 2 days while monitoring by LC/MS. Additional NaH (5 g, 60% dispersion in mineral oil) was added and refluxing was continued for another day. After the starting material was consumed, the reaction mixture was cooled to rt ("room temperature") and the solvent was removed under vacuum. Water was added, and the mixture was neutralized with acetic acid until a solid precipitated. The solid Compound (15) was collected and dried under high vacuum. ¹H NMR (DMSO-d₆) δ 3.28 (s, 3H), δ 3.61 (t, 2H), δ 4.28 (t, 2H), δ 7.08 (bs, 2H), δ 7.88 (s, 1H), δ 145 (bs, 1H); MS: 210.0 (M+H)⁺, 208.1 (M−1).

Step 2: Preparation of (2-(6-amino-2-(2-methoxyethoxy)-purin-9-yl)-ethoxymethyl)phosphonic acid diisopropyl ester (16)

To a solution of diisopropyl (2-hydroxyethoxy)phosphonate (413 mg, 1.71 mmol) in DMF (10 ml) was added 2-(2-methoxyethoxy)adenine (15), prepared in Step 1 (300 mg, 1.43 mmol). Triphenylphosphine (830 mg, 3.15 mmol) and diisopropyl azodicarboxylate (420 µl, 34 mmol) were then added. The reaction mixture was stirred at rt for 1 h, after which the solvent was removed under vacuum and the residue was dissolved in DCM ("dichloromethane"). The organic layer was washed with brine, and the water layer was extracted with DCM. The organic layers were combined and dried over Na₂SO₄, filtered, and concentrated, then purified by silica gel chromatography (eluting a linear gradient of 0-10% methanol in dichloromethane) to obtain 320 mg of Compound (16). ¹H NMR (CDCl₃) δ 1.26-1.32 (m, 12H), δ 3.43 (s, 3H), δ 3.71-3.77 (m, 4H), δ 3.91 (t, 2H), δ 4.31 (t, 2H), δ 4.48 (t, 2H), δ 4.67-4.74 (m, 2H), δ 5.62 (bs, 2H), δ 7.77 (s, 1H); MS: 432.0 (M+H)⁺, 430.2 (M−1).

Step 3: Preparation of (2-(6-amino-8-bromo-2-(2-methoxyethoxy)purin-9-yl)-ethoxymethyl)phosphonic acid diisopropyl ester (17)

To a solution of the phosphonate Compound (16) prepared in Step 2 (295 mg, 0.68 mmol) in acetonitrile (5 ml) was added NBS ("N-bromosuccinamide") (182 mg, 1.0 mmol). The reaction mixture was stirred at rt for 20 min. The solvent was removed under vacuum and the residue was washed with saturated aq. Na₂SO₃. The aqueous phase was extracted with DCM. The organic layers were combined and dried over Na₂SO₄, filtered, and concentrated. The crude material was purified using silica gel chromatography (eluting a linear gradient of 0-10% methanol in dichloromethane) to obtain 280 mg of Compound (17). $^1$H NMR (CDCl$_3$) δ 1.22-1.28 (m, 12H), δ 3.42 (s, 3H), δ 3.71-3.75 (m, 4H), δ 3.94 (t, 2H), δ 4.32 (t, 2H), δ 4.50 (t, 2H), δ 4.62-4.70 (m, 2H), δ 5.85 (bs, 2H); MS: 510.0 (M+H)$^+$.

Step 4: Preparation of (2-(6-amino-8-hydroxy-2-(2-methoxyethoxy)-purin-9-yl)ethoxymethyl)phosphonic acid (Example E)

A mixture of bromide Compound (17) prepared in Step 3 (21 mg) in 1 N HCl (1.5 ml) was reacted at 150° C. in a microwave for 15 min. The solvent was removed under vacuum and the residue was dissolved in water, and purified by prep HPLC on a C18 column (eluting 5-95% CH$_3$CN in H$_2$O) on a C18 column to give Example (E). $^1$H NMR (D$_2$O) 63.31 (s, 3H), δ 3.56 (d, 2H), 63.70-3.73 (m, 2H), δ 3.80 (t, 2H), δ 3.97 (t, 2 h), δ 4.45-4.48 (m, 2H); MS 364.1 (M+H)$^+$, 362.0 (M−1).

Example F

Scheme 19

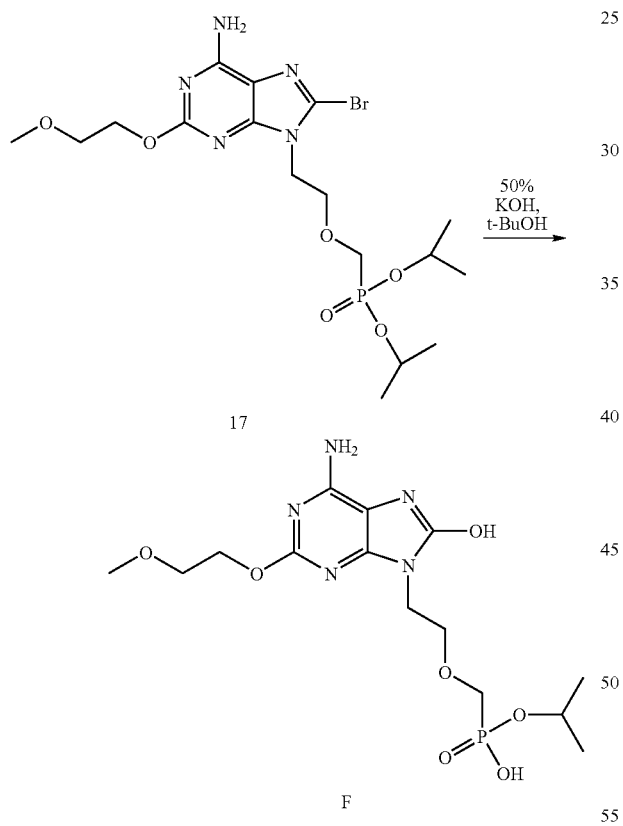

17

F (2-(6-amino-8-hydroxy-2-(2-methoxyethoxy)-purin-9-yl)ethoxymethyl)phosphonic acid monoethyl ester (Example F)

A mixture of bromide Compound (17) (10 mg) in 50% KOH (1 ml) and t-BuOH (1 ml) was refluxed at 105° C. overnight. The mixture was cooled to rt and neutralized with acetic acid. The NaOAc ("sodium acetate") was removed by filtration, and the product was purified by prep HPLC on a C18 column (eluting 5-95% CH$_3$CN in H$_2$O) to give Example (F). $^1$H NMR (CD$_3$OD) δ 1.11 (d, 6H), δ 3.405 (s, 3H), δ 3.61 (d, 2H), δ 3.71-3.74 (m, 2H), δ 3.84 (t, 2H), δ 4.04 (t, 2H), δ 4.30-4.40 (m, 1H), δ 4.11-4.43 (m, 2H); MS: 406.1 (M+H)$^+$, 404.0 (M−1).

Examples G and H

Scheme 20

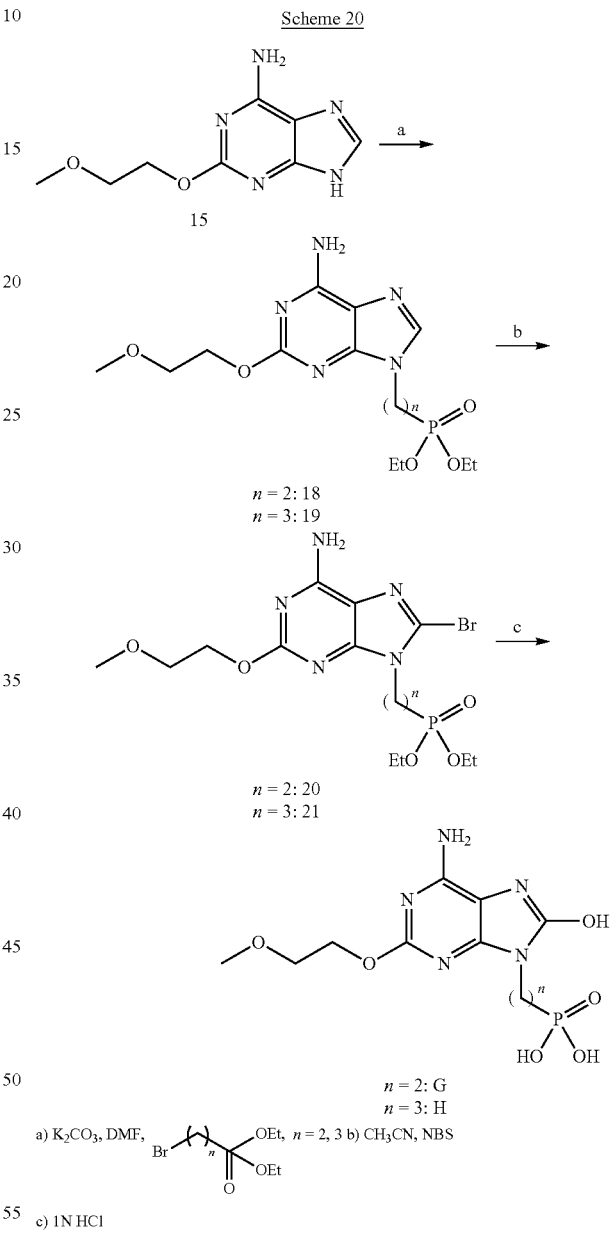

$n$ = 2: 18
$n$ = 3: 19

$n$ = 2: 20
$n$ = 3: 21

$n$ = 2: G
$n$ = 3: H a) K$_2$CO$_3$, DMF, Br(CH$_2$)$_n$P(O)(OEt)$_2$, $n$ = 2, 3 b) CH$_3$CN, NBS
c) 1N HCl

Example H

Step 1: Preparation of (3-(6-amino-2-(2-methoxyethoxy)purin-9-yl)propyl)phosphonic acid diethyl ester (19)

To a suspension of 2-(2-methoxyethoxy)adenine Compound (15) (200 mg, 0.96 mmol) in DMF (5 ml) was added K$_2$CO$_3$ (132 mg 0.96 mmol). Then diethyl (3-bromopropyl)

phosphonate (265 μl, 1.44 mmol) was added. The reaction mixture was stirred at 70° C. for 1 h, and the solvent was removed under vacuum. The residue was dissolved in DCM and washed with brine. The aqueous phase was extracted again with DCM. The combined organic layers were dried over Na$_2$SO$_4$, filtered, and concentrated under vacuum. The residue was purified by silica gel chromatography (eluting using a linear gradient of 0-10% MeOH in DCM) to give 293 mg of Compound (19). $^1$H NMR (CDCl$_3$) δ 1.10-1.16 (m, 6H), δ 1.52-1.59 (m, 2H), δ 1.90-2.09 (m, 2H), δ 3.25 (s, 3H), δ 3.51-3.57 (m, 2H), δ 3.89-3.92 (m, 4H), δ 4.04 (t, 2H), δ 4.28 (t, 2H), δ 6.60 (M, 2H), δ 7.53 (s, 1H); MS: 388.1 (M+H)$^+$, 386.0 (M−1).

Step 2: Preparation of (3-(6-amino-8-bromo-2-(2-methoxyethoxy)purin-9-yl)propyl)phosphonic acid diethyl ester (21)

To a solution of the phosphonate Compound (19) prepared in Step 1 (293 mg, 0.76 mmol) in CH$_3$CN (5 ml) was added NBS (200 mg, 1.14 mmol). The reaction mixture was stirred at room temperature for 30 min. The solvent was removed under vacuum, and the residue was washed with saturated aq. Na$_2$SO$_3$ solution. The aqueous phase was extracted again with DCM. The combined organic layers were dried over Na$_7$SO$_4$, filtered, concentrated and purified by silica gel chromatography (eluting a linear gradient of 0-10% MeOH in DCM) to give 308 mg of Compound (21). $^1$H NMR (CDCl$_3$) δ 1.31 (t, 6H), δ 1.76-1.83 (m, 2H), δ 2.09-38 (m, 2H), δ 3.43 (s, 3H), δ 3.76 (t, 2H), δ 4.04-4.14 (M, 4H), δ 4.20 (t, 2H), δ 4.46 (t, 2H), δ 5.66 (bs, 2H). MS: 466.1 (M+H)$^+$.

Step 3: Preparation of (3-(6-Amino-8-hydroxy-2-(2-methoxyethoxy)purin-9-yl)propyl)phosphonic acid (Example H)

A mixture of bromide Compound (21) prepared in Step 2 (37 mg) in 1 N HCl (3 ml) was reacted at 150° C. in a microwave for 12 min. The solvent was removed under vacuum, and the residue was purified by HPLC on a C18 column (eluting a linear gradient of 0-10% MeOH in DCM) to give Example (H). $^1$H NMR (D$_2$O) 61.44-1.56 (m, 2H), δ 1.80-1.90 (m, 2H), δ 3.30 (s, 3H), δ 3.70-3.72 (m, 2H), δ 3.79 (t, 2H), δ 4.46 (t, 2H); MS 348.1 (M+H)$^+$, 345.9 (M−1).

Example G

Example (G) with a two carbon linker (n=2) was prepared using procedures similar to those used to prepare Example (H), except that diethyl (2-bromoethyl)phosphonate was used instead of diethyl (3-bromopropyl)phosphonate in step 1.

(2-(6-amino-2-(2-methoxyethoxy)purin-9-yl)ethyl)phosphonic acid diethyl ester (18)

$^1$H NMR (CDCl$_3$) δ 1.22 (t, 6H), δ 51-2.42 (m, 2H), δ 3.40 (s, 3H), δ 3.72 (t, 2H), δ 3.98-4.06 (m, 4H), δ 4.30-4.4.40 (m, 2H), δ 4.44 (t, 2H), δ 6.20 (bs, 2H), δ 7.65 (s, 1H); MS: 374.1 (M+H)$^+$.

(2-(6-amino-8-bromo-2-(2-methoxyethoxy)-purin-9-yl)ethyl)phosphonic acid diethyl ester (20)

$^1$H NMR (CDCl$_3$) δ 1.33 (t, 6H), 649-2.40 (m, 2H), δ 3.44 (s, 3H), δ 3.76 (t, 2H), δ 4.07-4.18 (m, 4H), δ 4.36-4.44 (m, 2H), δ 4.48 (t, 2H), δ 5.69 (bs, 2H); MS: 452.0 (M+H)$^+$.

(2-(6-Amino-8-hydroxy-2-(2-methoxyethoxy)-purin-9-yl)ethyl)phosphonic acid (G)

$^1$H NMR (CD$_3$OD) δ 2.05-38 (m, 2H), δ 3.42 (s, 3H), δ 3.76 (t, 2H), δ 4.05-4.14 (m, 2H), 64.43-4.49 (m, 2H); MS: 334.1 (M+H)$^+$, 331.9 (M−1).

Examples I and J

Scheme 21

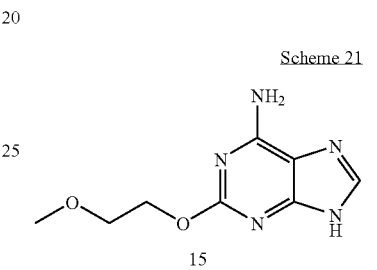

15

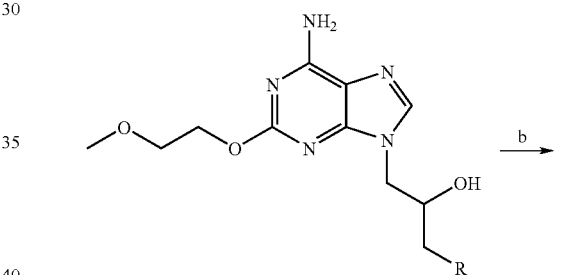

R = Ph: 22
R = H: 23

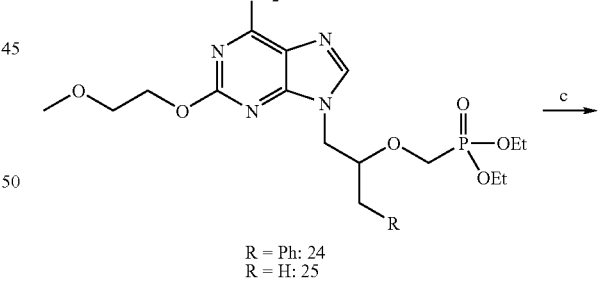

R = Ph: 24
R = H: 25

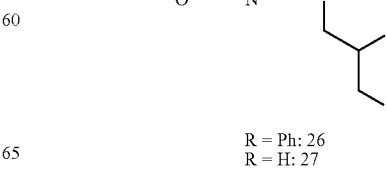

R = Ph: 26
R = H: 27

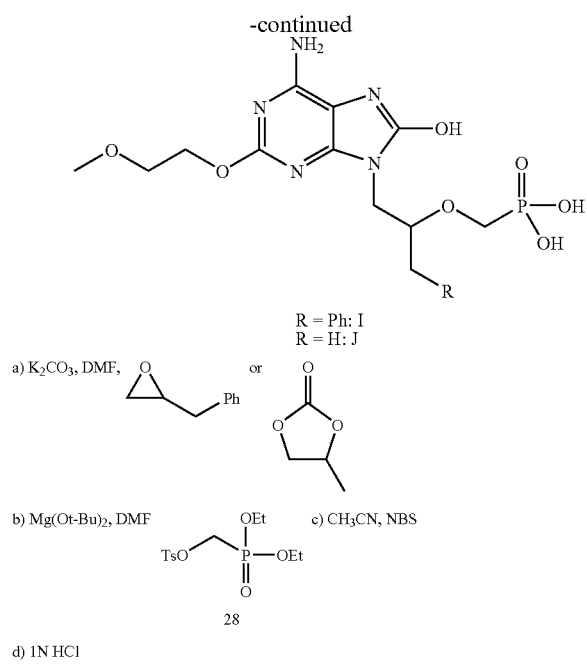

Step 1: Preparation of 1-(6-Amino-2-(2-methoxy-ethoxy)purin-9-yl)-3-phenylpropan-2-ol (22)

To a suspension of 6-amino-2-(2-methoxyethoxy)adenine Compound (15) (300 mg, 1.43 mmol) in DMF (3 ml) was added $K_2CO_3$. Then (2,3-epoxypropyl)benzene (285 μl, 34 mmol) was added and the reaction mixture was stirred at 70° C. for 5 h. The solvent was removed under vacuum and the residue was washed with brine. The aqueous phase was extracted with DCM and the combined organic layers were dried over $Na_2SO_4$, filtered, concentrated, and purified by silica gel chromatography (eluting a linear gradient of 0-10% MeOH in DCM) to give 170 mg of Compound (22). $^1$H NMR ($CDCl_3$) δ 2.82-2.85 (dd, 2H), δ 3.43 (s, 3H), δ 3.74 (t, 2H), δ 4.00-4.10 (m, 1H), δ 4.25-4.29 (m, 2H), δ 4.42 (t, 2H), δ 5.76 (bs, 2H), δ 7.21-7.34 (m, 5H), δ 7.50 (s, 1H); MS: 494.2 $(M+H)^+$.

Step 2: Preparation of (2-(6-Amino-2-(2-methoxy-ethoxy)-purin-9-yl)-1-benzyl-ethoxymethyl)phosphonic acid diethyl ester (24)

To a solution of the adenine derivative Compound (22) prepared in Step 1 (190 mg, 0.55 mmol) in DMF (2 ml) was added magnesium di-tert-butoxide (68 mg, 0.72 mmol) at room temperature. The temperature was raised to 75° C. and the tosylate reagent (28) (242 mg) was added. After stirring at 75° C., approximately 50% of the starting material was converted to product. The reaction mixture was quenched with water and extracted with DCM. The organic layer was dried over $Na_2SO_4$, filtered, concentrated, and purified by silica gel chromatography (eluting a linear gradient of 0-10% MeOH in DCM). The starting material (Compound (22)) and product (Compound (24)) were not separable, so the mixture was used in the next step without further purification. MS: 494.2 $(M+H)^+$.

Step 3: Preparation of (2-(6-Amino-8-bromo-2-(2-methoxyethoxy)purin-9-yl)-1-benzyl-ethoxymethyl) phosphonic acid diethyl ester (26)

To a solution of the phosphonate Compound (24) prepared in Step 2 (210 mg) in $CH_3CN$ (3 ml) was added NBS (115 mg) at room temperature. The reaction mixture was stirred at room temperature for 20 min. The solvent was removed and the residue was taken up in DCM and washed with saturated aq. $Na_2SO_3$. The aqueous phase was extracted again with DCM. The combined organic layers were dried over $Na_2SO_4$, filtered, concentrated and purified by prep HPLC on a C18 column (eluting a using a gradient of 5-95% $CH_3CN$ in $H_2O$) to give Compound (26).

$^1$H NMR ($CDCl_3$) δ 1.19-1.28 (m, 6H), δ 2.81-2.87 (dd, 1H), δ 3.00-3.06 (dd, 1H), δ 3.43 (s, 3H), δ 3.52-3.60 (m, 1H), δ 3.69-3.76 (m, 4H), δ 3.90-4.03 (m, 4H), δ 4.12-4.23 (m, 4H), δ 4.39 (t, 2H), δ 5.52 (bs, 2H), δ 7.24-7.31 (m, 5H); MS: 574 $(M+H)^+$.

Step 4: preparation of (2-(6-Amino-8-hydroxy-2-(2-methoxyethoxy)purin-9-yl)-1-benzyl-ethoxymethyl) phosphonic acid (Example I)

A mixture of bromide Compound (26) prepared in Step 3 (20 mg) in 1 N HCl (1.5 ml) was stirred at 150° C. in a microwave for 12 min. The solvent was removed under vacuum and the residue was purified by prep HPLC on a C18 column (eluting a using a gradient of 5-95% $CH_3CN$ in $H_2O$) to give Example (I). $^1$H NMR ($CD_3OD$) δ 2.80-2.86 (dd, 1H), δ 3.00-3.06 (dd, 1H), δ 3.40 (s, 3H), δ 3.56-3.72 (m, 4H), δ 3.85-3.4.02 (m, 2H), δ 4.15-4.22 (m, 1H), δ 4.37 (t, 2H), δ 7.14-7.32 (m, 5H); MS: 454.2 $(M+H)^+$.

Example J

Example (J) with R=H was prepared using procedures similar to those used to prepare a compound (1), except that propylene carbonate was used instead of the epoxide in Step 1.

1-(6-Amino-2-(2-methoxyethoxy)purin-9-yl)-propan-2-ol (23)

$^1$H NMR ($CDCl_3$) δ 1.24 (d, 3H), δ 3.43 (s, 3H), 3.72 δ (t, 2H), 3.92 δ (q, 1H), δ 4.14-4.25 (m, 2H), δ 4.07 (t, 2H), δ 6.10 (bs, 2H), δ 7.56 (s, 1H); MS: 268.1 $(M+H)^+$.

(2-(6-Amino-2-(2-methoxyethoxy)purin-9-yl-1-methyl-ethoxymethyl)phosphonic acid diethyl ester (25)

$^1$H NMR ($CDCl_3$) δ 1.20-1.34 (m, 9H), δ 3.43 (s, 3H), δ 3.56-3.64 (m, 1H), δ 3.74-3.3.92 (m, 4H), δ 4.01-4.13 (m, 6H), δ 4.47 (t, 2H), δ 5.67 (bs, 2H), δ 7.78 (s, 1H); MS: 418.2 $(M+H)^+$.

(2-(6-Amino-8-bromo-2-(2-methoxyethoxy)purin-9-yl)-1-methyl-ethoxymethyl)phosphonic acid diethyl ester (27)

$^1$H NMR ($CDCl_3$) δ 1.16-1.26 (m, 9H), δ 3.38 (s, 3H), δ 3.55-3.82 (m, 4H), δ 3.90-4.16 (m, 7H), δ 4.38-4.40 (m, 2H), δ 6.27 (bs, 2H); MS: 496.1 $(M+H)^+$.

(2-(6-Amino-8-hydroxy-2-(2-methoxyethoxy)purin-9-yl)-1-methyl-ethoxymethyl)phosphonic acid (Example J)

$^1$H NMR ($CD_3OD$) δ 1.22 (d, 3H), δ 3.40 (s, 3H), δ 3.67-3.83 (m, 6H), δ 3.93-4.01 (m, 2H), δ 4.43 9 (t, 2H); MS: 378.1 $(M+H)^+$, 376.0 $(M-1)$.

Example K

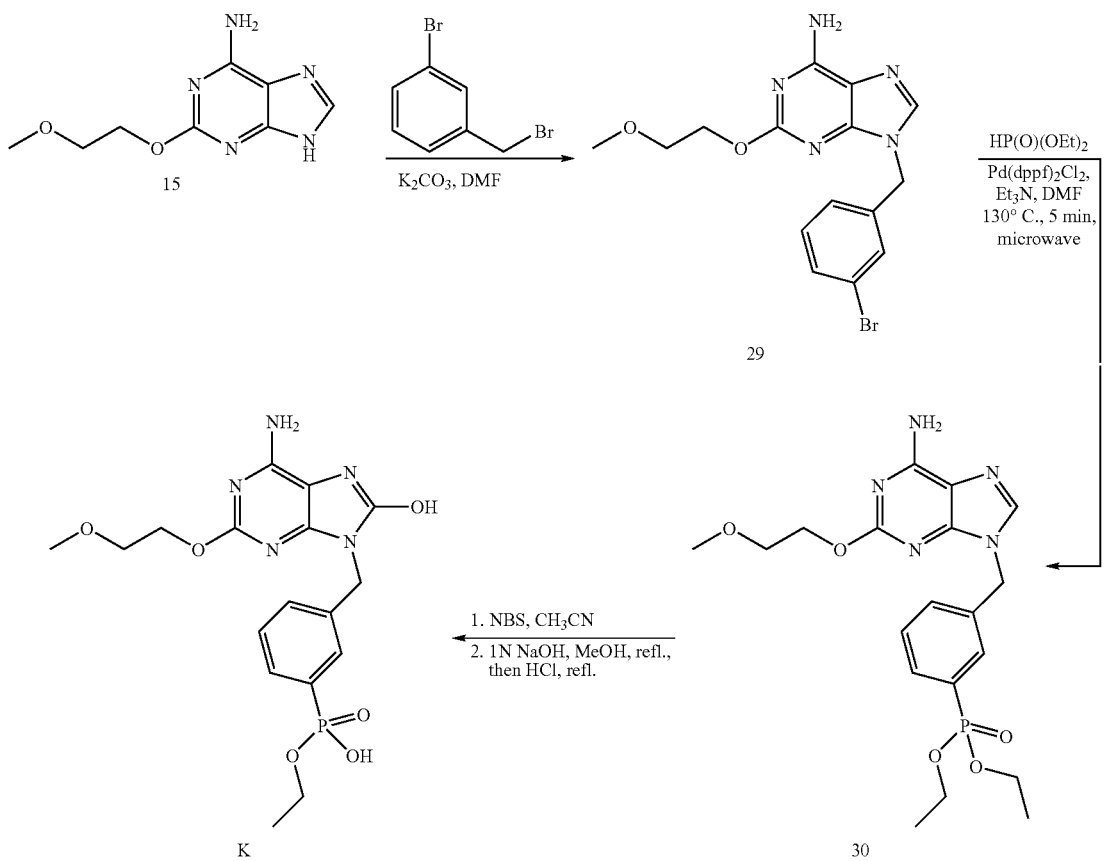

Scheme 22

Synthesis of 9-(3-bromobenzyl)-2-(2-methoxyethoxy)-9H-purin-6-amine (29)

2-(2-methoxyethoxy)-9H-purin-6-amine (15) (1.0 g, 4.78 mmol), 3-bromobenzyl bromide (1.5 g, 6.00 mmol) and anhydrous potassium carbonate (0.85 g, 6.15 mmol) were combined in DMF (15 mL) and stirred at room temperature for 16 h. The mixture was diluted with ethyl acetate (150 mL) and washed with water and brine. The organic phase was dried with sodium sulfate and the solvent was removed under vacuum. The resulting residue was triturated with a mixture of diethylether and ethyl acetate (4:1) and filtered. 9-(3-bromobenzyl)-2-(2-methoxyethoxy)-9H-purin-6-amine, Compound (39) (0.77 g, 43%) was obtained as a yellowish solid. $^1$H-NMR (DMSO) δ: 8.07 (s, 1H), 7.57 (s, 1H), 7.52-7.46 (m, 1H), 7.34-7.22 (m, 4H), 5.26 (s, 2H), 4.32 (t, J=4.5 Hz, 2H), 3.60 (t, J=4.5 Hz, 2H), 3.27 (s, 3H). MS: 378/380 (MH$^+$)

Synthesis of Diethyl 3-((6-amino-2-(2-methoxyethoxy)-9H-purin-9-yl)methyl)phenylphosphonate (30)

9-(3-bromobenzyl)-2-(2-methoxyethoxy)-9H-purin-6-amine (29) (500 mg, 1.32 mmol) was suspended in DMF (5 mL). Diethylphosphite (0.26 mL, 2.0 mmol), triethylamine (0.28 mL, 2.0 mmol) and (1,1'-Bis(diphenylphosphino)ferrocene)dichloropalladium(II), complex with CH$_2$Cl$_2$ (106 mg, 0.13 mmol) was added and the mixture was heated at 130° C. for 5 min in a microwave reactor. Then the reaction mixture was diluted with ethyl acetate (150 mL) and washed with water and brine. The organic solution was dried with sodium sulfate and the solvent was removed under vacuum. The residue was redissolved in ethyl acetate (10 mL) and adsorbed on a short column of silica gel. The product was eluted with dichloromethane/methanol 1:0 to 1:1 giving diethyl 3-((6-amino-2-(2-methoxyethoxy)-9H-purin-9-yl)methyl)phenylphosphonate (30) (400 mg, 70%) as a dark brown oil after evaporation of the solvent. MS: 436 (MH$^+$).

Synthesis of Diethyl 3-(((6-amino-8-bromo-2-(2-methoxyethoxy)-9H-purin-9-yl)methyl)phenylphosphonate Diethyl 3-((6-amino-2-(2-methoxyethoxy)-9H-purin-9-yl)methyl)phenylphosphonate (30) (400 mg, 0.92 mmol) was dissolved in acetonitrile and N-bromosuccinimide (500 mg, 2.8 mmol) was added in one portion. After stirring at room temperature for 2 h, the reaction mixture was diluted with ethyl acetate (150 mL) and washed with water, 0.2 M sodium thiosulfate solution and brine. The organic phase was dried with sodium sulfate and the solvent was removed under vacuum. The crude diethyl 3-(((6-amino-8-bromo-2-(2-methoxyethoxy)-9H-purin-9-yl)methyl)phenylphosphonate (450 mg, 95%) was used in the next step without further purification.

Synthesis of Ethyl hydrogen 3-((6-amino-8-hydroxy-2-(2-methoxyethoxy)-9H-purin-9-yl)methyl)phenylphosphonate (Example K)

Diethyl 3-((6-amino-8-bromo-2-(2-methoxyethoxy)-9H-purin-9-yl)methyl)phenylphosphonate (100 mg, 0.194 mmol) was dissolved in methanol (5 mL) and 1 N aqueous NaOH solution was added. The reaction mixture was heated at reflux and progress was monitored by HPLC. As soon as all the starting material had been consumed, the reaction mixture was acidified with conc. HCL. After heating at reflux for 1 h, the mixture was evaporated to dryness under vacuum. The product was purified by preparative reverse phase HPLC, yielding ethyl hydrogen 3-((6-amino-8-hydroxy-2-(2-methoxyethoxy)-9H-purin-9-yl)methyl)phenylphosphonate Example (K) (18 mg, 22%) as a white powder. $^1$H-NMR (DMSO) δ: 10.0 (s, 1H), 7.65-7.42 (m, 5H), 6.51 (br, 2H), 4.90 (s, 2H), 4.25 (t, J=4.5 Hz, 2H), 3.84 (quint, J=7 Hz, 2H), 3.57 (t, J=4.5 Hz, 2H), 3.26 (s, 3H), 1.13 (t, J=7 Hz, 3H). $^{31}$P-NMR (DMSO) δ: 13.04. MS: 424 (MH$^+$).

Example L

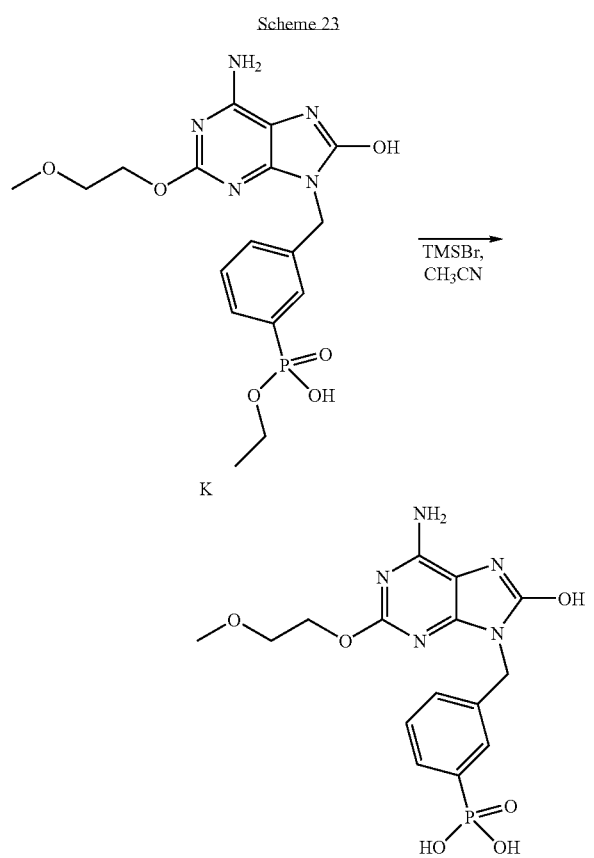

Synthesis of 3-((6-amino-8-hydroxy-2-(2-methoxyethoxy)-9H-purin-9-yl)methyl)phenylphosphonic acid (L)

Ethyl hydrogen 3-((6-amino-8-hydroxy-2-(2-methoxyethoxy)-9H-purin-9-yl)methyl)phenylphosphonate (K) (10 mg, 0.0236 mmol) was suspended in anhydrous acetonitrile (3 mL). Bromotrimethylsilane (0.2 mL) was added. After stirring at room temperature overnight, the mixture was concentrated under vacuum and treated with water (2 mL). Acetonitrile (1 mL) was added and the product was purified by preparative reverse phase HPLC, yielding 3-((6-amino-8-hydroxy-2-(2-methoxyethoxy)-9H-purin-9-yl)methyl)phenylphosphonic acid (L) (1.5 mg) as a white solid. $^1$H-NMR (DMSO) δ: 10.0 (s, 1H), 7.64-7.35 (m, 5H), 6.48 (br, 2H), 4.86 (s, 2H), 4.25 (t, J=4.5 Hz, 2H), 3.57 (t, J=4.5 Hz, 2H), 3.25 (s, 3H). MS: 396 (MH$^+$).

Examples M and N

Examples M and N were prepared using procedures similar to those shown in Scheme 22, except that 4-bromobenzyl bromide was used instead of 3-bromobenzyl bromide in step 1:

Synthesis of Ethyl hydrogen 4-((6-amino-8-hydroxy-2-(2-methoxyethoxy)-9H-purin-9-yl)methyl)phenylphosphonate (M)

$^1$H-NMR (DMSO) δ: 10.0 (s, 1H), 7.63 (dd, J=7.8 Hz, J=12.6 Hz, 2H), 7.37 (dd, J=3.3 Hz, J=7.8 Hz, 2H), 6.50 (br, 2H), 4.90 (s, 2H), 4.24 (t, J=4.5 Hz, 2H), 3.84 (quint, J=7 Hz, 2H), 3.56 (t, J=4.5 Hz, 2H), 3.25 (s, 3H), 1.15 (t, J=7 Hz, 3H). $^{31}$P-NMR (DMSO) δ: 14.97. MS: 424 (MH$^+$).

Synthesis of 4-((6-amino-8-hydroxy-2-(2-methoxyethoxy)-9H-purin-9-yl)methyl)phenylphosphonic acid (N)

$^1$H-NMR (DMSO) δ: 10.0 (s, 1H), 7.63 (dd, J=7.5 Hz, J=12.6 Hz, 2H), 7.38 (dd, J=3.3 Hz, J=7.5 Hz, 2H), 6.49 (br,

2H), 4.90 (s, 2H), 4.24 (t, J=4.5 Hz, 2H), 3.56 (t, J=4.5 Hz, 2H), 3.25 (s, 3H). $^{31}$P-NMR (DMSO) δ: 16.34. MS: 396 (MH$^+$).

Example O

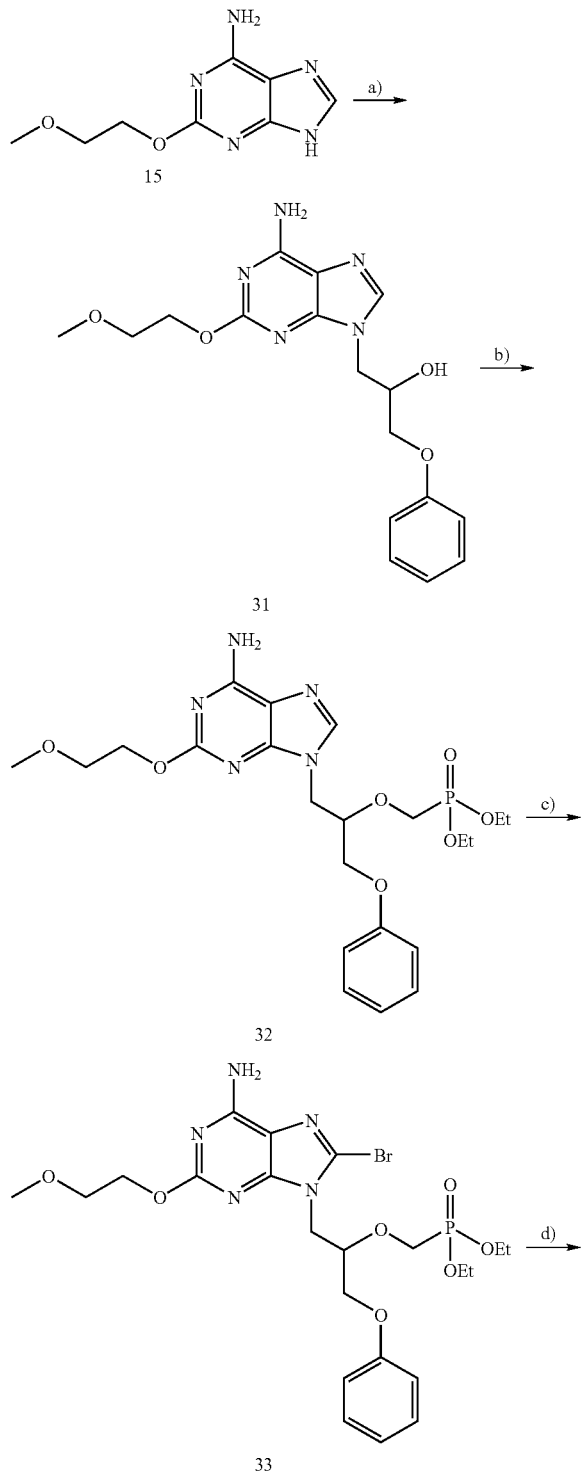

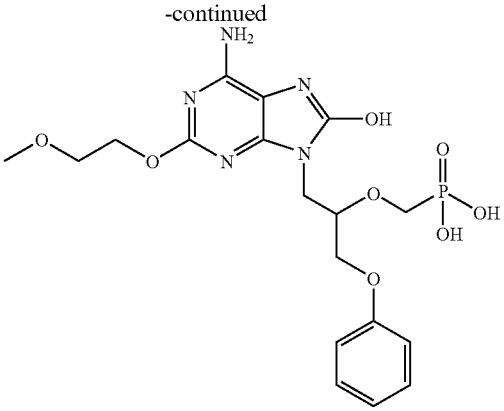

a) K$_2$CO$_3$, DMF, 70° C.,
b) Mg(O-tBu)$_2$, TsO-CH$_2$-P(=O)(OEt)$_2$, DMF, 75° C.
c) NBS, CH$_3$CN
d) 1N HCl, microwave, 150° c., 10 min Step 1: Preparation of 1-(6-amino-2-(2-methoxy-ethoxy)purin-9-yl)-3-phenoxy-propan-2-ol. (31)

To a suspension of 6-amino-2-(2-methoxyethoxy)adenine (300 mg, 1.43 mmol) in DMF (3 ml) was added K$_2$CO$_3$ (200 mg, 1.43 mmol). Then 1,2-epoxy-3-phenoxy-propane (321 mg, 2.14 mmol) was added. The reaction mixture was stirred at 70° C. overnight. The solvent was removed and the residue was taken up in CH$_2$Cl$_2$ and washed with water. The aqueous phase was extracted with DCM. The organic layer was dried over NaSO$_4$, filtered, concentrated, and purified by silica gel chromatography, using linear gradient of MeOH in DCM as eluent to give 350 mg product. $^1$H NMR (CDCl$_3$): δ 3.43 (s, 3H), δ 3.74 (t, 2H), δ 3.90-4.06 (m, 2H), δ 4.30-4.35 (m, 1H), δ 4.30-4.50 (m, 4H), δ 6.00 (bs, 2H), δ 6.88-7.01 (m, 3H), δ 7.27-7.32 (m, 2H), δ 7.70-7.73 (m, 1H); MS: 360.2 (M+1).

Step 2: Preparation of (2-(6-amino-2-(2-methoxy-ethoxy)purin-9-yl)-1-phenoxymethylethoxymethyl)-phosphonic acid diethyl ester. (32)

To a solution of the purine analog prepared in step 1 (350 mg, 0.97 mmol) in DMF (3 ml) was added magnesium di-tert-butoxide (165 mg, 0.97 mmol) at room temperature. The mixture was heated to 75° C. and the tosylate reagent (468 mg) was added, followed by stirring at that temperature. LC/MS after 3 h indicated that the reaction was finished. The reaction was quenched with ether and extracted with DCM. The organic layer was dried over Na$_2$SO$_4$, filtered, concentrated, and purified by silica gel chromatography, using linear gradient of MeOH in DCM as eluent. $^1$H NMR (CDCl$_3$) δ 1.17-1.23 (m, 6H), δ 3.35 (s, 3H), δ 3.64 (t, 2H), δ 3.78-3.86 (m, 1H), δ 3.91-3.4.15 (m, 8H), δ 4.22-4.44 (m, 4H), δ 6.54 (bs, 2H), δ 6.79-6.92 (m, 3H), δ 7.18-7.24 (m, 2H), δ 7.72 (s, 1H); MS: 510.3 (M+1).

Step 3: Preparation of (2-(6-amino-8-bromo-2-(2-methoxy-ethoxy)purin-9-yl)-1-(phenoxymethyl)ethoxymethyl)phosphonic acid diethyl ester. (33)

To a solution of the phosphonate prepared in step 2 (300 mg, 0.59 mmol) in CH$_3$CN (5 ml) was added NBS (157 mg, 0.88 mmol) at room temperature. The reaction mixture was stirred at room temperature for 1 h. The solvent was removed and the residue was washed with sat. aq Na$_2$SO$_3$ solution. The aqueous phase was extracted again with DCM. The organic layer was dried over Na$_2$SO$_4$, filtered, concentrated, and purified by prep HPLC on a C18 column, eluting with a gradient of 5-95% CH$_3$CN in H$_2$O as solvent. $^1$H NMR (CDCl$_3$) δ 1.19-1.27 (m, 6H), δ 3.40 (s, 3H), δ 3.68 (t, 2H), δ 3.84-3.3.88 (m, 1H), δ 3.93-4.10 (m, 8H), δ 4.30-4.36 (m, 4H), δ 6.30 (bs, 2H), δ 6.83-6.97 (m, 3H), δ 7.23-7.28 (m, 2H); MS: 588.2 (M+1).

Step 4: preparation of (2-(6-Amino-8-hydroxy-2-(2-methoxy-ethoxy)-purin-9-yl)-1-(phenoxymethyl) ethoxymethyl)phosphonic acid. (Example O)

A mixture of bromide prepared in step 3 (50 mg) in 1 N HCl (2.5 ml) was heated at 150° C. in a microwave reactor for 12 min. The solvent was removed under vacuum and the product was purified by prep HPLC on a C18 column, eluting with a gradient of 5-95% CH$_3$CN in H$_2$O. $^1$H NMR (CDCl$_3$) δ 3.37 (s, 3H), 63.65 (t, 2H), δ 3.91-3.96 (m, 2H), δ 3.10-3.20 (m, 4H), δ 4.23-4.4.27 (m, 1H), δ 4.32 (t, 2H), δ 6.85-6.94 (m, 3H), δ 7.21-7.27 (M, 1H); MS: 470.2 (M+1), 468.1 (M−1).

Example P

Scheme 25

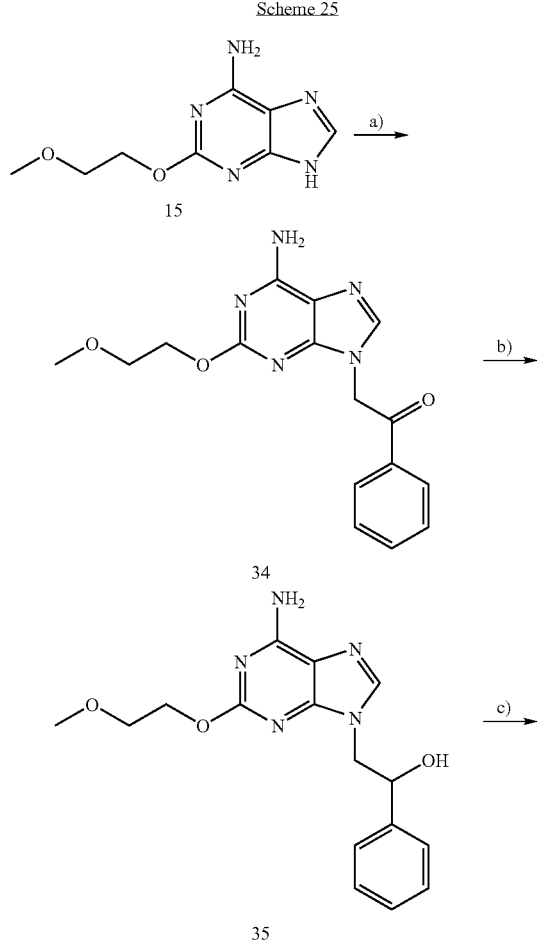

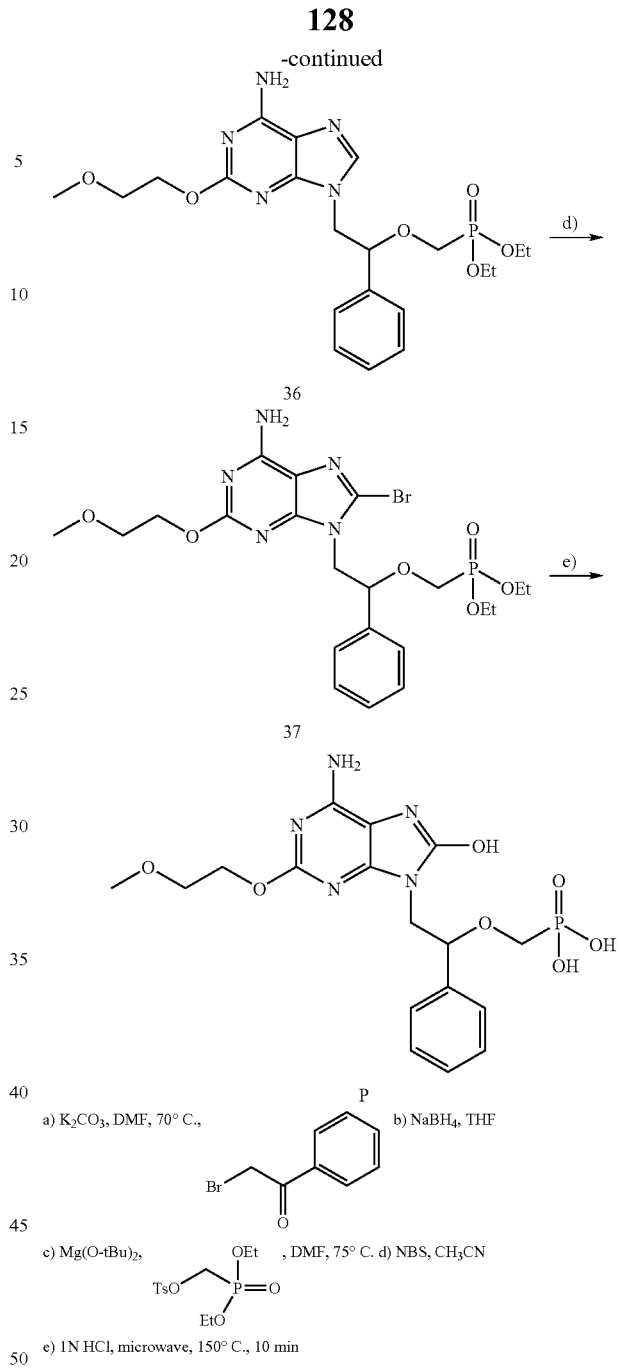

a) K$_2$CO$_3$, DMF, 70° C., b) NaBH$_4$, THF c) Mg(O-tBu)$_2$, [phosphonate reagent], DMF, 75° C. d) NBS, CH$_3$CN e) 1N HCl, microwave, 150° C., 10 min Step 1: Preparation of 2-(6-amino-2-(2-methoxy-ethoxy)purin-9-yl)-1-phenylethanone. (34)

To a suspension of 6-amino-2-(2-methoxyethoxy)adenine (500 mg, 2.39 mmol) in DMF (5 ml) was added K$_2$CO$_3$ (330 mg, 2.39 mmol). Then 2-bromoacetophenone was added and the reaction mixture was heated to 70° C. with stirring for 30 min. The solvent was removed under vacuum and the residue was washed with brine. The aqueous phase was extracted with DCM and the organic layer was dried over Na$_2$SO$_4$, filtered, concentrated, and purified by silica gel chromatography using linear gradient of MeOH in DCM as eluent. $^1$H NMR (CDCl$_3$) δ 3.40 (s, 3H), δ 3.72 (t, 2H), δ 4.45 (t, 2H), δ 5.58 (s, 2H), δ 5.67 (bs, 2H), δ 7.53-7.74 (m, 4H), δ 8.03 (s, 1H), δ 8.06 (s, 1H); MS: 328.2 (M+1), 326.0 (M−1).

Step 2: 2-(6-amino-2-(2-methoxyethoxy)purin-9-yl)-1-phenylethanol. (35)

To a suspension of ethanone prepared in step 1 (60 mg, 0.18 mmol) in THF, was added NaBH$_4$ at room temperature. The reaction was complete after stirring at room temperature for 1 h. The solvent was removed under vacuum and the residue was washed with sat. aq. NaHCO$_3$ solution. The aqueous phase was extracted with DCM. The organic layer was dried over Na$_2$SO$_4$, filtered, concentrated, and purified by silica gel chromatography using a liner gradient of MeOH in DCM as eluent. $^1$H NMR (CDCl$_3$) δ 3.36 (s, 3H), δ 3.68 (t, 2H), δ 4.07-4.38 (m, 4H), δ 5.12-5.14 (m, 1H), δ 6.36 (bs, 2H), δ 7.26-7.38 (m, 5H), δ 7.51 (s, 1H); MS: 330.1 (M+1).

The other steps were carried out according to the procedures used in preparing Example O.

(2-(6-Amino-2-(2-methoxyethoxy)purin-9-yl)-1-phenylethoxymethyl)phosphonic acid diethyl ester. (36) $^1$H NMR (CDCl$_3$): δ 1.09-1.16 (m, 6H)>3.30 δ (s, 3H), δ 3.38-3.63 (m, 4H), δ 3.84-3.98 (m, 4H), δ 4.14-4.34 (m, 4H), δ 4.65-4.71 (m, 1H), δ 6.57 (bs, 2H), δ 7.20-7.24 (m, 5H), δ 7.60 (s, 1H); MS: 480.2 (M+1).

(2-(6-Amino-8-bromo-2-(2-methoxyethoxy)purin-9-yl)-1-phenylethoxymethyl)phosphonic acid diethyl ester. (37) $^1$H NMR (CDCl$_3$): δ 1.20-1.31 (m, 6H), δ 3.42-3.77 (m, 5H), δ 3.78 (t, 2H), δ 3.91-4.06 (m, 4H), δ 4.16-4.51 (m, 4H), δ 4.96-5.00 (m, 1H), δ 5.73 (bs, 2H), δ 7.30-7.40 (m, 5H); MS: 480.2 (M+1).

(2-(6-Amino-8-hydroxy-2-(2-methoxyethoxy)purin-9-yl)-1-phenylethoxymethyl)phosphonic acid. (Example P) $^1$H NMR (CD$_3$OD): δ 3.42 (s, 3H), δ 3.45-3.59 (m, 2H), δ 3.74 (t, 2H), δ 3.92-4.22 (m, 2H), δ 4.41 (t, 2H), δ 4.93-4.98 (m, 1H), δ 7.30-7.43 (m, 5H); MS: 440.1 (M+1), 438.2 (M−1).

Example Q

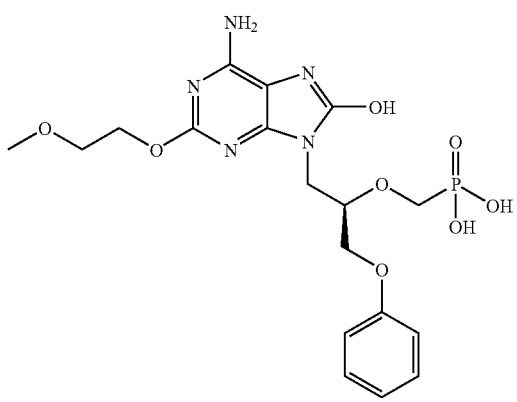

(2-(6-Amino-8-hydroxy-2-(2-methoxy-ethoxy)-purin-9-yl)-1-(R)-phenoxymethylethoxymethyl)-phosphonic acid (Example Q)

Example Q were prepared using procedures similar to those used to prepare Example O, except that R-2-epoxy-3-phenoxy-propane was used instead of racemic 2-epoxy-3-phenoxy-propane in step a). Enantiomerically pure 2-epoxy-3-phenoxy-propane was made from chiral glycidyl tosylate according to the procedure described in *Journal of Organic Chemistry*, 1989, 54, 1295-1304. $^1$H NMR (CD$_3$OD) δ 3.37 (s, 3H), δ 3.64 (t, 2H), δ 3.91-3.96 (m, 2H), δ 4.12-4.25 (m, 5H), δ 4.32 (t, 2H), δ 6.85-6.94 (m, 3H), δ 7.21-7.27 (m, 2H); $^{31}$P NMR (CD$_3$OD) 18.48 (s); MS: 470.2 (M+H)$^+$, 468.1 (M−1).

Example R

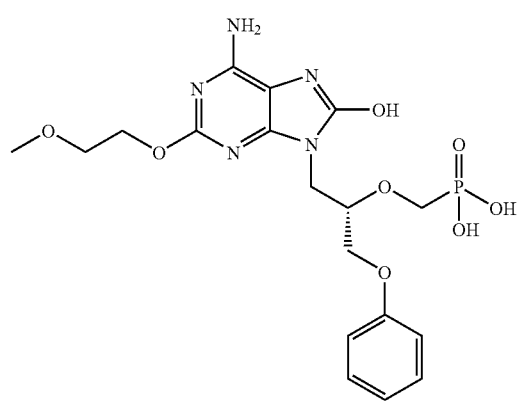

(2-(6-Amino-8-hydroxy-2-(2-methoxy-ethoxy)-purin-9-yl)-1-(S)-phenoxymethylethoxymethyl)-phosphonic acid (Example R)

Example R was prepared using procedures similar to those used to prepare Example O, except that S-2-epoxy-3-phenoxy-propane was used instead of racemic 2-epoxy-3-phenoxy-propane in step a). Enantiomerically pure 2-epoxy-3-phenoxy-propane was made from chiral glycidyl tosylate according to the procedure described in *Journal of Organic Chemistry*, 1989, 54, 1295-1304. $^1$H NMR (CD$_3$OD) δ 3.37 (s, 3H), δ 3.65 (t, 2H), δ 3.91-3.96 (m, 2H), δ 4.12-4.25 (m, 5H), δ 4.32 (t, 2H), δ 6.85-6.94 (m, 3H), δ 7.21-7.27 (m, 2H); $^{31}$P NMR (CD$_3$OD) δ 18.62 (s); MS: 470.1 (M+H)$^+$, 468.1 (M−1).

Examples S and T

Examples S and T were prepared using procedures similar to those used to prepare Example O except cis-stilbene oxide or cyclopentene oxide were used in the step 1, respectively. The spectral data of the two compounds (Example S and T) and intermediates are listed below.

Scheme 26

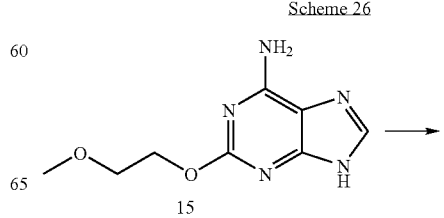

-continued

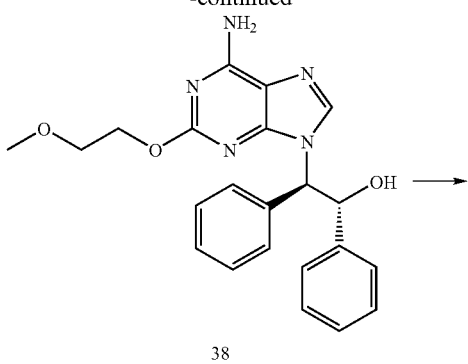

38

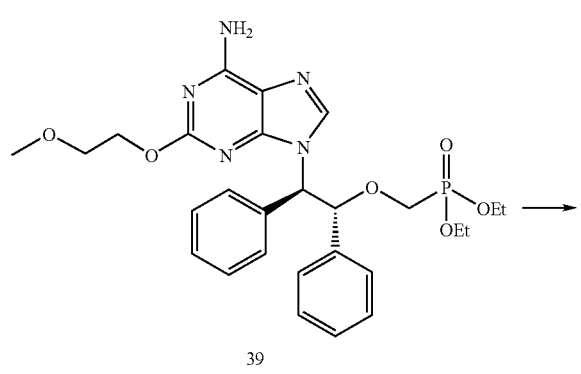

39

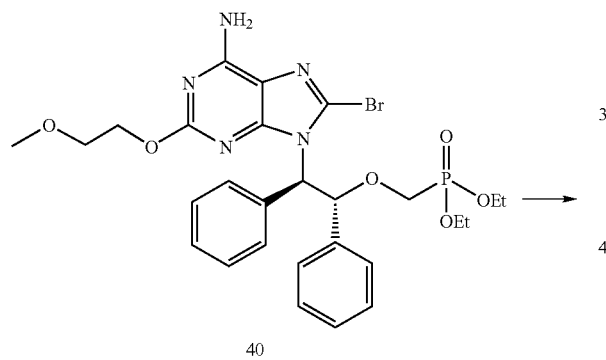

40

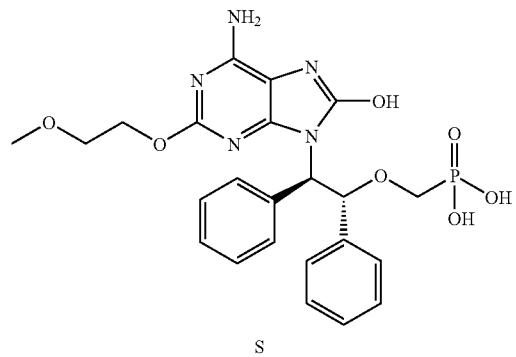

S 2-(6-Amino-2-(2-methoxy-ethoxy)-purin-9-yl)-1,2-diphenyl-ethanol (38)

$^1$H NMR (CDCl$_3$): δ 3.42 (s, 3H), δ 3.73 (t, 2H), δ 4.41-4.44 (m, 1H), δ 5.75 (s, 2H), δ 5.88 (bs, 2H), δ 7.18-7.28 (m, 10H), δ 7.75 (s, 1H); MS: 406.1 (M+H)$^+$.

(2-(6-Amino-2-(2-methoxy-ethoxy)-purin-9-yl)-1,2-diphenyl-ethoxymethyl)-phosphonic acid diethyl ester (39)

$^1$H NMR (CDCl$_3$): δ 1.21-1.29 (m; 6H), δ 3.42 (s, 3H), δ 3.57-3.74 (m, 5H), δ 3.95-4.04 (m, 4H), δ 4.37-4.42 (m, 2H), δ 5.56 (d, 1H), δ 5.76 (d, 1H), δ 5.93 (bs, 2H), δ 7.12-7.31 (m, 10H), δ 8.21 (s, 1H); MS: 554.1 (M−1).

(2-(6-Amino-8-bromo-2-(2-methoxy-ethoxy)-purin-9-yl)-1,2-diphenyl-ethoxymethyl)-phosphonic acid diethyl ester (40)

$^1$H NMR (CDCl$_3$): δ 1.11-1.19 (m, 6H), δ 3.50 (s, 3H), δ 3.61 (d, 2H), δ 3.76-3.96 (m, 6H), δ 4.59-4.68 (m, 2H), δ 6.59 (d, 1H), δ 5.80 (bs, 2H), δ 6.15 (d, 1H), δ 7.14-7.37 (m, 10H); MS: 634.0 (M+H)$^+$.

(2-(6-Amino-8-hydroxy-2-(2-methoxy-ethoxy)-purin-9-yl)-1,2-diphenyl-ethoxymethyl)-phosphonic acid (Example S)

$^1$H NMR (CD$_3$OD): δ 3.45 (s, 3H), δ 3.48-3.57 (m, 2H), δ 3.82 (t, 2H), δ 4.60 (t, 3H), δ 5.56 (d, 1H), δ 5.92 (d, 1H), δ 7.16-7.41 (m, 10H); MS: 516.1 (M+H)$^+$, 514.1 (M−1).

Example T

Scheme 27

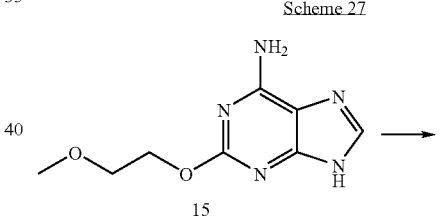

15

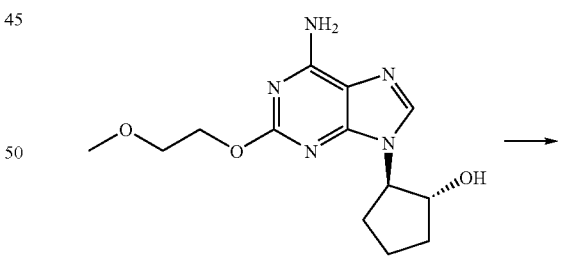

41

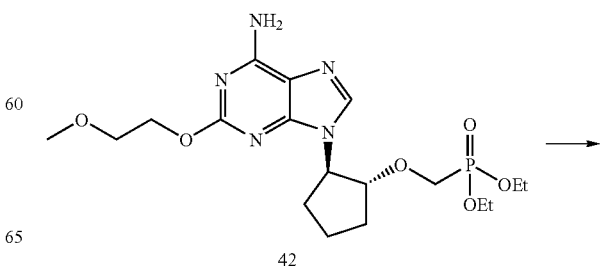

42

133
-continued

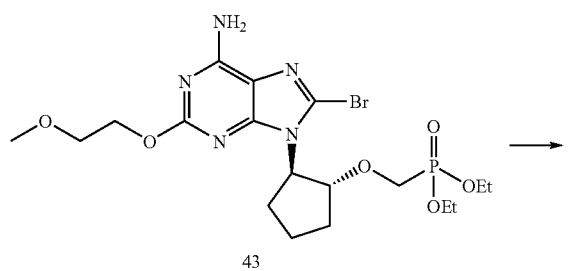
43

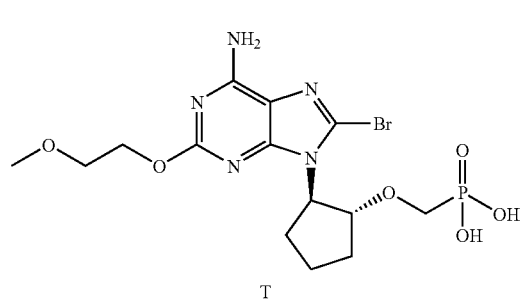
T 2-(6-Amino-2-(2-methoxy-ethoxy)-purin-9-yl)-cyclopentanol (41)

$^1$H NMR (CDCl$_3$): δ 1.82-2.27 (m, 6H), δ 2.46-2.49 (m, 1H), δ 3.44 (s, 3H), δ 3.77 (t, 2H), δ 4.37-4.41 (m, 1H), δ 4.44 (t, 2H), δ 4.48-4.53 (m, 1H), δ 5.80 (bs, 2H), δ 7.63 (s, 1H); MS: 294.1 (M+H)$^+$.

(2-(6-Amino-2-(2-methoxy-ethoxy)-purin-9-yl)-cyclopentyloxymethyl)-phosphonic acid diethyl ester (42)

$^1$H NMR (CDCl$_3$): δ 1.25-1.30 (M, 4H), δ 1.84-2.34 (m, 6H), δ 3.45 (s, 3H), δ 3.73-3.80 (m, 4H), δ 4.05-4.11 (m, 2H), δ 4.44-4.49 (m, 3H), δ 4.68-4.69 (m, 1H), δ 5.78 (bs, 2H), δ 7.70 (s, 1H); MS: 444.1 (M+H)$^+$.

(2-(6-Amino-8-bromo-2-(2-methoxy-ethoxy)-purin-9-yl)-cyclopentyloxymethyl)-phosphonic acid diethyl ester (43)

$^1$H NMR (CDCl$_3$): δ 1.23-1.30 (m, 4H), δ 1.82-2.36 (m, 6H), δ 3.45 (s, 3H), δ 3.64-3.76 (m, 2H), δ 3.77 (t, 2H), δ 4.04-4.13 (m, 2H), δ 4.45 (t, 2H), δ 4.73-4.78 (m, 2H), δ 5.77 (bs, 2H); MS: 522.0 (M+H)$^+$.

(2-(6-Amino-8-hydroxy-2-(2-methoxy-ethoxy)-purin-9-yl)-cyclopentyloxymethyl)-phosphonic acid (Example T)

$^1$H NMR (CD$_3$OD): δ 1.81-1.87 (m, 2H), δ 1.95-2.13 (m, 2H), δ 2.18-2.28 (m, 2H), δ 3.41 (s, 3H), δ 3.60-3.71 (m, 2H), δ 3.74 (t, 2H), δ 4.43 (t, 2H), δ 4.59-4.68 (m, 2H); MS: 404.0 (M+H)$^+$, 403.1 (M−1).

134
Example U

Scheme 28

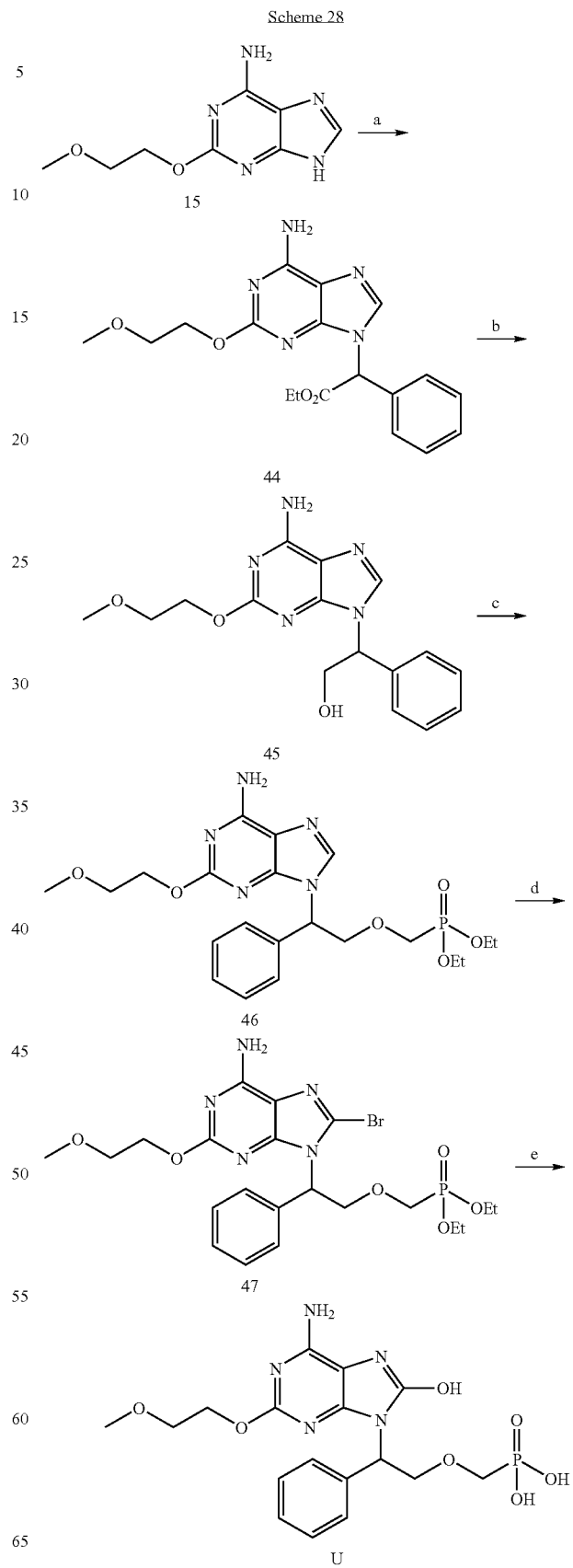

a) 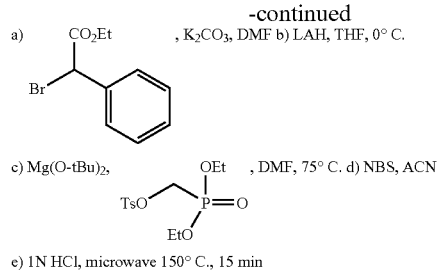, K₂CO₃, DMF b) LAH, THF, 0° C.

c) Mg(O-tBu)₂, TsO-CH₂-P(=O)(OEt)(OEt), DMF, 75° C. d) NBS, ACN e) 1N HCl, microwave 150° C., 15 min

Step 1: synthesis of (6-Amino-2-(2-methoxy-ethoxy)-purin-9-yl)-phenyl-acetic acid ethyl ester (44)

To a suspension of 2-methoxylethoxyadenine (500 mg, 2.39 mmol) in DMF (5 ml), was added K₂CO₃ (329 mg, 2.39 mmol) and ethyl α-bromophenylacetate (460 μl, 2.68 mmol). The reaction mixture was allowed to react at 70° C. for 2 h. The reaction mixture was washed with water and extracted by DCM. The organic later was dried over Na₂SO₄. The organic layer then was filtered, concentrated and purified by silica gel column, using dichlormethane and MeOH as the solvent in a linear gradient. $^1$H NMR (CDCl₃): δ 1.31 (t, 3H), δ 3.45 (s, 3H), δ 3.78 (t, 2H), δ 4.29-4.33 (m, 2H), δ 4.51 (t, 2H), δ 5.83 (bs, 2H), δ 7.41-7.42 (m, 5H), δ 7.78 (s, 1H); MS: 372.1 (M+H)⁺, 370.1 (M−1).

Step 2: synthesis of 2-(6-Amino-2-(2-methoxy-ethoxy)-purin-9-yl)-2-phenyl-ethanol (45)

To a solution of ester made above (360 mg, 0.89 mmol) in THF (5 ml), was added LAH (101 mg, 2.67 mmol) in one portion at 0° C. The reaction mixture was stirred at 0° C. for ½ h, until reaction finished. The reaction was quenched with a few drops of 1N HCl, then washed with water and extracted with dichlormethane. The organic was dried over Na₂SO₄, filtered, concentrated and purified by silica gel chromatography, using dichloromethane and MeOH as the solvent in a linear gradient to give 260 mg product. $^1$H NMR (CDCl₃): δ 3.42 (s, 3H), δ 3.76 (t, 2H), δ 4.32 (d, 2H), δ 4.52-4.59 (m, 3H), δ 7.37-7.43 (m, 5H); MS: 372.1 (M+H)⁺.

(2-(6-Amino-2-(2-methoxy-ethoxy)-purin-9-yl)-2-phenyl-ethoxymethyl)-phosphonic acid diethyl ester (46)

$^1$H NMR (CDCl₃): δ 1.24-1.28 (m, 6H), δ 3.43 (s, 3H), δ 3.75 (t, 2H), δ 3.81-3.87 (m, 2H), δ 4.03-4.09 (m, 4H), δ 4.20-4.23 (M, 1H), δ 4.17 (t, 2H), δ 4.56-4.60 (m, 1H), δ 5.84-5.87 (m, 1H), δ 5.88 (bs, 2H), δ 7.34-7.36 (m, 5H), δ 7.92 (s, 1H); MS: 480.1 (M+H)⁺.

(2-(6-Amino-8-bromo-2-(2-methoxy-ethoxy)-purin-9-yl)-2-phenyl-ethoxymethyl)-phosphonic acid diethyl ester (47)

$^1$H NMR (CDCl₃): δ 1.22-1.27 (m, 6H), δ 3.45 (s, 3H), δ 3.82-3.85 (m, 2H), δ 3.99-4.07 (m, 4H), δ 4.30-4.34 (m, 1H), δ 4.48 (t, 2H), δ 5.11 (t, 1H), δ 5.82-5.85 (m, 3H), δ 7.28-7.36 (m, 3H), δ 7.47-7.49 (m, 2H); MS: 558.0 (M+H)⁺.

(2-(6-Amino-8-hydroxy-2-(2-methoxy-ethoxy)-purin-9-yl)-2-phenyl-ethoxymethyl)-phosphonic acid (Example U)

$^1$H NMR (CD₃OD) δ 3.40 (s, 3H), δ 3.72 (t, 2H), δ 3.77-3.79 (q, 2H), δ 4.20-4.23 (q, 1H), δ 4.42 (t, 3H), δ 4.90-4.94 (m, 2H), δ 5.70-5.74 (q, 1H), δ 7.30-7.36 (m, 3H), δ 7.52 (d, 2H); MS: 440.1 (M+H)⁺, 438.1 (M−1).

Example V

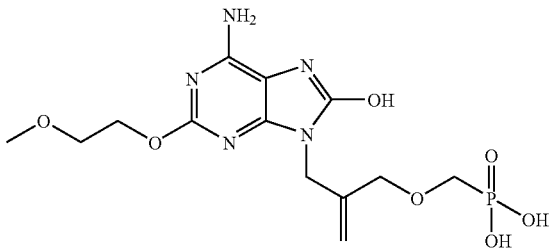

V

Scheme 29

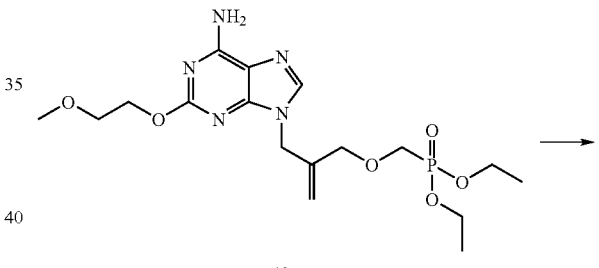

48

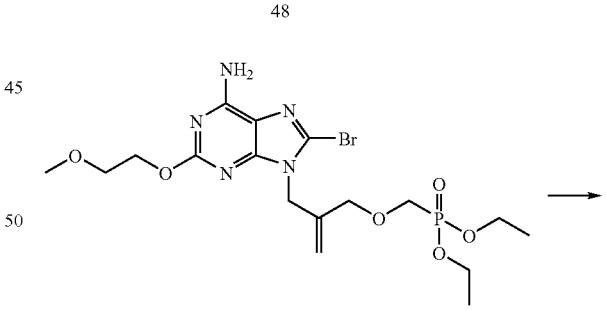

49

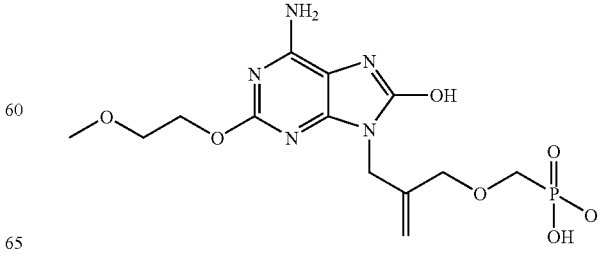

V (2-(6-Amino-2-(2-methoxy-ethoxy)-purin-9-ylm-ethyl)-allyloxymethyl)-phosphonic acid diethyl ester (48)

Compound 48 was prepared by alkylating Compound 15 with the corresponding bromide, using the procedures similar to those shown in Scheme 28.
$^1$H NMR (CDCl$_3$): δ 1.35 (t, 3H), δ 3.42 (s, 3H), δ 3.73 (s, 2H), δ 3.76 (s, 2H), δ 4.06 (s, 2H), δ 4.13-4.23 (m, 4H), δ 4.45 (t, 2H), δ 4.75 (t, 2H), δ 4.75 (s, 2H), δ 5.02 (s, 1H), δ 5.24 (s, 1H), δ 5.94 (bs, 2H), δ 7.71 (s, 1H).

(2-(6-Amino-8-bromo-2-(2-methoxy-ethoxy)-purin-9-ylmethyl)-allyloxymethyl)-phosphonic acid diethyl ester (49)

$^1$H NMR (CDCl$_3$): δ 1.34 (t, 6H), δ 3.41 (s, 3H), 63.70-3.79 (m, 4H), δ 4.13-4.23 (m, 6H), δ 4.43 (t, 2H), δ 4.72 (s, 3H), δ 5.21 (s, 1H), δ 6.04 (s, 2H); MS: 508.2 (M+H)$^+$.

(2-(6-Amino-8-hydroxy-2-(2-methoxy-ethoxy)-purin-9-ylmethyl)-allyloxymethyl)-phosphonic acid (Example V)

$^1$H NMR (CD$_3$OD) δ 3.39 (s, 3H), δ 3.67-3.73 (m, 4H), δ 4.17 (s, 2H), δ 4.40 (t, 2H), 64.47 (s, 2H), 64.88 (s, 1H, which is cover by the H$_2$O peak in CD$_3$OD), δ 5.21 (s, 1H); MS: 390.1 (M+H)$^+$, 388.0 (M−1).

Example W

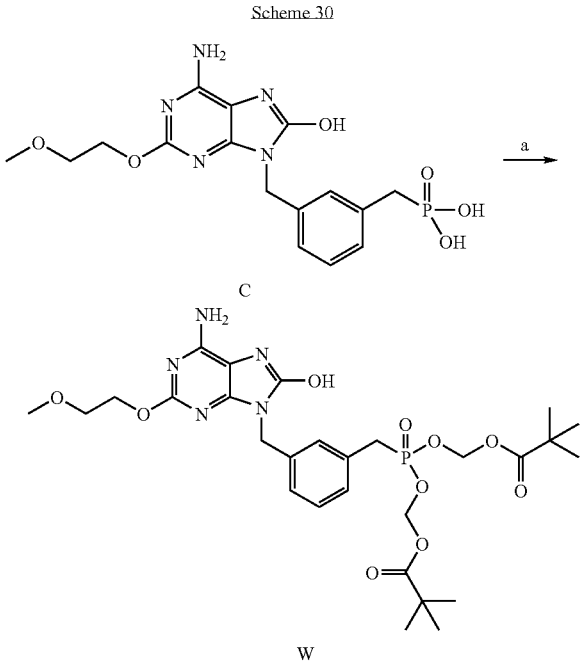

a) N,N'-dicyclohexyl-4-morpholine-carboxamidine, chloromethyl pivalate, DMF, 60° C.

Synthesis of 2,2-Dimethyl-propionic acid (3-(6-amino-8-hydroxy-2-(2-methoxy-ethoxy)-purin-9-ylmethyl)-benzyl)-(2,2-dimethyl-propionyloxymethoxy)-phosphinoyloxymethyl ester (Example W)

To a suspension of (3-(6-Amino-8-hydroxy-2-(2-methoxy-ethoxy)-purin-9-ylmethyl)-benzyl)-phosphonic acid (Example C)(50 mg, 0.12 mmol) in DMF (2 ml) was added N,N'-dicyclohexyl-4-morpholine-carboxamidine (71 mg, 0.24 mmol) and chloromethyl pivalate (90 L$^1$, 0.60 mmol). The reaction mixture was stirred at 60° C. overnight. The reaction mixture was purified by Prep-HPLC on a C18 column, eluting with a gradient of 5-95% acetonitrile in water as solvent. $^1$H NMR (CDCl$_3$, 300 MHz) δ 1.19 (s, 18H), δ 3.21 (d, 2H), δ 3.41 (s, 3H), δ 3.72 (t, 3H), δ 4.44 (s, 2H), δ 5.01 (s, 2H), δ 5.59 (d, 4H), δ 5.77 (bs, 2H), δ 7.18-7.34 (m, 4H), δ 10.43 (bs, 1H); $^{31}$P NMR (CDCl$_3$, 300 MHz): δ 27.18 (s); MS: 638.2 (M+H)$^+$.

Example X

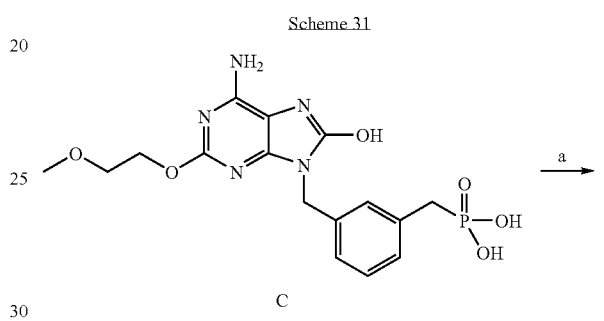

a) diesopropylethyl amine, chloromethyl povalate, DMF, 60° C.

Synthesis of 2,2-Dimethyl-propionic acid (3-(6-amino-8-hydroxy-2-(2-methoxy-ethoxy)-purin-9-ylmethyl)-benzyl)-hydroxy-phosphinoyloxymethyl ester (X)

To a solution of (3-(6-Amino-8-hydroxy-2-(2-methoxy-ethoxy)-purin-9-ylmethyl)-benzyl)-phosphonic acid (Example C) (50 mg, 0.12 mmol) in DMF, was added diisopropylethylamine (110 µl, 0.60 mmol), and chloromethyl pivalate. The reaction mixture stirred at 60° C. After checking the reaction after 6 h by LC/MS, about 60% starting material was converted to desired product. The product was isolated by prep-HPLC on a C18 column, eluting with a gradient of 5-95% acetonitrile in water as solvent. $^1$H NMR (CDCl$_3$, 300 MHz) δ 1.21 (s, 9H), δ 3.01 (d, 2H), δ 3.39 (s, 3H), δ 3.17 (t, 3H), δ 4.42 (t, 3H), δ 4.92 (s, 2H), δ 5.60 (d, 2H), δ 7.17-7.37 (m, 4H), δ 10.64 (s, 1H); MS: 524.1 (M+H)$^+$, 531.9 (M−1).

Example Y

Scheme 32

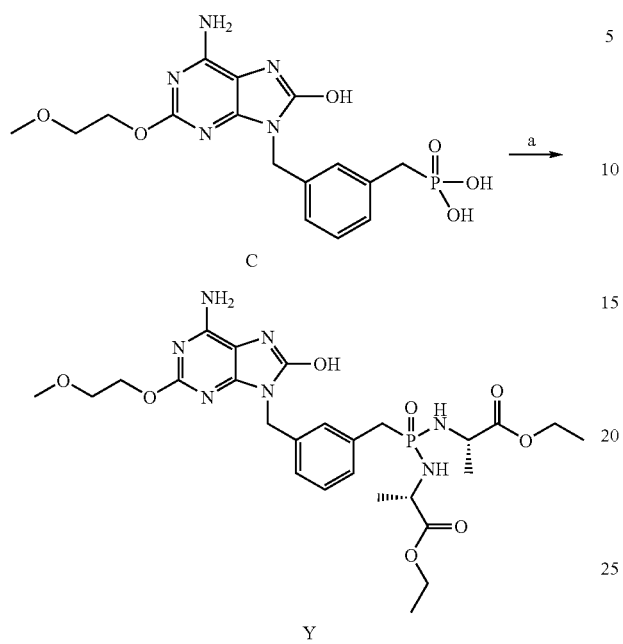

a) PPh3, Aldrithiol-2, Ala-OEt·HCl, pyridine

Synthesis of Example Y

To a solution of L-alanine ethyl ester hydrochloride (56 mg, 0.36 mmol) in pyridine, was added triphenyl phosphate (190 mg, 0.72 mmol), aldrithiol-2 (160 mg, 0.72 mmol), and (3-(6-Amino-8-hydroxy-2-(2-methoxy-ethoxy)-purin-9-yl-methyl)-benzyl)-phosphonic acid (30 mg, 0.073 mmol). The reaction mixture was stirred at 60° C. for 4 h. After the reaction was finished, NaHCO$_3$ (60 mg) was added and the mixture was stirred at RT for 10 min. The solvent was removed, and the residue was dissolved in DCM and purified by 4 g silica gel column. The column was eluted with 50% EtOAc/hexane to wash out all yellow color. Then the product was eluted with 20% EtOH/EtOAc. The fraction with product (Example Y) was concentrated and purified again by prep HPLC using 5-100% acetonitrile in water. $^1$H NMR (CDCl$_3$, 300 MHz): δ 1.20 (t, 6H), 61.27-1.34 (m, 6H), δ 3.14 (d, 2H), δ 3.28-3.44 (m, 5H), δ 3.71 (t, 2H), δ 3.87-3.98 (M, 2 h), δ 4.08-4.14 (M, 4H), δ 4.43 (t, 2H), δ 4.97 (s, 2H), δ 5.99 (bs, 2H), δ 7.16-7.40 (m, 4H), δ 10.54 (s, 1H); $^{31}$P NMR (CDCl$_3$, 300 MHz): δ 25.65 (s); MS: 608.2 (M+H), 606.2 (M−1).

Example Z was isolated from the reaction above.

Z

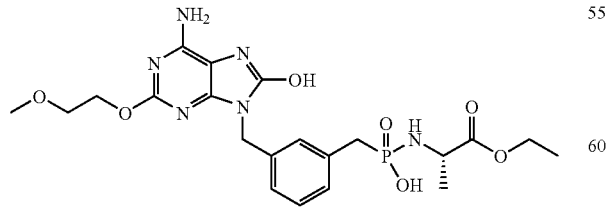

$^1$H NMR (CDCl$_3$) δ 1.33 (t, 3H), δ 1.50 (d, 3H), δ 3.01 (d, 2H), δ 3.39 (s, 3H), δ 3.70 (t, 2H), δ 3.92 (m, 1H), δ 4.05-4.29 (m, 4 h), δ 4.46 (s, 2H), δ 4.90 (s, 2H), δ 7.16-7.40 (m, 4H); MS: 509.1 (M+H)$^+$, 507.0 (M−1).

Examples AA and AB

Examples AA and AB were prepared using procedures similar to those used to prepare Example Y, except that different amino acids were used during the reaction.

AA

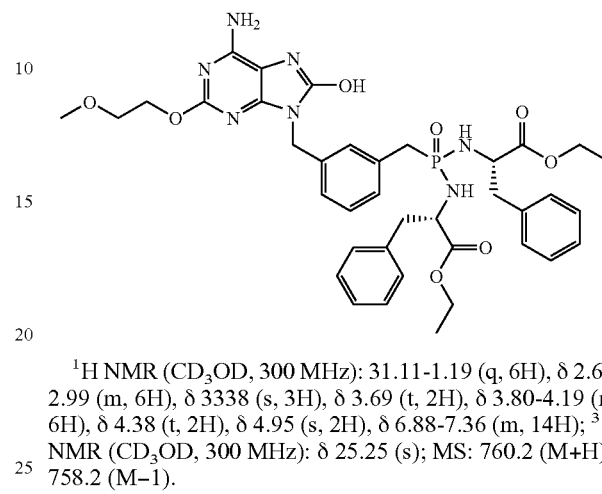

$^1$H NMR (CD$_3$OD, 300 MHz): 31.11-1.19 (q, 6H), δ 2.62-2.99 (m, 6H), δ 3338 (s, 3H), δ 3.69 (t, 2H), δ 3.80-4.19 (m, 6H), δ 4.38 (t, 2H), δ 4.95 (s, 2H), δ 6.88-7.36 (m, 14H); $^{31}$P NMR (CD$_3$OD, 300 MHz): δ 25.25 (s); MS: 760.2 (M+H)$^+$, 758.2 (M−1).

AB

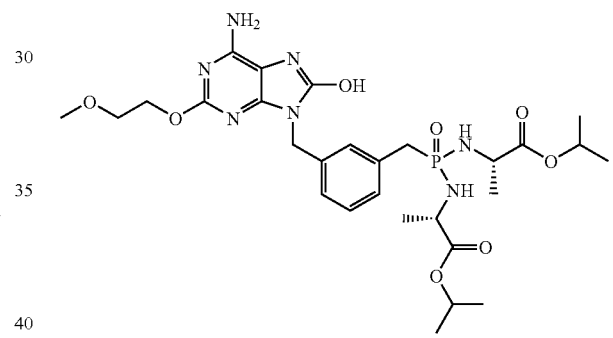

$^1$H NMR (CD$_3$OD, 300 MHz) δ 1.15-1.28 (m, 18H), δ 3.15 (d, 2H), δ 3.39 (s, 3H), δ 3.70-3.76 (m, 3H), δ 3.82-3.88 (m, 1), δ 4.44 (t, 2H), δ 4.88-4.96 (m, 2H), δ 4.98 (s, 2H), δ 7.27-7.39 (m, 4H); $^{31}$P NMR (CD$_3$OD, 300 MHz): 27.14 (s); MS: 636.1 (M+H)$^+$, 634.2 (M−1).

Example AC

Scheme 33

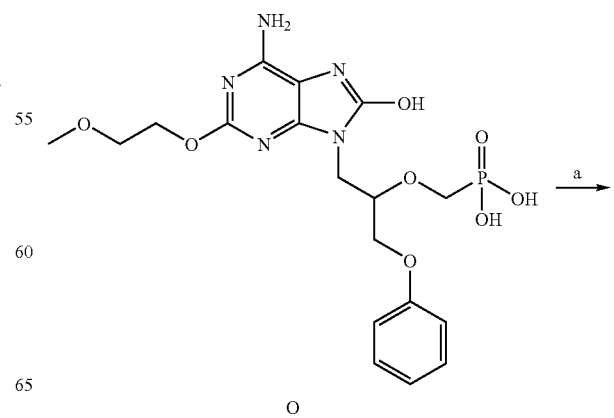

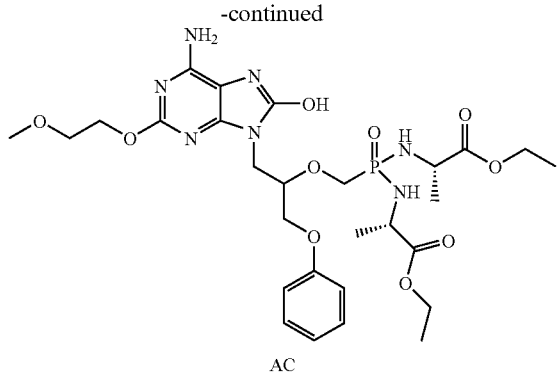

AC a) PPh3, Aldrithiol-2, Ala-OEt•HCl, pyridine

Synthesis of Example AC

To a solution of L-alanine ethyl ester hydrochloride (37 mg, 0.24 mmol) in pyridine (2 ml) was added triphenylphosphate (256 mg, 0.98 mmol), aldrithiol-2 (440 mg, 0.98 mmol) and (2-(6-Amino-8-hydroxy-2-(2-methoxy-ethoxy)-purin-9-yl)-1-phenoxymethyl-ethoxymethyl)-phosphonic acid (Example O) (23 mg, 0.049 mmol). The reaction mixture stirred at 60° C. for 4 h and cooled to rt. NaHCO$_3$ (50 mg) was added to the reaction mixture and it was stirred at rt for 10 min. The solvent was evaporated and the residue was dissolve in dichloromethane. The mixture was purified by 4 g silica gel chromatography. The column was eluted with 50% EtOAc/ hexane to get rid of yellow impurities. Then the desired product was eluted with 20% EtOH/ EtOAc. The fraction with product (Example AC) was concentrated and purified by prep-HPLC by 5-100% acetonitrile in water. $^1$H NMR (CDCl$_3$, 300 MHz): δ 1.19-1.22 (m, 6H), δ 1.35-1.38 (m, 6H), δ 3.38 (s, 3H), δ 3.54-3.64 (m, 2H), δ 3.87-4.30 (m, 18H), δ 5.99 (s, 2H), δ 6.87-7.26 (m, 5H), δ 10.52 (d, 1H); $^{31}$P NMR (CDCl$_3$, 300 MHz): δ 22.26 (s), δ 22.33 (s); MS: 668.2 (M+H)$^+$, 666.2 (M−1).

Examples AD, AE, and AF

Examples AD, AE, and AF were prepared using procedures similar to shown in Scheme 32 except that different amino acid esters were used in the reaction.

AD

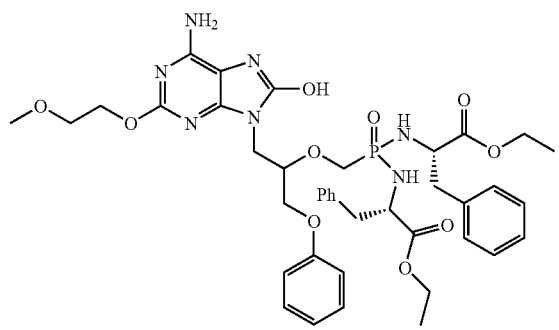

$^1$H NMR (CD$_3$OD, 300 MHz) δ 1.10-1.21 (m, 6H), (2.72-3.05 (m, 4H), δ 3.36 (d, 3H), δ 3.43-3.74 (m, 4H), δ 3.93-4.14 (m, 11H), δ 4.27-4.31 (m, 2H), (6.84-7.28 (m, 15H); 31P NMR (CD$_3$OD, 300 MHz): (23.17 (s), (23.25 (s); MS: 820.3 (M+H)$^+$, 818.3 (M−1).

AE

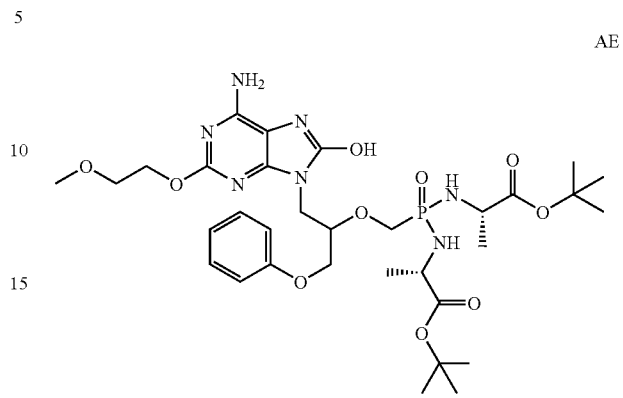

1H NMR (CD3OD, 300 MHz): (1.30 (s, 3H), (1.32 (s, 3H), (1.42 (s, 9H), (1.45 (s, 9H), (3.37 (s, 3H), (3.65 (t, 3H), (3.78-3.87 (m, 2H), (3.95-3.98 (m, 2H), (4.12-4.16 (m, 2H), (4.20-4.24 (m, 2H), (4.21-4.33 (m, 2H), (6.90-6.95 (m, 3H), (7.23-7.28 (m, 2H); 31P NMR (CD3OD, 300 MHz): (23.55 (s), (23.75 (s); MS: 724.2 (M+H)$^+$, 722.2 (M−1).

AF

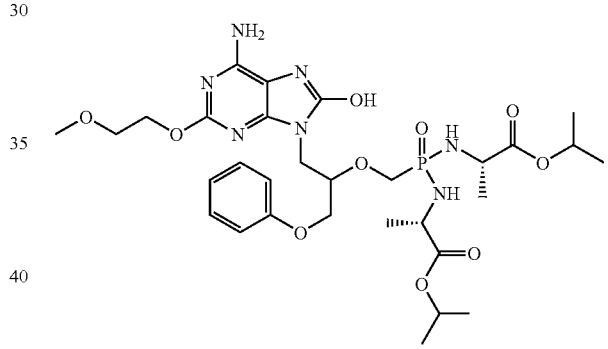

1H NMR (CD3OD, 300 MHz) (1.19-1.24 (m, 12H), (1.31-1.34 (m, 6H), (3.37 (d, 3H), (3.63-3.67 (m, 2H), (3.90-4.00 (m, 4H), (4.12-4.15 (m, 3H), (4.32-4.34 (m, 2H), (4.90-4.97 (m, 2H), (6.90-6.96 (m, 3H), (7.23-7.28 (m, 2H); 31P NMR (CD3OD, 300 MHz): (23.52 (s), (23.74 (s); MS: 696.2 (M+H)+, 694.1 (M−1).

Example AG

Scheme 34

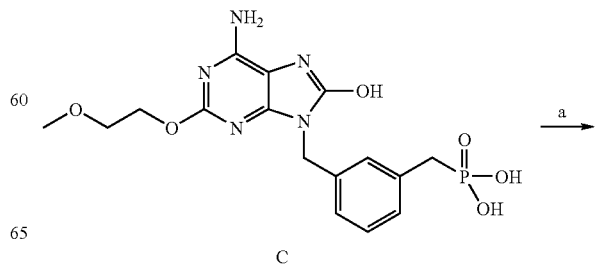

C

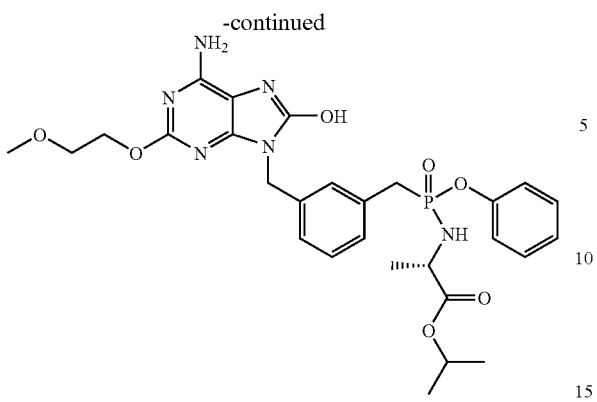

AG a) Ala-OiPr•HCl, Phenol, TEA, PPh₃, aldrithiol-2, pyridine, 60° C.

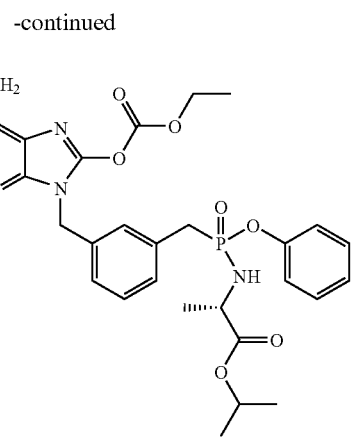

AH a) TEA, ethyl chloroformate, DCM

Synthesis of Example AG

To a solution of (3-(6-Amino-8-hydroxy-2-(2-methoxyethoxy)-purin-9-ylmethyl)-benzyl)-phosphonic acid (40 mg, 0.098 mmol) in pyridine (2 ml), was added L-alanine isopropyl ester hydrochloride (33 mg, 0.19 mmol), triethyl amine (170 μl, 1.16 mmol), phenol (46 mg, 4.85 mmol), triphenylphosphate (180 mg, 0.69 mmol), aldrithiol-2 (150 mg, 0.69 mmol). The reaction mixture was stirred at 60° C. overnight. The solvent was removed, and the residue was dissolved in dichloromethane and purified using 4 g silica gel chromatography. The column was eluted with 50% EtOAc/hexane to wash out the yellow impurities and then the product was eluted with 20% EtOH/EtOAc. The organic fraction with product (Example AG) was concentrated and purified again by prep-HPLC using 5-100% acetonitrile in water. $^1$H NMR (CDCl$_3$, 300 MHz): (1.12-1.17 (m, 9H), (3.38 (s, 3H), (3.49-3.53 (m, 1H), (3.70 (t, 2H), (3.88-3.92 (m, 1H), (4:45 (t, 2H), (4.89-4.94 (m, 1H), (4.99 (s, 2H), (6.26 (bs, 1H), (7.00-7.46 (m, 9H), (10.41 (s, 1H); $^1$H NMR (CD$_3$OD): (1.00-1.20 (m, 9H), (3.34-3.38 (m, 5H), (3.69 (t, 2H), (3.72-3.81 (m, 1H), (4.41 (t, 3H), (4.86 (m, 1H), (5.00 (s, 2H), (6.98-7.41 (m, 9H); $^{31}$P NMR (CDCl$_3$, 300 MHz): (27.06 (s), (27.11 (s); $^{31}$P NMR (CD$_3$OD): (28.36 (s), (28.76 (s); MS: 599.2 (M+H)$^+$, 597.2 (M−1);

Example AH

Scheme 35

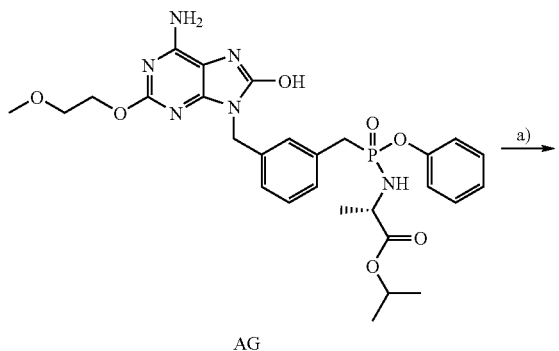

AG

Synthesis of Example AH

To a solution of compound AH (5.7 mg, 0.0096 mmol) in dichloromethane (0.5 ml) was added triethylamine (30 μl) and ethyl chloroformate (20 μl). The reaction mixture was stirred at rt for 10 min. The solvent was removed, and the residue was dissolved in DMF and purified by prep-HPLC using 5-100% acetonitrile in water. $^1$H NMR (CDCl$_3$): (1.10-1.20 (m, 9H), (1.22-1.46 (m, 3H), (3.13-3.36 (m, 4H), (3.41 (s, 3H), (3.71 (t, 2H), (3.92-4.00 (m, 1H), (4.42-4.50 (m, 4H), (4.86-4.99 (m, 3H), (7.01-7.52 (m, 9H); $^{31}$P NMR (CDCl$_3$): (25.61 (s), (25.86 (s); MS: 671.2 (M+H)$^+$.

Examples AI, AJ, AK, AL, AM, AN, AO, and AP

Examples AI, AJ, AK, AL, AM, AN, AO, and AP were prepared from chiral phosphonic acid example Q and R using procedures similar to those used to prepare Example AC.

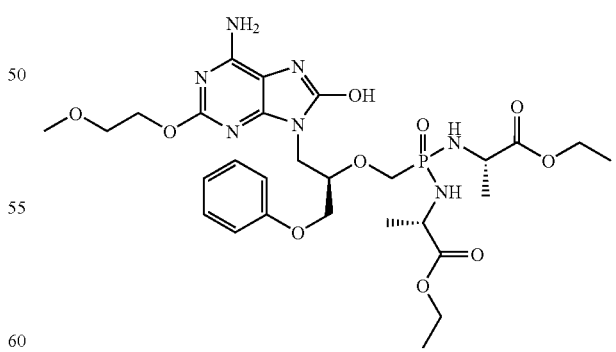

AI $^1$H NMR (CD$_3$OD, 300 MHz): δ 1.19-1.27 (m, 6H), (1.32-1.36 (m, 6H), (3.37 (s, 3H), (3.65 (t, 2H), (3.90-4.00 (m, 4H), (4.03-4.23 (m, 9H), (4.32 (t, 2H), (6.89-6.96 (m, 3H), (7.23-7.29 (m, 2H); $^{31}$P NMR (CD$_3$OD, 3001 Hz): (23.58; MS: 668.2 (M+H)$^+$; 666.2 (M−1).

145
AJ
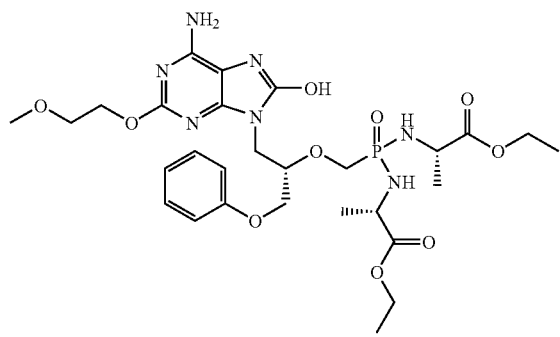
1H NMR (CD3OD, 300 MHz): (1.20-1.27 (m, 6H), (1.33-1.36 (m, 6H), (3.38 (s, 3H), (3.65 (t, 2H), (3.93-4.01 (m, 4H), (4.07-4.16 (m, 7H), (4.20-4.28 (m, 2H), (4.32 (t, 2H), (6.89-6.96 (m, 3H), (7.26 (t; 2H); 31P NMR (CD3OD, 300 MHz): (23.84; MS: 668.1 (M+H)+, 666.1 (M−1).
AK
1H NMR (CD3OD, 300 Hz): (1.19-1.22 (m, 12H), (1.24-1.34 (m, 6H), (3.37 (s, 3H), (3.65 (t, 2H), (3.85-4.00 (m, 4H), (4.12-4.15 (m, 3H), (4.20-4.24 (m, 2H), (4.31 (t, 2H), (4.88-4.99 (M, 2H), (6.90-6.95 (m, 3H), (7.26 (t, 2H); 31P NMR (CD3OD, 300 MHz): (23.54; MS: 696.1 (M+H)+, 694.2 (M−1).
AL
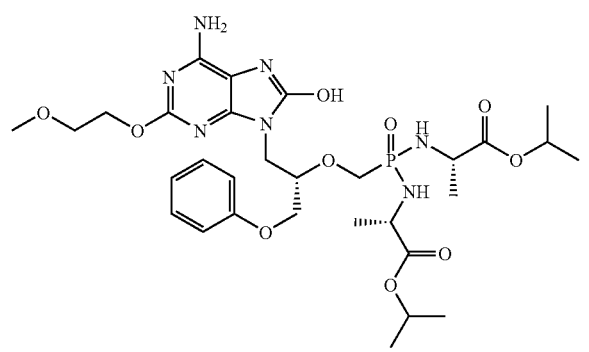
$^1$H NMR (CD3OD, 300 MHz): (1.20-1.24 (m, 12H), (1.32-1.35 (m, 6H), (3.38 (s, 3H), (3.66 (t, 2H), (3.90-4.01 (m, 4H), (4.09-4.15 (m, 3H), (4.20-4.25 (m, 2H), (4.32 (t, 2H), (4.90-4.99 (m, 2H), (6.90-6.96 (m, 3H), (7.26 (t, 2H); $^{31}$P NMR (CD3OD, 300 MHz): (23.77; MS: 696.1 (M+H)+, 694.1 (M−1).
146
AM
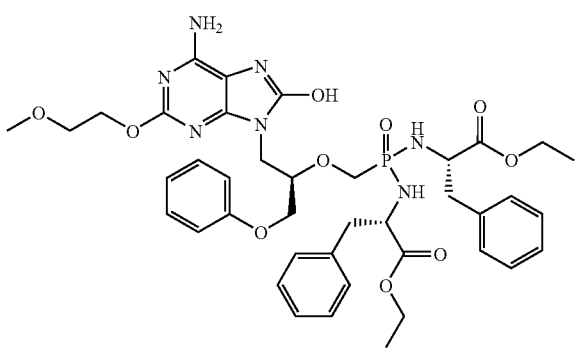
1H NMR (CD3OD, 300 MHz): (1.11-1.22 (m, 6H), (2.73-3.04 (m, 4H), (3.36 (s, 3H), (3.49-3.55 (m, 2H), (3.64 (t, 2H), (3.98-4.17 (m, 11H), (4.29 (t, 2H), (6.84-6.93 (m, 3H), (7.10-7.28 (m, 12H); 31P NMR (CD3OD, 300 MHz): (23.16; MS: 820.2 (M+H)+, 818.2 (M−1).
AN
1H NMR (CD3OD, 300 MHz): (1.14-1.20 (m, 6H), (2.72-3.07 (m, 4H), (3.36 (s, 3H), (3.43-3.74 (m, 4H), (3.95-4.15 (m, 11H), (4.27-4.29 (m, 2H), (6.86-6.96 (m, 3H), (7.09-7.29 (m, 12H); 31P NMR (CD3OD, 300 MHz): (23.24; MS: 820.1 (M+H)+, 818.2 (M−1).
AO
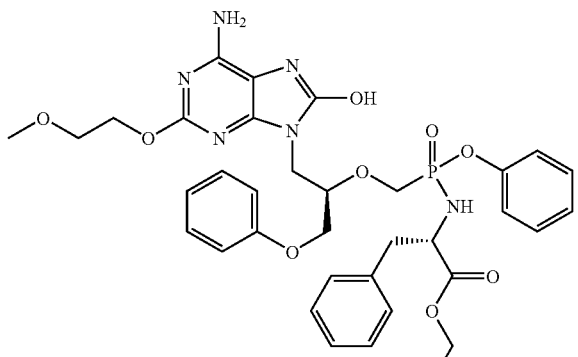
$^1$H NMR (CD$_3$OD, 300 MHz): δ 1.16 (d, 6H), δ 1.25 (d, 3H), δ 3.37 (s, 3H), δ 3.96-4.33 (m, 10H), δ 4.90-4.91 (m, partly covered by water peak, 1H), δ 6.92-7.32 (m, 10H); $^{31}$P NMR (CD$_3$OD, 300 MHz): δ 24.26; MS: 659.2 (M+H)$^+$, 657.1 (M−1).

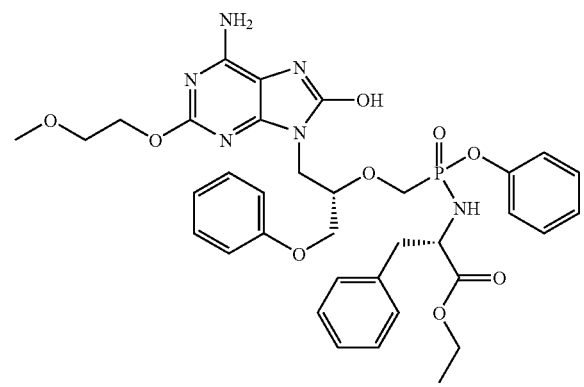

AP $^1$H NMR (CD$_3$OD, 300 MHz): δ 1.16-1.20 (m, 6H), δ 1.25 (d, 3H), δ 3.37 (s, 3H), δ 3.65 (t, 2H), δ 3.94-4.25 (m, 7H), δ 4.30-4.33 (m, 3H), δ 4.90-4.91 (m, partly covered by water peak, 1H), δ 6.92-7.29 (m, 10H); $^{31}$P NMR (CD$_3$OD, 300 MHz): δ 23.36 (s), δ 24.55 (s); MS: 659.2 (M+H)$^+$, 657.1 (M−1).

Examples AQ and AR

Scheme 36

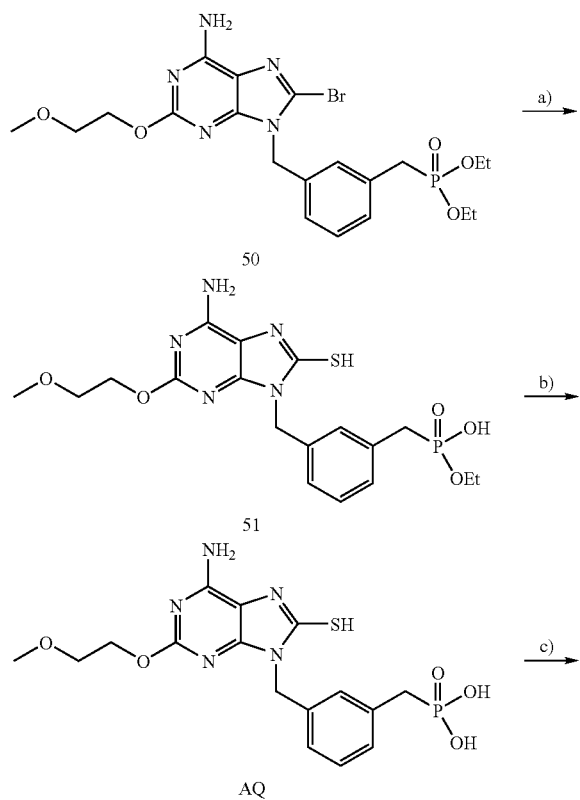

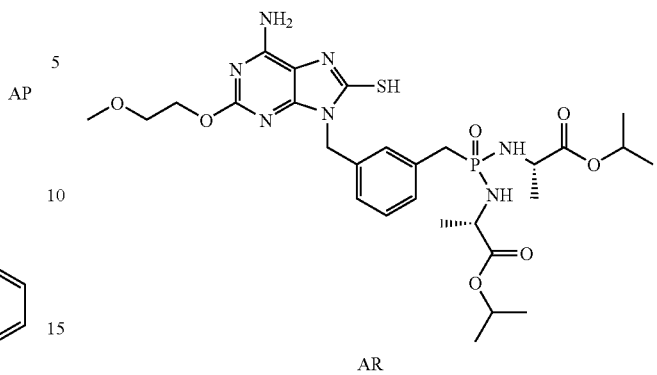

AR a) patossium thioacetate, DMF, 100° C. b) TMSBr, CH$_3$CN
c) aldrithiol, PPh$_3$, L-Ala-OiPr•HCl, pyridine Step 1: Synthesis of (3-(6-Amino-8-mercapto-2-(2-methoxy-ethoxy)-purin-9-ylmethyl)-benzyl)-phosphonic acid monoethyl ester (51)

To a solution of (3-(6-Amino-8-bromo-2-(2-methoxy-ethoxy)-purin-9-ylmethyl)-benzyl)-phosphonic acid diethyl ester (50) (180 mg, 0.34 mmol) in DMF (2 ml) was added potassium thioacetate (778 mg, 6.8 mmol). The reaction mixture stirred at 100° C. for 24 h. After cooling to rt, the reaction mixture was filtered and purified by reversed phase prep-HPLC using a linear gradient of acetonitrile in water from 5% to 95%. $^1$H NMR (DMSO, 300 MHz): (1.08 (t, 3H), (3.00 (d, 2H), (3.25 (s, 3H), (3.58 (t, 2H), (3.77-3.84 (m, 2H), (4.29 (t, 2H), (5.23 (s, 2H), (6.87 (bs, 2H), (7.16-7.28 (m, 4H); $^{31}$P NMR (DMSO, 300 MHz): (23.20; MS: 454.1 (M+H)$^+$, 452.0 (M−1).

(3-(6-Amino-8-mercapto-2-(2-methoxy-ethoxy)-purin-9-ylmethyl)-benzyl)-phosphonic acid (Example AQ)

1H NMR (CD3OD, 300 MHz): (3.07 (d, 2H), (3.38 (s, 3H), (3.71 (t, 2H), (4.44 (t, 2H), (5.36 (s, 2H), (7.21-7.47 (m, 4H); 31P NMR (CD3OD, 300 MHz): (23.48; MS: 426.1 (M+H)+, 424.0 (M−1).

Example AR

1H NMR (CD3OD, 300 MHz): δ 1.14-1.29 (m, 18H), δ 3.15 (d, 2H), δ 3.38 (s, 3H), δ 3.69-3.89 (m, 4H), δ 4.44 (t, 2H), (4.90-4.96 (m, 2H), (5.37 (s, 2H), (7.24-7.48 (m, 4H); 31P NMR (CD$_3$OD, 300 MHz): (27.23. MS: 652.0 (M+H)$^+$, 650.2 (M−1).

Examples AS, AT, and AU

Example AS, AT, and AU were prepared from Example C using procedures as shown in Scheme 17, except that phenol was replaced with cyclic amines or oxime.

AS

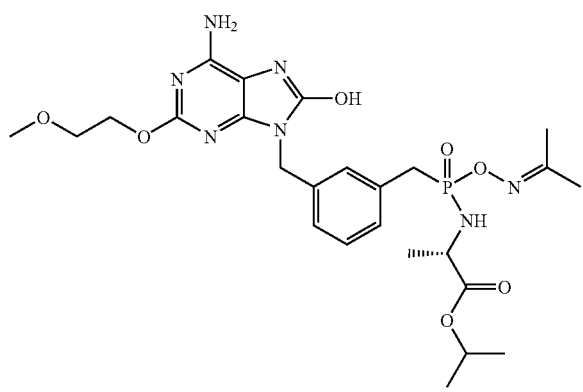

¹H NMR (CDCl3, 300 MHz): (1.18-1.33 (m, 9H), (1.85-1.95 (m, 6H), (3.25-3.35 (m, 2H), (3.39 (s, 3H), (3.49-3.67 9 m, 1H), (3.72 (t, 2H), (3.95-3.98 (m, 1H), (4.46 (t, 2H), (4.96-5.00 (m, 3H), (6.25 (bs, 2H), (7.15-7.35 (m, 4H), (10.40 (bs, 1H); ³¹P NMR (CDCl3, 300 MHz): (33.51 (s), (33.38 (s); MS: 578.2 (M+H)+, 576.1 (M−1).

AT

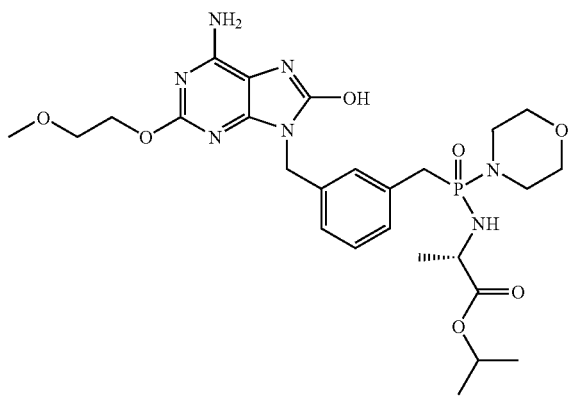

¹H NMR (CDCl3, 300 MHz): δ 1.16-1.35 (m, 9H), δ 2.90-3.17 (m, 4H), δ 3.40 9 s, 3H), δ 3.46-3.50 (m, 4H), δ 3.73 (t, 2H), δ 3.86-3.89 (m, 1H), δ 4.52 (t, 2H), δ 4.96-5.03 (m, 3H), δ 7.14-7.37 (m, 4H), δ 10.63 (s, 1H); ³¹P NMR (CDCl₃, 300 MHz): δ 27.07 (s), δ 28.11 (s); MS: 592.1 (M+H)⁺, 590.2 (M−1).

AU

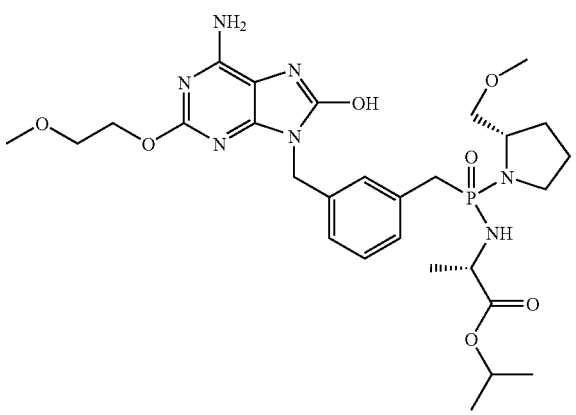

Synthesis of Example AU

To a solution of (3-(6-Amino-8-hydroxy-2-(2-methoxyethoxy)-purin-9-ylmethyl)-benzyl)-phosphonic acid (Example C) (100 mg, 0.24 mmol) in pyridine (1 ml) was added (s)-2-(methoxymethyl)pyrrolidine (28 mg, 0.24 mmol), triphenylphosphane (314 mg, 1.2 mmol) and aldrithiol-2 (264 mg, 1.2 mmol). The reaction mixture was reacted at 65° C. for 2 h. After starting material was consumed, L-alanine isopropyl ester hydrogen chloride (80 mg, 0.48 mmol), triphenylphosphine (314 mg, 1.2 mmol), adrithiol-2 (264 mg, 1.2 mmol) and molecular sieves (50 mg) were added to the reaction mixture. The mixture was stirred at 65° C. until LC/MC indicated that the reaction was complete, and then the mixture was cooled and the solvent was removed. The residue was loaded on silica gel column, eluted with EtOAc/Hexane (1/1) to remove a yellow impurity and then with 20% EtOH/EtOAC to elute the product. The fractions containing product were concentrated and purified by reversed phase HPLC, using 5-85% acetonitrile in water as solvent. ¹H NMR (CDCl₃, 300 MHz): δ 1.19-1.33 (m, 12H), 61.72-1.75 (m, 3H), δ 2.90-3.01 (m, 2H), δ 3.03-3.20 (m, 6H), δ 3.38 (s, 3H), δ 3.71-3.82 (m, 4H), δ 4.08-4.10 (m, 1H), δ 4.46 (t, 2H), 64.94-5.00 (m, 3H), δ 6.55 (bs, 2H), δ 7.16-7.33 (m, 4H), δ 10.72 (b, 1H); ³¹P NMR (CDCl₃, 300 MHz): δ 26.65 (s), δ 28.78 (s); MS: 620.2 (M+H)⁺, 618.2 (M−1).

Example AV

Scheme 37

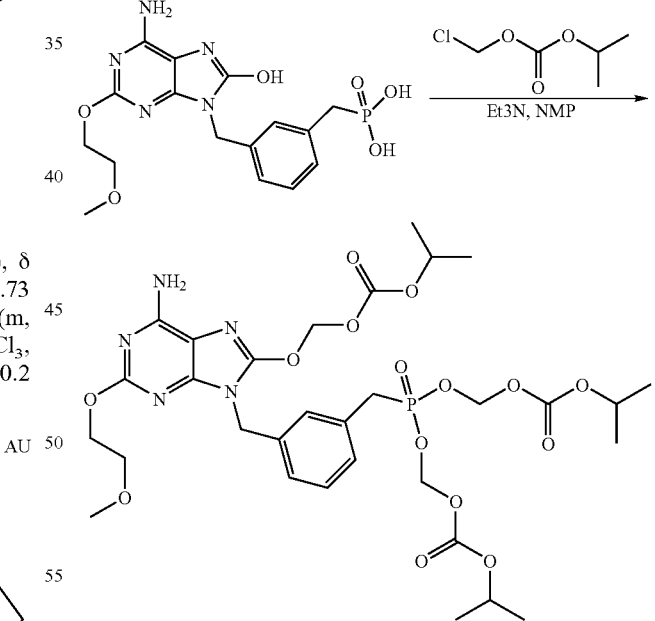

Synthesis of Example AV

Example C (95 mg, 0.232 mmol) was suspended in NMP (0.5 mL). Triethylamine (0.22 mL) was added and the mixture was heated to 62° C. A solution of chloromethyl isopropyl carbonate (0.22 mL) in NMP (1.5 mL) was added with a syringe pump over 90 minutes. The mixture was heated at 62°

C. for 5 more hours, and then diluted with ethyl acetate, washed with water and brine, dried with Na$_2$SO$_4$ and evaporated under vacuum. The crude product was purified by flash chromatography on silica gel (Eluent 50% to 100% hexane/ethyl acetate) giving AV (20 mg) as colorless oil. MS: 758.2 (M+H)$^+$.

Example AW

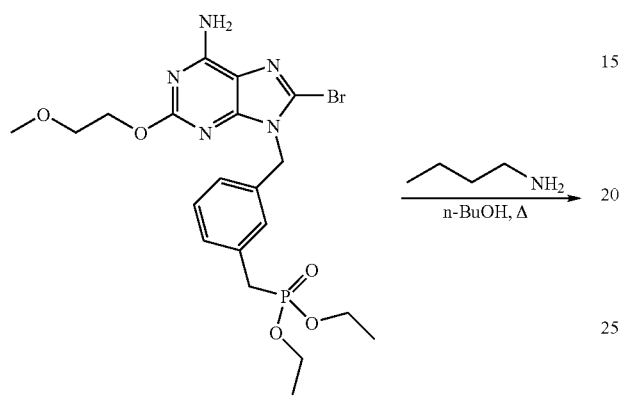

Synthesis of Example AW

Diethyl (3-((6-amino-8-bromo-2-(2-methoxyethoxy)-9H-purin-9-yl)methyl)phenyl)methylphosphonate 50 from the synthesis of Example C (40 mg, 0.076 mmol), n-butylamine (0.1 mL) and n-butanol (1 mL) were combined and heated in the microwave at 200° C. for 10 minutes. The solvent was evaporated under vacuum and the residue was partitioned between brine and dichloromethane. The aqueous layer was extracted with dichloromethane (4×). The combined organic layers were dried with Na$_2$SO$_4$ and evaporated under vacuum. The crude product 56 was dissolved in acetonitrile (1 mL) and bromotrimethylsilane (1 mL) was added. The mixture was stirred at ambient temperature overnight. After evaporation to dryness the crude product was purified by preparative reverse phase HPLC giving Example AW (6 mg) was white powder. MS: 465.2 (M+H).

Example AX

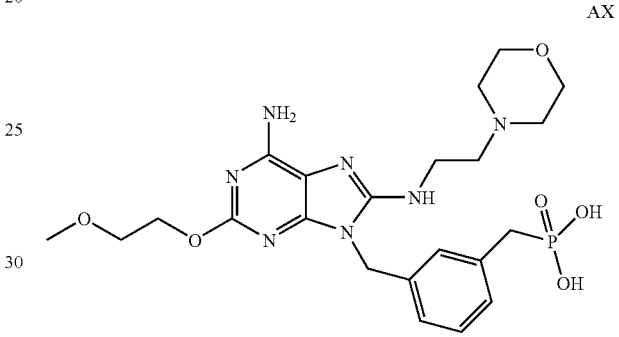

Example AX was prepared using procedures similar to those used to prepare Example AW except that n-butylamine was replaced with 2-morpholinoethanamine. MS: 522.2 (M+H).

Example AY

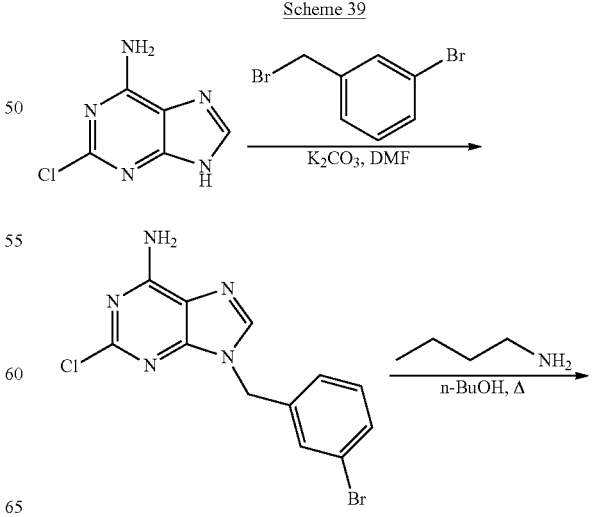

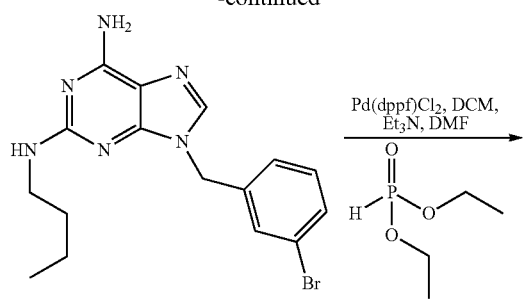

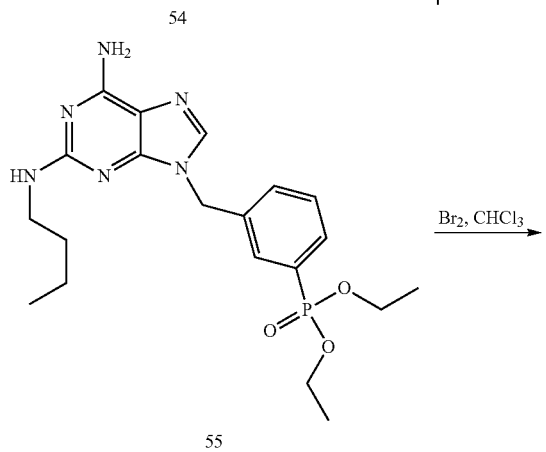

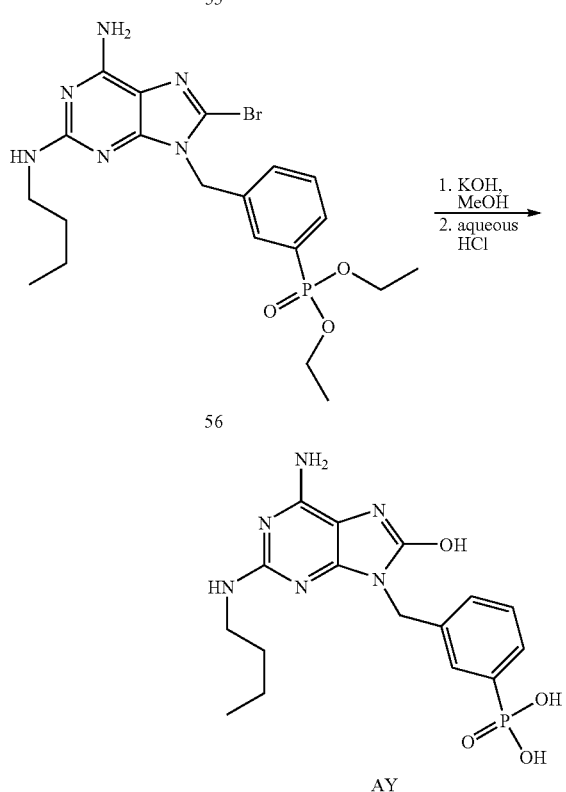

Synthesis of 9-(3-bromobenzyl)-2-chloro-9H-purin-6-amine (53)

2-Chloroadenine (1.53 g, 9.0 mmol), 3-bromobenzyl bromide (2.48 g, 9.92 mmol), potassium carbonate (1.38 g, 10 mmol) were combined in DMF (10 mL) and stirred at ambient temperature overnight. The mixture was diluted with ethyl acetate (200 mL) and washed with water and brine. The organic layer was dried with $Na_2SO_4$ and evaporated to dryness. The residue was triturated with diethyl ether/ethyl acetate 4:1 and filtered giving 9-(3-bromobenzyl)-2-chloro-9H-purin-6-amine (Compound 53) (2.3 g) as off-white solid.

Synthesis of 9-(3-bromobenzyl)-$N^2$-butyl-9H-purine-2,6-diamine (54)

9-(3-bromobenzyl)-2-chloro-9H-purin-6-amine (2.3 g) (100 mg, 0.295 mmol), n-butylamine (0.5 mL) and n-butanol (1 mL) were combined and heated in the microwave at 170° C. for 15 minutes. The solvent was evaporated under vacuum and the residue was partitioned between water and ethylacetate. The organic layer was washed with brine, dried with $Na_2SO_4$ and evaporated under vacuum. The crude product was triturated with diethylether and filtered giving 9-(3-bromobenzyl)-$N^2$-butyl-9H-purine-2,6-diamine (Compound 54) (60.9 mg) as off-white solid.

Synthesis of Example AY 9-(3-Bromobenzyl)-$N^2$-butyl-9H-purine-2,6-diamine (50 mg, 0.133 mmol), diethylphosphite (0.026 mL, 0.2 mmol), triethylamine (0.028 mL, 0.2 mmol), Pd(dppf)$Cl_2$.DCM (15 mg, 0.018 mmol) were combined in DMF (1 mL) and heated in the microwave at 130° C. for 5 minutes. The mixture was diluted with ethyl acetate (50 mL) and washed with water and brine, dried with $Na_2SO_4$ and evaporated. The crude product (Compound 55) was dissolved in chloroform (2 mL) and a 10% solution of bromine in chloroform was added dropwise until the bromine color remained. After stirring for additional 10 minutes the mixture was diluted with ethyl acetate (50 mL) and washed with 0.1N sodium thiosulfate solution, water, sodium bicarbonate solution and brine, dried with $Na_2SO_4$ and evaporated under vacuum to dryness. The crude product (Compound 56) was dissolved in methanol (10 mL) and 50% aqu. KOH solution (2 mL) was added. The mixture was heated under reflux until HPLC analysis showed complete disappearance of the bromide. Then the mixture was acidified with conc. HCl and heated under reflux for 2 hours. All solvents were removed under vacuum and the solid residue was extracted with methanol three times. The combined methanol extracts were evaporated under vacuum. The crude monoester was dissolved in acetonitrile (2 mL), bromotrimethylsilane (2 mL) was added and the mixture was stirred at ambient temperature overnight. After evaporation to dryness the crude product was dissolved in 1N HCl/acetonitrile and precipitated by slowly neutralizing with 1N NaOH to pH~5. The precipitate was filtered and dried giving Example AY (11.3 mg) as tan solid. MS: 393.2 (M+H)$^+$.

Examples AZ and BA were prepared using procedures similar to those as shown in Schemes 39 and 40 except that n-butylamine was replaced with benzylamine or sodium n-butoxide.

Example AZ 427.3 (M+H)+

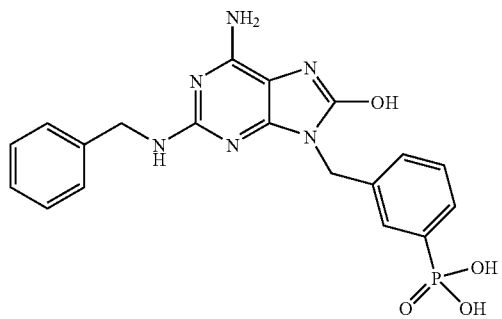

Example BA 394.2 (M+H)+

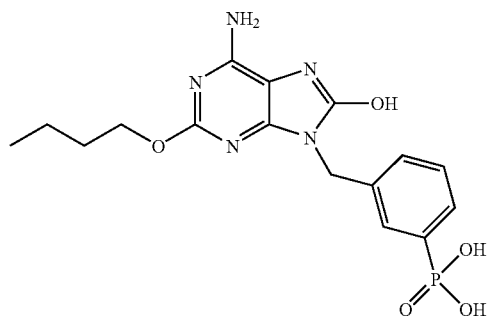

Example BB

Scheme 40

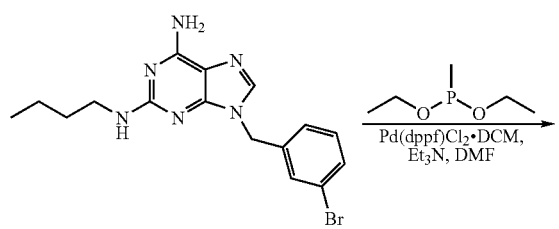

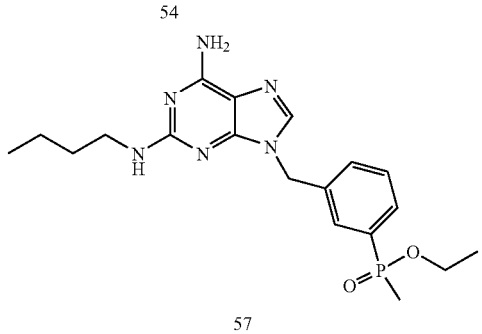

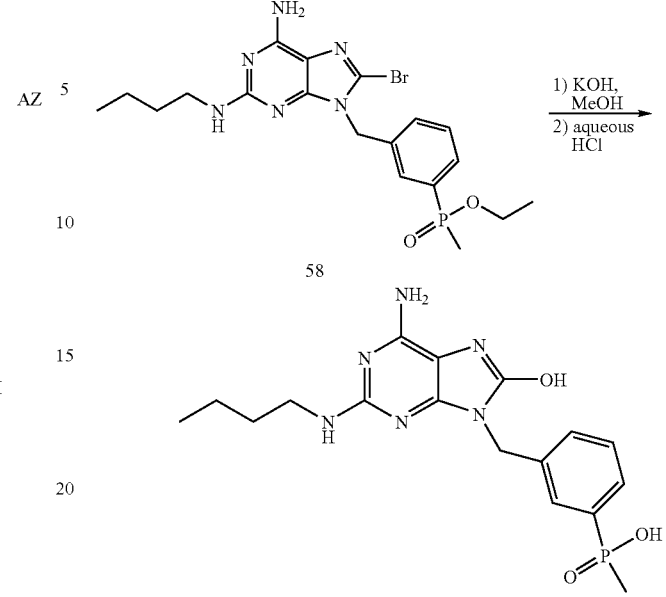

Synthesis of Example BB 9-(3-Bromobenzyl)-$N^2$-butyl-9H-purine-2,6-diamine (200 mg, 0.532 mmol), diethylmethylphosphonite (0.1 mL), triethylamine (0.12), Pd(dppf)Cl$_2$.DCM (50 mg) were combined in DMF (2 mL) and heated in the microwave at 130° C. for 5 minutes. The mixture was diluted with ethyl acetate (150 mL) and washed with water and brine, dried with Na$_2$SO$_4$ and evaporated. The crude product was dissolved in ethyl acetate and filtered through a pad of silica gel (3 g), eluting with 25% methanol in ethyl acetate. After evaporation to dryness the product was dissolved in chloroform (10 mL) and a 5% solution of bromine in chloroform was added dropwise until the bromine color remained. After stirring for additional 10 minutes the mixture was diluted with ethyl acetate (50 mL) and washed with 0.1N sodium thiosulfate solution, water, sodium bicarbonate solution and brine, dried with Na$_2$SO$_4$ and evaporated under vacuum to dryness. The crude product was dissolved in methanol (5 mL) and 50% aqu. KOH solution (1 mL) was added. The mixture was heated under reflux for 2 hours. Then the mixture was acidified with conc. HCl and heated under reflux overnight. All solvents were removed under vacuum and the solid residue was extracted with methanol. The methanol extract was evaporated under vacuum and the residue was purified by preparative reverse phase HPLC giving Example BB (87 mg) as white powder. MS: 391.2 (M+H).

Example BC

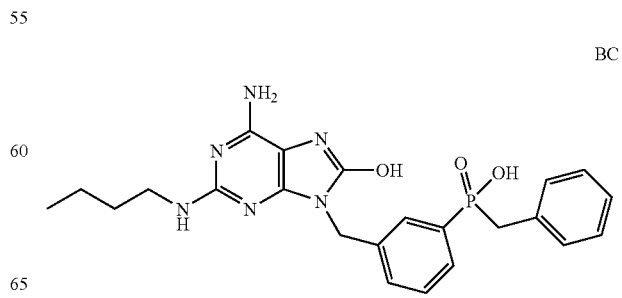

Example BC was prepared using procedures similar to those shown in Scheme 40 expect that diethylmethylphosphonite was replaced with ethyl benzylphosphinate. MS: 467.3 (M+H).

Example BD

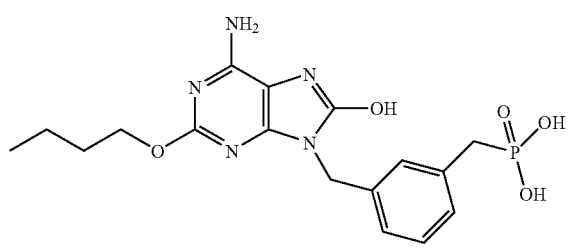

Scheme 41

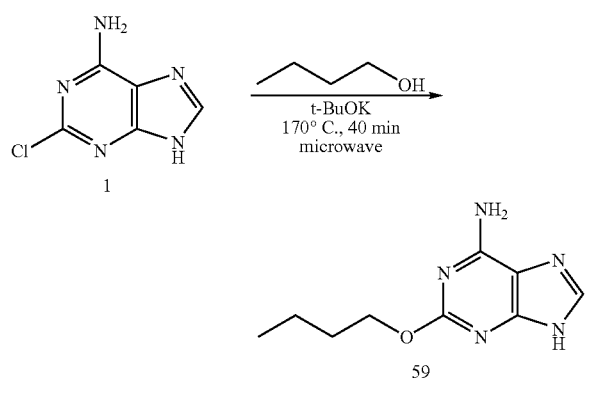

Synthesis of 2-butoxy-9H-purin-6-amine (59)

2-chloroadenine (1) (1.53 g, 9.03 mmol) was divided among three microwave vials (10-20 mL), each containing 1-butanol (10 mL) and t-BuOK (5 mL, 1M in THF). Each vial was heated to 170° C. for 40 minutes. After reaction completion the solvent was removed by rotary evaporation and the product was purified on flash column eluting 10% methanol in ethylacetate. Evaporation of solvent gave 1.33 g (70%) of 59 as an off white solid. $^1$H NMR (300 MHz, DMSO) δ 0.919 (t, 3H), 1.39 (m, 2H), 1.62 (m, 2H), 4.09 (t, 2H), 6.00 (s, 2H), 7.44 (s, 1H). LCMS: m/z for $C_9H_{13}N_5O^+$+H observed 208.1 at 1.34 minutes of a 3.5 minute run, gradient 5-95% $CH_3CN$ in $H_2O$.

Scheme 42

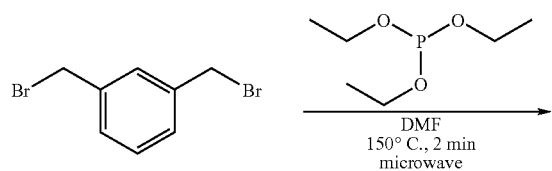

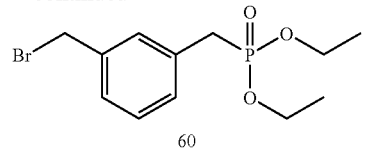

Synthesis of diethyl 3-(bromomethyl)benzylphosphonate (60)

To a solution of α,α'-Bisbromo-m-xylene (10.02 g, 37.95 mmol) in DMF (20 mL) was added triethyl phosphite (3.15 g, 3.3 mL, 19.98 mmol) via syringe. The mixture was heated to 150° C. for 2 minutes in a microwave. The reaction mixture was poured into water and product extracted with diethyl ether (3×25 mL). The combined organics were washed with water (2×50 mL) and brine (50 mL), and dried over $Na_2SO_4$. Reduced volume in vacuo and purified product by flash column eluting 30-100% ethyl acetate in hexanes to give 4.64 g (76%) 60 as a colorless oil. LCMS: m/z for $C_{12}H_{18}BrO_3P^+$+H observed 321.0 and 323.0 at 2.29 minutes of a 3.5 minute run, gradient 5-95% $CH_3CN$ in $H_2O$.

Scheme 43

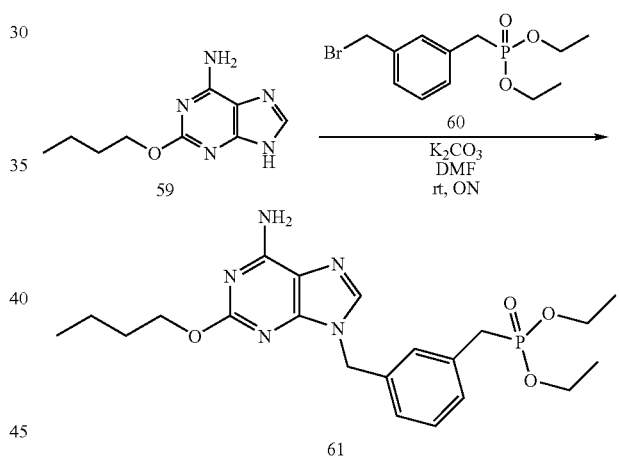

Synthesis of diethyl (3-((6-amino-2-butoxy-9H-purin-9-yl)methyl)phenyl)methylphosphonate (61)

A mixture of 59 (348.7 mg, 1.68 mmol) and $K_2CO_3$ (232.56 mg, 1.68) was dissolved in DMF (5 mL) and to it was added -60 (540.4 mg, 1.68 mmol). The mixture was left to stir over night at room temperature, solvent was evaporated by rotary evaporation. The remaining solid was taken up in water and the product extracted with DCM (3×50 mL). Combined organic layers were washed with water (1×50 mL) and brine (2×50 mL) and dried over $Na_2SO_4$. Product was purified by flash column eluting 0-15% methanol in ethyl acetate to give 165.8 mg (22%) 61 as a solid. $^1$H NMR (300 MHz, CDCl$_3$) δ 0.969 (t, 3H), 1.21 (m, 6H), 1.51 (m, 2H), 1.80 (m, 2H), 3.11 (d, 2H), 3.98 (m, 4H), 4.36 (t, 2H), 5.27 (s, 2H), 7.26 (m, 4H), 7.67 (s, 1H). LCMS: m/z for $C_{21}H_{30}N_5O_4P^+$+H observed 448.1 at 2.28 minutes of a 3.5 minute run, gradient 5-95% $CH_3CN$ in $H_2O$.

Scheme 44

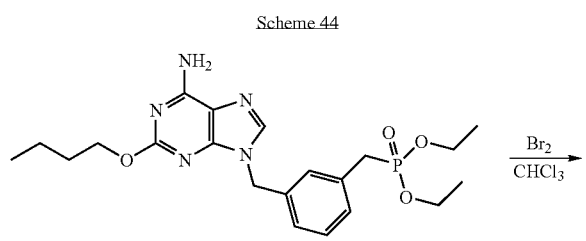

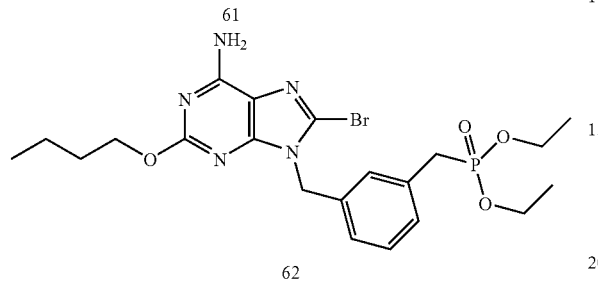

Synthesis of diethyl (3-((6-amino-8-bromo-2-butoxy-9H-purin-9-yl)methyl)phenyl)methylphosphonate (62)

To a solution of 61 (134.9 mg, 0.30 mmol) in CHCl$_3$ (5 mL) was added a 10% (v) solution of Br$_2$ in chloroform. The reaction was stopped when starting material was consumed, monitored by HPLC. Bromine was quenched with a saturated Na$_2$SO$_3$ solution and product extracted with DCM (2×10 mL). Organics were washed with water (2×10 mL) and brine (1×10 mL) and dried over Na$_2$SO$_4$. Purified by flash column eluting 100% ethyl acetate. Evaporation of solvent gave 76.0 mg (49%) of 62 as a yellow solid. LCMS: m/z for C$_{21}$H$_{29}$BrN$_5$O$_4$P$^+$+H observed 526.1 and 528.1 at 2.37 minutes of a 3.5 minute run, eluting 5-95% CH$_3$CN in H$_2$O.

Scheme 45

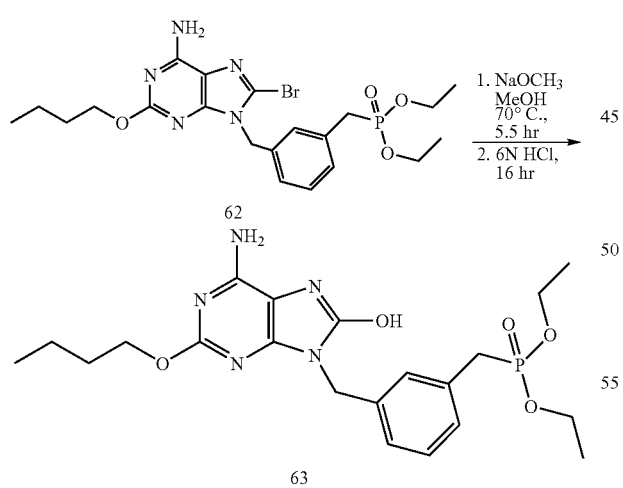

Synthesis of methyl (3-((6-amino-2-butoxy-8-hydroxy-9H-purin-9-yl)methyl)phenyl)methyl(methyl)phosphinate (63)

To a solution of 62 (76.0 mg, 0.144 mmol) in methanol (10 mL) was slowly added sodium methoxide (155.9 mg, 2.88 mmol). The mixture was heated to 70° C. for 5.5 hours at which time Dowex resin was added to quench any remaining methoxide. The resin was filtered off and the solvent evaporated. The product was stirred in 6N HCl over night after which time the solvent was evaporated to give 61 mg (93%) 63 as a white solid, the crude product was carried through to the next step. LCMS: m/z for C$_{21}$H$_{30}$N$_5$O$_5$P$^+$+H observed 464.1 at 2.10 minutes of a 3.5 minute run, eluting 5-95% CH$_3$CN in H$_2$O.

Scheme 46

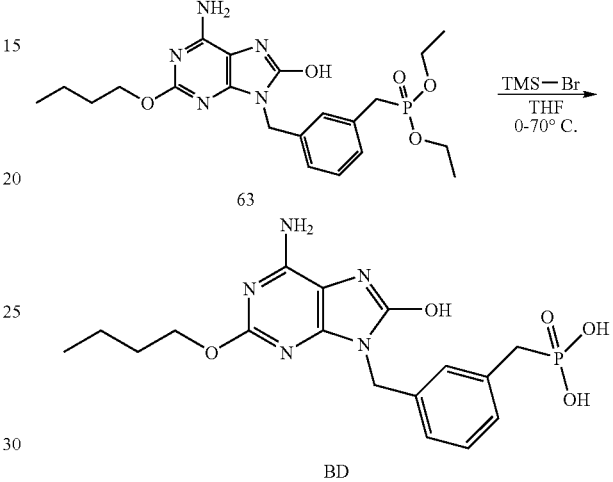

Synthesis of (3-((6-amino-2-butoxy-8-hydroxy-9H-purin-9-yl)methyl)phenyl)methylphosphonic acid (BD)

TMS-Br was added to a solution of 63 (61 mg, 0.13 mmol) in CH$_3$CN was cooled to 0° C. The mixture was stirred at 0° C. for 30 minutes, then heated to 70° C. for 6.5 hours. The solvent and TMS-Br were removed by rotary evaporation, and the resulting product was purified by prep. HPLC giving 1.6 mg of BD as a white solid. $^1$H NMR (300 MHz, CD$_3$OD) δ 0.972 (t, 3H), 1.49 (m, 2H), 1.74 (m, 2H), 2.97 (d, 2H), 4.28 (t, 2H), 4.98 (s, 2H), 7.18 (m, 2H), 7.29 (d, 1H), 7.36 (s. 1H). LCMS: m/z for C$_{17}$H$_{22}$N$_5$O$_5$P$^+$+H observed 408.2 at 1.70 minutes of a 3.5 minute run, eluting 5-95% CH$_3$CN in H$_2$O.

Example BE

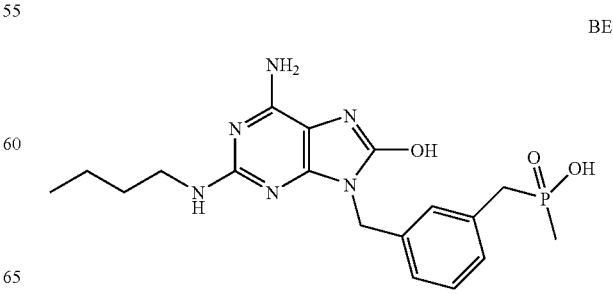

Scheme 47

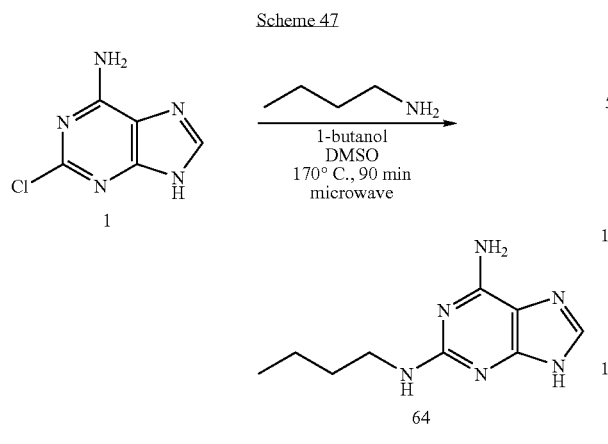

Synthesis of N²-butyl-9H-purine-2,6-diamine (64)

2-chloroadenine (1) (1.60 g, 9.44 mmol) was divided among three microwave vials (10-20 mL), each containing Butylamine (4 mL), 1-Butanol (10 mL,), and DMSO (1 mL). Each vial was heated to 170° C. for 90 minutes. After reaction completion the solvent was removed by rotary evaporation and the product was purified on flash column eluting 10% methanol in ethylacetate. Evaporation of solvent gave 1.62 g (83%) of 64 as an off white solid. $^1$H NMR (300 MHz, DMSO) δ 0.877 (t, 3H), 1.29 (m, 2H), 1.45 (m, 2H), 3.17 (t, 2H), 6.49 (s, 2H), 7.61 (s, 1H), 12.1 (s, 1H). LCMS: m/z for $C_9H_{14}N_6^+$+H observed 207.2 at 1.40 minutes of a 3.5 minute run, gradient 5-95% $CH_3CN$ in $H_2O$.

Scheme 48

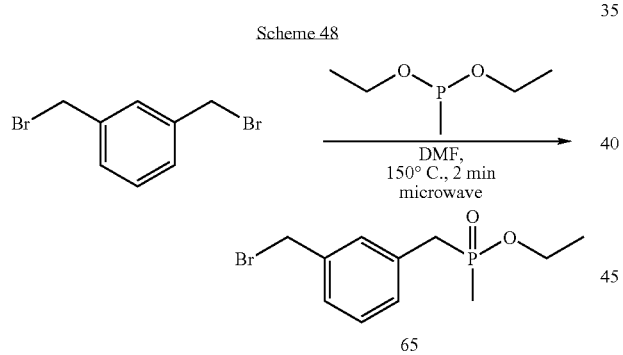

Synthesis of ethyl 3-(bromomethyl)benzyl(methyl)phosphinate (65)

To a solution of α,α'-Bisbromo-m-xylene (7.75 g, 29.38 mmol) in DMF (10 mL) was added diethyl methylphosphonite (2.0 g, 14.69 mmol) via syringe. The mixture was heated to 150° C. for 2 minutes in a microwave. The reaction mixture was poured into water and product extracted with ethyl acetate (3×25 mL). The combined organics were washed with water (2×50 mL) and brine (50 mL), and dried over $Na_2SO_4$. Reduced volume in vacuo and purified product by flash column eluting 20-100% ethyl acetate in hexanes to give 1.89 g mg (44%) 65 as a colorless oil. $^1$H NMR (300 MHz, $CDCl_3$) δ 1.24 (t, 3H), 1.33 (d, 3H), 3.08 (d, 2H), 3.97 (dt, 2H), 4.44 (s, 2H), 7.25 (m, 4H). LCMS: m/z for $C_{11}H_{16}BrO_2P^+$+H observed 291.0 and 293.0 at 2.09 minutes of a 3.5 minute run, gradient 5-95% $CH_3CN$ in $H_2O$.

Scheme 49

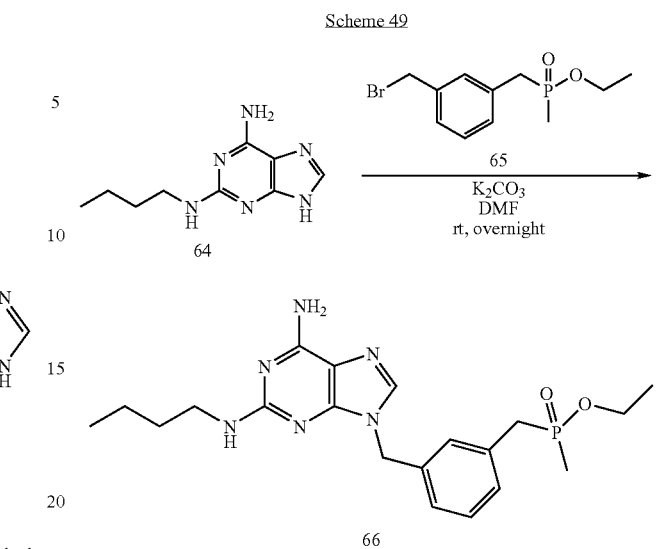

Synthesis of ethyl (3-((6-amino-2-(butylamino)-9H-purin-9-yl)methyl)phenyl)methyl(methyl)phosphinate (66)

A mixture of 64 (300.0 mg, 1.45 mmol) and $K_2CO_3$ (200.0 mg, 1.45 mmol) was dissolved in DMF (5 mL) and to it was added 65 (420.0 mg, 1.45 mmol). The mixture was left to stir over night at room temperature, solvent was evaporated by rotary evaporation. The remaining solid was taken up in water and the product extracted with DCM (3×50 mL). Combined organic layers were washed with water (1×50 mL) and brine (2×50 mL) and dried over $Na_2SO_4$. Product was purified by flash column eluting 0-20% methanol in ethyl acetate to give 299.4 mg (50%) 66 as a solid. $^1$H NMR (300 MHz, $CDCl_3$) δ 0.818 (t, 3H), 1.15 (t, 3H), 1.24 (d, 3H), 1.27 (m, 2H), 1.43 (m, 2H), 2.99 (d, 2H), 3.28 (m, 2H), 3.87 (m, 2H), 4.01 (m, 2H), 5.09 (s, 2H), 7.11 (m, 4H), 7.36 (s, 1H). LCMS: m/z for $C_{20}H_{29}N_6O_2P^+$+H observed 417.3 at 1.76 minutes of a 3.5 minute run, gradient 5-95% $CH_3CN$ in $H_2O$.

Scheme 50

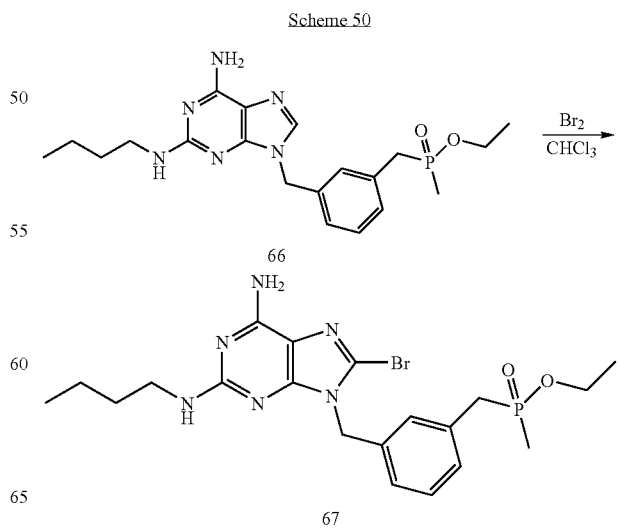

Synthesis of ethyl (3-((6-amino-8-bromo-2-(butylamino)-9H-purin-9-yl)methyl)phenyl)methyl(methyl)phosphinate (67)

To a solution of 66 (299.4 mg, 0.72 mmol) in CHCl$_3$ (5 mL) was added a 10% (v) solution of Br$_2$ in chloroform. The reaction was stopped when starting material was consumed, monitored by HPLC. Bromine was quenched with a saturated Na$_2$SO$_3$ solution and product extracted with DCM (2×10 mL). Organics were washed with water (2×10 mL) and brine (1×10 mL) and dried over Na$_2$SO$_4$. Purified by flash column eluting 10% methanol in ethyl acetate. Evaporation of solvent gave 223.6 mg (63%) of 67 as a yellow solid. LCMS: m/z for C$_{20}$H$_{28}$BrN$_6$O$_2$P$^+$+H observed 495.2 and 497.2 at 1.98 minutes of a 3.5 minute run, eluting 5-95% CH$_3$CN in H$_2$O.

Scheme 51

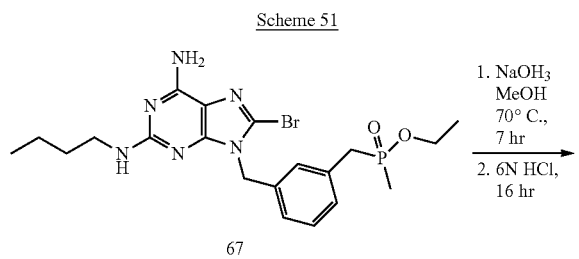

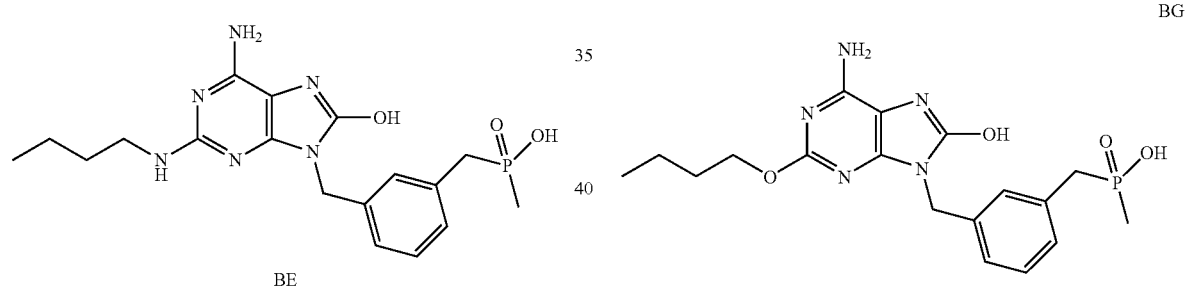

BE

Synthesis of methyl (3-((6-amino-2-butoxy-8-hydroxy-9H-purin-9-yl)methyl)phenyl)methyl(methyl)phosphinate (Example BE)

To a solution of 67 (223.6, 0.45 mmol) in methanol (10 mL) was slowly added sodium methoxide (487.7 mg, 5.25 mmol). The mixture was heated to 70° C. for 7 hours at which time Dowex resin was added to quench any remaining methoxide. The resin was filtered off and the solvent evaporated. The product was stirred in 6N HCl over night (16 hr) after which time the solution was heated to reflux for 2 hr. The pH was adjusted to 4, 90.6 mg (50%) of BE was collected by filtration as a white solid. $^1$H NMR (300 MHz, DMSO) δ 0.86 (t, 3H), 1.15 (d, 3H), 1.25 (m, 2H), 1.43 (m, 2H), 2.96 (d, 2H), 3.19 (s, 2H), 4.78 (s, 2H), 7.19 (m, 4H). LCMS: m/z for C$_{18}$H$_{25}$N$_6$O$_3$P$^+$+H observed 405.3 at 1.65 minutes of a 3.5 minute run, eluting 5-95% CH$_3$CN in H$_2$O.

Example BF

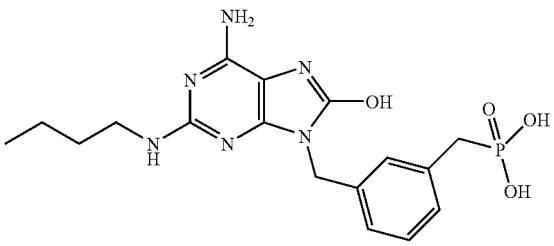

Example BF was prepared using procedures similar to those shown in Schemes 39 and 40 except that n-butylamine was replaced with sodium n-butoxide.

$^1$H NMR (300 MHz, DMSO) δ 0.88 (t, 3H), 1.32 (m, 2H), 1.47 (m, 2H), 2.87 (d, 2H), 3.27 (t, 2H), 4.80 (s, 2H), 7.13 (m, 4H). LCMS: m/z for C$_{17}$H$_{23}$N$_6$O$_4$P$^+$+H observed 407.2 at 1.57 minutes of a 3.5 minute run, gradient 5-95% CH$_3$CN in 1H$_2$O Example BG

BG

Scheme 52

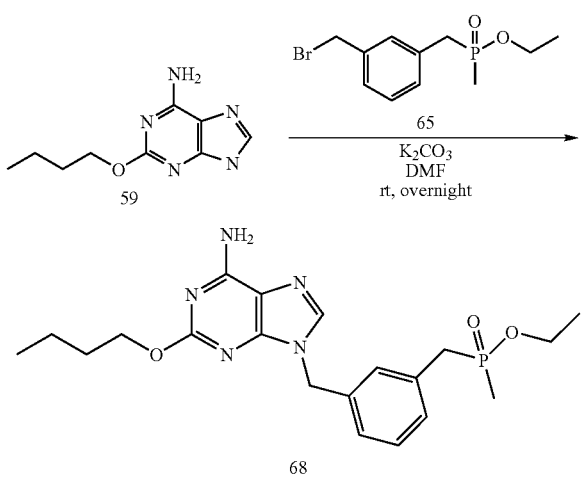

Synthesis of ethyl (3-((6-amino-2-butoxy-9H-purin-9-yl)methyl)phenyl)methyl(methyl)phosphinate (68)

A mixture of 59 (300.0 mg, 1.45 mmol) and K₂CO₃ (200.0 mg, 1.45 mmol) was dissolved in DMF (5 mL) and to it was added 65 (421.0 mg, 1.45 mmol). The mixture was left to stir over night at room temperature, solvent was evaporated by rotary evaporation. The remaining solid was taken up in water and the product extracted with DCM (3×50 mL). Combined organic layers were washed with water (1×50 mL) and brine (2×50 mL) and dried over Na₂SO₄. Product was purified by flash column eluting 0-10% methanol in ethyl acetate to give 204.0 mg (34%) 68 as a solid. ¹H NMR (300 MHz, CDCl₃) δ 0.923 (t, 3H), 1.19 (t, 3H), 1.31 (d, 3H), 1.44 (m, 2H), 1.73 (m, 2H), 3.07 (dd, 2H), 3.94 (m, 2H), 4.28 (t, 2H), 5.24 (s, 2H), 7.17 (m, 4H), 7.59 (s, 1H). LCMS: m/z for C₂₀H₂₈N₅O₃P⁺+H observed 418.2 at 2.03 minutes of a 3.5 minute run, gradient 5-95% CH₃CN in H₂O.

Synthesis of ethyl (3-((6-amino-8-bromo-2-butoxy-9H-purin-9-yl)methyl)phenyl)methyl(methyl)phosphinate (69)

To a solution of 68 (204.0 mg, 0.488 mmol) in CHCl₃ (5 mL) was added a 10% (v) solution of Br₂ in chloroform. The reaction was stopped when starting material was consumed, monitored by HPLC. Bromine was quenched with a saturated Na₂SO₃ solution and product extracted with DCM (2×10 mL). Organics were washed with water (2×10 mL) and brine (1×10 mL) and dried over Na₂SO₄. Purified by flash column eluting 10% methanol in ethyl acetate. Evaporation of solvent gave 130.4 mg (54%) of 69 as a yellow solid. LCMS: m/z for C₂₀H₂₇BrN₅O₃P⁺+H observed 496.2 and 498.1 at 2.18 minutes of a 3.5 minute run, eluting 5-95% CH₃CN in H₂O.

Synthesis of methyl (3-((6-amino-2-butoxy-8-hydroxy-9H-purin-9-yl)methyl)phenyl)methyl(methyl)phosphinate (70)

To a solution of 69 (130.4, 0.26 mmol) in methanol (10 mL) was slowly added sodium methoxide (283.8 mg, 5.25 mmol). The mixture was heated to 70° C. for 3 hours at which time Dowex resin was added to quench any remaining methoxide. The resin was filtered off and the solvent evaporated. The product was stirred in 6N HCl over night (16 hr) after which time the solvent was evaporated to give 70 as a white solid, the crude product was carried through to the next step. LCMS: m/z for C₂₀H₂₈N₅O₄P⁺+H observed 420.2 at 1.92 minutes of a 3.5 minute run, eluting 5-95% CH₃CN in H₂O.

Scheme 54

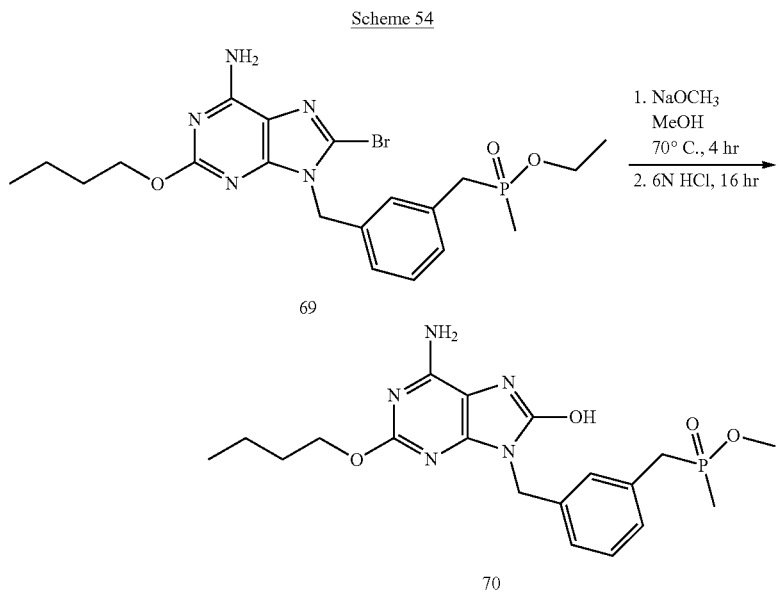

Scheme 53

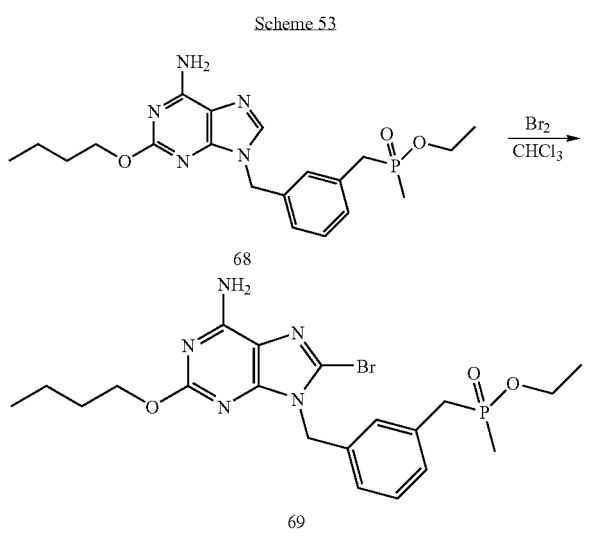

Scheme 55

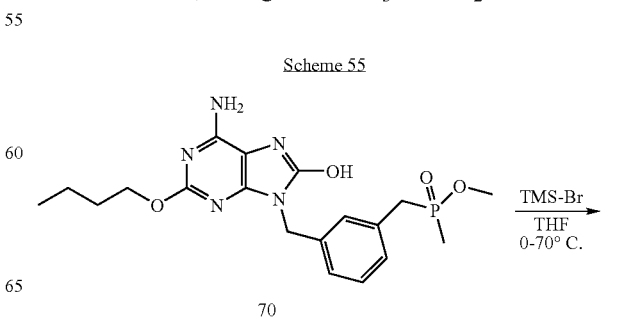

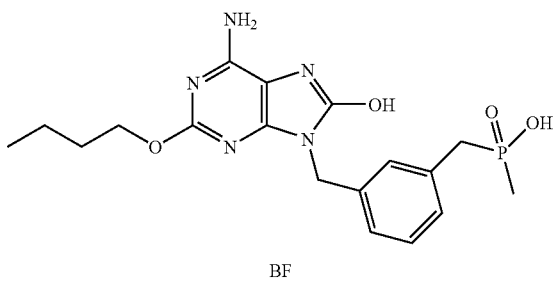

BF

Synthesis of (3-((6-amino-2-butoxy-8-hydroxy-9H-purin-9-yl)methyl)phenyl)methyl(methyl)phosphinic acid (Example BF)

TMS-Br was added to a solution of 70 in $CH_3CN$ was cooled to 0° C. The mixture was stirred at 0° C. for 30 minutes, then heated to 70° C. for 2.5 hours. The solvent and TMS-Br were removed by rotary evaporation, and the resulting product was purified by prep. HPLC giving 13.2 mg (13%) of BF as a white solid. $^1$H NMR (300 MHz, $CD_3OD$) δ 0.973 (t, 3H), 1.35 (d, 3H), 1.49 (m, 2H), 1.79 (m, 2H), 3.14 (d, 2H), 4.53 (t, 2H), 5.04 (s, 2H), 7.26 (m, 4H). LCMS: m/z for $C_{18}H_{24}N_5O_4P^+$+H observed 406.1 at 1.76 minutes of a 3.5 minute run, eluting 5-95% $CH_3CN$ in $H_2O$.

Example BG

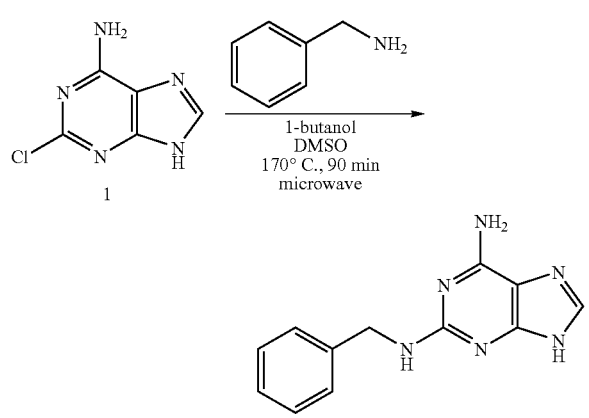

BG

Synthesis of $N^2$-benzyl-9H-purine-2,6-diamine (71)

2-chloroadenine (1) (2.81 g, 16.67 mmol) was divided among three microwave vials (10-20 mL), each containing Benzylamine (6 mL), 1-Butanol (8 mL,), and DMSO (1 mL). Each vial was heated to 170° C. for 90 minutes. After reaction completion the solvent was removed by rotary evaporation and triteration with diethylether gave 5.85 g of 71 as an off white solid pure enough for the next step. LCMS: m/z for $C_{12}H_{12}N_6^+$+H observed 241.2 at 1.45 minutes of a 3.5 minute run, gradient 5-95% $CH_3CN$ in $H_2O$.

Example BG was prepared from 71 using procedures similar to those used to prepare Example BD.

$^1$H NMR (300 MHz, DMSO) δ 2.85 (d, 2H), 4.39 (s, 2H), 4.75 (s, 2H), 6.44 (s, 2H), 7.13 (m, 9H), 10.2 (s, 1H). LCMS: m/z for $C_{20}H_{21}N_6O_4P^+$+H observed 441.2 at 1.61 minutes of a 3.5 minute run, gradient 5-95% $CH_3CN$ in $H_2O$.

Example BH

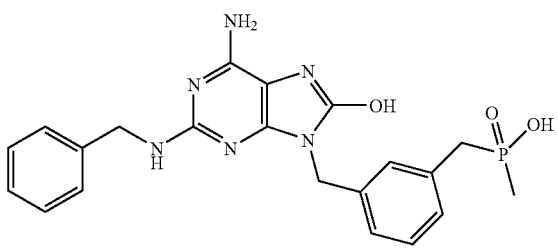

BH

Example BH was prepared using procedures similar to those used to prepare BG except that 71 was replaced with 59.

$^1$H NMR (300 MHz, DMSO) δ 1.15 (d, 3H), 2.94 (d, 2H), 4.41 (s, 2H), 4.76 (s, 2H), 7.03 (m, 9H), 9.72 (s, 1H). LCMS: m/z for $C_{21}H_{23}N_6O_3P^+$+H observed 439.2 at 1.67 minutes of a 3.5 minute run, gradient 5-95% $CH_3CN$ in $H_2O$.

TLR7 Reporter Assay protocol
A. HEK293 Assay
1. Cell Culture:

HEK293 cells stably transfected with the human TLR7 gene and a pNiFty™ NF-kB inducible luciferase reporter plasmid were obtained from Invivogen (San Diego, Calif.). DMEM/F12 medium, fetal bovine serum (FBS), Penicillin-Streptomycin (Pen-Strep), Blasticidin and Zeocine were from Invitrogen (Carlsbad, Calif.). The HEK293/TLR7/Luciferase cell line was constructed by transfecting stably the HEK293/TLR7 cells with the pNiFty plasmid. Cells were grown in the DMEM/F12 medium with 10% heat-inactivated FBS, supplemented with 1× Pen-Strep, 10 µg/mL Blasticidin and 51 g/mL Zeocin.

2. Assay Procedure:

For the determination of the EC50 and Emax values of TLR7 agonists in the reporter assay, 20 µL of 2× test concentration of serial diluted compound in cell culture medium was added to each well of a white, clear-bottomed 384-well cell culture plate from Corning (Corning, N.Y.). To this plate, 20 µL of cell culture medium containing 12,000 HEK293/TLR7/Luciferase cells was dispensed to each well. The plate was then placed in incubator (37° C. and 5% $CO_2$) and incubated for 2 days. After the incubation, 40 µL of the pre-mixed lysis buffer/luciferase substrate solution was dispensed into each well. The lysis buffer (5×) and luciferase substrate was obtained from Promega (Madison, Wis.) and they were mixed at 2:3 (v/v) ratio immediately prior to use. After 10 minutes of incubation at room temperature, the luminescence signal was measured using a VictorLight plate reader (Perkin Elmer, Wellesley, Mass.) with an integration time of 0.1 seconds per sample.

Data analysis was performed with Prism software from GraphPad (San Diego, Calif.) using a single site binding algorithm. The maximum signal for each test compound ($E_{max}$) was normalized with the maximum signal for the positive control, Resiquimod, on each plate. The concentration of a compound that corresponds to 50% of the maximum signal is defined as the $EC_{50}$.

The compounds of the present invention have HCV EC50 values (μM) in the range of about 0.01 to about 1000, or about 0.1 to about 500, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10.

B. PBMC Assay

Assays were conducted to determine cytokine stimulation at 24 hours from human Peripheral Blood Mononuclear Cell (PMBC) using the compounds of the present invention. The assays were run in duplicate, with 8-point, half-log dilution curves. The compounds of the present invention were diluted from 10 μM DMSO solution. Cell supernatants are assayed directly for IFNα and 1:10 dilution for TNFα. The assays were performed in a similar fashion as described in Bioorg. Med. Chem. Lett. 16, 4559, (2006). Specifically, cryo-preserved PBMCs were thawed and seeded 96 well plates with 750,000 cells/well in 190 μL/well cell media. The PBMCs were then incubated for 1 hour at 37° C. at 5% $CO_2$. Then, the compounds of the present invention were added in 10 μL cell media at 8 point, half-log dilution titration. The plates were incubated at 37° C. and 5% $CO_2$ for 24 hours and then spinned at 1200 rpm for 10 min, which was followed by collecting supernatant and storing the same at −80° C. Cytokine secretion was assayed with Luminex and Upstate multi-plex kits, using a Luminex analysis instrument.

The compounds of the present invention have IFN ECmax values (μM) in the range of about 0.01 to about 1000, or about 0.1 to about 500, or about 0.1 to about 300, or about 0.1 to about 200, or about 0.1 to about 100, or about 0.1 to about 50, or less than about 500, or less than about 400, or less than about 300, or less than about 200, or less than about 100, or less than about 50, or less than about 20, or less than about 10.

What is claimed is:

1. A compound selected from the group consisting of:

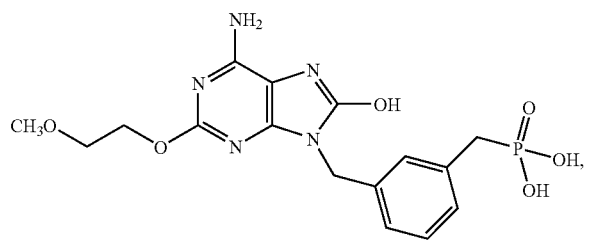

-continued

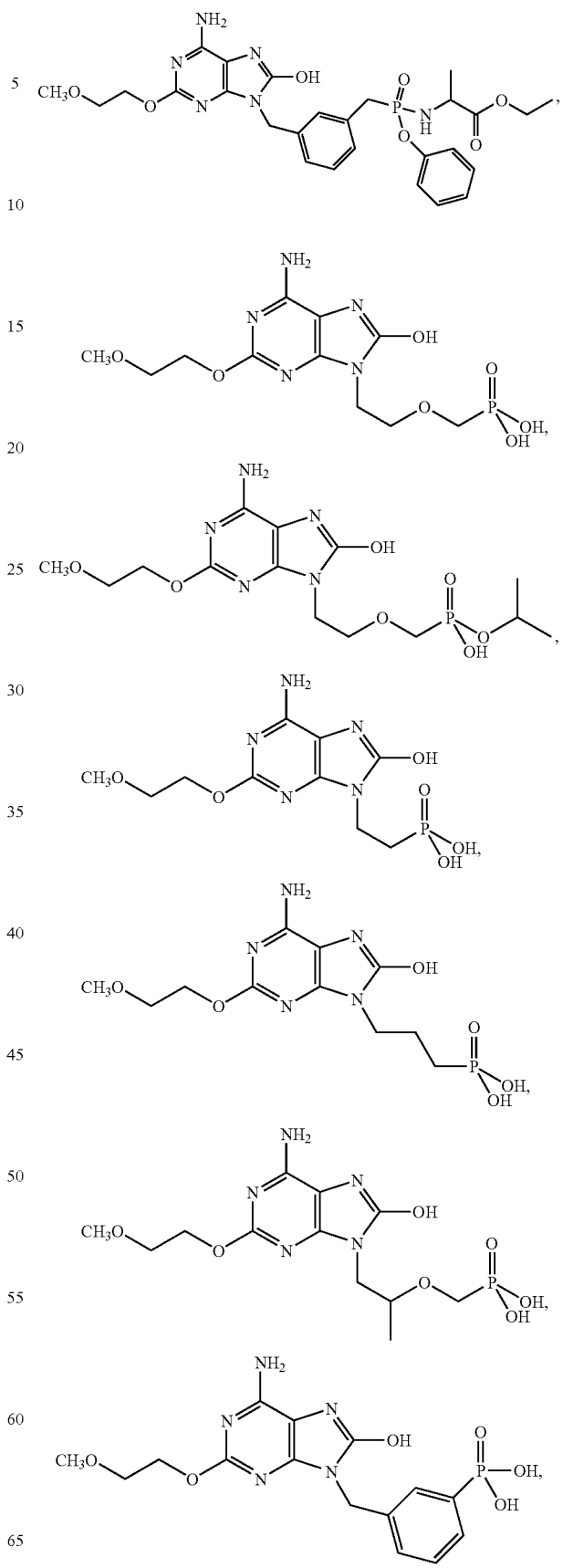

171
-continued
172
-continued
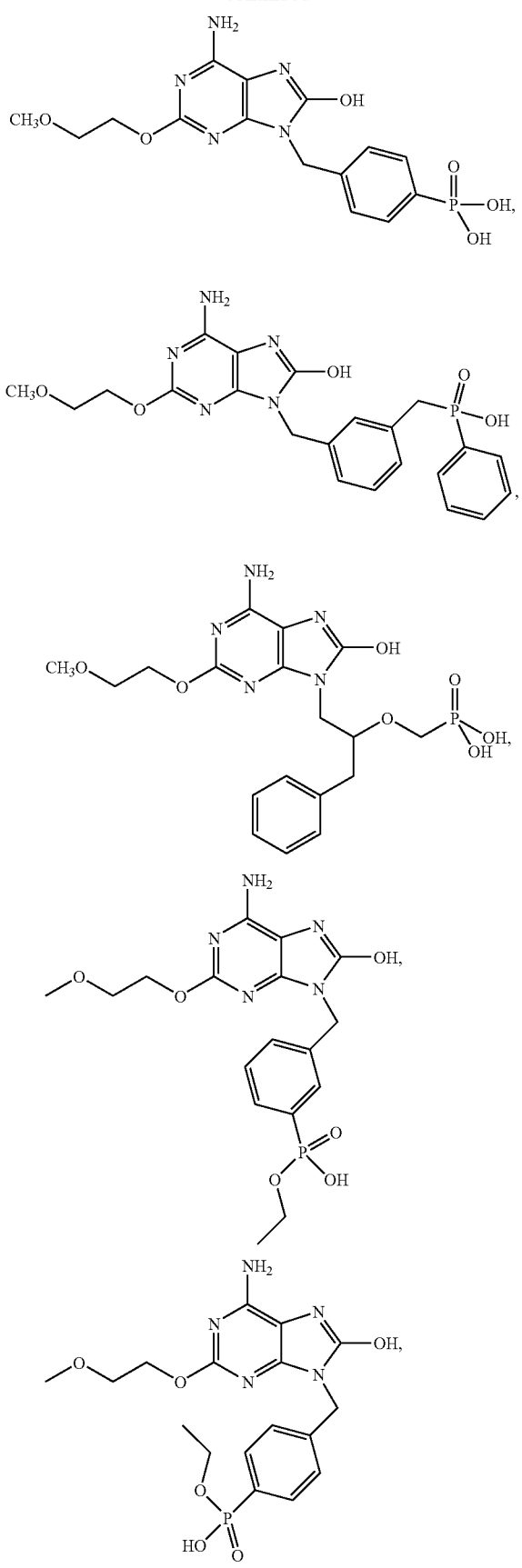
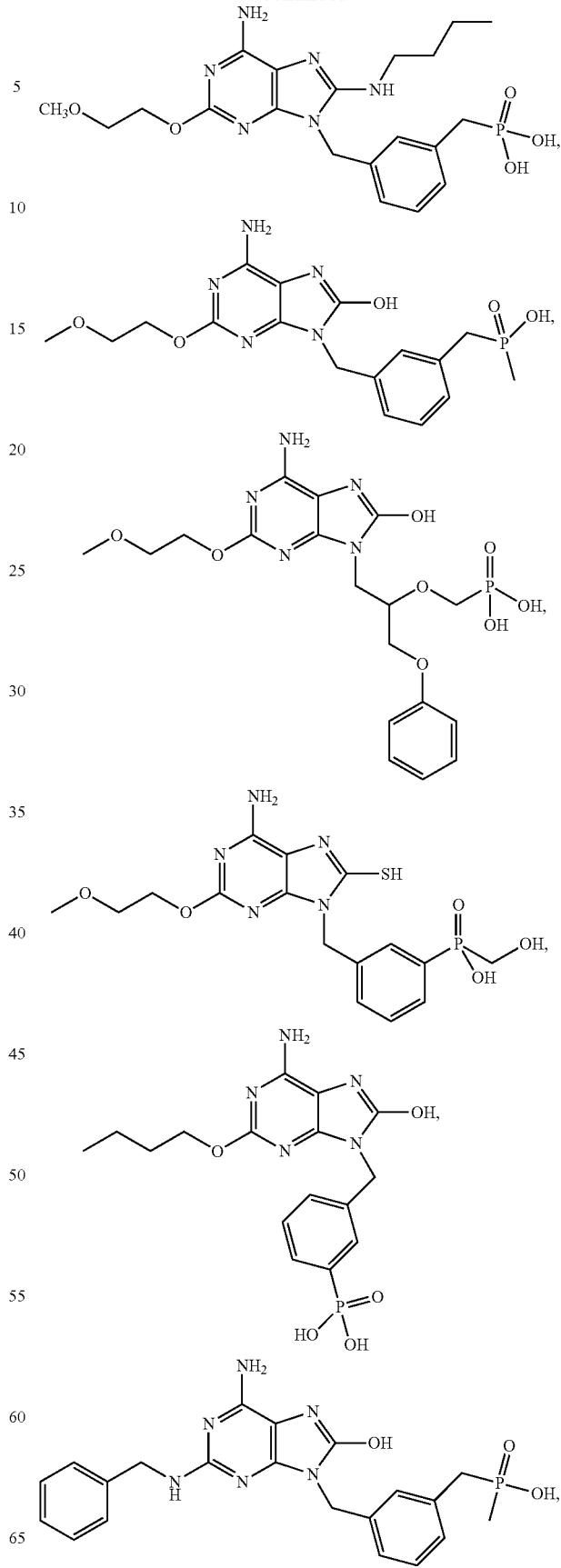

173
-continued
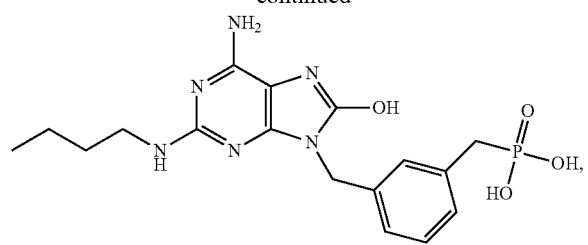
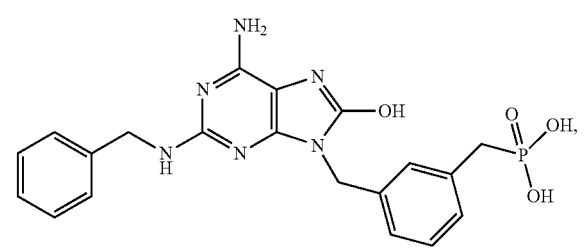
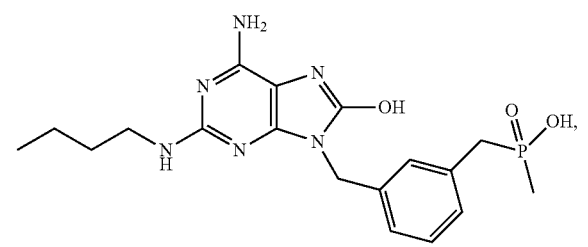
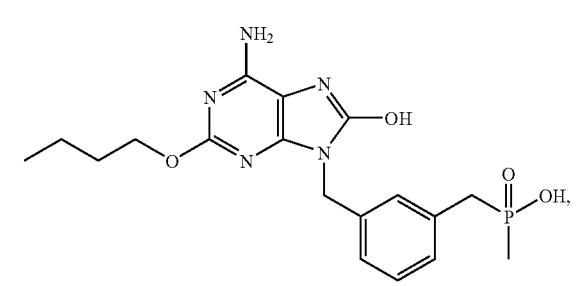
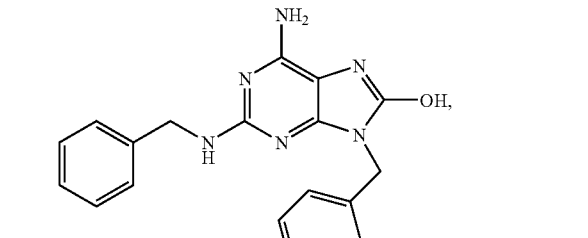
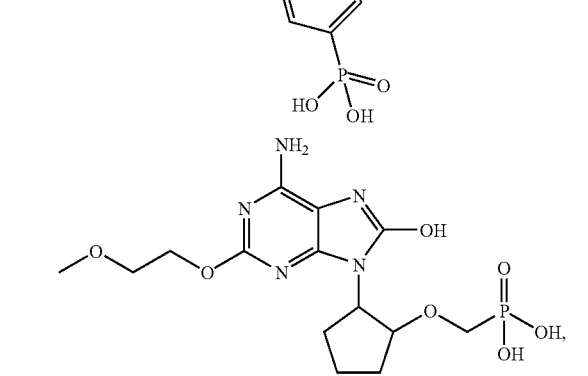
174
-continued
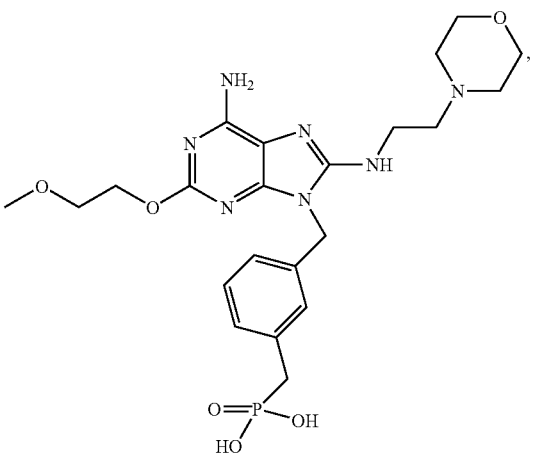
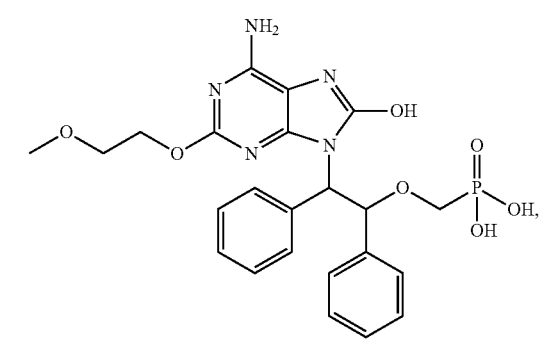
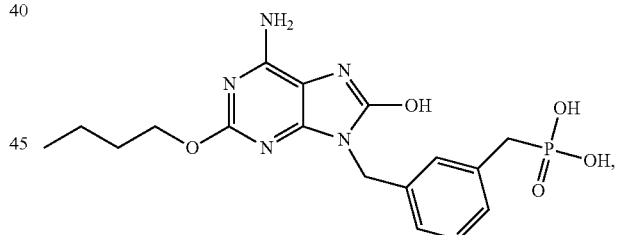
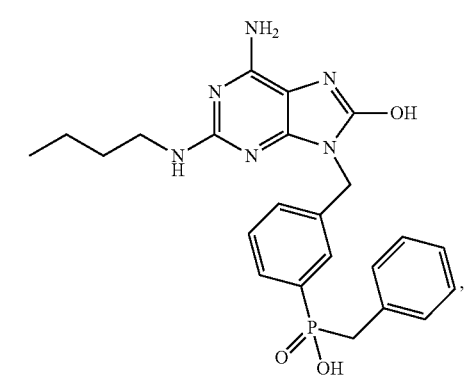

175
-continued
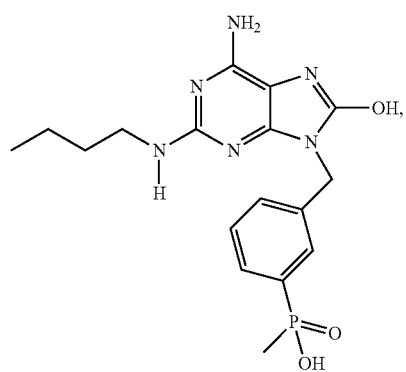
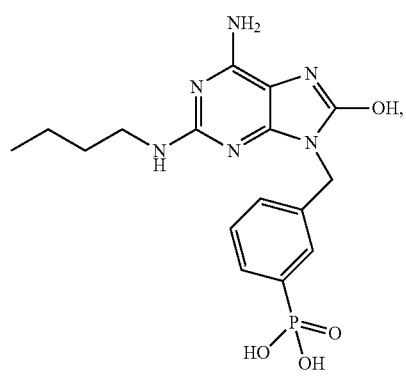
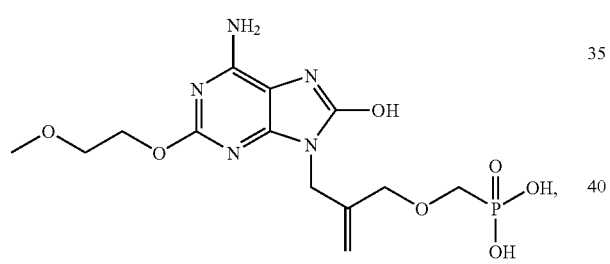
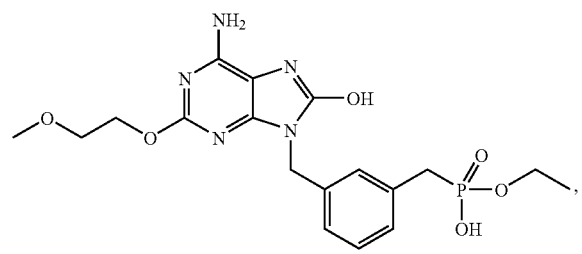
176
-continued
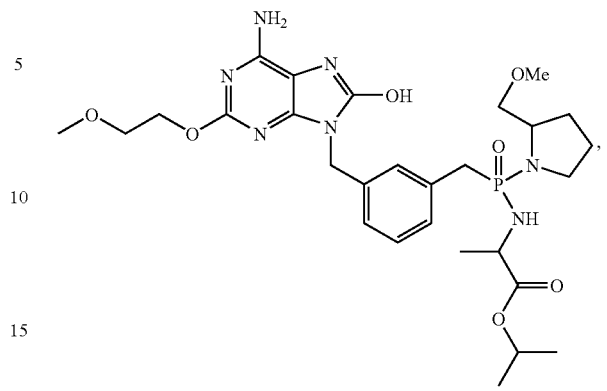
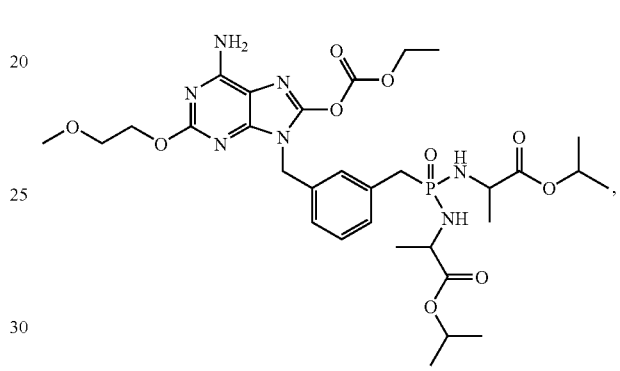
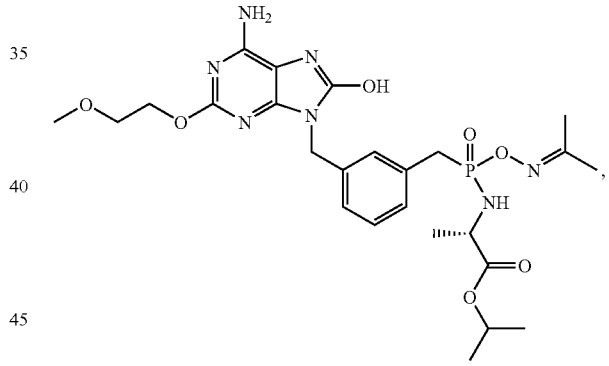
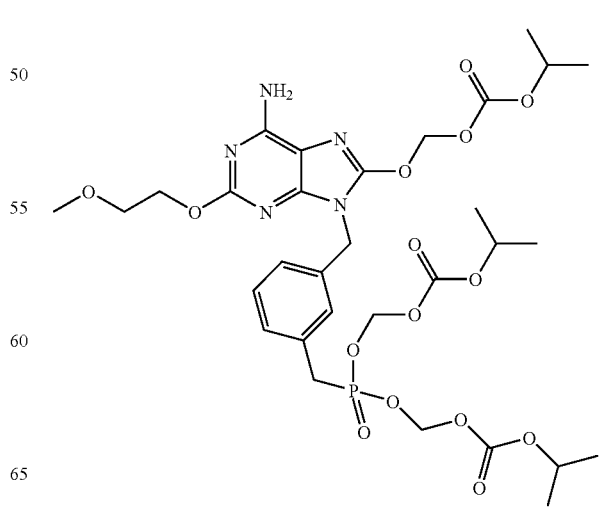

177
-continued
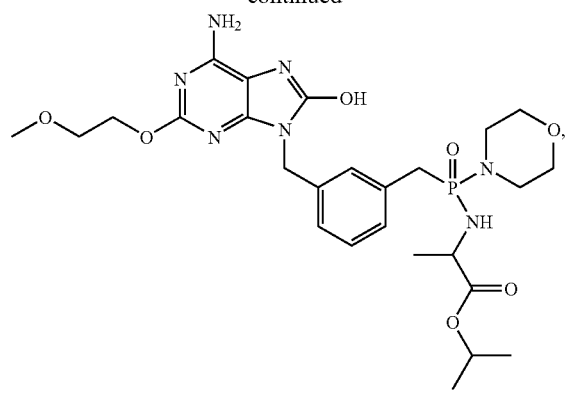
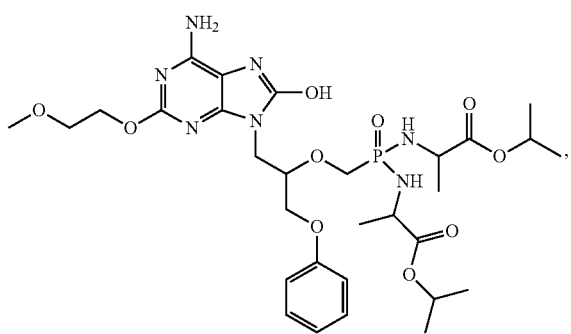
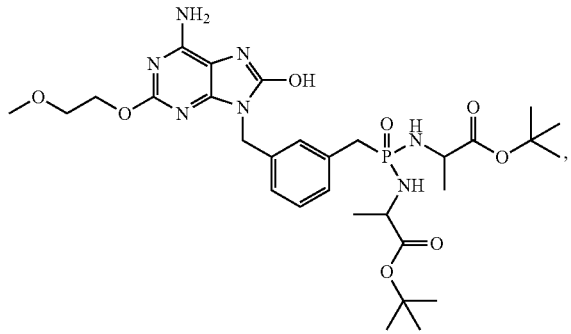
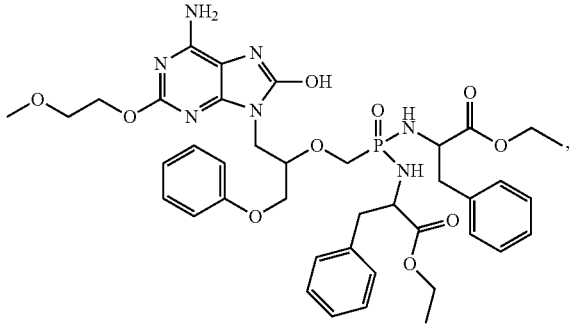
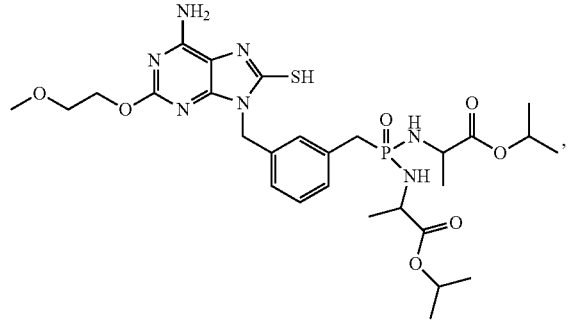
178
-continued
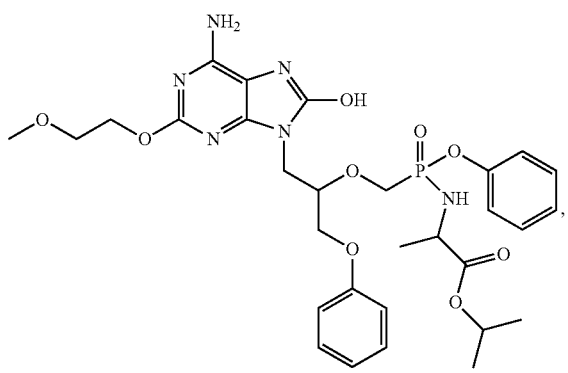
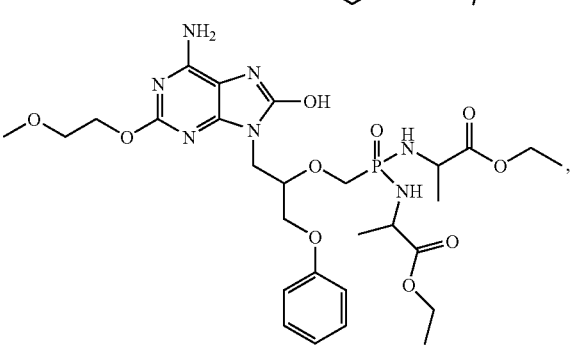
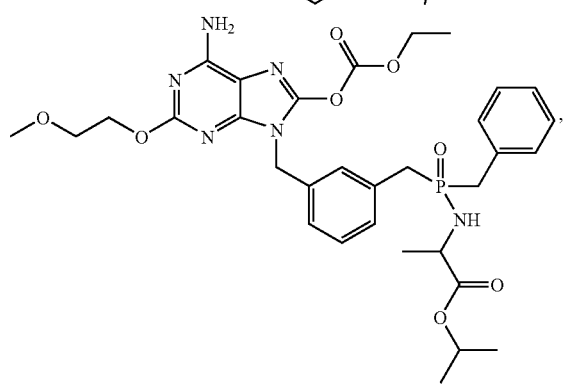
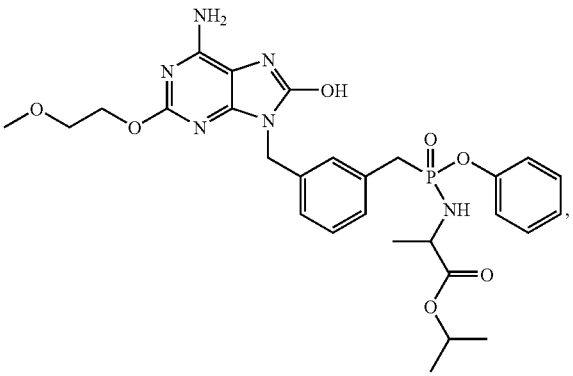
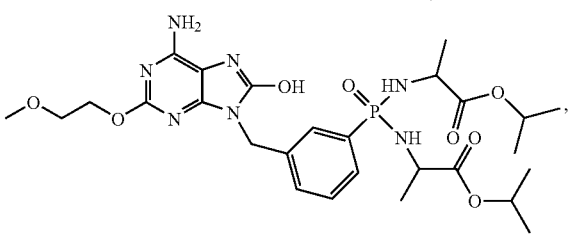

179
-continued
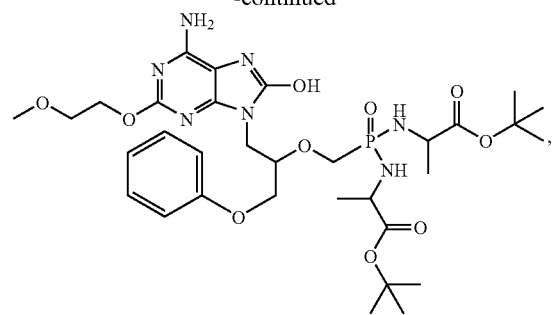
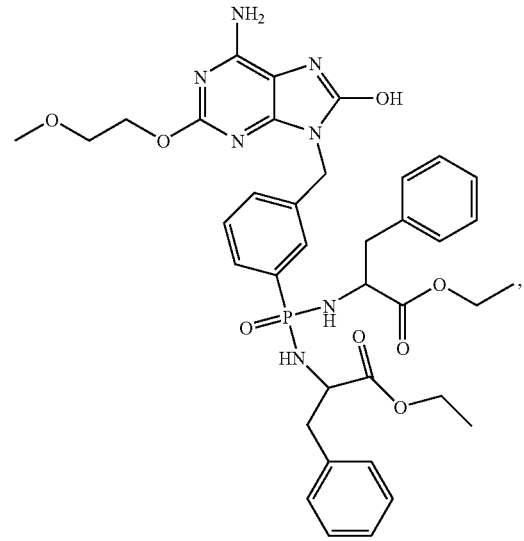
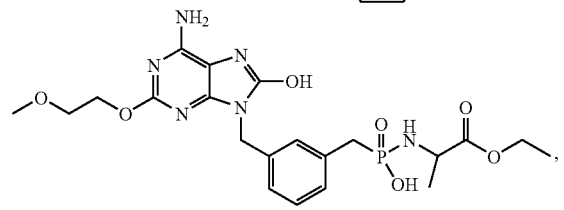
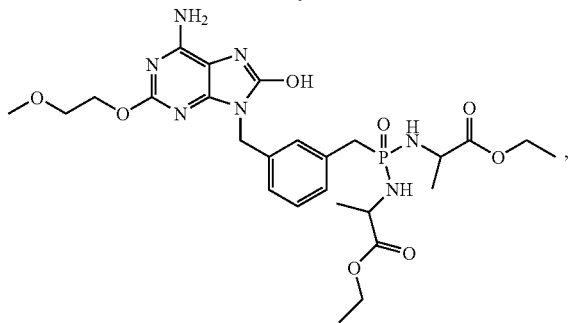
180
-continued
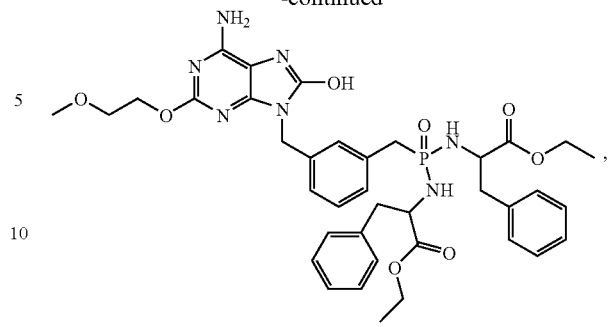
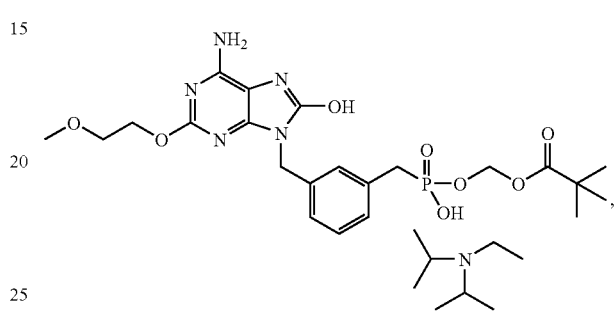
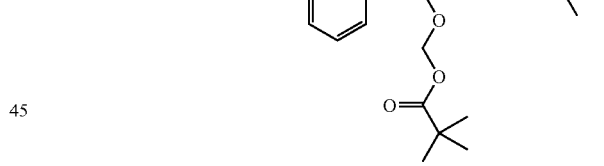
or pharmaceutically acceptable salts, solvates, and/or esters thereof.
* * * * *